(12) United States Patent
Lam et al.

(10) Patent No.: US 9,911,649 B1
(45) Date of Patent: Mar. 6, 2018

(54) PROCESS FOR MAKING AND USING MESH-STYLE NCEM PADS

(71) Applicant: PDF Solutions, Inc., San Jose, CA (US)

(72) Inventors: Stephen Lam, Freemont, CA (US); Dennis Ciplickas, San Jose, CA (US); Tomasz Brozek, Morgan Hill, CA (US); Jeremy Cheng, San Jose, CA (US); Simone Comensoli, Darfo Boario Terme (IT); Indranil De, Mountain View, CA (US); Kelvin Doong, Hsinchu (TW); Hans Eisenmann, Tutzing (DE); Timothy Fiscus, New Galilee, PA (US); Jonathan Haigh, Pittsburgh, PA (US); Christopher Hess, Belmont, CA (US); John Kibarian, Los Altos Hills, CA (US); Sherry Lee, Monte Sereno, CA (US); Marci Liao, Santa Clara, CA (US); Sheng-Che Lin, Hsinchu (TW); Hideki Matsuhashi, Santa Clara, CA (US); Kimon Michaels, Monte Sereno, CA (US); Conor O'Sullivan, Campbell, CA (US); Markus Rauscher, Munich (DE); Vyacheslav Rovner, Pittsburgh, PA (US); Andrzej Strojwas, Pittsburgh, PA (US); Marcin Strojwas, Pittsburgh, PA (US); Carl Taylor, Pittsburgh, PA (US); Rakesh Vallishayee, Dublin, CA (US); Larg Weiland, Hollister, CA (US); Nobuharu Yokoyama, Tokyo (JP)

(73) Assignee: PDF Solutions, Inc., San Jose, CA (US)

(*) Notice: Subject to any disclaimer, the term of this patent is extended or adjusted under 35 U.S.C. 154(b) by 0 days.

(21) Appl. No.: 15/259,309

(22) Filed: Sep. 8, 2016

Related U.S. Application Data

(60) Division of application No. 15/090,274, filed on Apr. 4, 2016, and a continuation-in-part of application No. 14/612,841, filed on Feb. 3, 2015.

(Continued)

(51) Int. Cl.
*H01L 21/66* (2006.01)
*H01L 23/58* (2006.01)
(Continued)

(52) U.S. Cl.
CPC .. *H01L 21/76895* (2013.01); *H01L 21/32139* (2013.01)

(58) Field of Classification Search
CPC ........................................................ H01L 22/32
(Continued)

(56) References Cited

U.S. PATENT DOCUMENTS 5,008,727 A 4/1991 Katsura et al.
5,576,223 A 11/1996 Zeininger et al.
(Continued)

FOREIGN PATENT DOCUMENTS

WO WO/2003/019456 3/2003
WO WO/2003/034492 4/2003
(Continued)

OTHER PUBLICATIONS

R. J. Baker, "CMOS: circuit design, layout, and simulation," 3rd et, John Wiley & Sons, Inc., 2010.
(Continued)

*Primary Examiner* — Calvin Lee
(74) *Attorney, Agent, or Firm* — David Garrod

(57) ABSTRACT

Wafers, chips, or dies that contain fill cells with structures configured to obtain in-line data via non-contact electrical
(Continued)

measurements ("NCEM"). Such NCEM-enabled fill cells may target/expose a variety of open-circuit, short-circuit, leakage, or excessive resistance failure modes, and may include NCEM pads that comprise a mesh of GATECNT and AACNT stripes. Such wafers, chips, or dies may include Designs of Experiments ("DOEs"), comprised of multiple NCEM-enabled fill cells, in at least two variants, all targeted to the same failure mode(s).

3 Claims, 141 Drawing Sheets

Related U.S. Application Data

(60) Provisional application No. 62/268,463, filed on Dec. 16, 2015.

(51) Int. Cl.
*H01L 21/768* (2006.01)
*H01L 21/3213* (2006.01)

(58) Field of Classification Search
USPC .................................. 438/11–18; 257/48
See application file for complete search history.

(56) References Cited

U.S. PATENT DOCUMENTS

| | | | |
|---|---|---|---|
| 5,576,833 A | 11/1996 | Miyoshi et al. |
| 5,773,315 A | 6/1998 | Jarvis |
| 5,959,459 A | 9/1999 | Satya et al. |
| 6,061,814 A | 5/2000 | Sugasawara et al. |
| 6,091,249 A | 7/2000 | Talbot et al. |
| 6,236,222 B1 | 5/2001 | Sur, Jr. et al. |
| 6,297,644 B1 | 10/2001 | Jarvis et al. |
| 6,348,808 B1 | 2/2002 | Yakura |
| 6,388,315 B1 | 5/2002 | Clark et al. |
| 6,433,561 B1 | 8/2002 | Satya et al. |
| 6,452,412 B1 | 9/2002 | Jarvis et al. |
| 6,509,197 B1 | 1/2003 | Satya et al. |
| 6,524,873 B1 | 2/2003 | Satya et al. |
| 6,539,106 B1 | 3/2003 | Gallarda et al. |
| 6,576,923 B2 | 6/2003 | Satya et al. |
| 6,633,174 B1 | 10/2003 | Satya et al. |
| 6,636,064 B1 | 10/2003 | Satya et al. |
| 6,815,345 B2 | 7/2004 | Yan et al. |
| 6,771,806 B1 | 8/2004 | Satya et al. |
| 6,844,550 B1 | 1/2005 | Yin et al. |
| 6,861,666 B1 | 3/2005 | Weiner et al. |
| 6,897,444 B1 | 5/2005 | Alder |
| 6,949,765 B2 | 9/2005 | Song et al. |
| 6,967,110 B2 | 11/2005 | Guldi et al. |
| 7,026,175 B2 | 4/2006 | Li et al. |
| 7,101,722 B1 | 9/2006 | Wang et al. |
| 7,105,436 B2 | 9/2006 | Zhao et al. |
| 7,137,092 B2 | 11/2006 | Maeda |
| 7,198,963 B2 | 4/2007 | Gaurav et al. |
| 7,217,579 B2 | 5/2007 | Ben-Porath et al. |
| 7,223,616 B2 * | 5/2007 | Duan ................. H01L 22/34 257/48 |
| 7,256,055 B2 | 8/2007 | Aghababazadeh et al. |
| 7,280,945 B1 | 10/2007 | Weiner et al. |
| 7,456,636 B2 | 11/2008 | Patterson et al. |
| 7,474,107 B2 | 1/2009 | Patterson et al. |
| 7,518,190 B2 | 4/2009 | Cote et al. |
| 7,514,681 B1 | 6/2009 | Marella et al. |
| 7,592,827 B1 | 9/2009 | Brozek |
| 7,642,106 B2 | 1/2010 | Choel-Hwyi et al. |
| 7,655,482 B2 | 2/2010 | Satya et al. |
| 7,656,170 B2 | 2/2010 | Pinto et al. |
| 7,679,083 B2 | 3/2010 | Sun et al. |
| 7,705,666 B1 | 4/2010 | Hsu et al. |
| 7,733,109 B2 | 6/2010 | Ishtiaq et al. |
| 7,736,916 B2 | 6/2010 | Aghababazadeh et al. |
| 7,739,065 B1 | 6/2010 | Lee et al. |
| 7,772,866 B2 | 8/2010 | Patterson et al. |
| 7,893,703 B2 | 2/2011 | Rzepiela et al. |
| 7,895,548 B2 | 2/2011 | Lin et al. |
| 7,902,548 B2 | 3/2011 | Lim et al. |
| 7,902,849 B2 | 3/2011 | Bullock |
| 7,930,660 B2 | 4/2011 | Ruderer et al. |
| 7,939,348 B2 | 5/2011 | Seng et al. |
| 8,001,516 B2 | 8/2011 | Smith et al. |
| 3,039,837 A1 | 10/2011 | Patterson et al. |
| 8,063,402 B2 | 11/2011 | Sokel et al. |
| 8,089,297 B2 | 1/2012 | Hong et al. |
| 8,178,876 B2 | 5/2012 | Hess et al. |
| 8,339,449 B2 | 12/2012 | Fong et al. |
| 8,344,745 B2 | 1/2013 | Aghababazadeh et al. |
| 8,350,583 B2 | 1/2013 | Cote et al. |
| 8,399,266 B2 | 3/2013 | Mo |
| 8,421,009 B2 | 4/2013 | Xiao |
| 8,575,955 B1 | 11/2013 | Brozek |
| 8,754,372 B2 | 6/2014 | Hong et al. |
| 8,779,400 B2 | 7/2014 | Shichi et al. |
| 8,927,989 B2 | 1/2015 | Arnold et al. |
| 9,222,969 B2 | 12/2015 | Liu et al. |
| 2002/0093350 A1 | 7/2002 | Yamada |
| 2004/0084671 A1 | 5/2004 | Song et al. |
| 2004/0133868 A1 | 6/2004 | Ichimiya |
| 2005/0272174 A1 | 12/2005 | Duan et al. |
| 2006/0164881 A1 | 7/2006 | Oki |
| 2006/0202231 A1 | 9/2006 | Yamamoto |
| 2007/0296435 A1 | 12/2007 | Eldridge et al. |
| 2008/0246030 A1 | 10/2008 | Satya et al. |
| 2008/0267489 A1 | 10/2008 | Xiao et al. |
| 2008/0312875 A1 | 12/2008 | Yu et al. |
| 2009/0037131 A1 | 2/2009 | Hess et al. |
| 2009/0057664 A1 | 3/2009 | Lim et al. |
| 2009/0102501 A1 | 4/2009 | Guldi et al. |
| 2010/0055809 A1 | 3/2010 | Pak et al. |
| 2010/0258798 A1 | 10/2010 | Sokel et al. |
| 2011/0006794 A1 | 1/2011 | Sellathamby et al. |
| 2011/0013826 A1 | 1/2011 | Xiao |
| 2011/0080180 A1 | 4/2011 | Lavoie et al. |
| 2012/0286341 A1 | 11/2012 | Chen et al. |
| 2013/0020639 A1 | 1/2013 | Thompson et al. |
| 2013/0292633 A1 | 11/2013 | Pellizzer et al. |
| 2014/0151699 A1 | 6/2014 | Wu et al. |
| 2015/0270181 A1 | 9/2015 | De et al. |
| 2015/0356232 A1 | 12/2015 | Bomholt et al. |
| 2016/0086863 A1 | 3/2016 | Won et al. |

FOREIGN PATENT DOCUMENTS

| | | |
|---|---|---|
| WO | WO/2003/104921 | 12/2003 |
| WO | WO/2004/057649 | 7/2004 |
| WO | 2005/020297 | 5/2005 |
| WO | WO/2006/123281 | 11/2006 |
| WO | 2009/090516 | 8/2009 |
| WO | WO/2015/192069 | 12/2015 |

OTHER PUBLICATIONS

X. Meng et al., "Layout of Decoupling Capacitors in IP Blocks for 90-nm CMOS," IEEE Trans. on VLSI, Oct. 3, 2008.
W. T. Lee, "Engineering a Device for Electron-Beam Probing," IEEE Design & Test of Computers, Jun. 1989.
B. Vandewalle et al., "Design technology co-optimization for a robust 10nm Metal1 solution for Logic design and SRAM," Proc. SPIE, Mar. 28, 2014.
A. J. Fixi et al., "Laser Stimulated Electron-Beam Prober for 15ps Resolution Internal Waveform Measurements of a 5 Gb/s ECL Circuit," Reliability Physics Symposium, Mar. 23, 1993.
J. M. Sebeson et al., "Noncontact Testing of Interconnections in Film Integrated Circuits Using an Electron Beam," Reliability Physics Symposium, Apr. 1973.
L. Remy et al., "Definition of an Innovative Filling Structure for Digital Blocks: the DFM Filler Cell," ICECS 2009, Dec. 13, 2009.

(56) References Cited

OTHER PUBLICATIONS

J. C. Eidson, "Fast electron-beam lithography: High blanking speeds may make this new system a serious challenger in producing submicrometer ICs," IEEE Spectrum, Jul. 1981.
M. T. Moreira, "Design and Implementation of a Standard Cell Library for Building Asynchronous Asics," Pontificia Universidade Católica Do Rio Grande Do Sul, 2010.
P. De Bisschop et al., "Joint-Optimization of Layout and Litho for SRAM and Logic towards the 20 nm node, using 193i," Proc. SPIE, Mar. 23, 2011.
Written Opinion of International Searching Authority, Applic. No. PCT/US2015/035647, dated Oct. 7, 2015.
International Search Report, Applic. No. PCT/US2015/035647, dated Oct. 7, 2015.
M. Gupta, "Design and Implementation of a Scribe Line Measurement Transistor Test Array Structure in 14nm FinFET CMOS Technology," M.S. Thesis, Univ. of Texas at Austin, May 2015.
O.D. Patterson et al., "In-Line Process Window Monitoring using Voltage Contrast Inspection," 2008 IEEE/SEMI Advanced Semiconductor Manufacturing Conference, May 5, 2008.
J. Jau et al., "A Novel Method for In-line Process Monitoring by Measuring the Gray Level Values of SEM Images," IEEE International Symposium on Semiconductor Manufacturing, Sep. 13, 2005.
M. Saito et al., "Study of ADI (After Develop Inspection) Using Electron Beam," Proc. of Spie vol. 6152, Feb. 19, 2006.
H.Y. Li et al., "Built-in Via Module Test Structure for Backend Interconnection In-line Process Monitor," Proceedings of the 12th International Symposium on the Physical and Failure Analysis of Integrated Circuits, Jun. 27, 2005.
Y. Hamamura et al., "An Advanced Defect-Monitoring Test Structure for Electrical Screening and Defect Localization," IEEE Transactions on Semiconductor Manufacturing, May 10, 2004.
S.-C. Lei et al., "Contact leakage and open monitoring with an advanced e-beam inspection system," Proc. SPIE 6518, Apr. 5, 2007.
H. Xiao et al., "Capturing Buried Defects in Metal Interconnections with Electron Beam Inspection System," Proc. SPIE 3681, Apr. 18, 2013.
T. Newell et al., "Detection of Electrical Defects with SEMVision in Semiconductor Production Mode Manufacturing," Proc. of SPIE vol. 9778, Feb. 21, 2016.
C. Hess et al., "Scribe Characterization Vehicle Test Chip for Ultra Fast Product Wafer Yield Monitoring," 2006 IEEE International Conference on Microelectronic Test Structures, Mar. 6, 2006.
J. Cong et al., "Optimizing routability in large-scale mixed-size placement," Design Automation Conference (ASP-DAC), Jan. 22, 2013.
C. Menezes et al., "Design of regular layouts to improve predictability," Proceedings of the 6th IEEE International Caribbean Conference on Devices, Circuits and Systems, Apr. 26, 2006.
X. Meng et al., "Novel Decoupling Capacitor Designs for sub-90nm CMOS Technology," Proceedings of the 7th IEEE International Symposium on Quality Electronic Design, Mar. 27, 2006.
T. Jungeblut et al., "A modular design flow for very large design space explorations," CDNLive! EMEA 2010, May 4, 2010.
J. Orbon et al., "Integrated electrical and SEM based defect characterization for rapid yield ramp," Proc. of SPIE, vol. 5378, 2004.
O.D. Patterson, "Use of Diodes to Enable μLoop® Test Structures for Buried Defects and Voltage to Grayscale Calibration," 25th Annual Semi Advanced Semiconductor Manufacturing Conference, May 19, 2014.
O.D. Patterson et al., "Voltage Contrast Test Structure for Measurement of Mask Misalignment," Advanced Semiconductor Manufacturing Conference (ASMC), 2010 IEEE/SEMI, pp. 334-340, Jul. 11, 2010.
O.D. Patterson et al., "Test Structure and e-Beam Inspection Methodology for In-line Detection of (Non-visual) Missing Spacer Defects," Advanced Semiconductor Manufacturing Conference, 2007 IEEE/SEMI, pp. 48-53, Jun. 11, 2007.
H. Xiao et al., "Inspection of 32nm imprinted patterns with an advanced e-beam inspection system," Proc. SPIE 7488, Photomask Technology 2009, Sep. 23, 2009.
S.-M. Chon et al., "Development of Automated Contact Inspection System using In-line CD SEM," 2001 IEEE International Semiconductor Manufacturing Symposium, Oct. 8, 2001.
O.D. Patterson et al., "Rapid Reduction of Gate-Level Electrical Defectivity using Voltage Contrast Test Structures," 2003 IEEEI/SEMI Advanced Semiconductor Manufacturing Conference and Workshop, Mar. 31, 2003.
J.-L. Baltzinger et al., "E-beam inspection of dislocations: product monitoring and process change validation," IEEE Conference and Workshop Advanced Semiconductor Manufacturing, May 4, 2004.
K. Mai et al., "SPC Based In-line Reticle Monitoring on Product Wafers," 2005 IEEE/SEMI Advanced Semiconductor Manufacturing Conference and Workshop, Apr. 11, 2005.
C. Holfeld et al., "Wafer Inspection as Alternative Approach to Mask Defect Qualification," Proc. SPIE 6730, Photomask Technology 2007, Oct. 25, 2007.
O.D. Patterson et al., "Detection of Resistive Shorts and Opens using Voltage Contrast Inspection," 17th Annual SEMI/IEEE Advanced Semiconductor Manufacturing Conference, May 22, 2006.
O.D. Patterson et al., "Enhancement of Voltage Contrast Inspection Signal Using Scan Direction," International Symposium on Semiconductor Manufacturing, Oct. 15, 2007.
O.D. Patterson et al., "In-Line Process Window Monitoring using Voltage Contrast Inspection," IEEE/SEMI Advanced Semiconductor Manufacturing Conference, May 5, 2008.
O.D. Patterson et al., "Methodology for Trench Capacitor Etch Optimization using Voltage Contrast Inspection and Special Processing," ASMC 2010, Jul. 11, 2010.
X.J. Zhou et al., "Characterization of Contact Module Failure Mechanisms for SOI Technology using E-beam Inspection and In-line TEM," ASMC 2010, Jul. 11, 2010.
H.-C. Liao et al., "Blind Contact Detection in the Irregularly Periphery Area Using Leap & Scan e-Beam Inspection," Presentation Slides, International Symposium on Semiconductor Manufacturing (ISSM) and e-Manufacturing and Design Collaboration Symposium (eMDC), Sep. 5, 2011.
C. Boye et al., "E-Beam Inspection for Combination Use of Defect Detection and CD Measurement," 23rd Annual SEMI Advanced Semiconductor Manufacturing Conference (ASMC), May 15, 2012.
O.D. Patterson et al., "E-Beam Inspection for Detection of Sub-Design Rule Physical Defects," ASMC 2012, May 15, 2012.
O.D. Patterson et al., "Early Detection of Systematic Patterning Problems for a 22nm SOI Technology using E-Beam Hot Spot Inspection," ASMC 2013, May 14, 2013.
B. Donovan et al., "Early Detection of Electrical Defects in Deep Trench Capacitors using Voltage Contrast Inspection," ASMC 2013, May 14, 2013.
Presentation entitled, "tau-Metrix, Inc: A Product Yield Enhancement Company," 2009.
Li, "Innovative E-Beam Applications for Advanced Technology Nano-defect Era," SEMATECH Symposium Taiwan 2012, Oct. 18, 2012.
T. Marwah, "System-on-Chip Design and Test with Embedded Debug Capabilities," M.S. Thesis, Univ. of Tenn. at Knoxville, Aug. 2006.
M. Bhushan et al., "Microelectronic Test Structures for CMOS Technology," DOI 10.1007/978-1-4419-9377-9_1, (c) Springer Science+Business Media, LLC, 2011.
M. Muehlberghuber et al., "Red Team vs. Blue Team Hardware Trojan Analysis: Detection of a Hardware Trojan on an Actual ASIC," Proceedings of the 2nd International Workshop on Hardware and Architectural Support for Security and Privacy, Jun. 24, 2013.

* cited by examiner

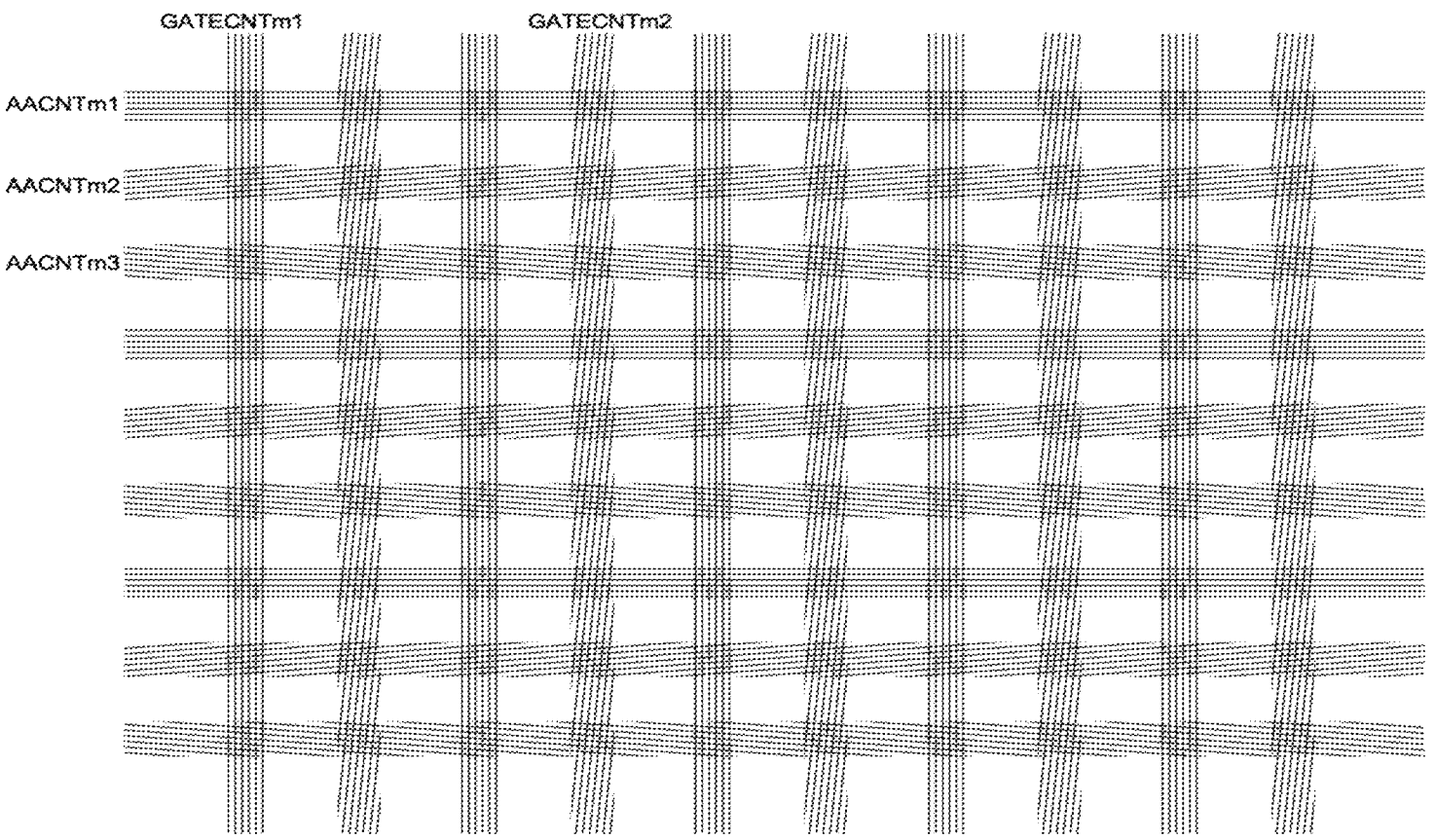

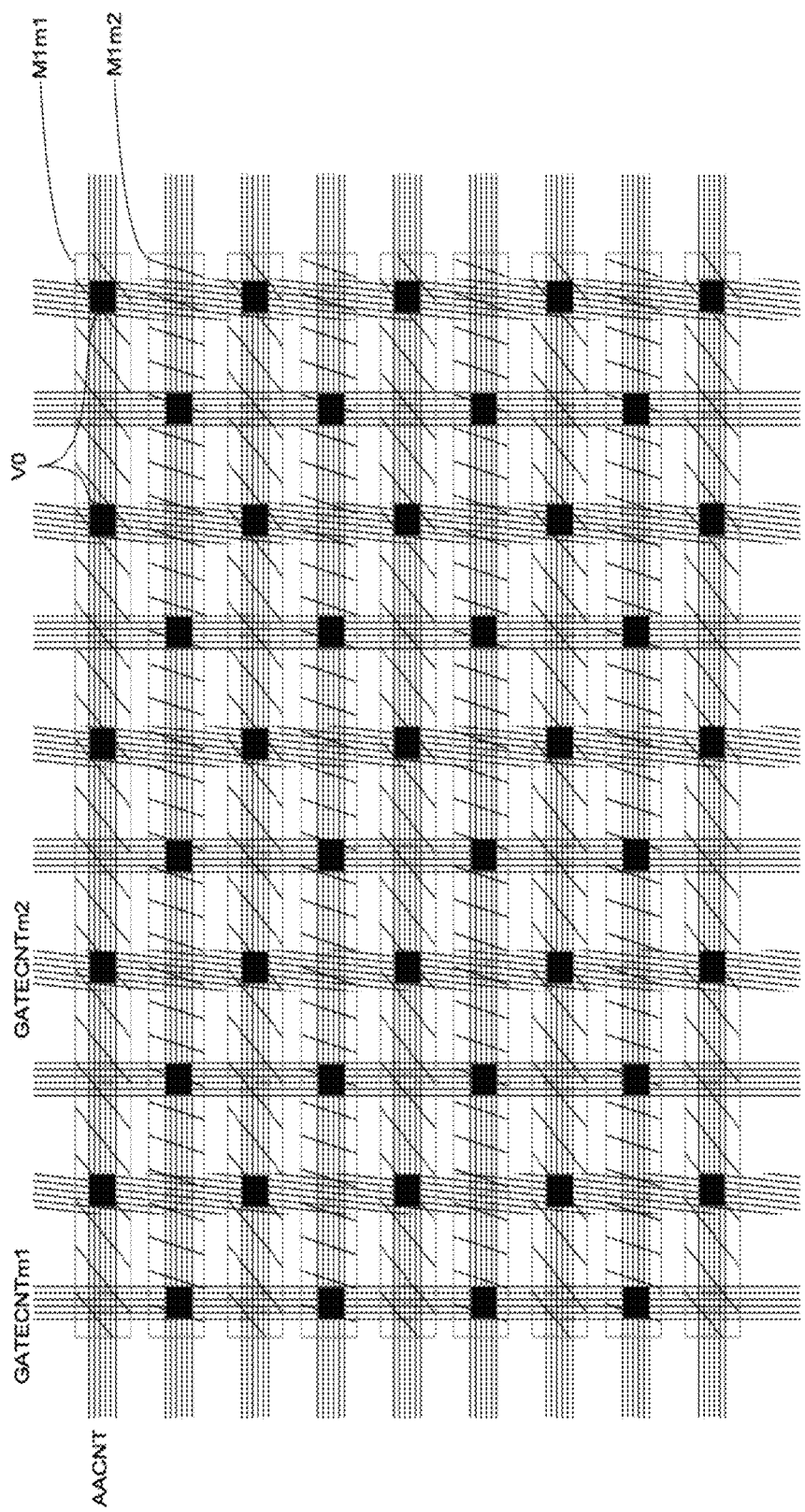
FIG. 9AAA

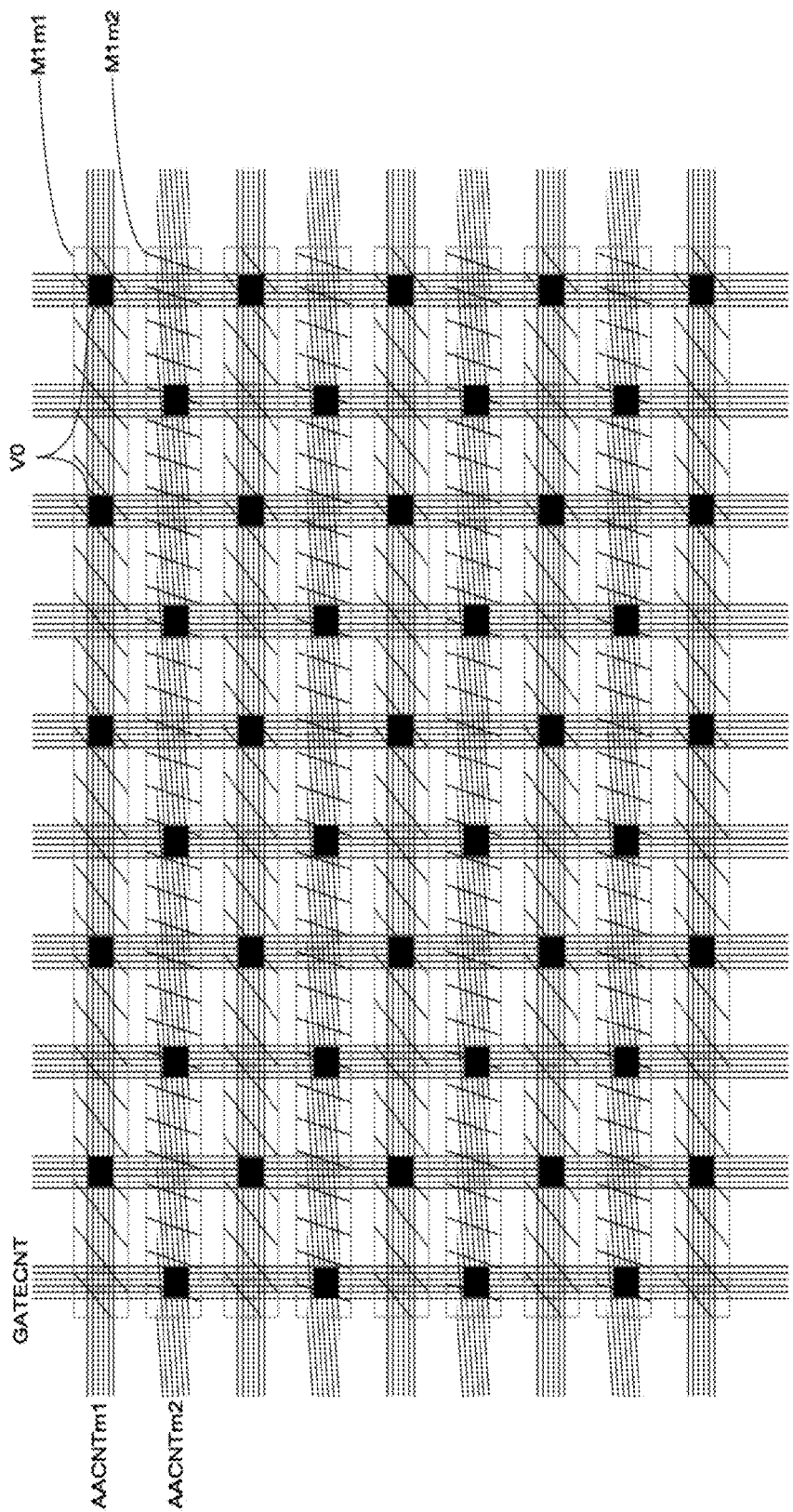
FIG. 9BBB

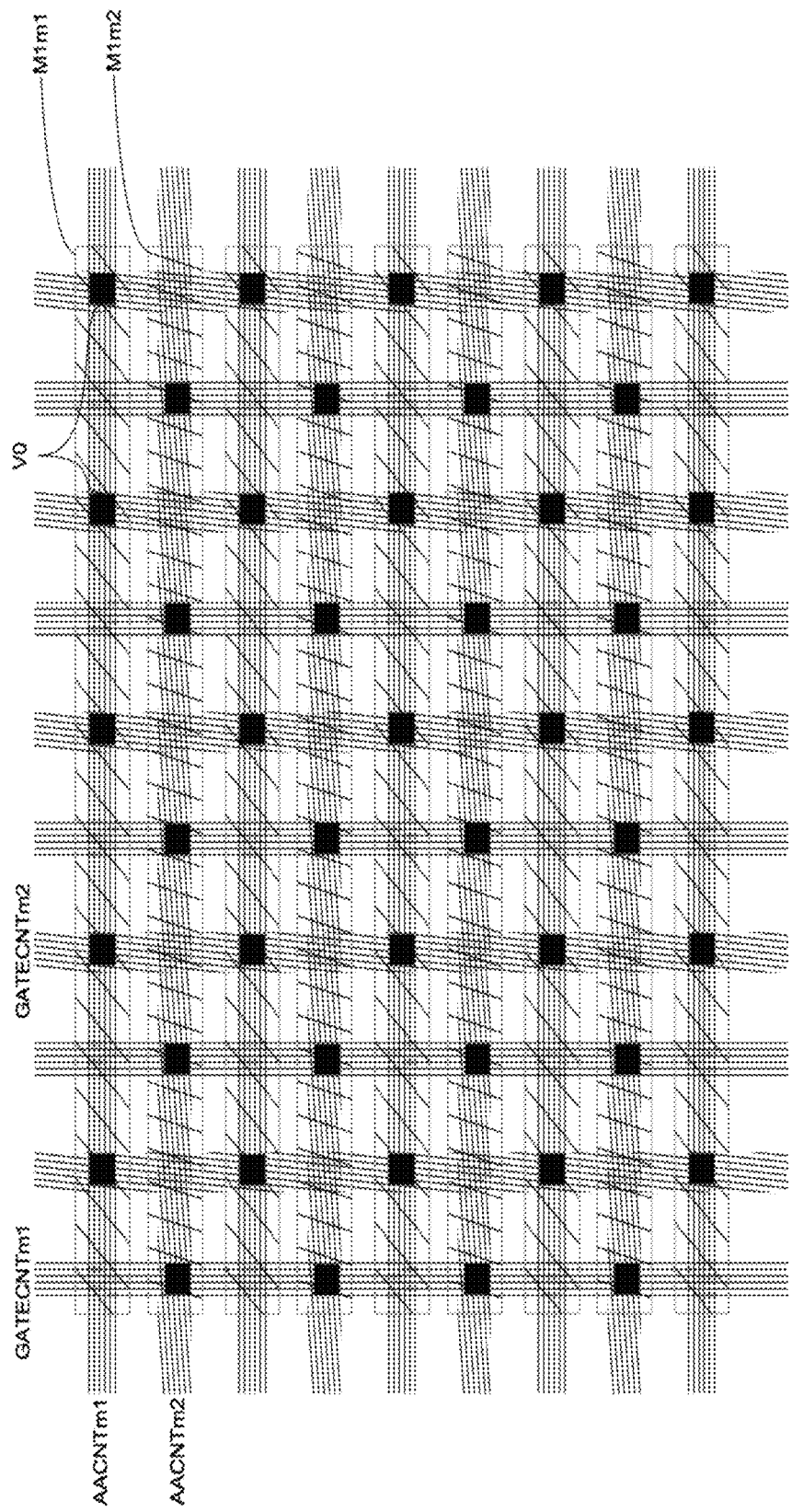
FIG. 9CCC

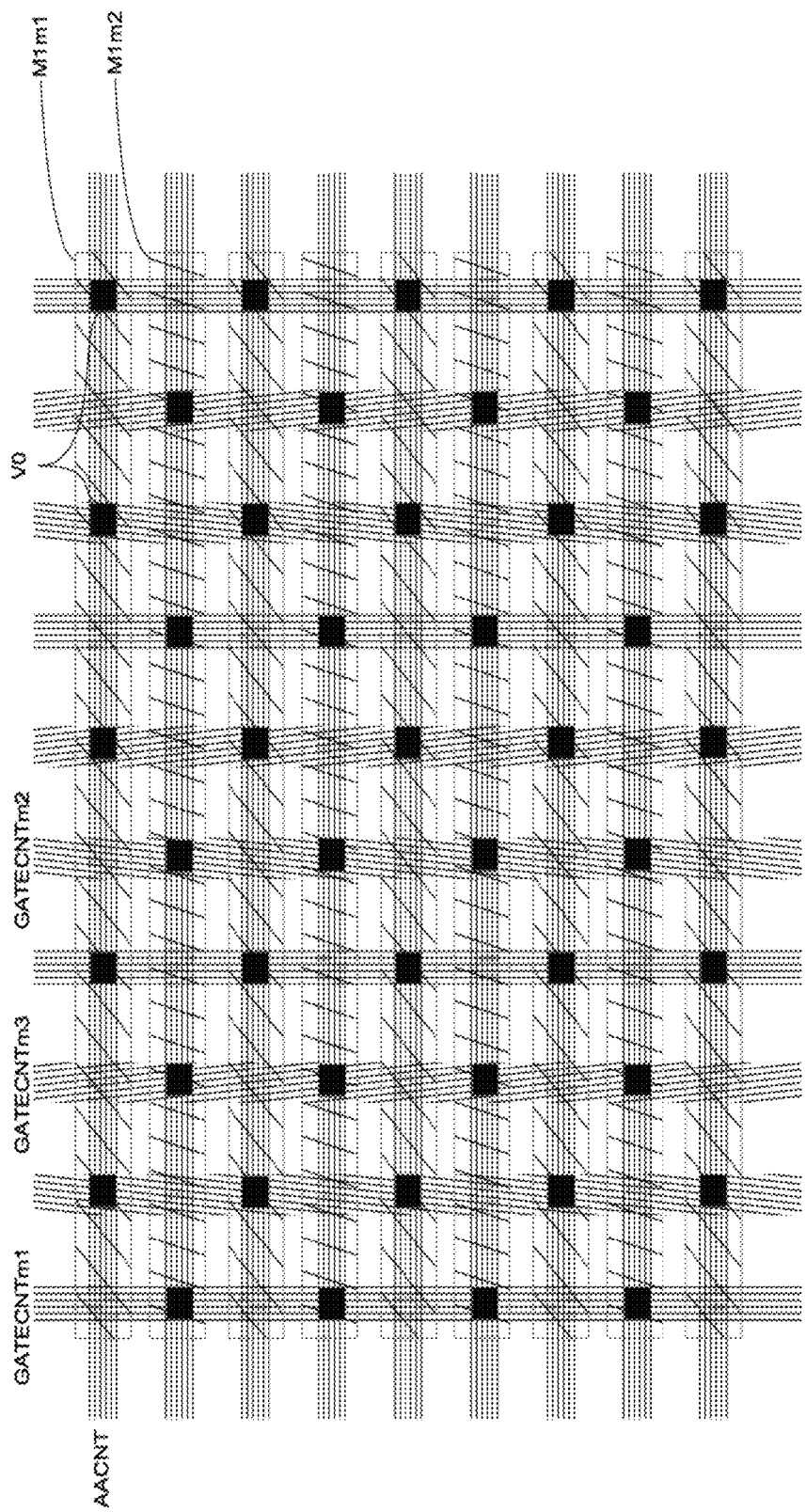
FIG. 9DDD

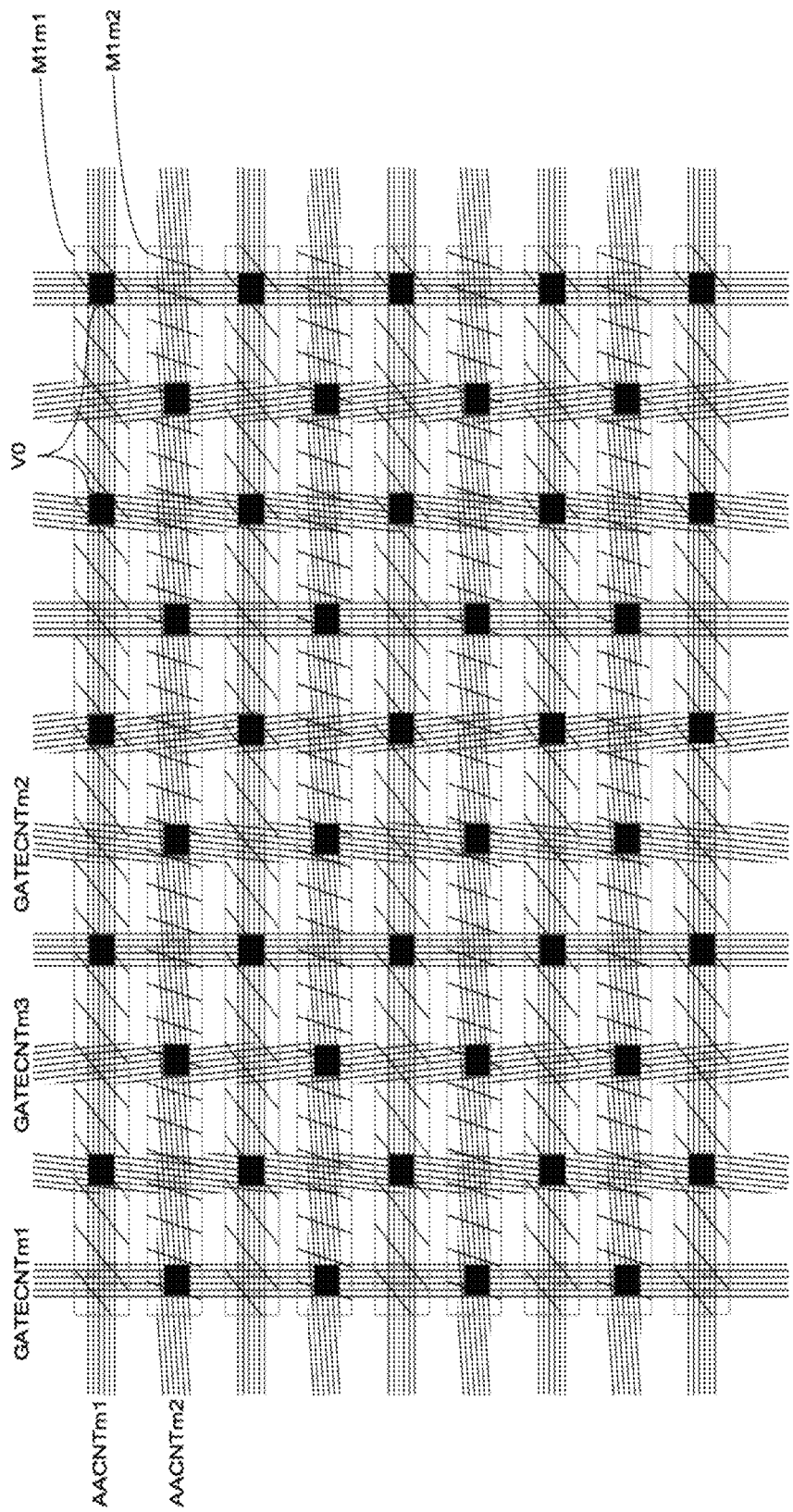
FIG. 9EEE

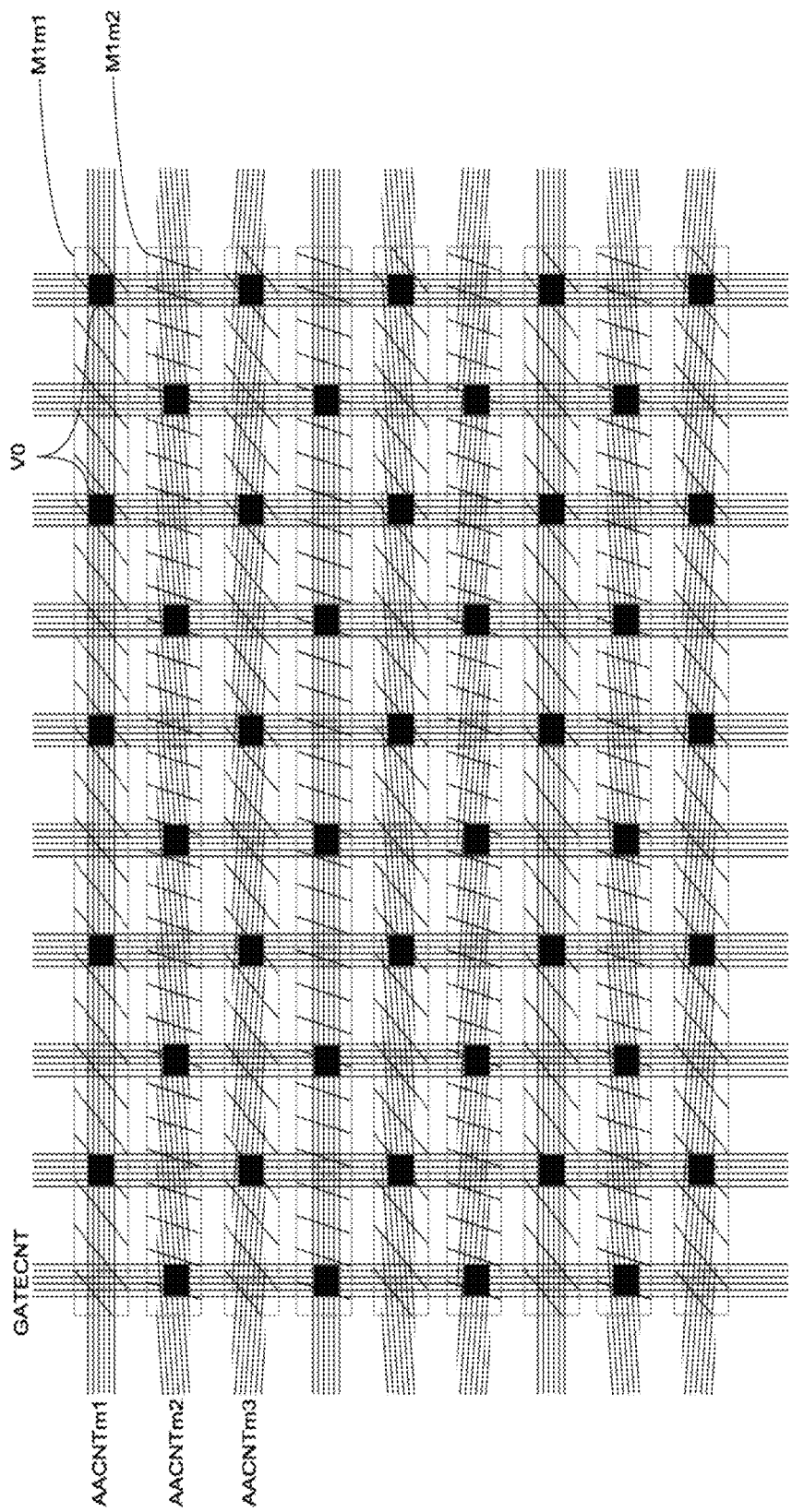
FIG. 9FFF

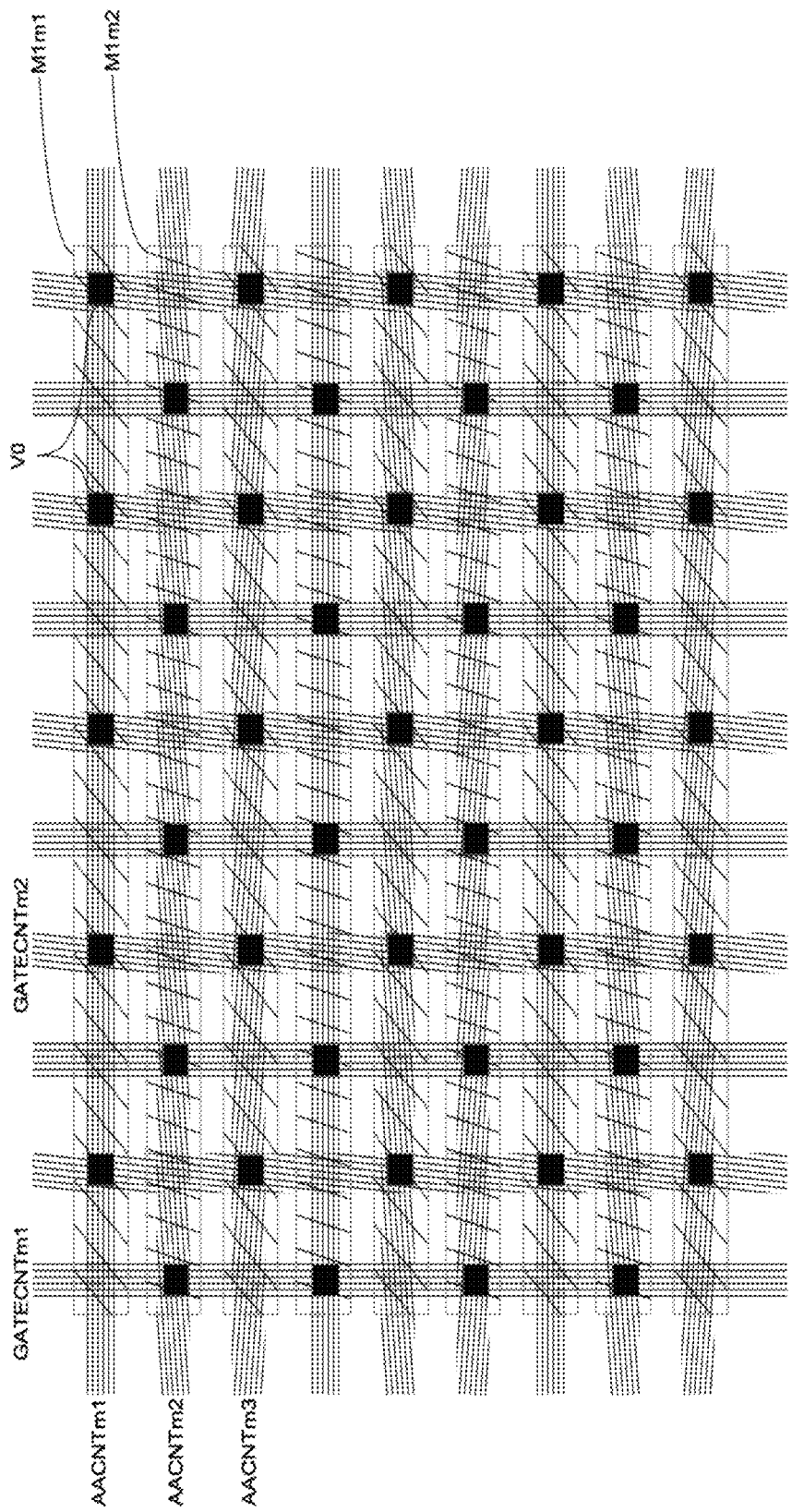
FIG. 9GGG

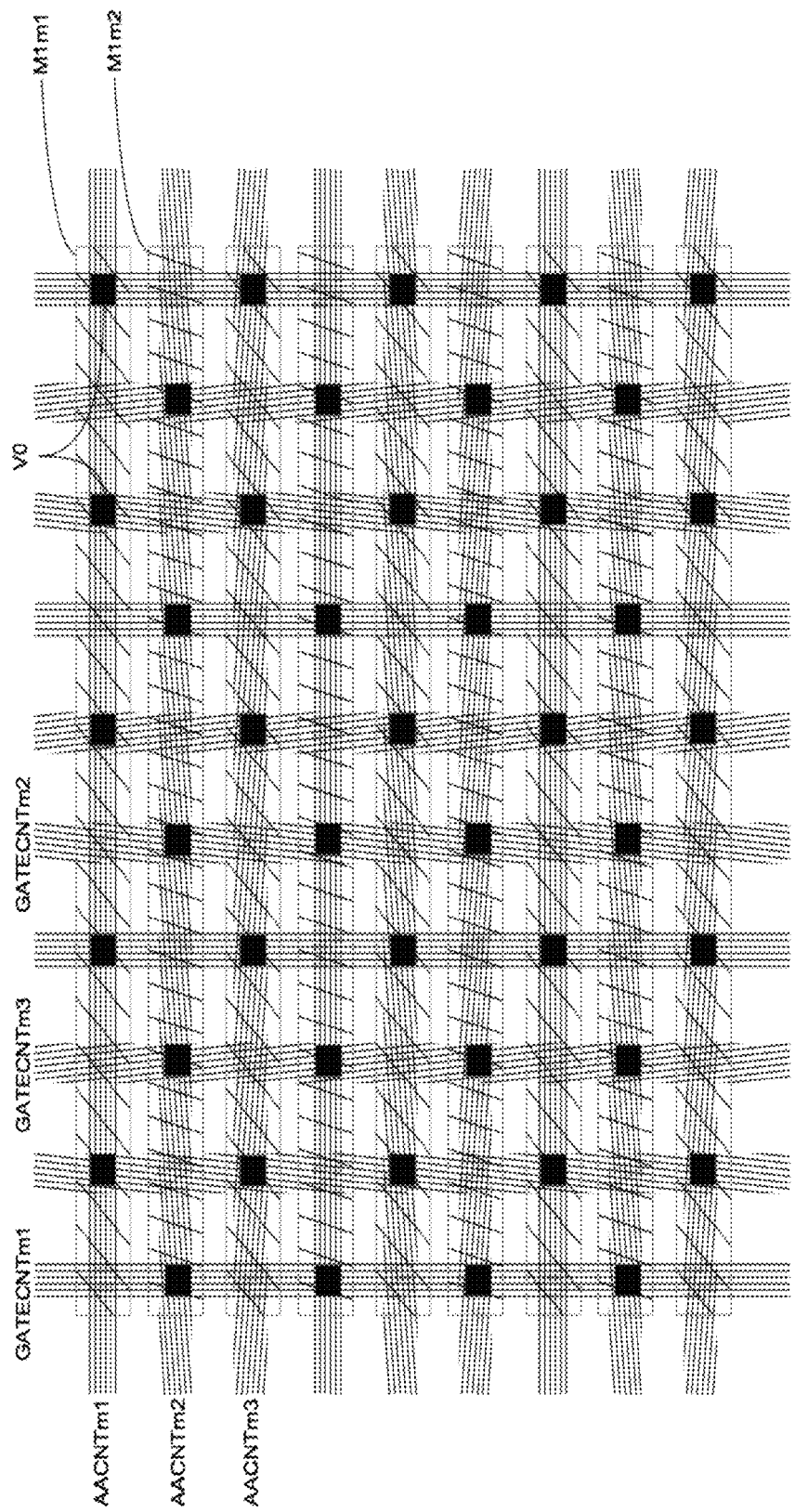
FIG. 9HHH

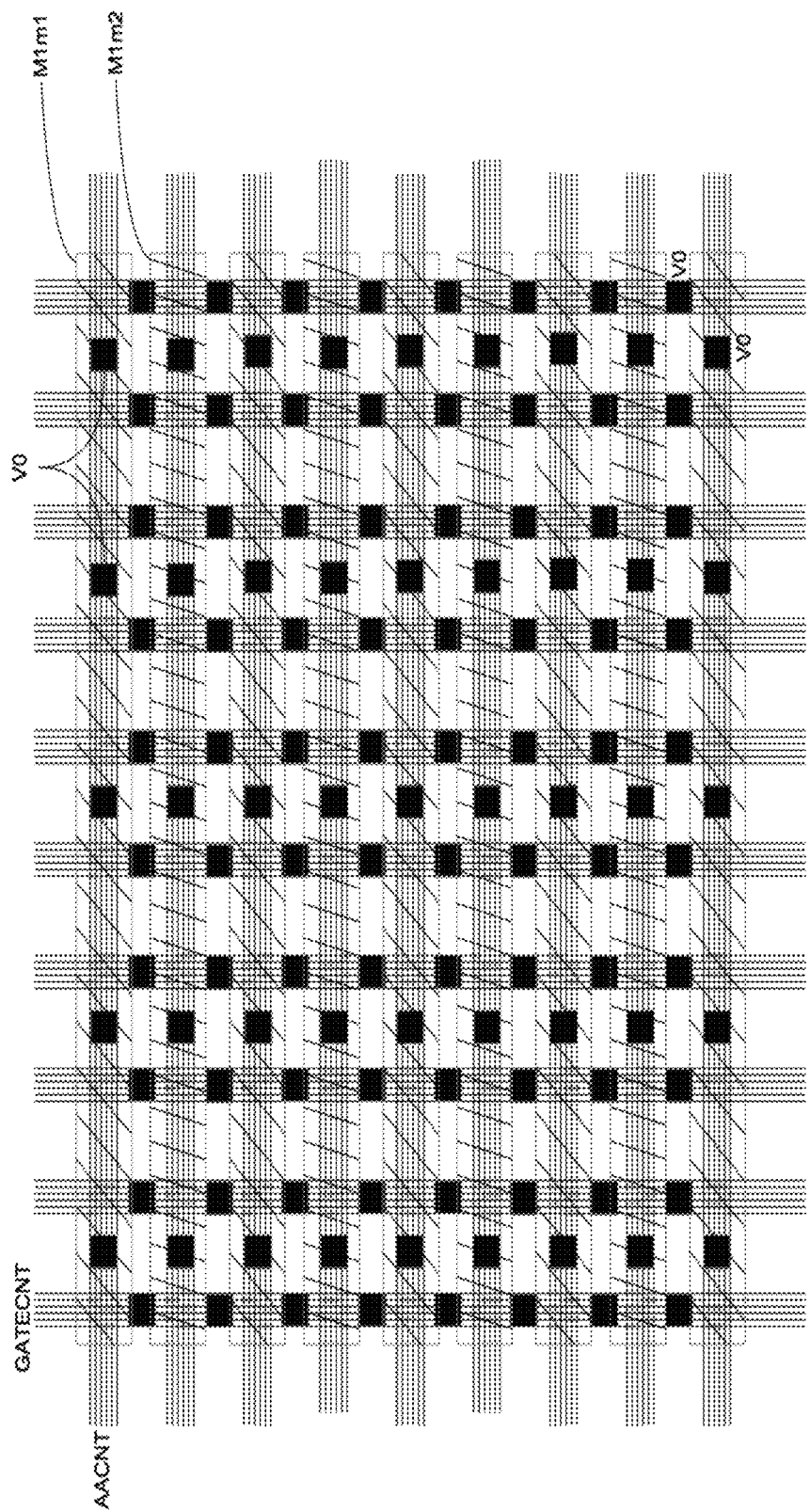
FIG. 9III

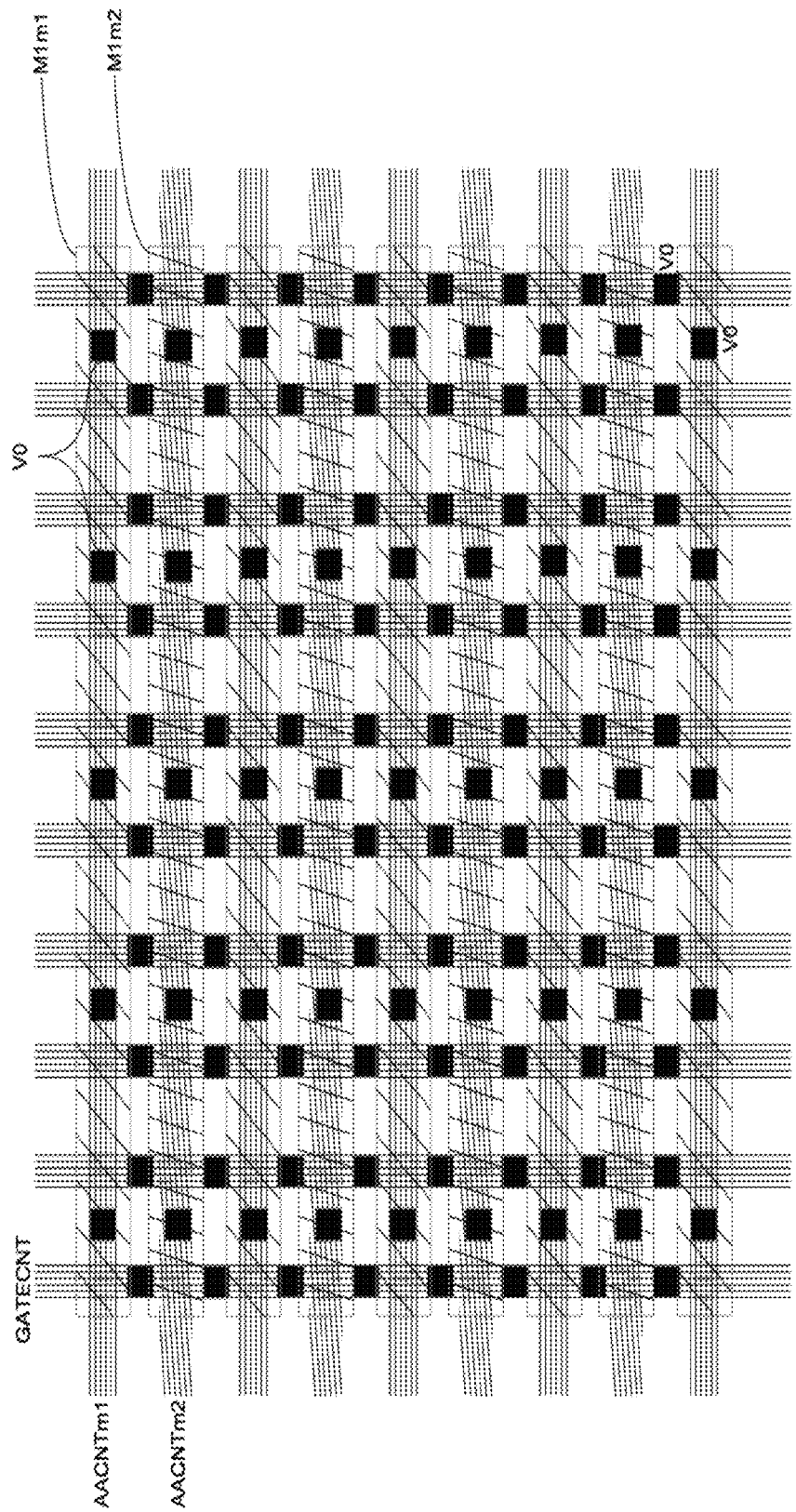
FIG. 9KKK

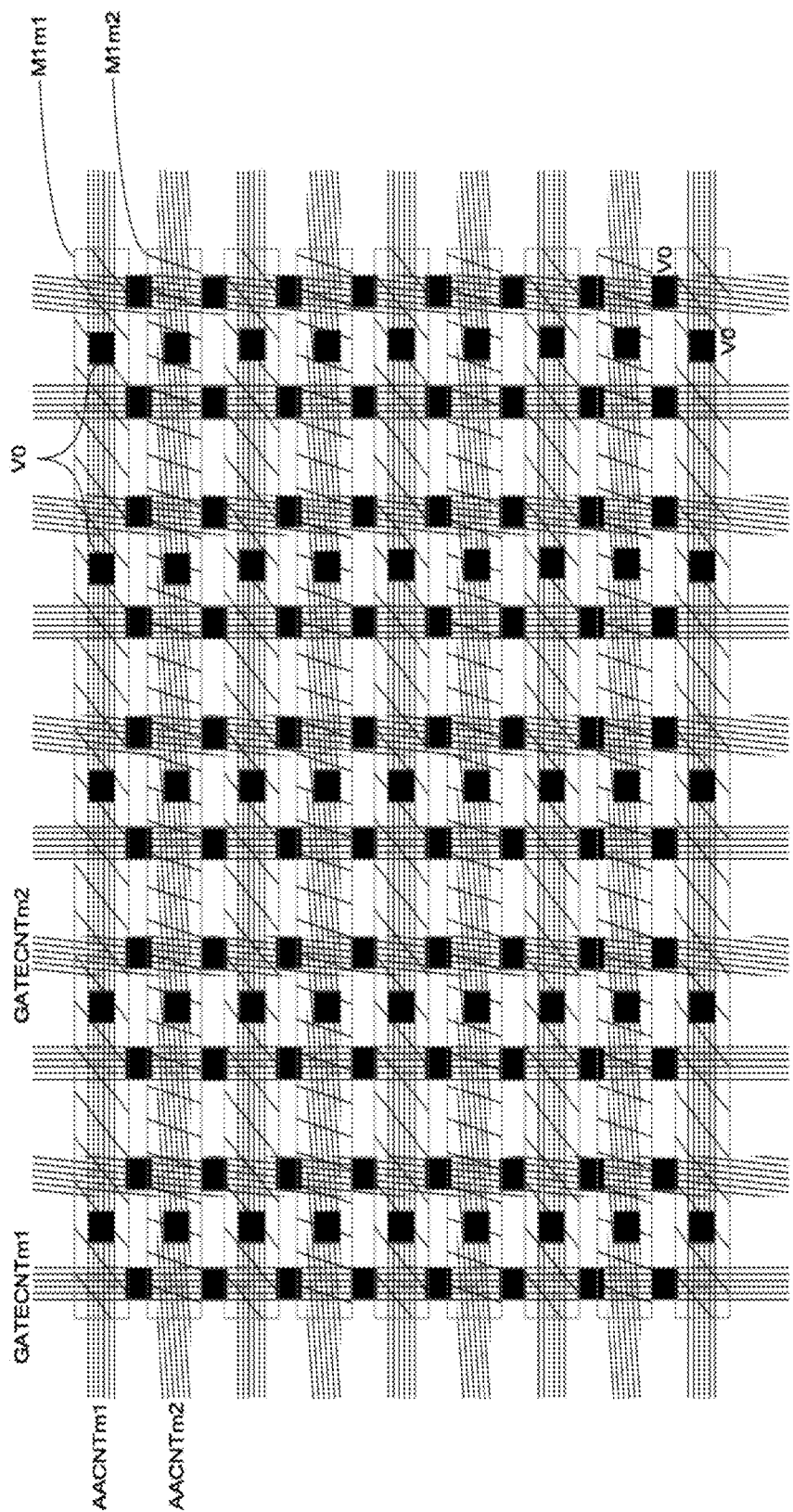
FIG. 9LLL

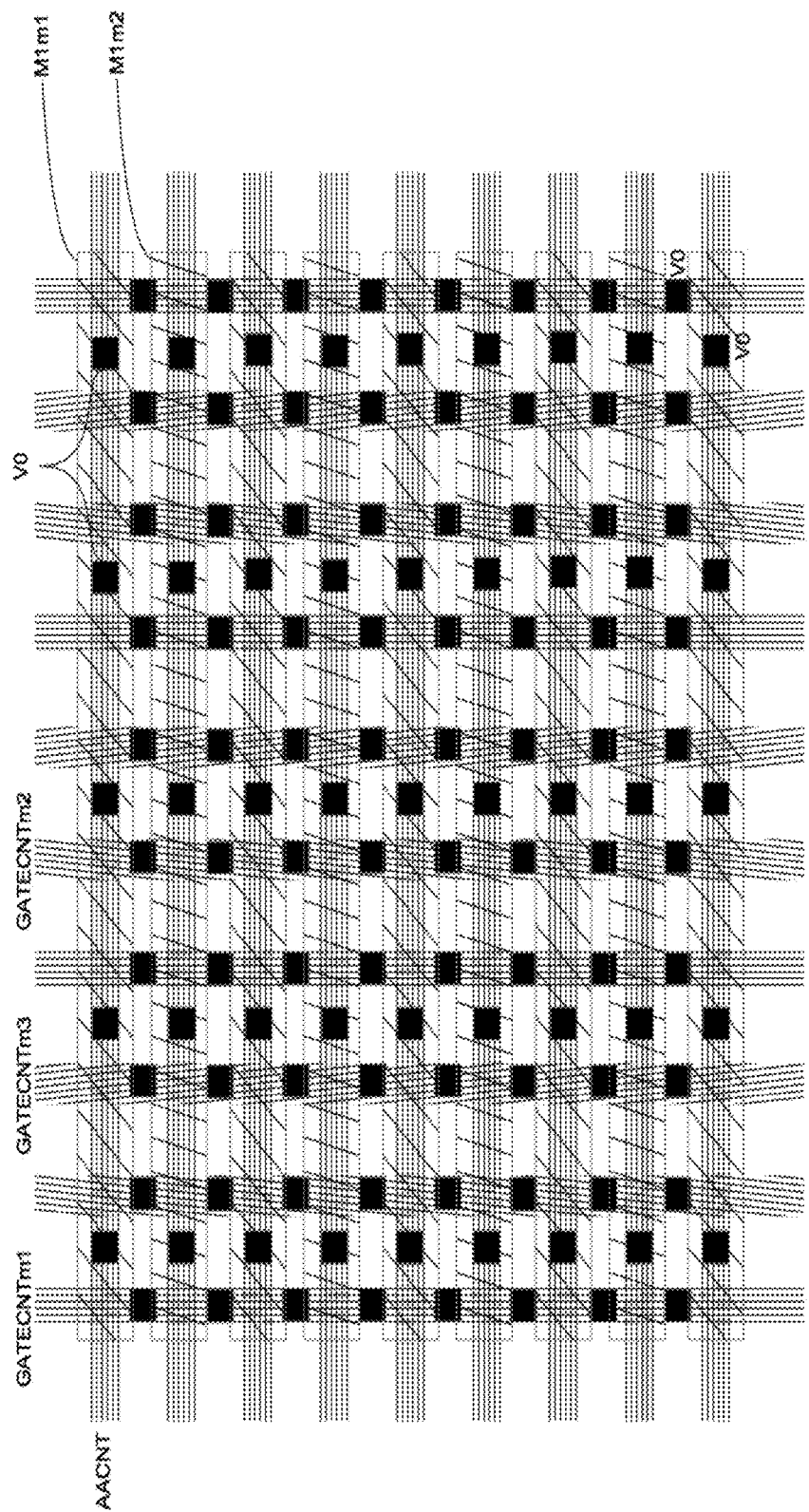
FIG. 9MMM

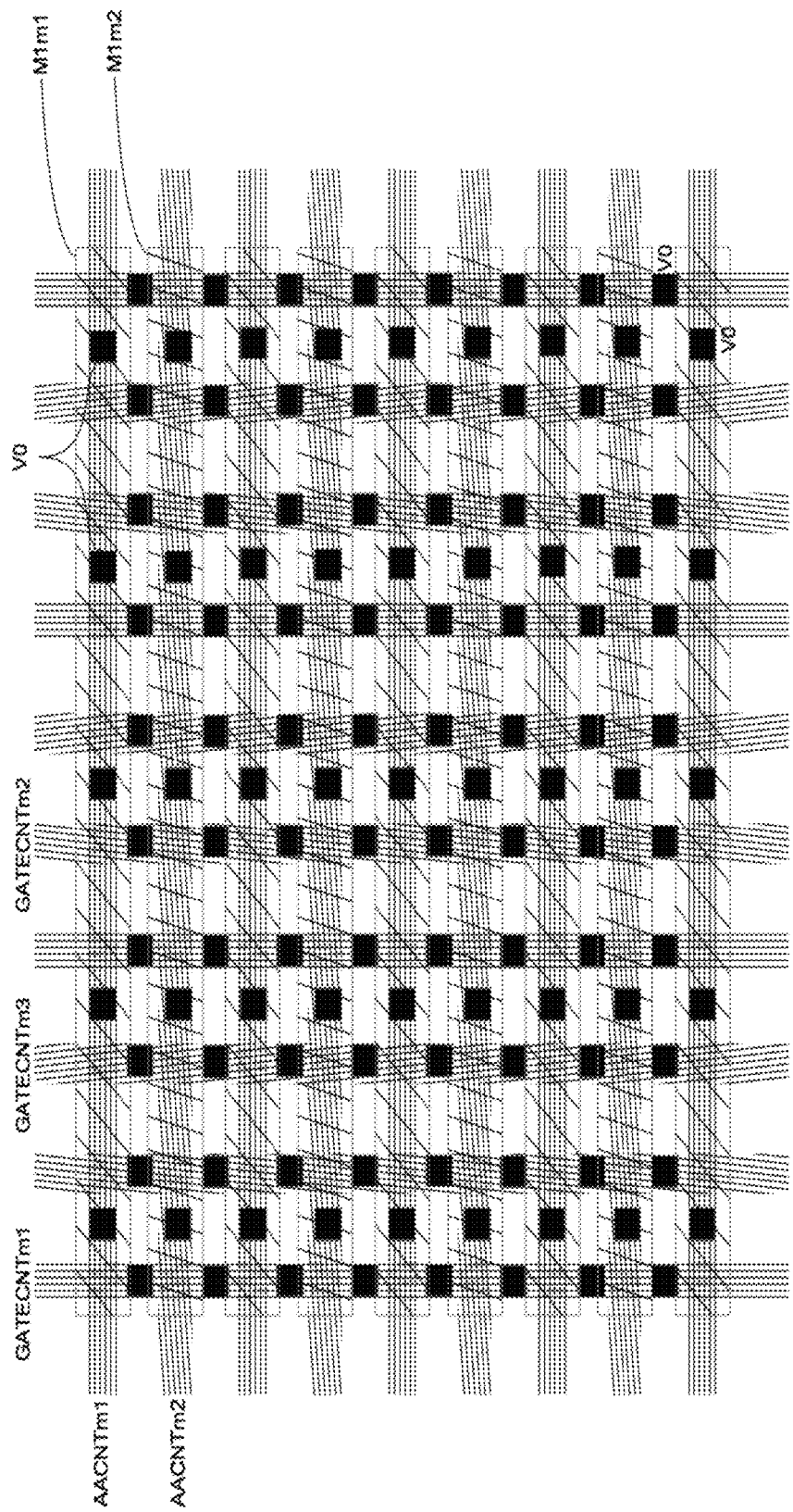
FIG. 9NNN

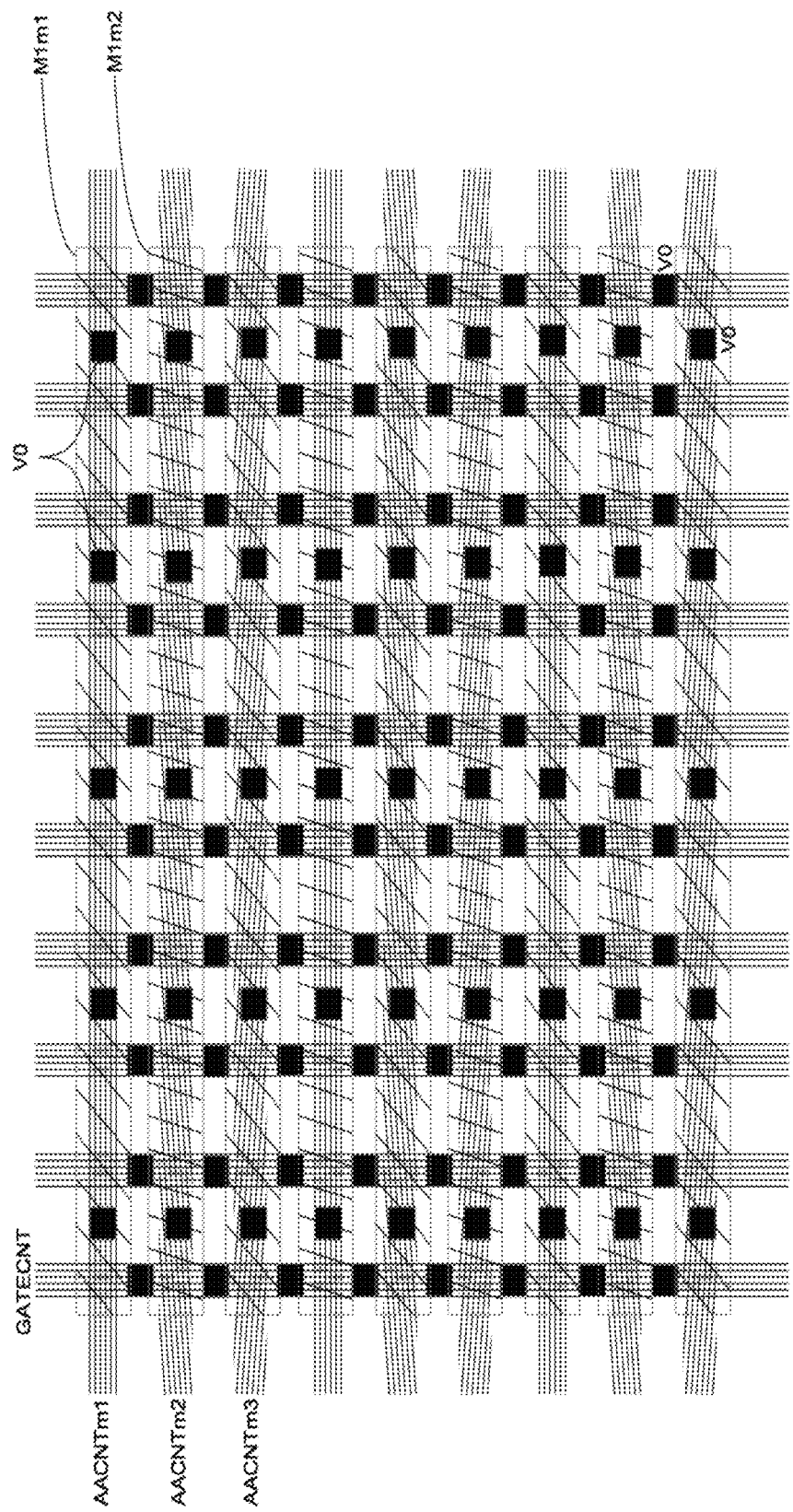
FIG. 9000

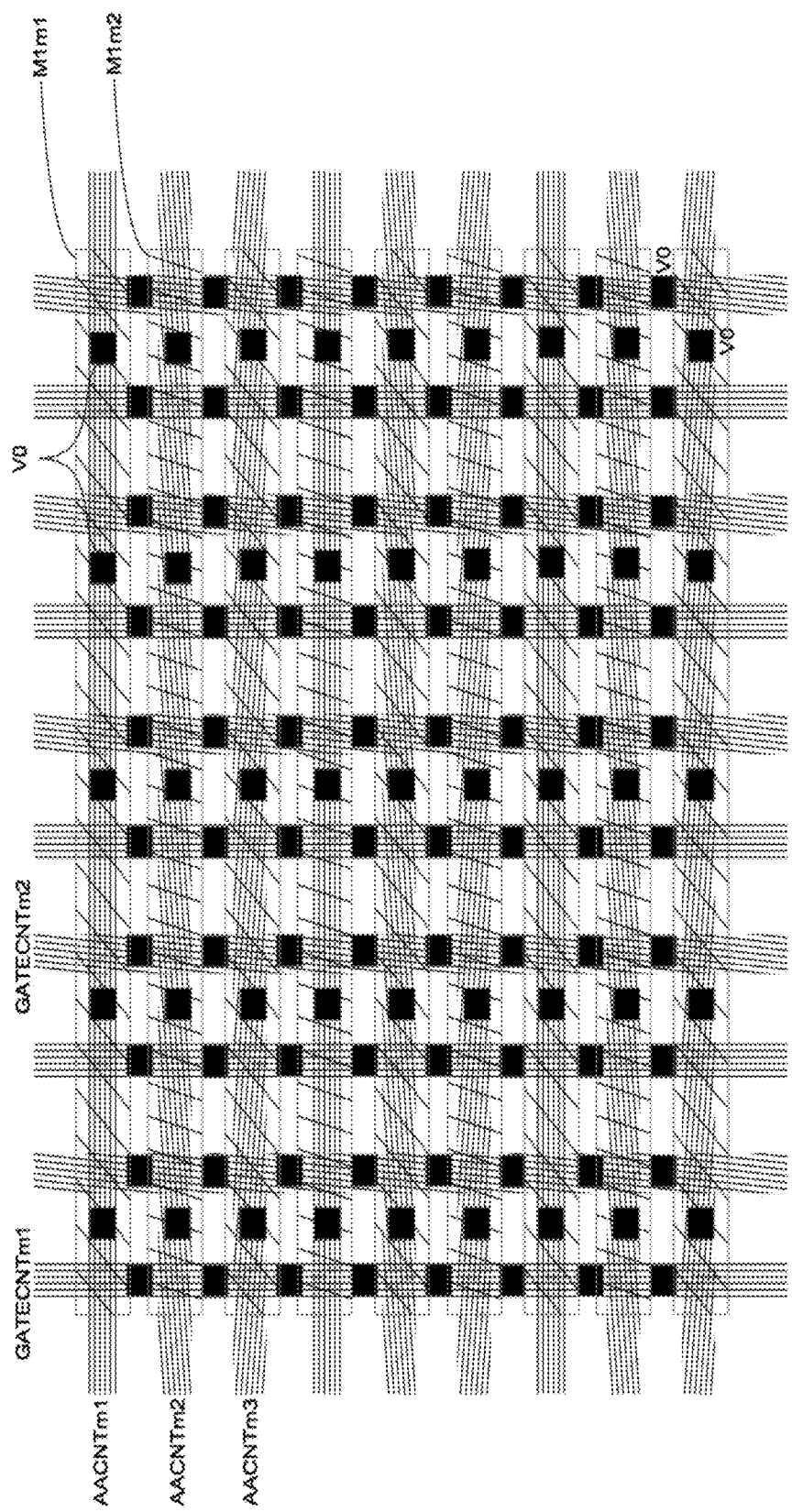
FIG. 9PPP

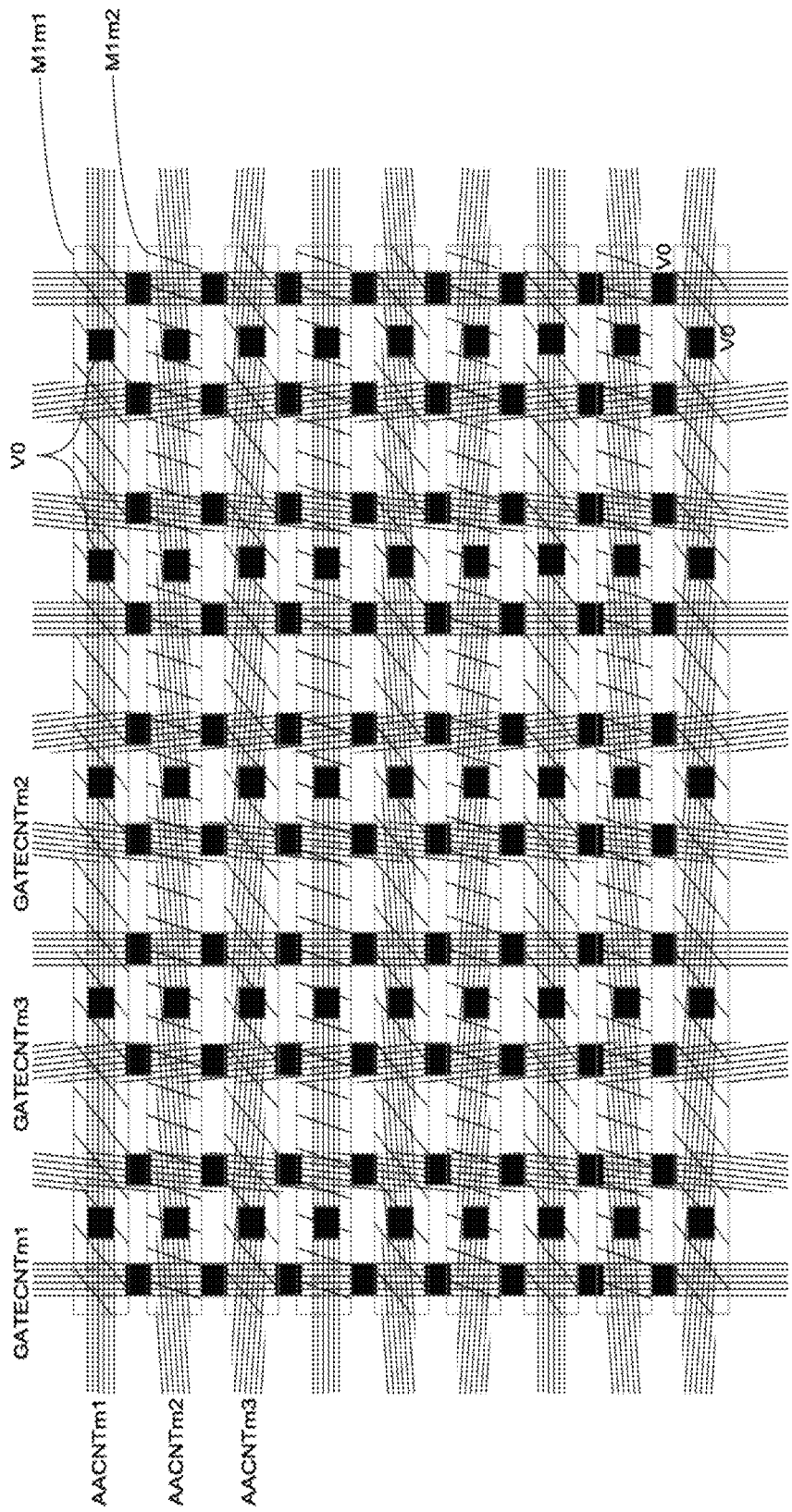
FIG. 9QQQ

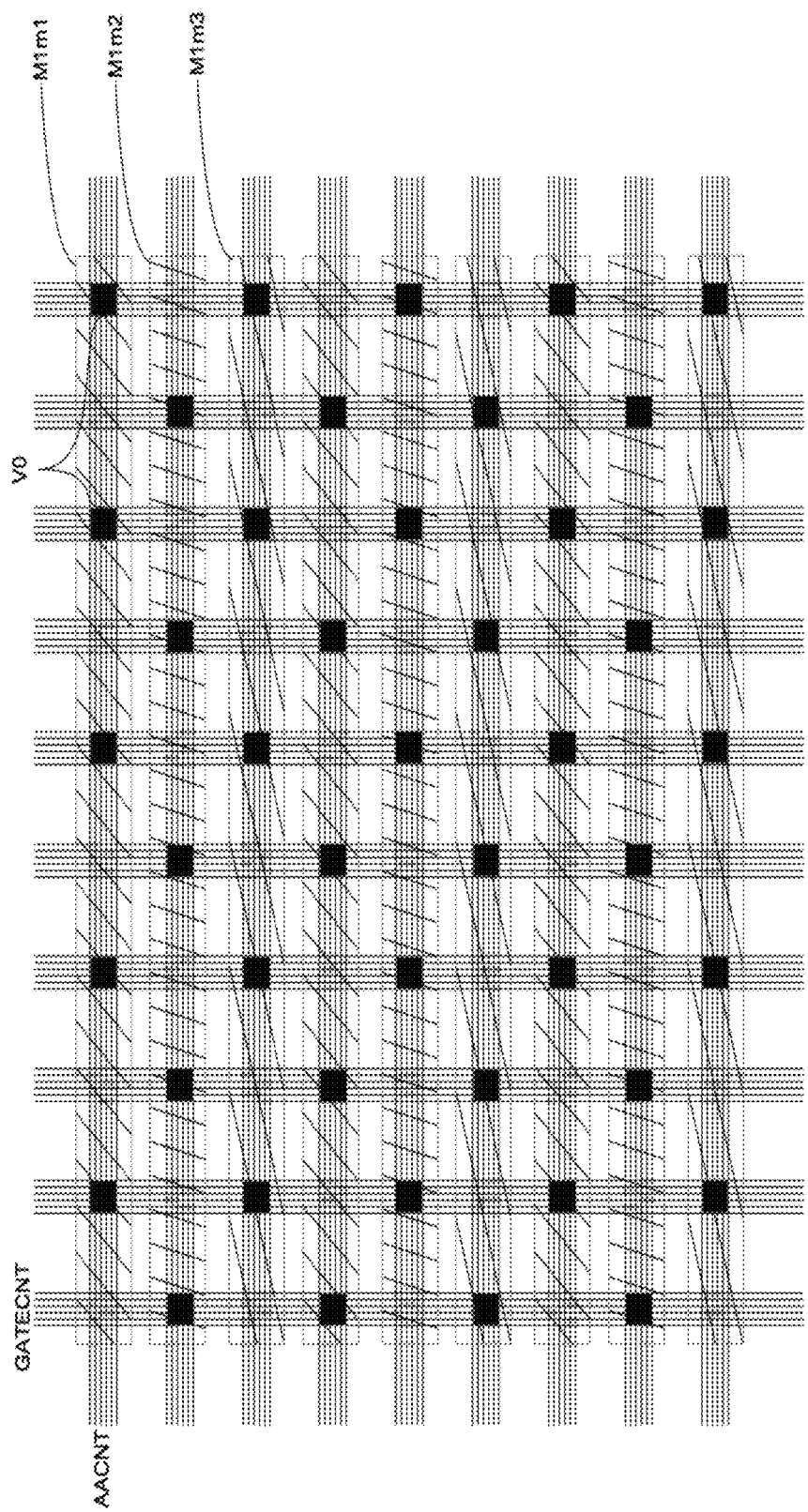
FIG. 9RRR

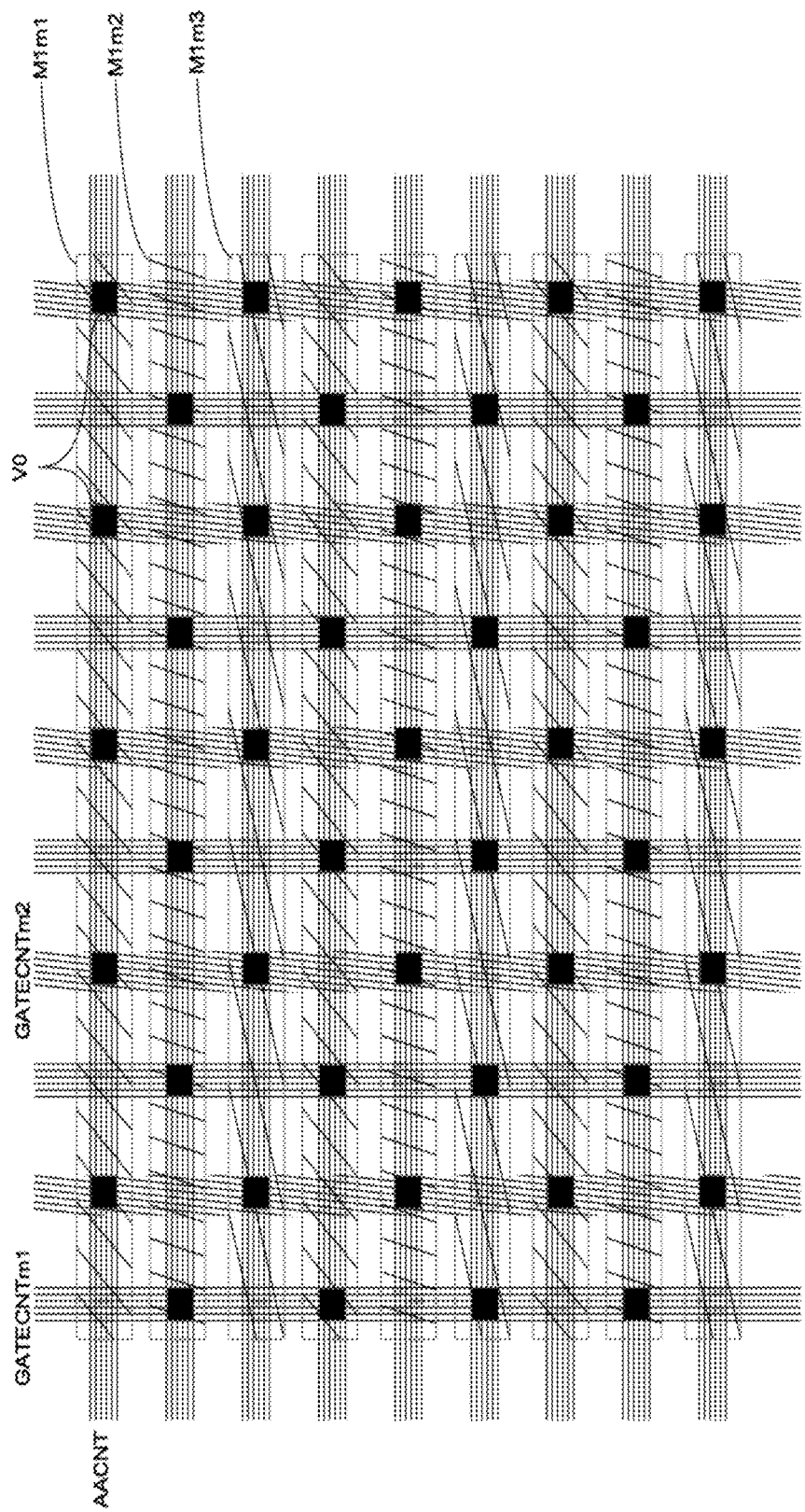
FIG. 9SSS

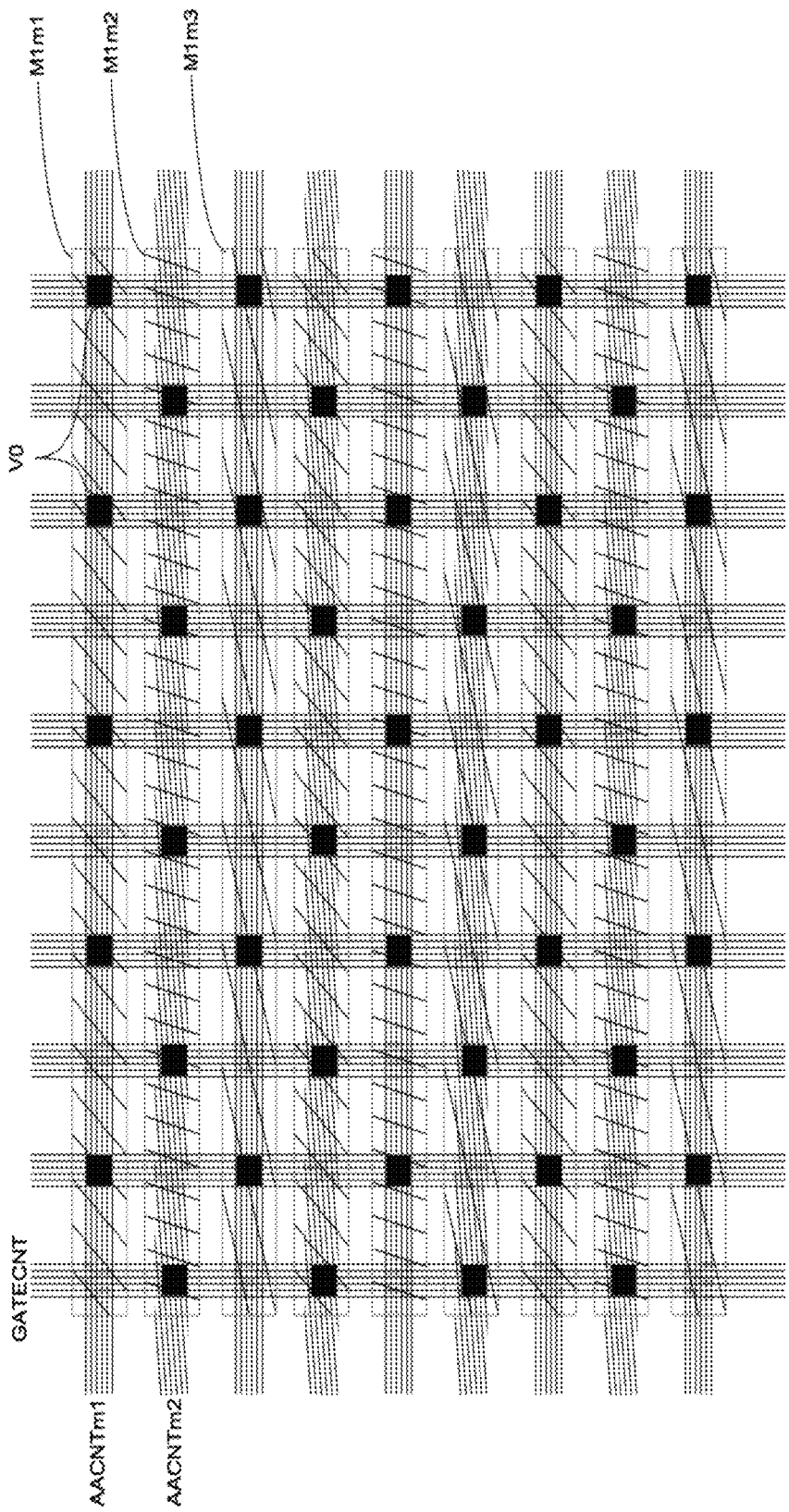
FIG. 9TTT

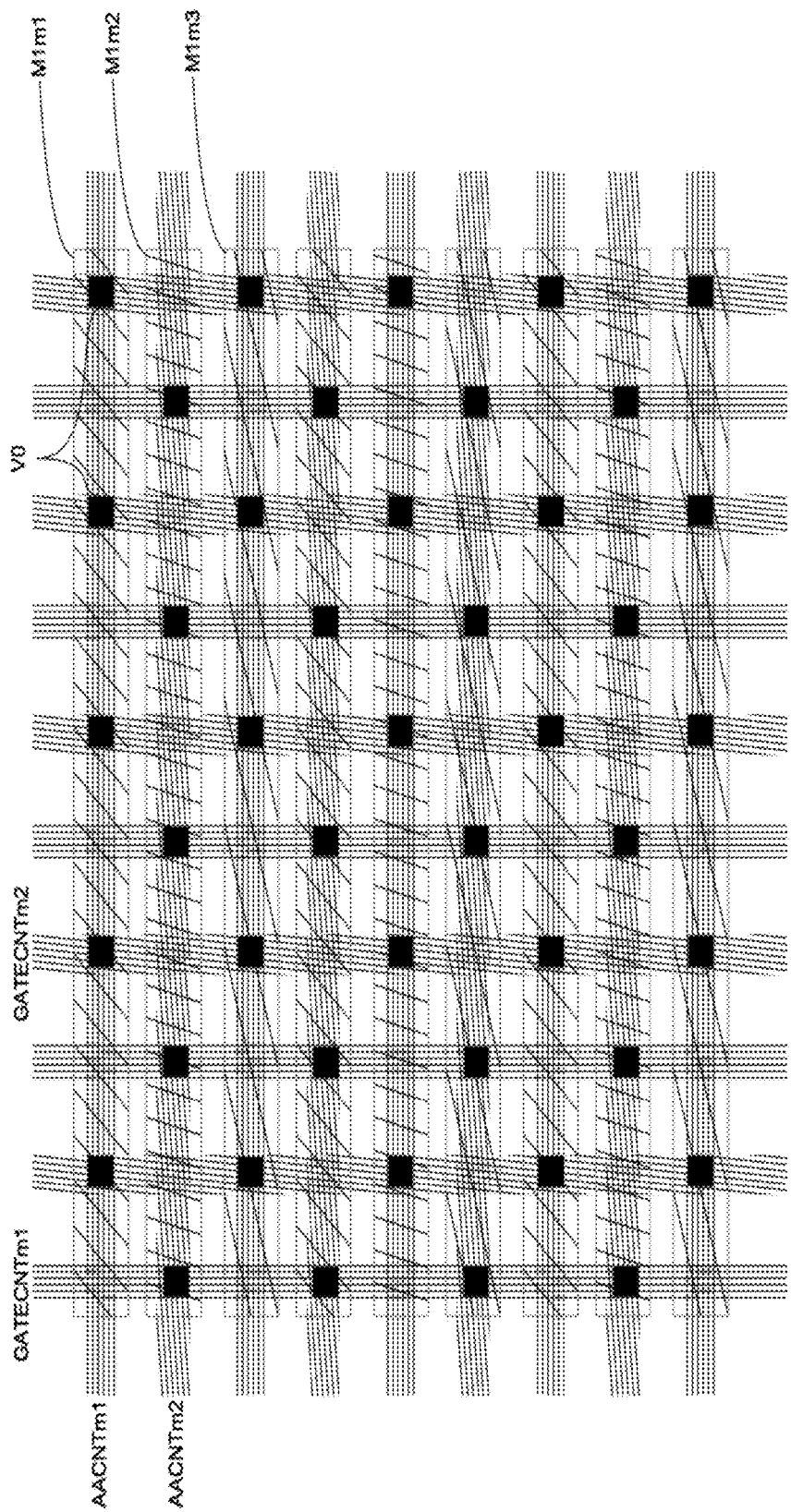
FIG. 9UUU

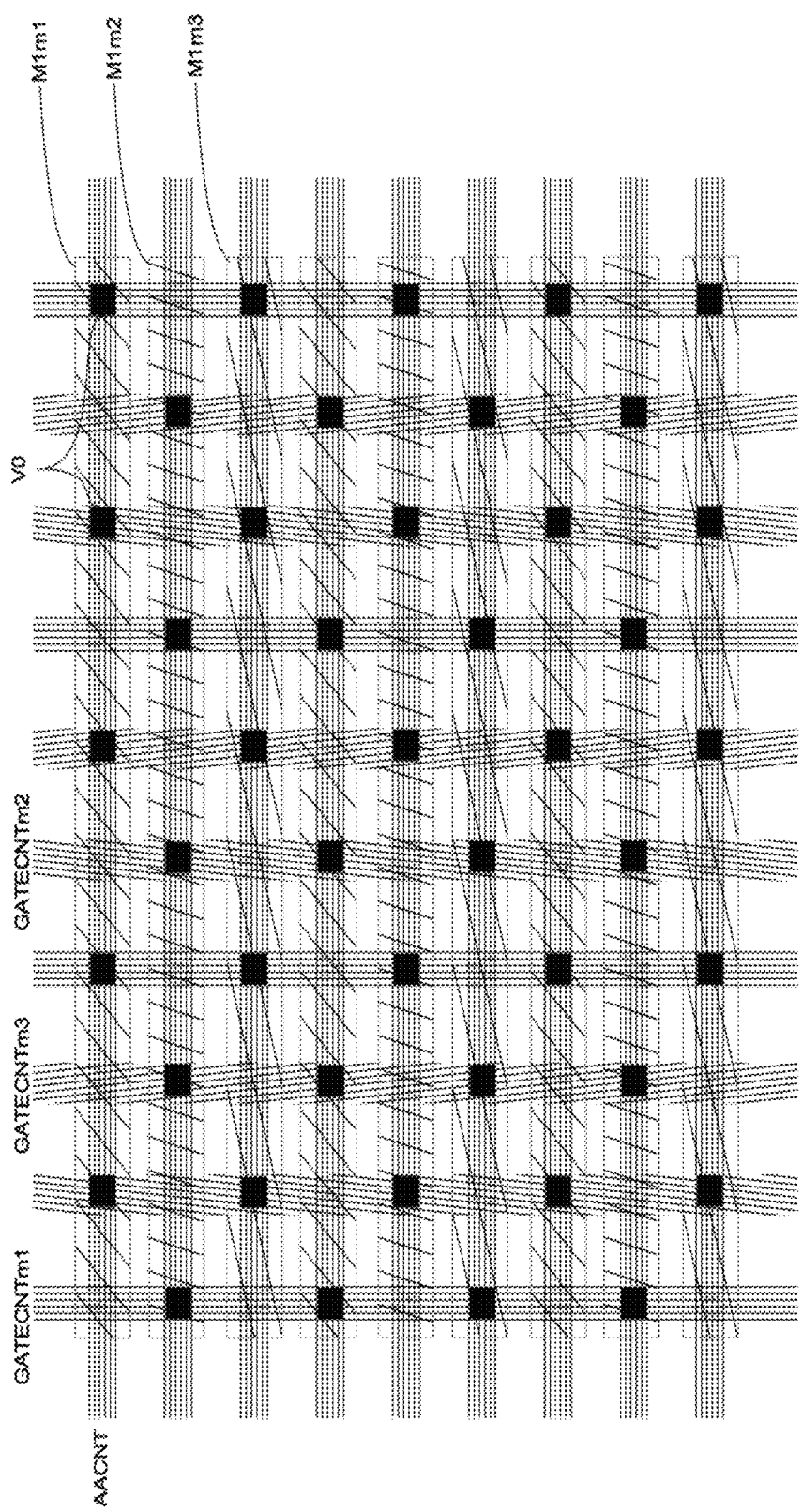
FIG. 9VVV

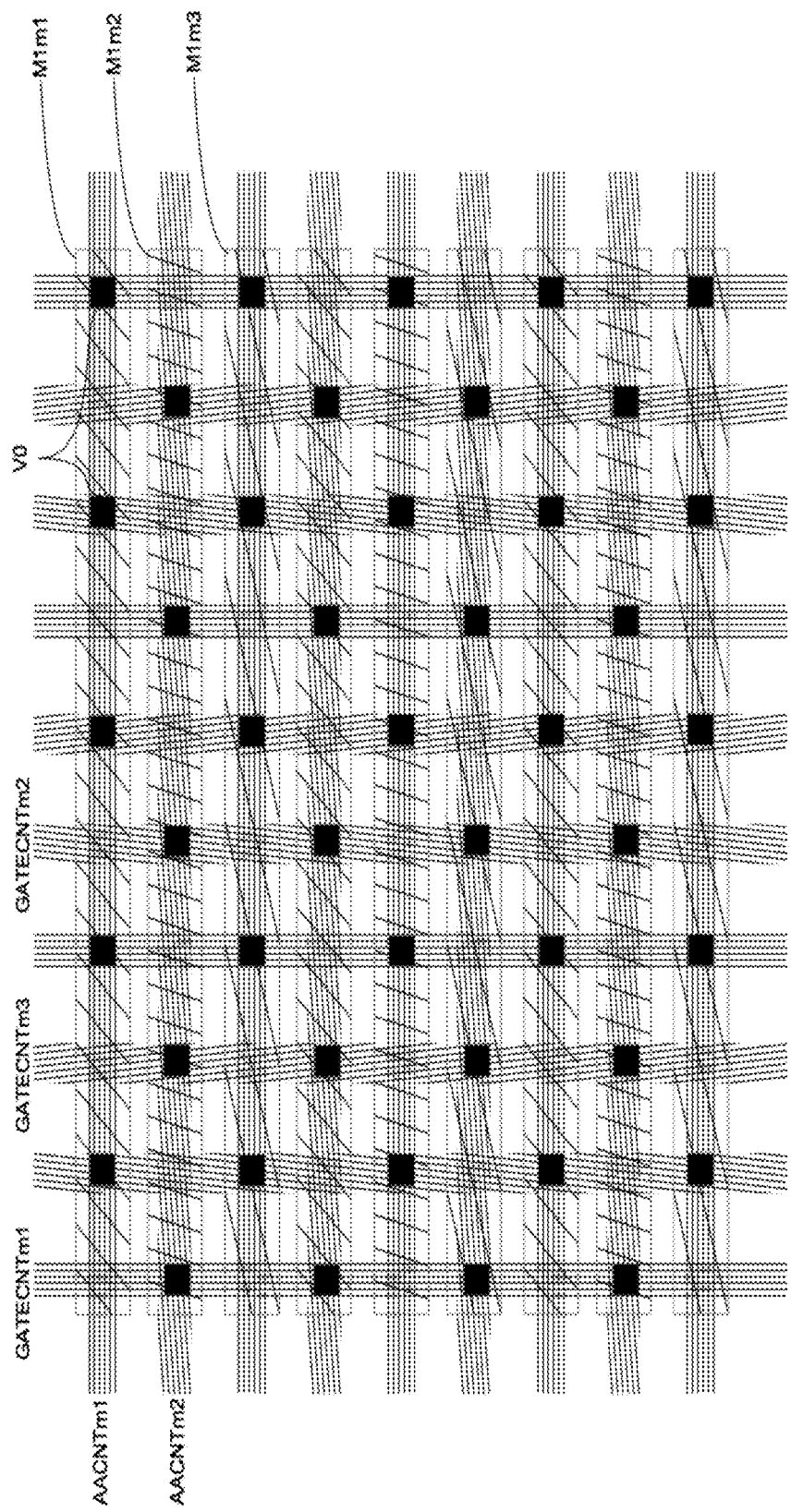
FIG. 9WWW

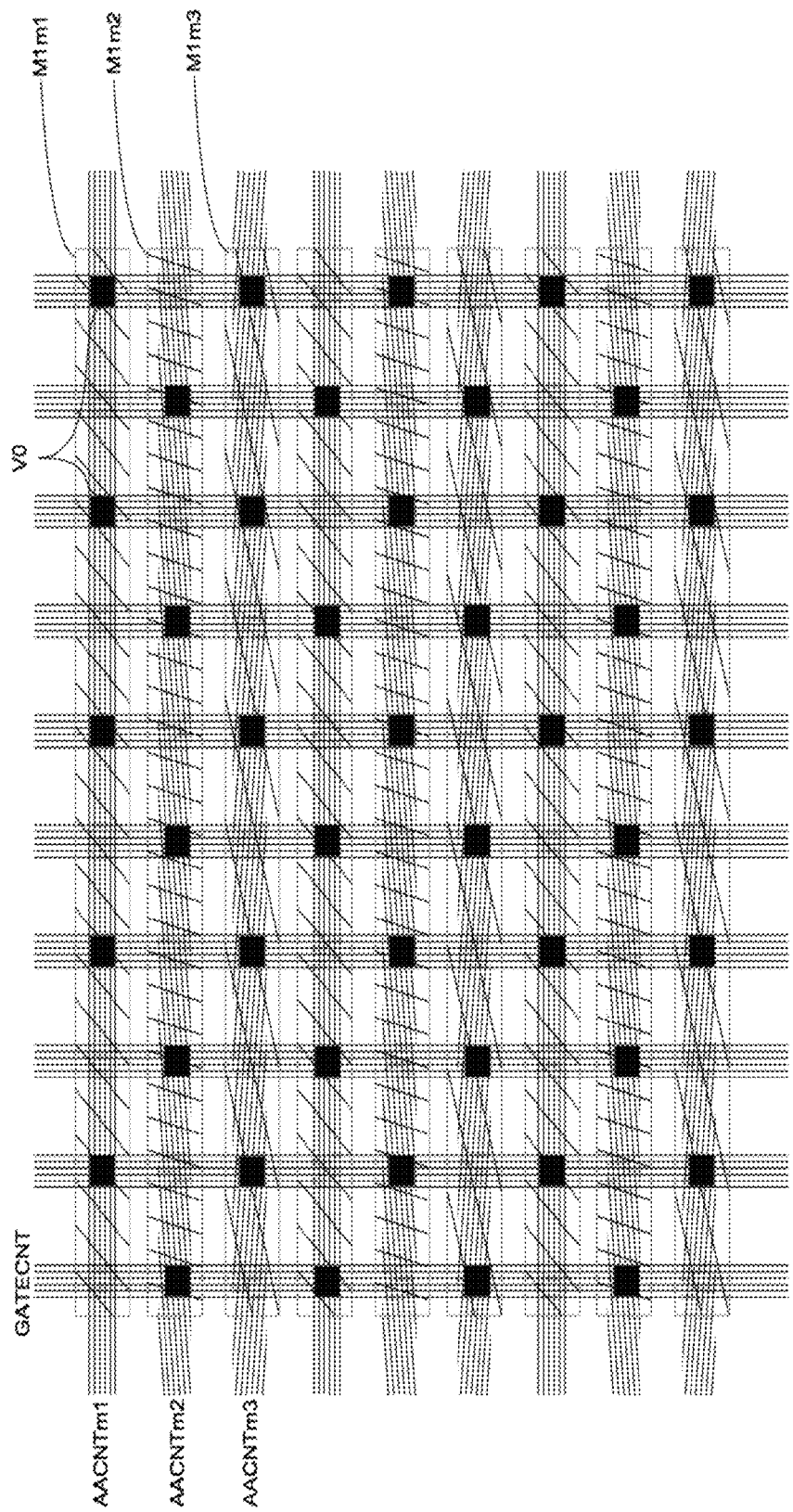
FIG. 9XXX

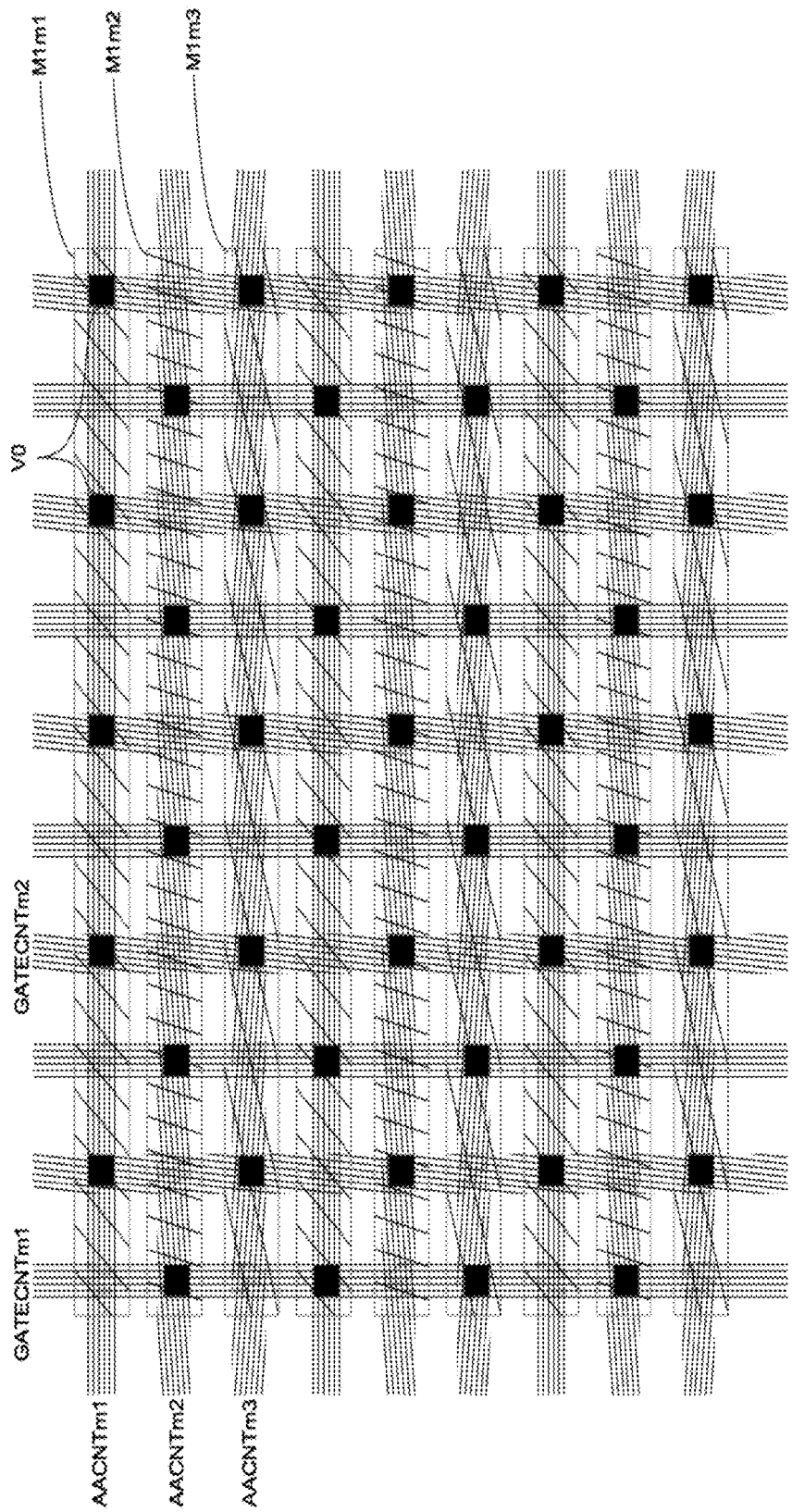
FIG. 9YYY

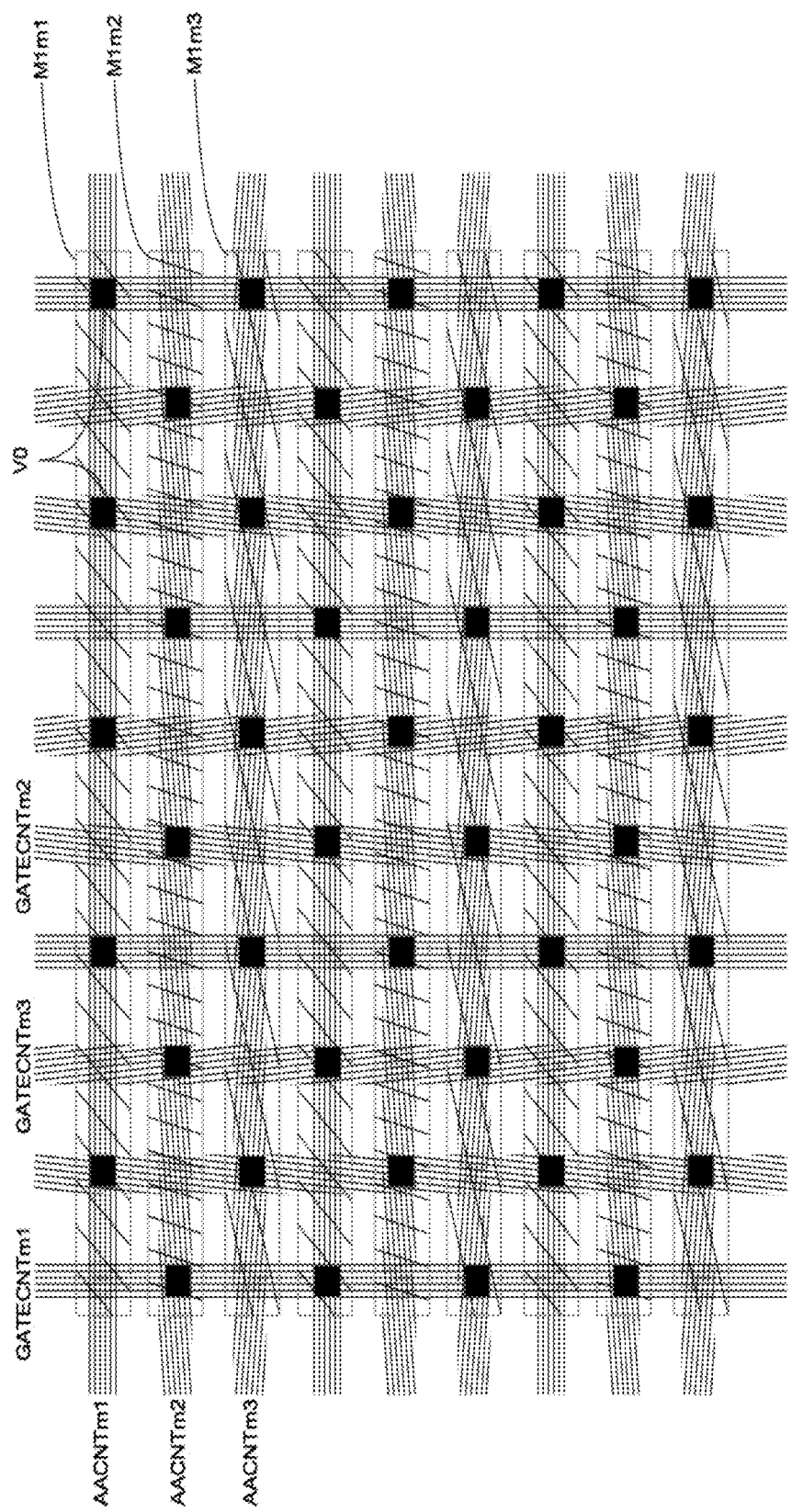
FIG. 9ZZZ

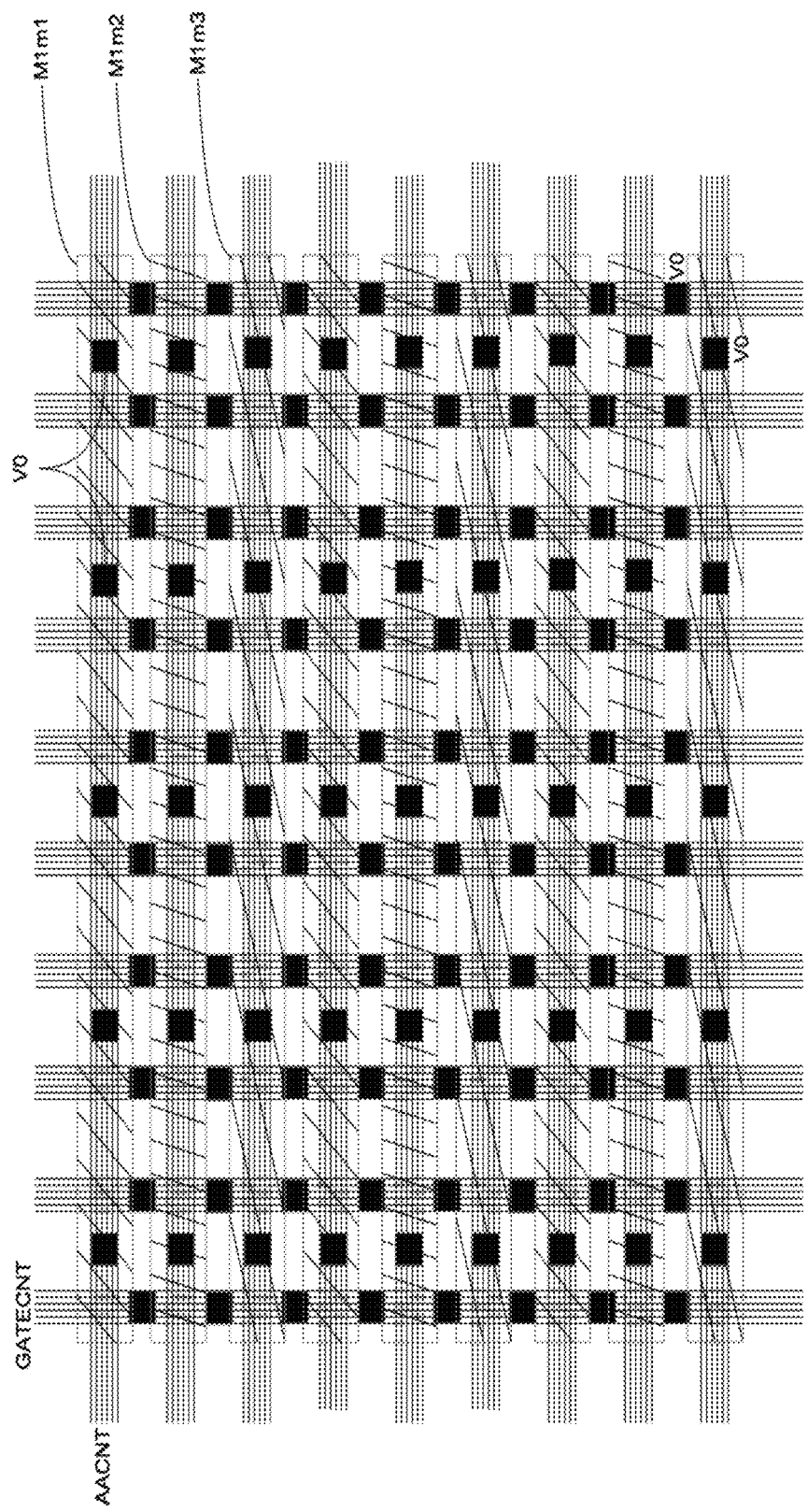
FIG. 9AAAA

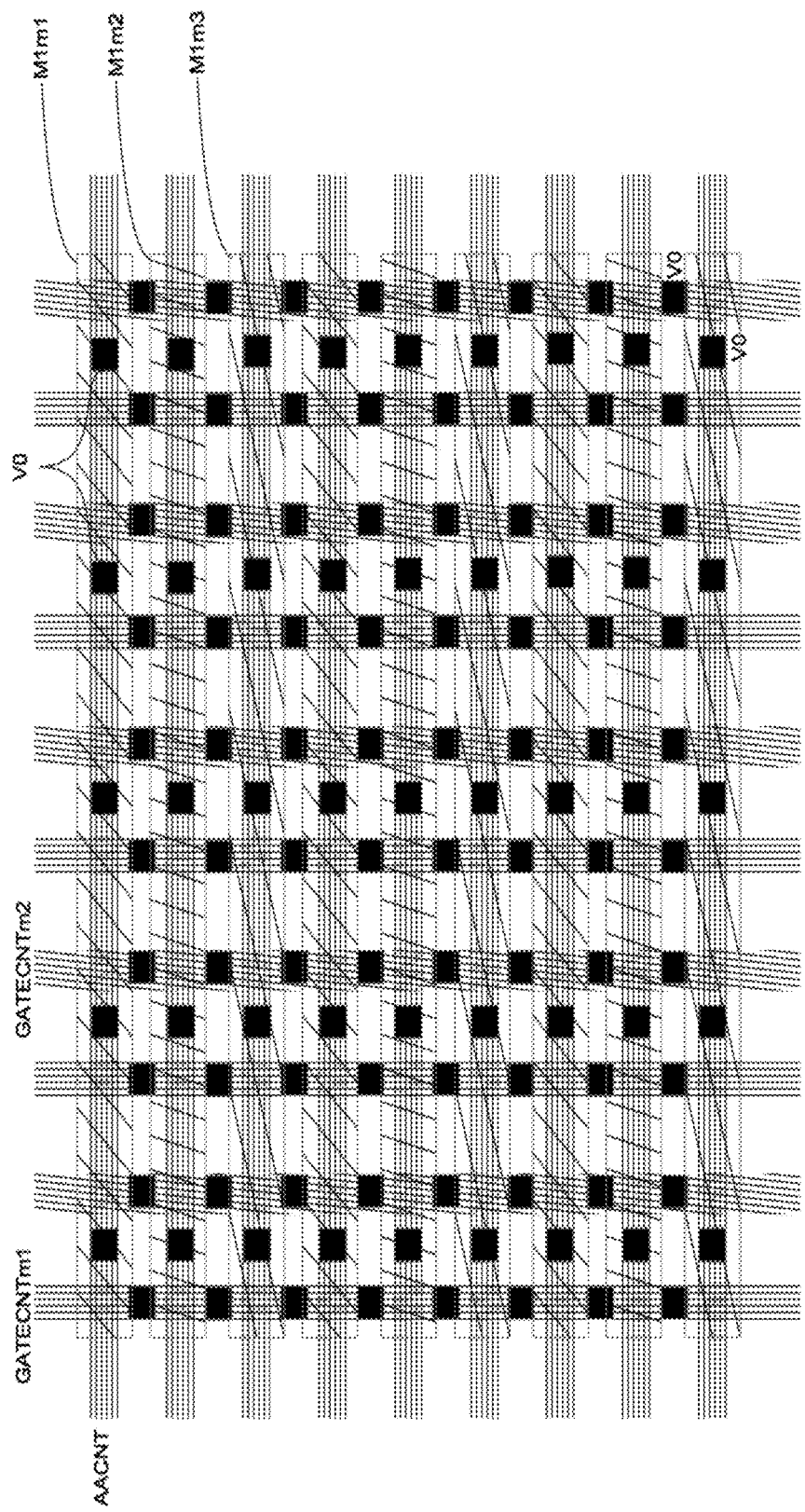
FIG. 9BBBB

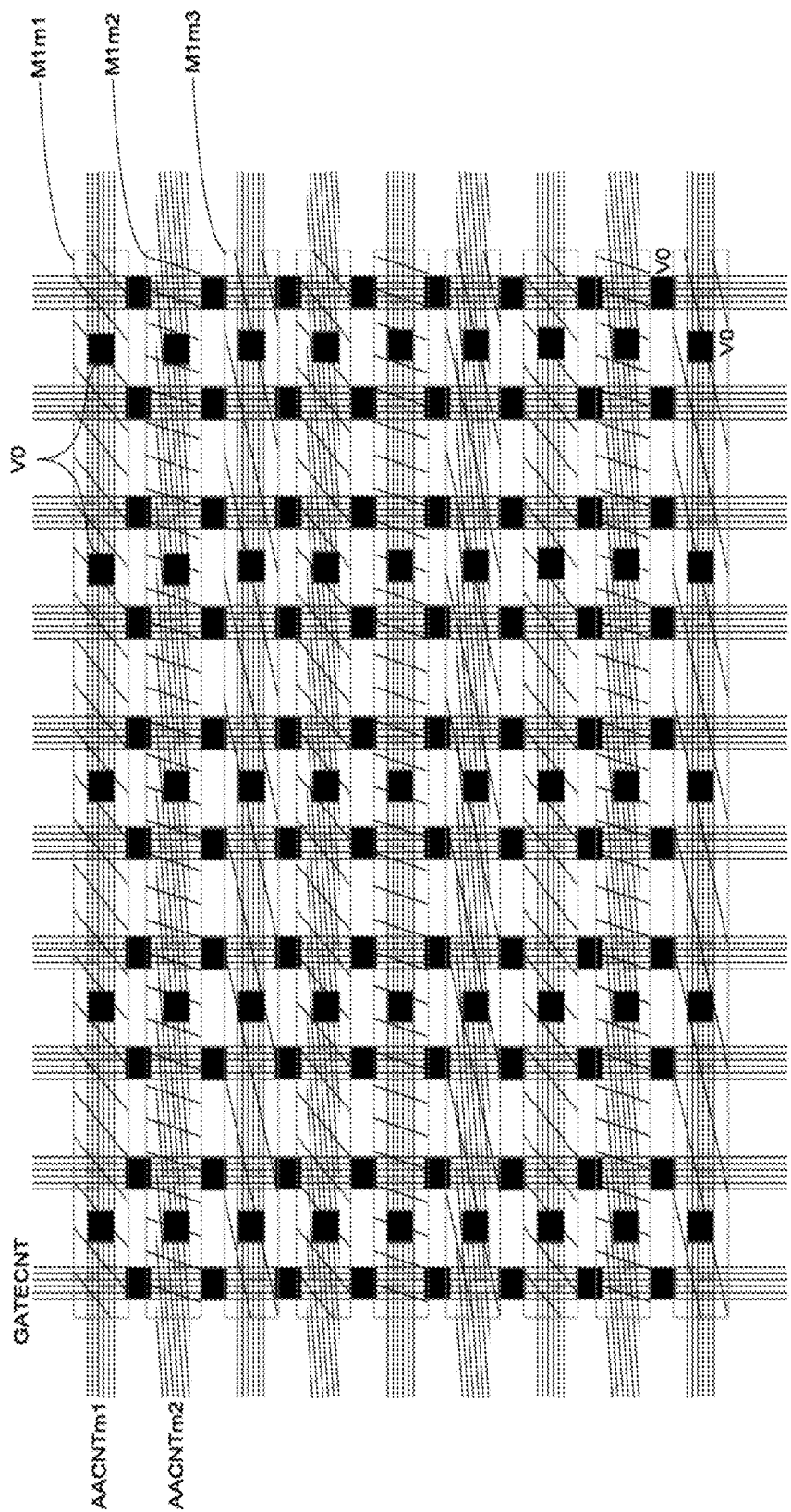
FIG. 9CCCC

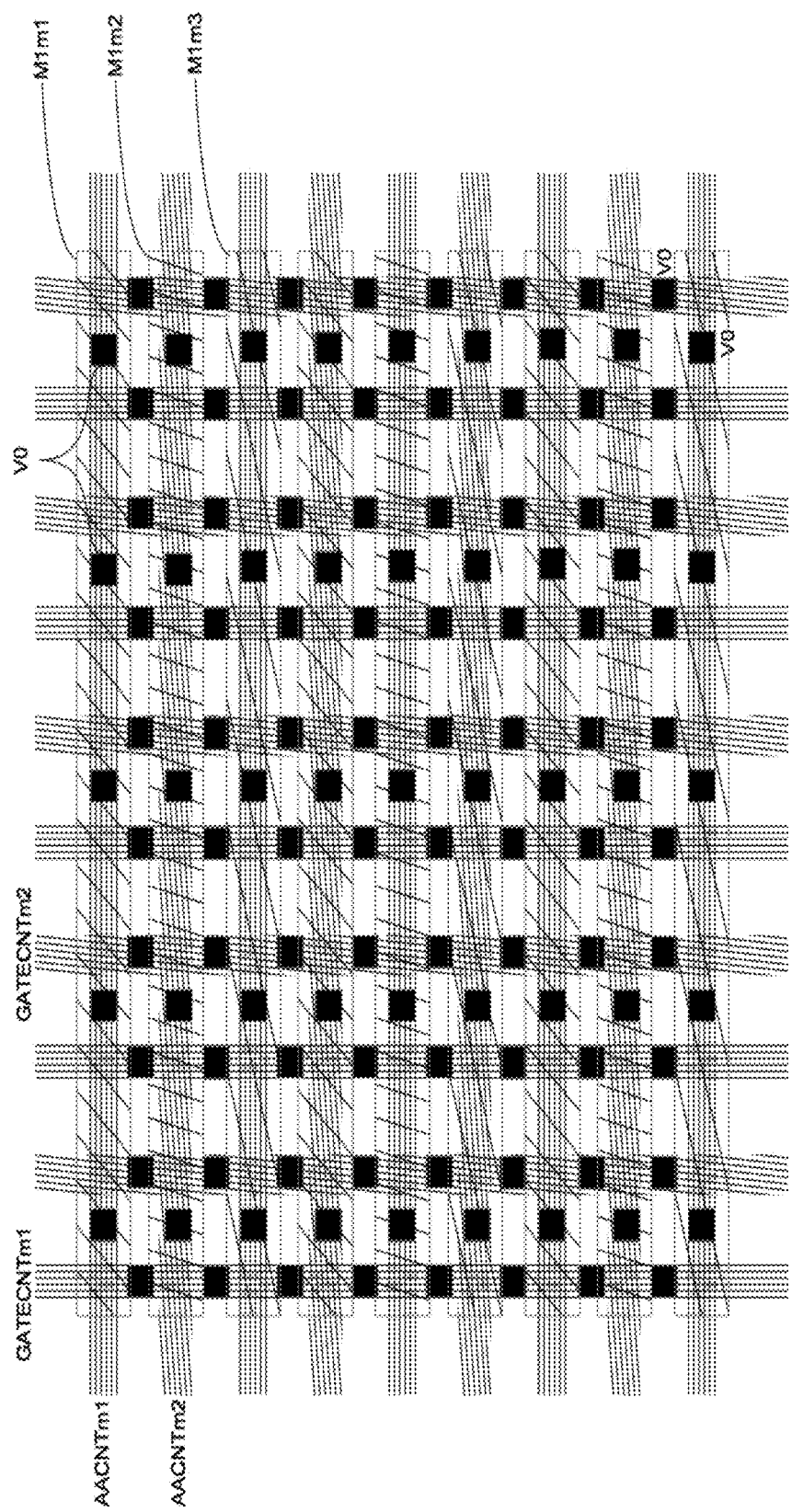
FIG. 9DDDD

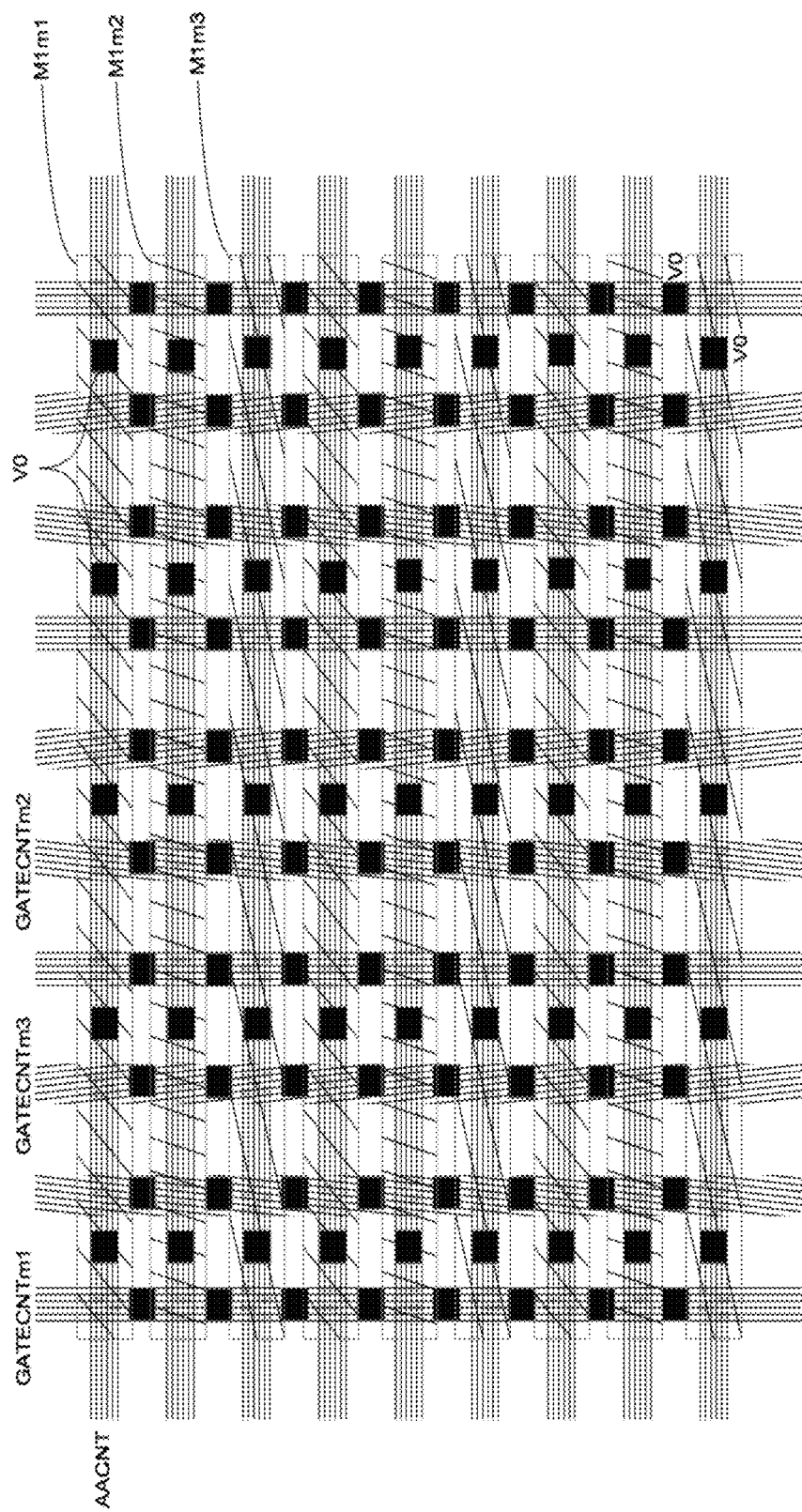
FIG. 9EEEE

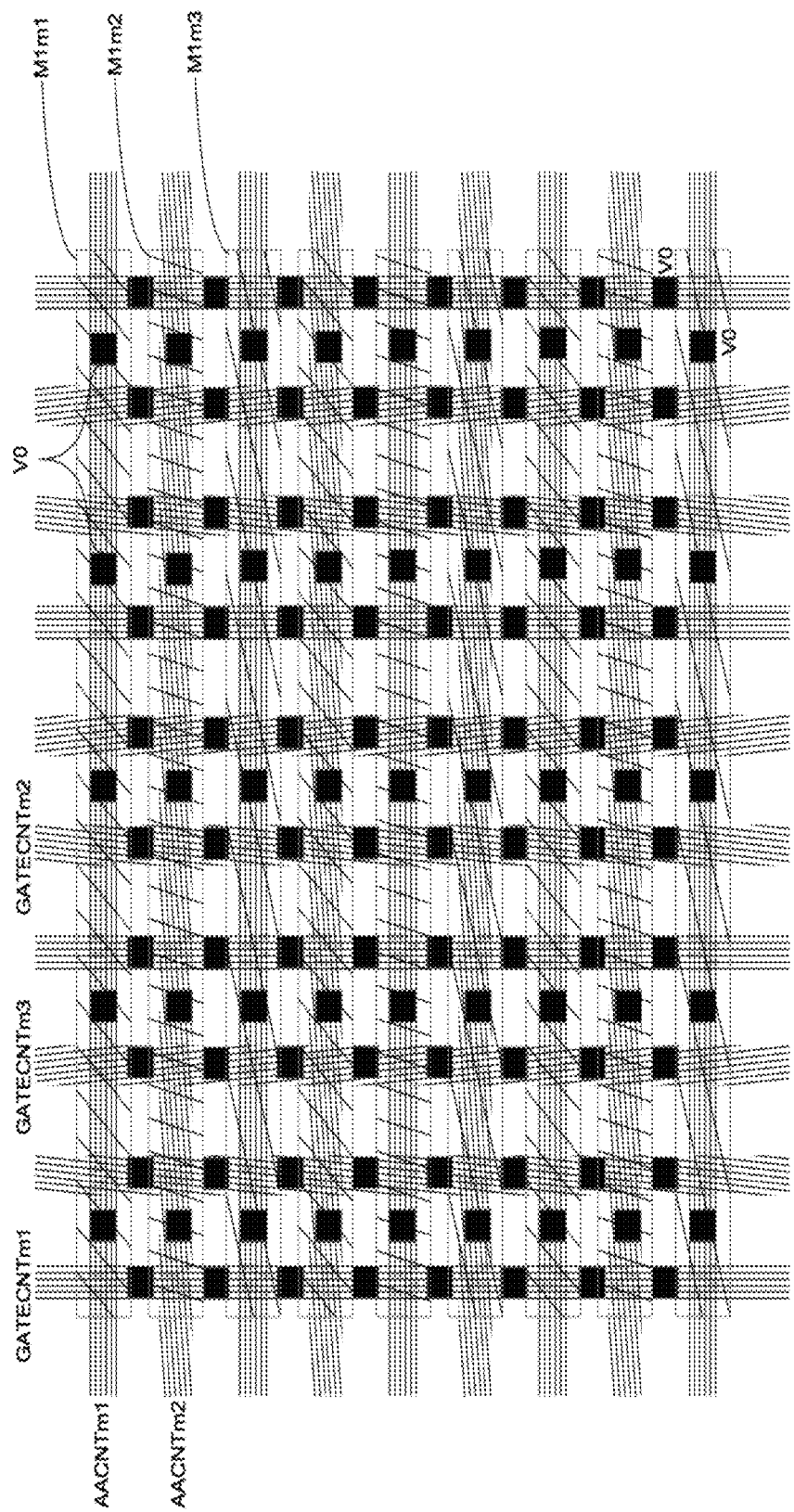
FIG. 9FFFF

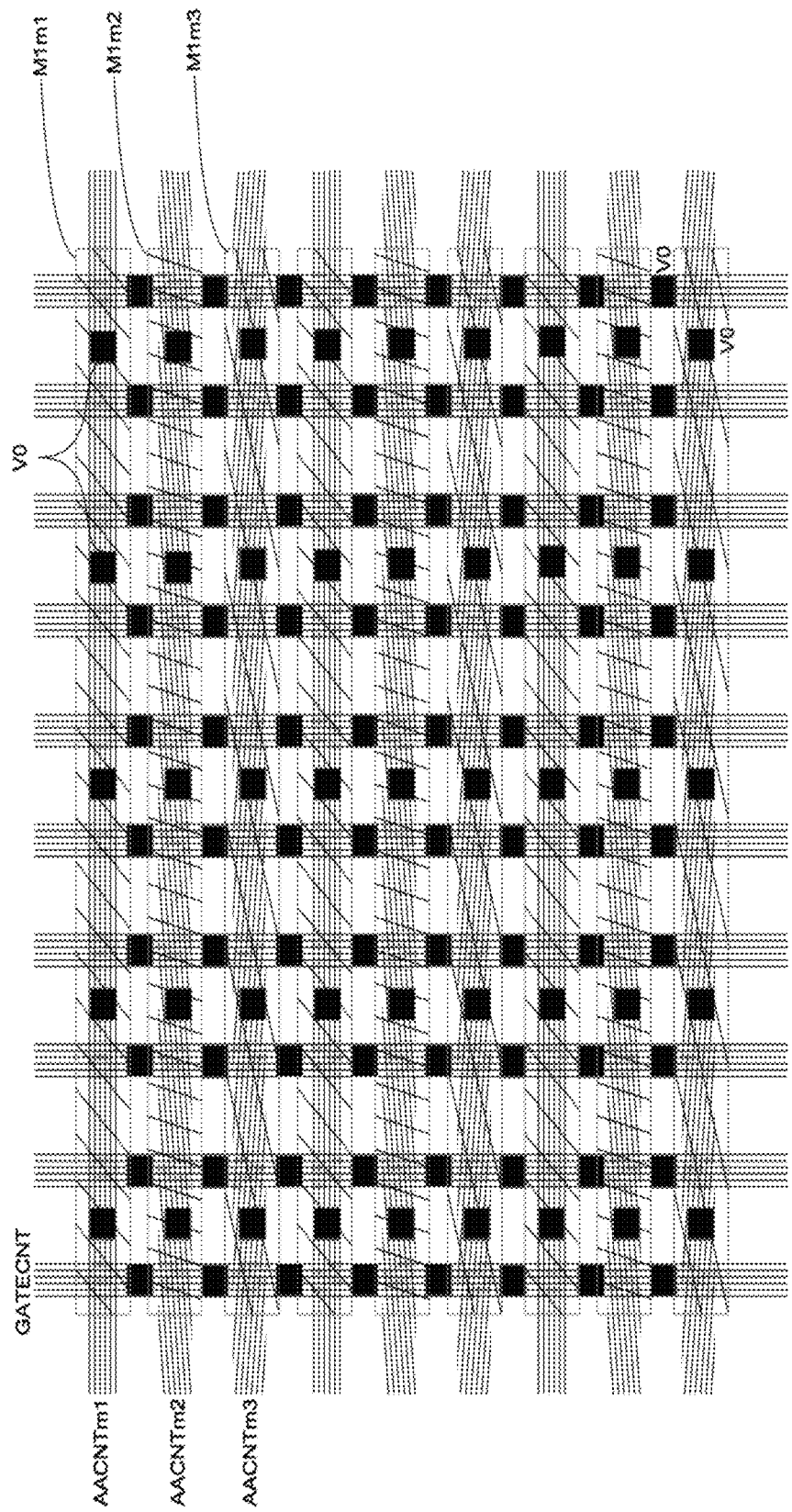
FIG. 9GGGG

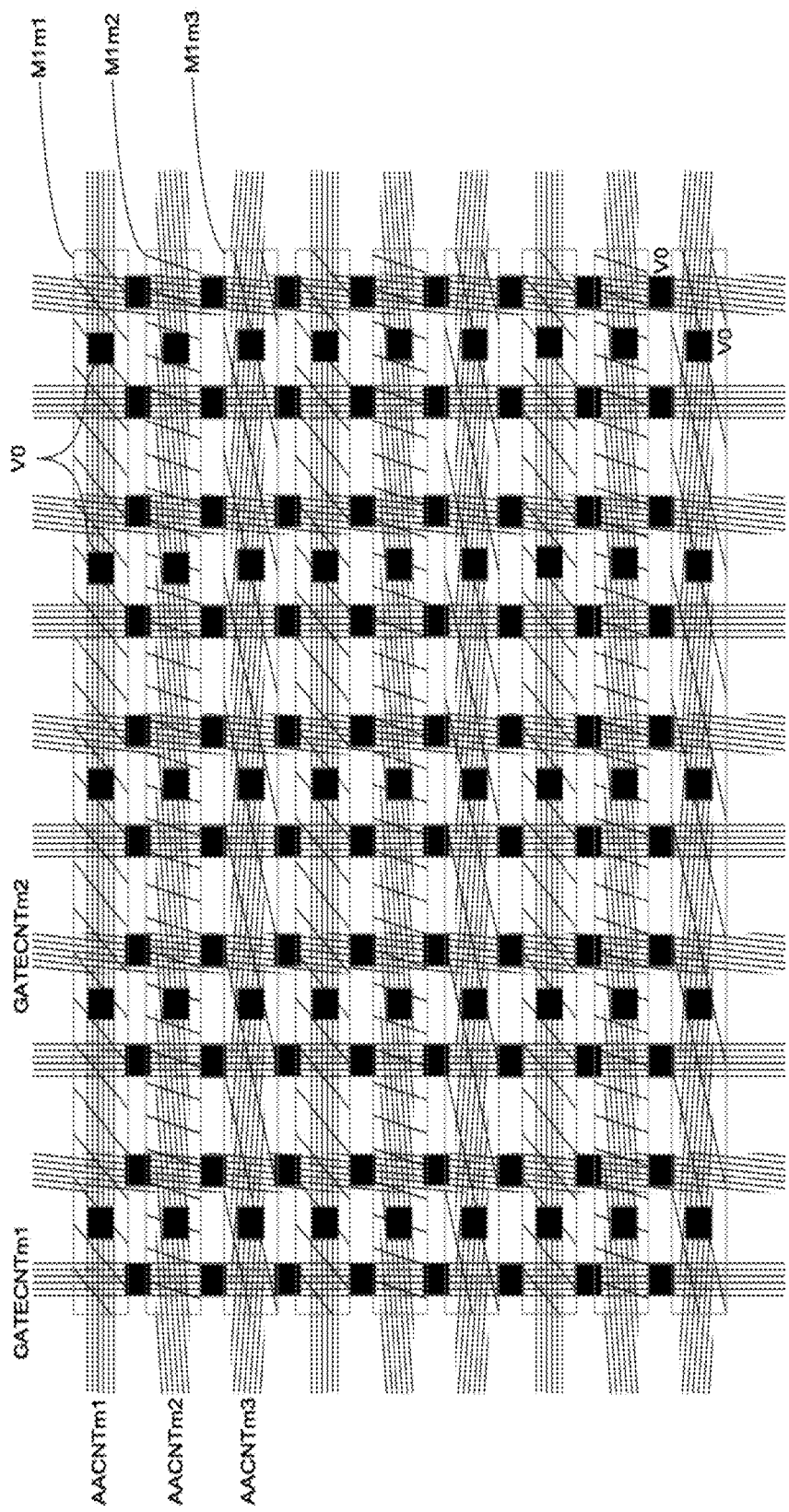
FIG. 9HHHH

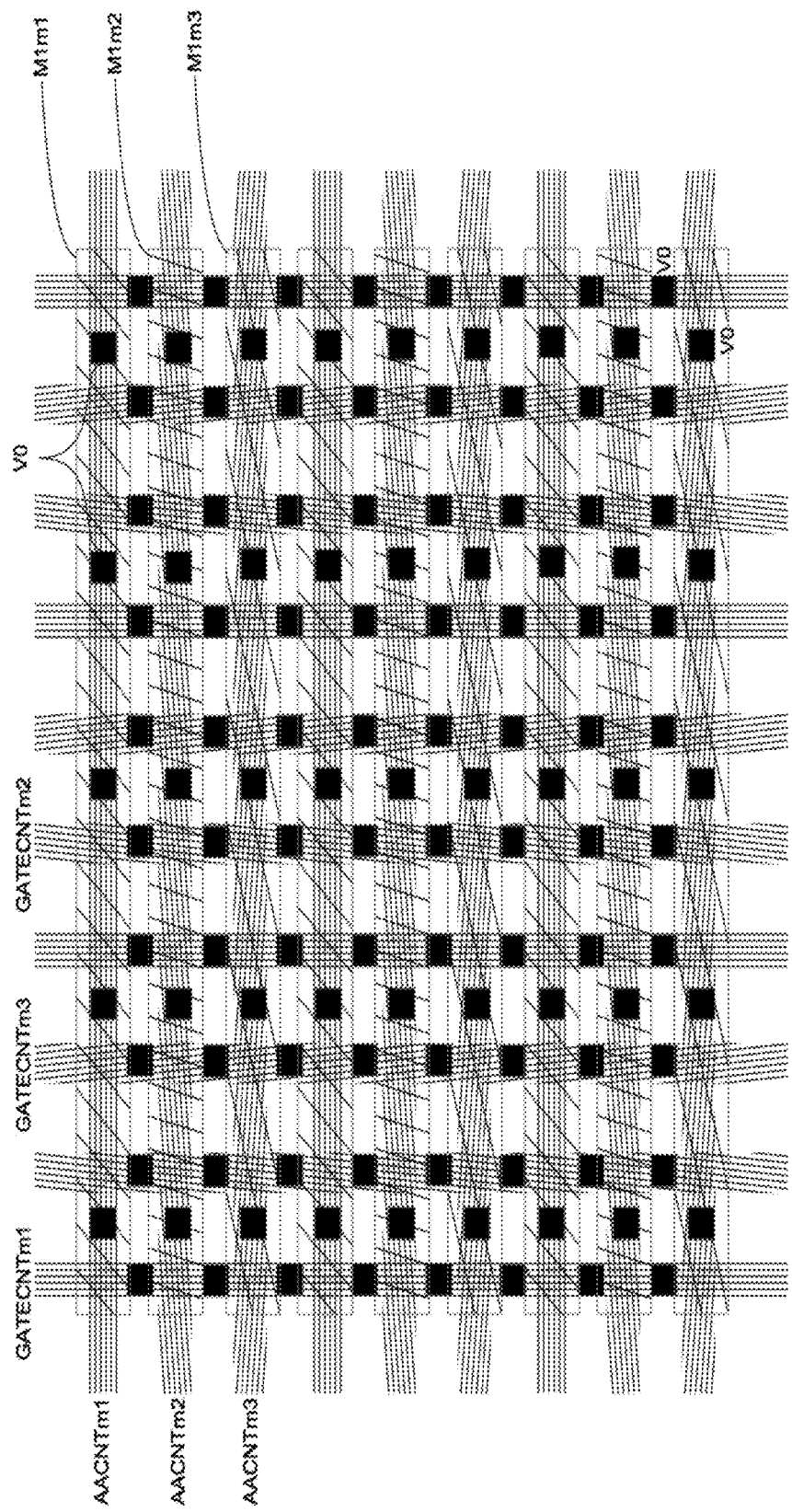
FIG. 9IIII

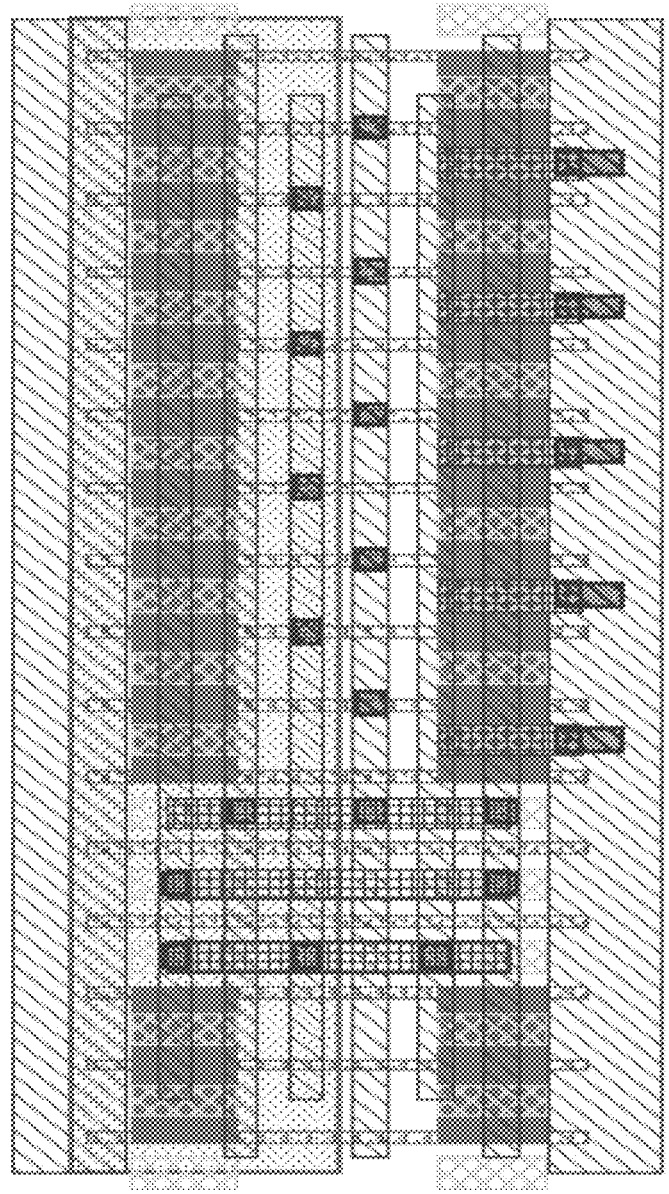
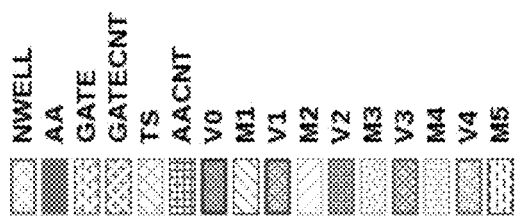
FIG. 46A

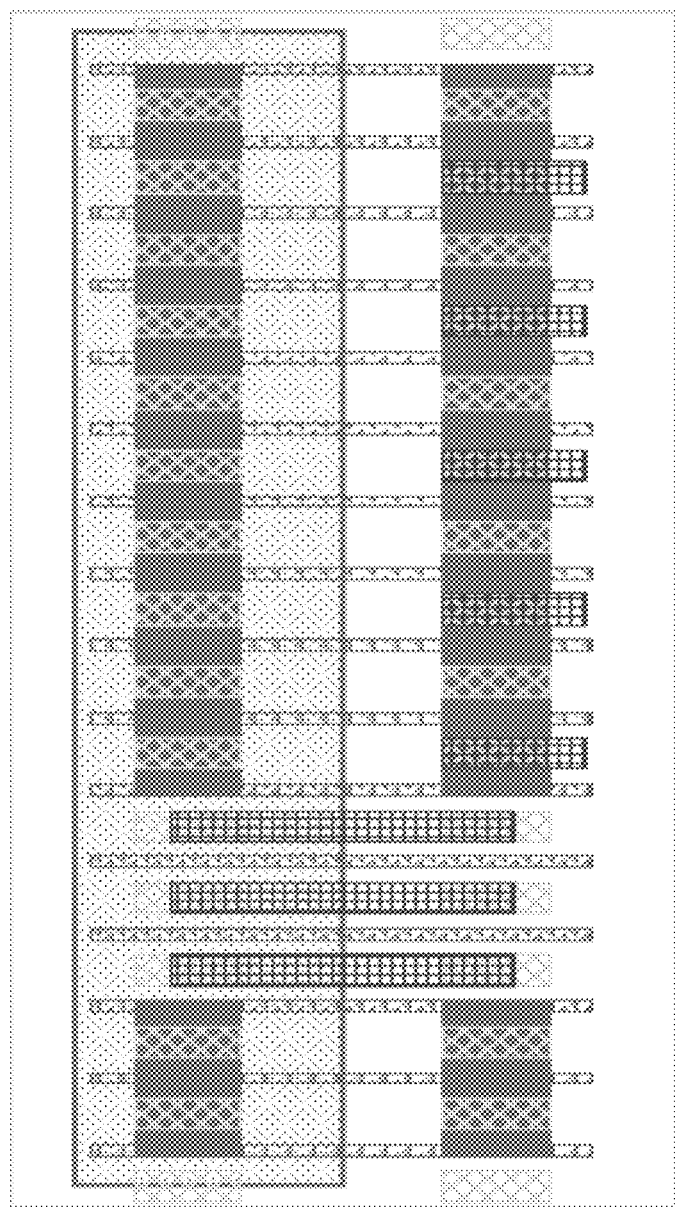
FIG. 46B

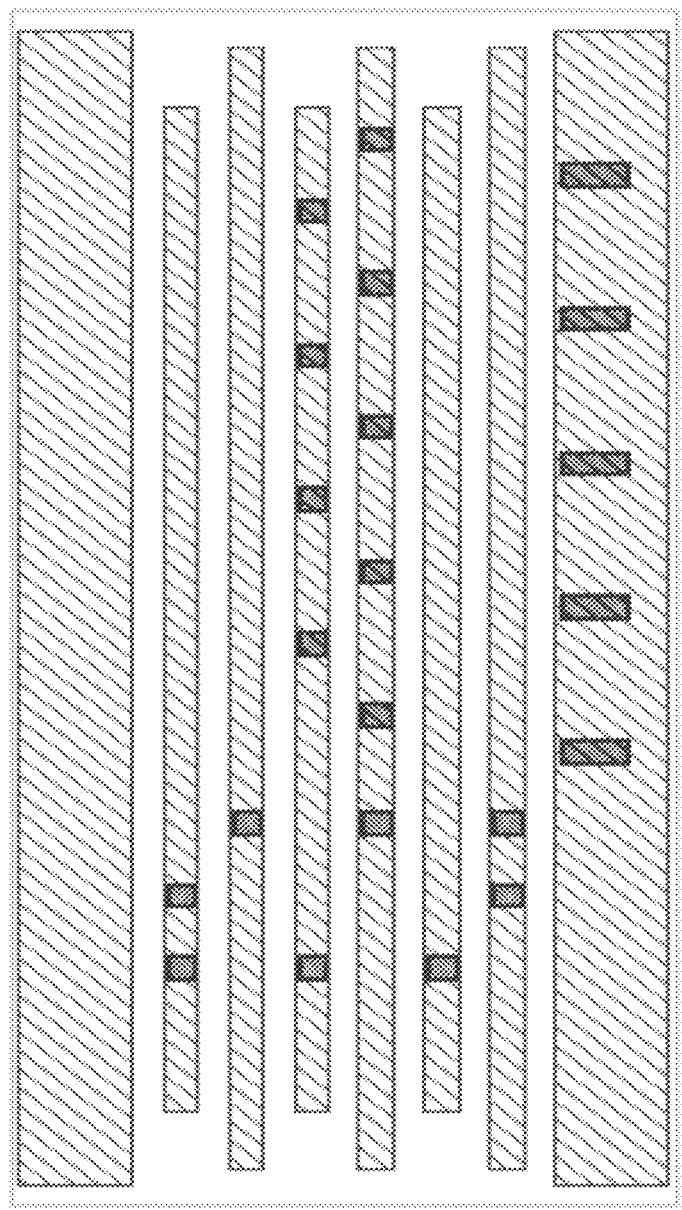
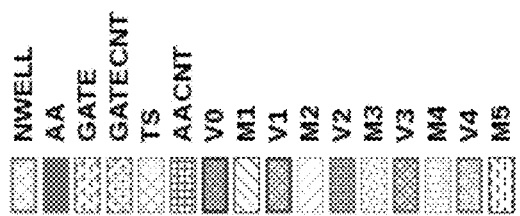
FIG. 46C

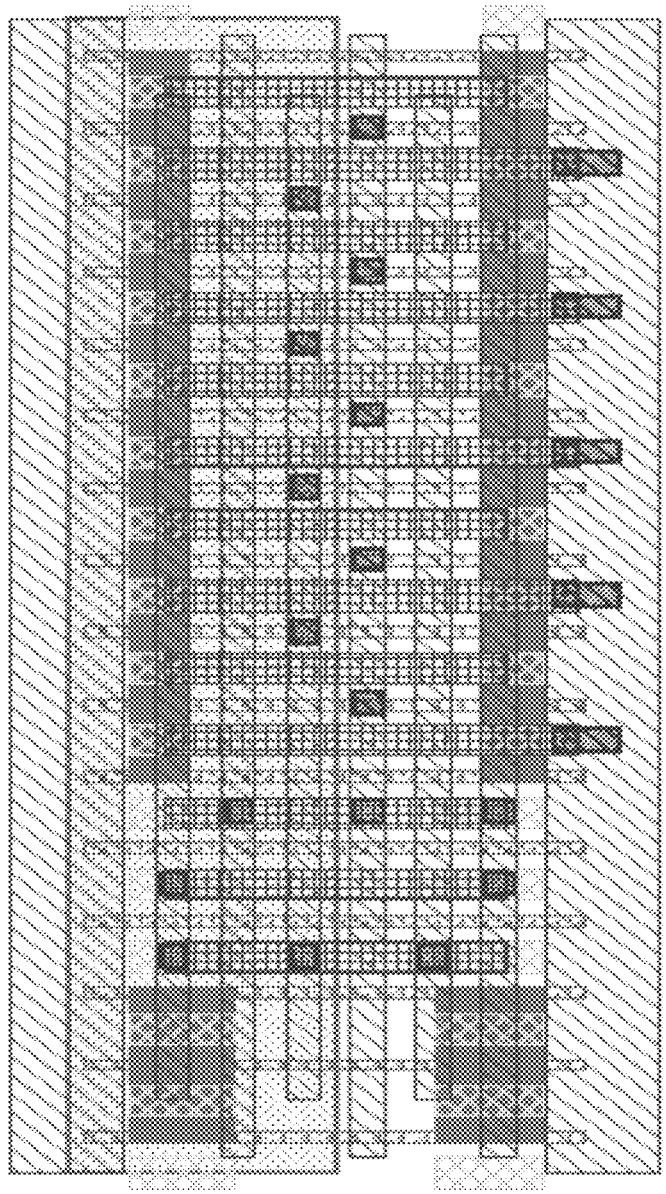
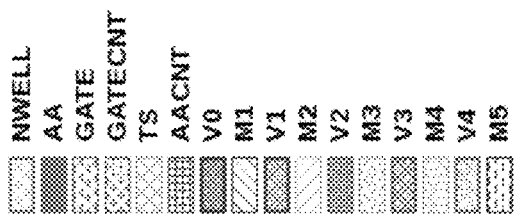
FIG. 47A

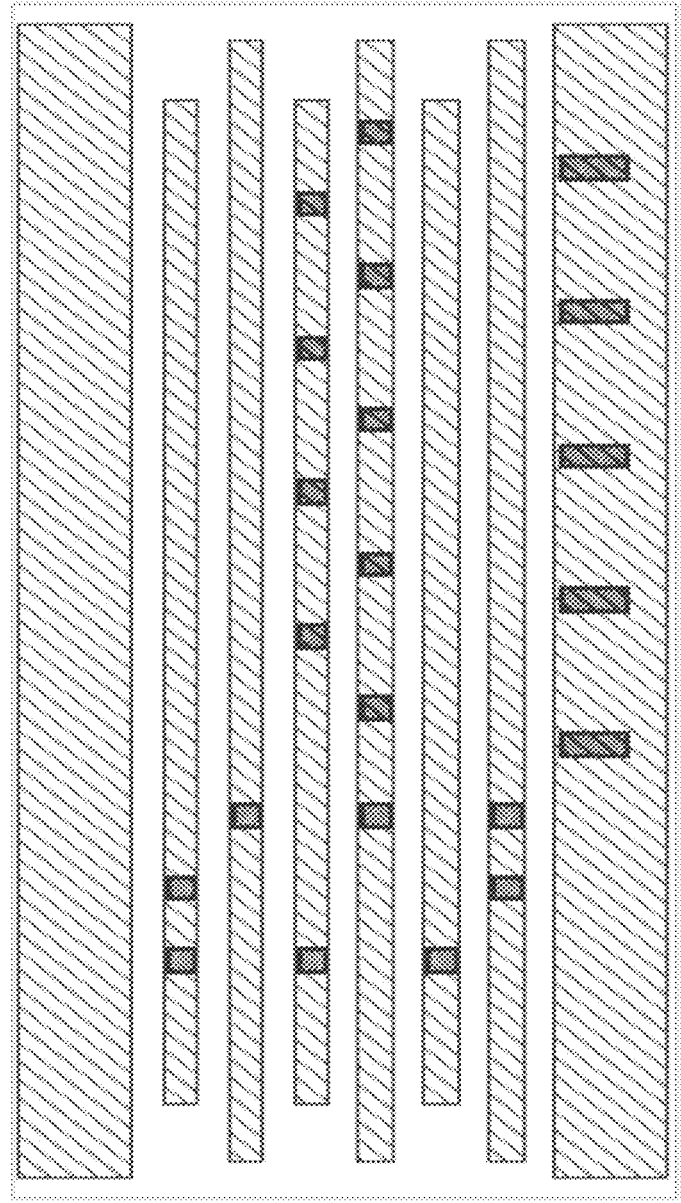
FIG. 47C

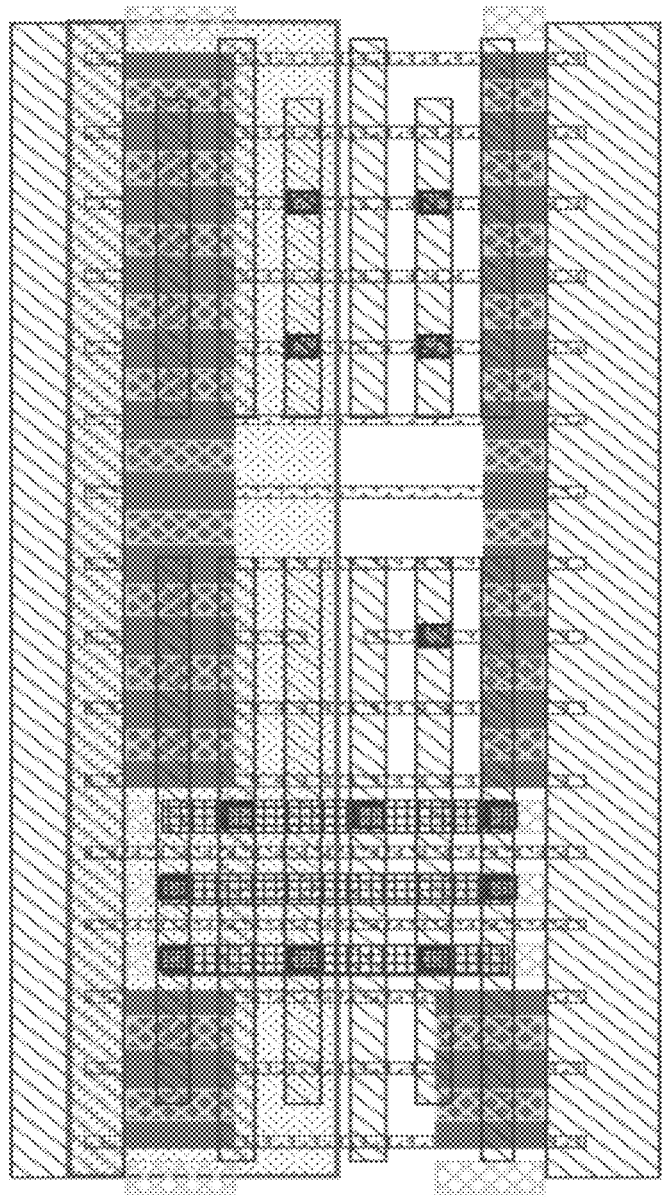
FIG. 48A

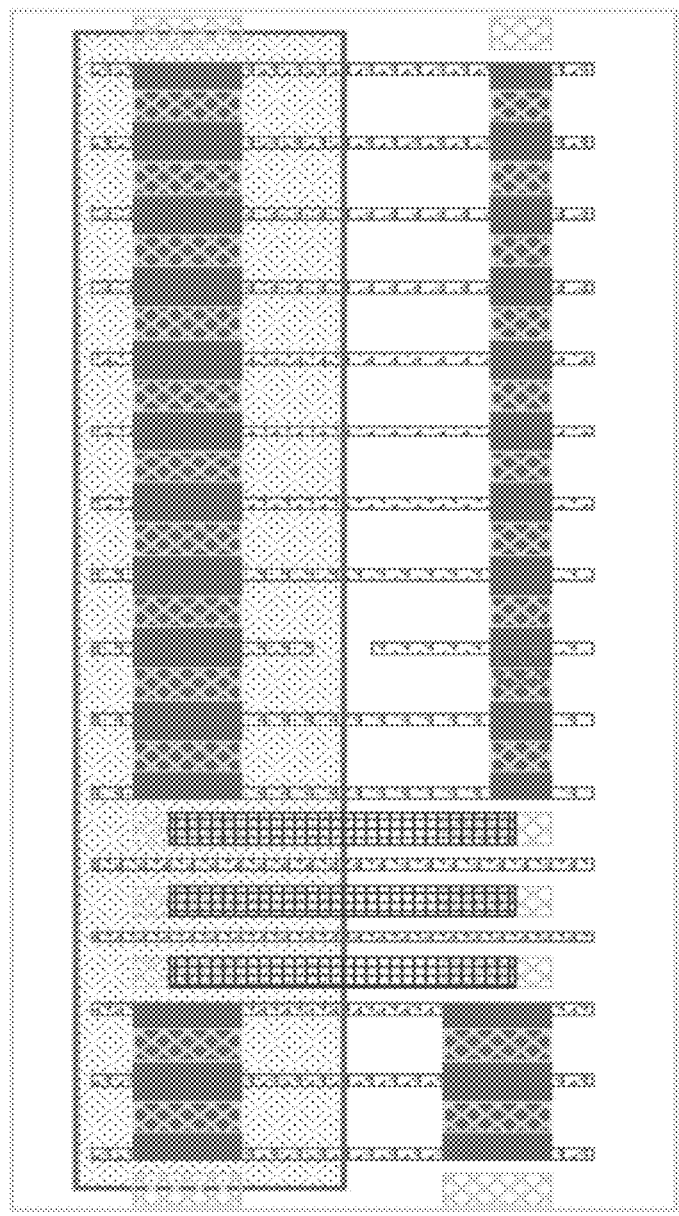
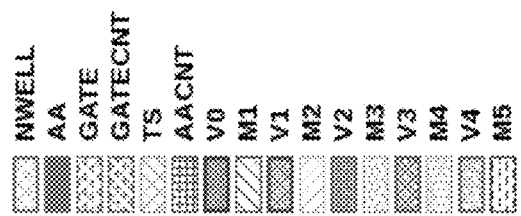
FIG. 48B

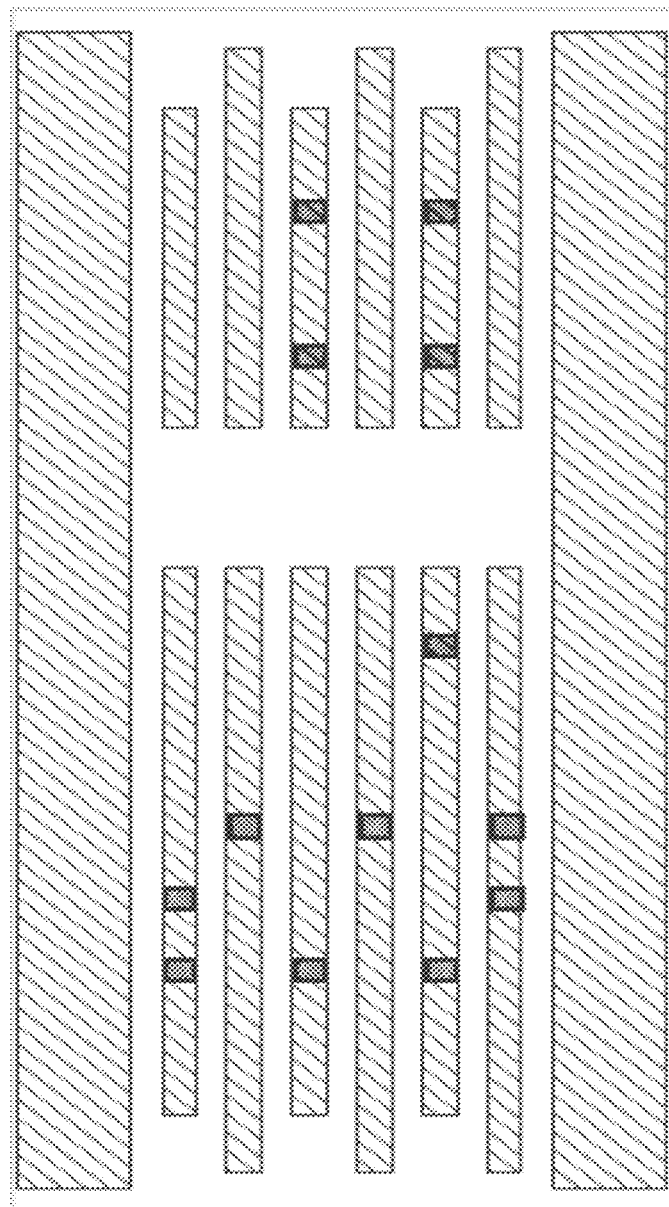
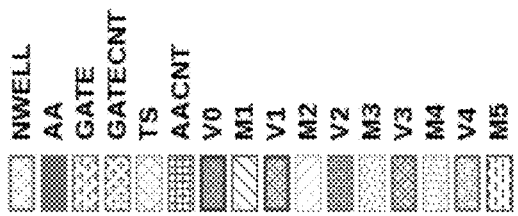
FIG. 48C

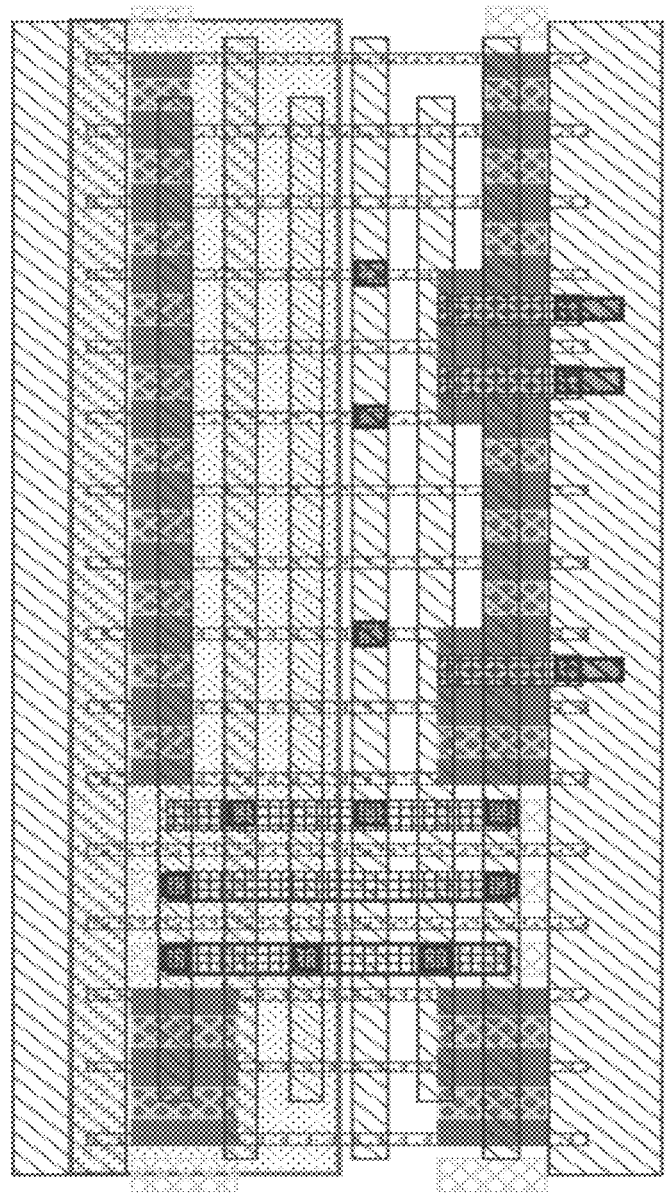
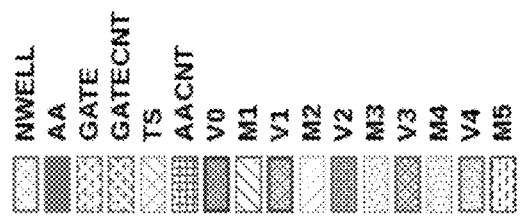
FIG. 49A

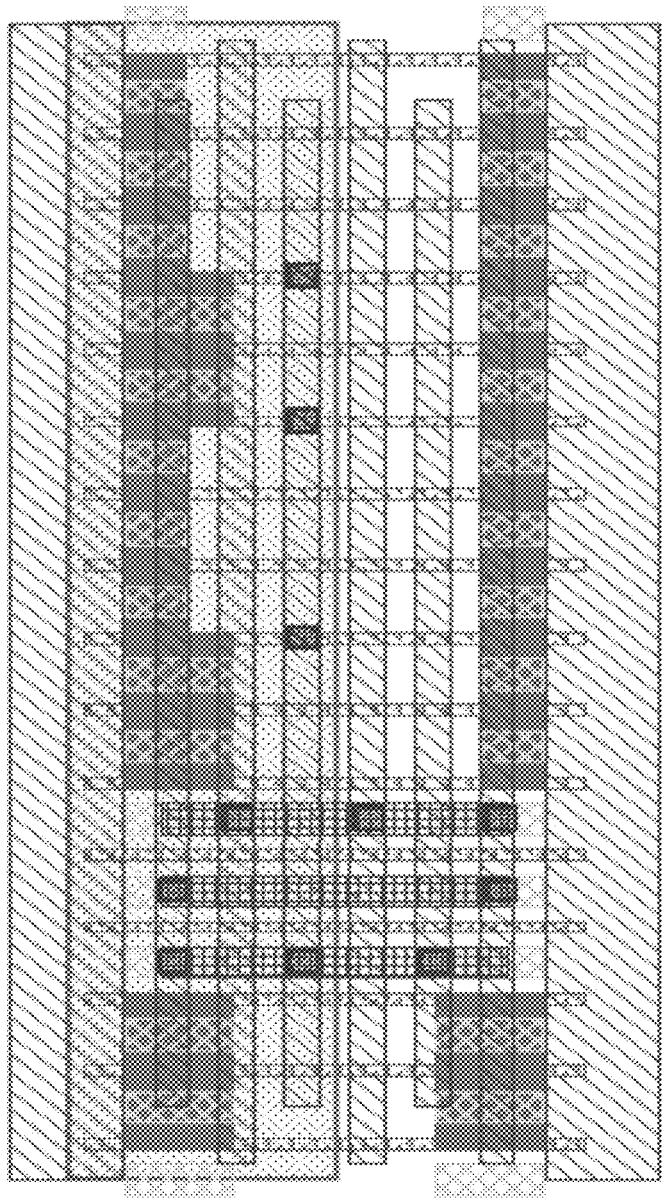
FIG. 50A

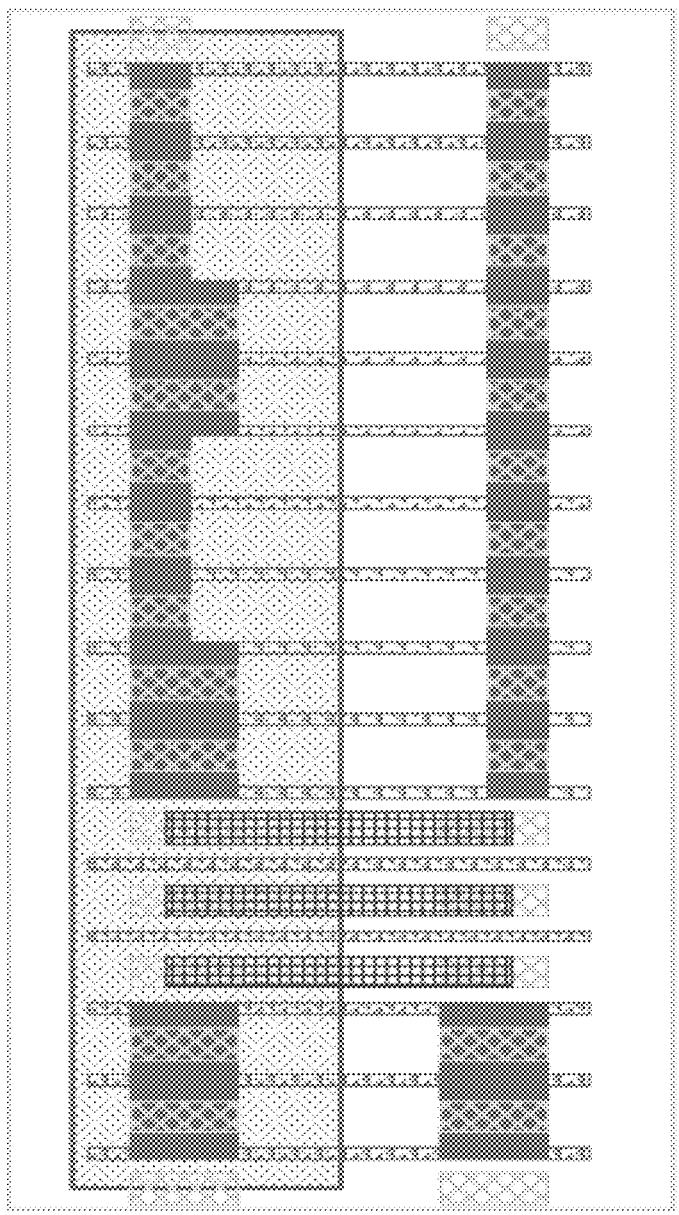
FIG. 50B

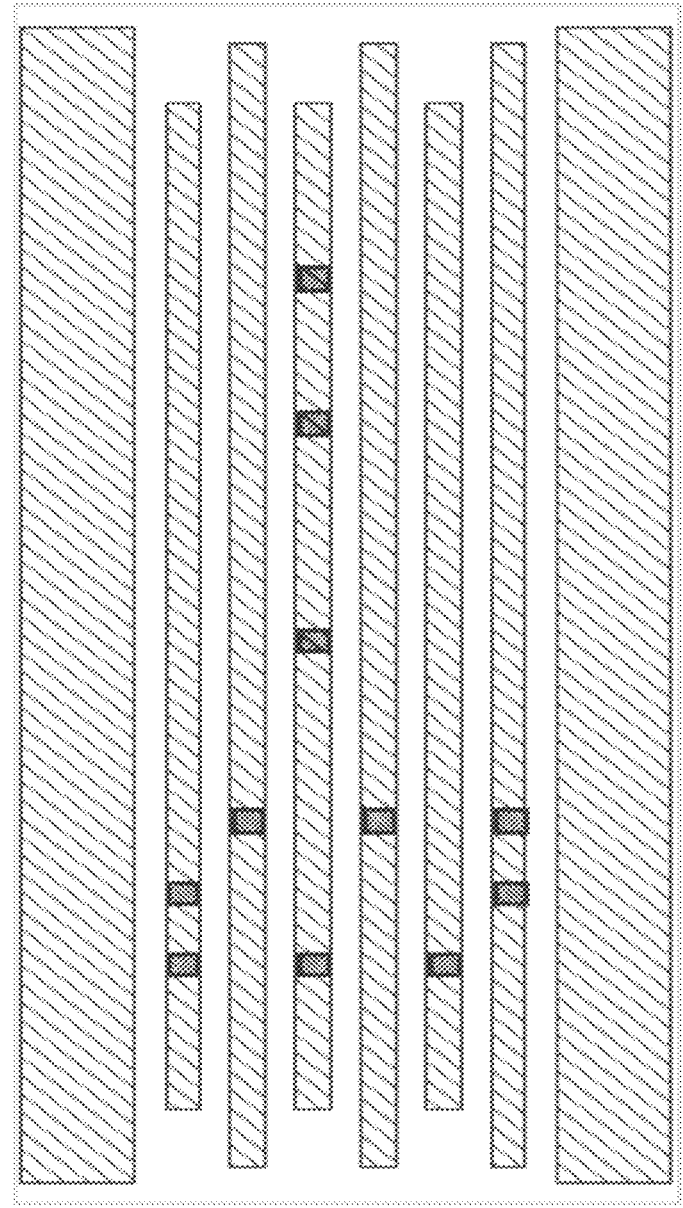
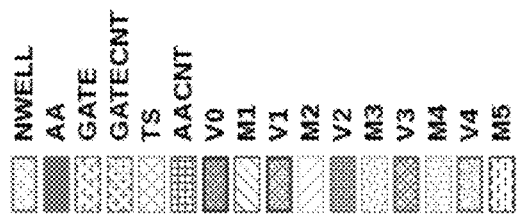
FIG. 50C

PROCESS FOR MAKING AND USING MESH-STYLE NCEM PADS

CROSS-REFERENCE TO RELATED APPLICATIONS

This application is a divisional of U.S. patent application Ser. No. 15/090,274, entitled "Mesh-Style NCEM Pads, and Process for Making Semiconductor Dies, Chips, and Wafers Using In-Line Measurements from Such Pads," filed Apr. 4, 2016, which '274 application is incorporated by reference herein. (Any references in the present application to FIGS. 51-2461 should be read as referring to the figures of the incorporated '274 application.)

This application also claims priority from U.S. Pat. Applic. Ser. 62/268,463, entitled "Integrated Circuit Containing DOEs of NCEM-enabled Fill Cells+Process for Making Semiconductor Dies, Chips, and Wafers Using In-Line Measurements Obtained From DOEs of NCEM-enabled Fill Cells," filed Dec. 16, 2015, which '463 application is incorporated by reference herein.

This application is also a continuation-in-part of U.S. patent application Ser. No. 14/612,841, filed Feb. 3, 2015, which '841 application is also incorporated by reference herein.

MASK WORK NOTICE

A portion of the disclosure of this patent document (including its incorporated documents) contains material which is subject to mask work protection, *M*, PDF Solutions, Inc. The mask work owner (PDF Solutions, Inc.) has no objection to the facsimile reproduction by anyone of the patent document (including its incorporated documents) or the patent disclosure, as it appears in the Patent and Trademark Office patent file or records, but otherwise reserves all mask work rights whatsoever.

FIELD OF THE INVENTION

This invention relates generally to improved processes for manufacturing semiconductor wafers and chips through use of in-line measurements obtained via non-contact electrical measurements ("NCEM"), to on-chip structures configured to provide useful information via NCEM, and to implementation of NCEM structures in library compatible fill cells.

BACKGROUND OF THE INVENTION

U.S. Pat. No. 5,008,727 ("Standard cell having test pad for probing and semiconductor integrated circuit device containing the standard cells") to Katsura et al., incorporated by reference herein, discloses placement of a testing pad in a standard cell.

U.S. Pat. No. 6,091,249 A ("Method and apparatus for detecting defects in wafers") to Graham et al., incorporated by reference herein, discloses structures and methods for testing certain defects using a non-contact ("NC") technique.

U.S. Pat. No. 6,452,412 B1 ("Drop-in test structure and methodology for characterizing an integrated circuit process flow and topography") to Jarvis et al., incorporated by reference herein, discloses structures and methods for testing certain defects using an NC technique.

U.S. Pat. No. 6,949,765 B2 ("Padless structure design for easy identification of bridging defects in lines by passive voltage contrast") to Song et al., incorporated by reference herein, discloses structures and methods for testing certain defects using an NC technique.

U.S. Pat. No. 7,101,722 B1 ("In-line voltage contrast determination of tunnel oxide weakness in integrated circuit technology development") to Wang et al., incorporated by reference herein, discloses structures and methods for testing certain defects using an NC technique.

U.S. Pat. No. 7,105,436 B2 ("Method for in-line monitoring of via/contact holes etch process based on test structures in semiconductor wafer manufacturing") to Zhao et al., incorporated by reference herein, discloses structures and methods for testing certain defects using an NC technique.

U.S. Pat. No. 7,518,190 B2 ("Grounding front-end-of-line structures on a 501 substrate") to Cote et al., incorporated by reference herein, discloses structures and methods for testing certain defects using an NC technique.

U.S. Pat. No. 7,930,660 B2 ("Measurement structure in a standard cell for controlling process parameters during manufacturing of an integrated circuit"), to Ruderer et al., incorporated by reference herein, describes the use of test structures in fill cells for manufacturing optimization.

U.S. Pat. No. 7,939,348 B2 ("E-beam inspection structure for leakage analysis"), to Seng et al., incorporated by reference herein, discloses structures and methods for testing certain defects using an NC technique.

U.S. Pat. No. 8,039,837 B2 ("In-line voltage contrast detection of PFET silicide encroachment") to Patterson et al., incorporated by reference herein, discloses structures and methods for testing certain defects using an NC technique.

U.S. Pat. No. 8,339,449 B2 ("Defect monitoring in semiconductor device fabrication"), to Fong et al., incorporated by reference herein, discloses structures and methods for testing certain defects using an NC technique.

U.S. Pat. No. 8,399,266 B2 ("Test structure for detection of gap in conductive layer of multilayer gate stack") to Mo et al., incorporated by reference herein, discloses structures and methods for testing certain defects using an NC technique.

U.S. Pat. No. 8,421,009 B2 ("Test structure for charged particle beam inspection and method for defect determination using the same") to Xiao, incorporated by reference herein, discloses structures and methods for testing certain defects using an NC technique.

U.S. Pat. No. 8,575,955 B1 ("Apparatus and method for electrical detection and localization of shorts in metal interconnect lines") to Brozek, incorporated by reference herein, discloses structures and methods for testing certain defects using an NC technique.

U.S. Patent Publication 20090102501 A1 ("Test structures for e-beam testing of systematic and random defects in integrated circuits") to Guldi et al., incorporated by reference herein, discloses structures and methods for testing certain defects using an NC technique.

SUMMARY OF THE INVENTION

The invention generally involves the placement of NC-testable structures, and DOEs (Designs of Experiments) based on such structures, preferably within the "fill cells" typically used in standard cell logic regions. As used in this application, "fill cells" (or "filler cells") refer to cells configured for placement in standard cell rows, but not configured to perform any logical or information storage function(s). Modern, standard-cell layouts commonly use such fill cells to relieve routing congestion. See, e.g., Cong, J., et al. "Optimizing routability in large-scale mixed-size placement," ASP-DAC, 2013; and Menezes, C., et al. "Design of regular layouts to improve predictability," Proceedings of the 6th IEEE International Caribbean Conference on Devices, Circuits and Systems, 2006. See also U.S. Pat. No. 8,504,969 ("Filler Cells for Design Optimization in a Place-and-Route System") to Lin et al., incorporated by reference herein. As used herein "fill cells" may include structures designed to perform ancillary (i.e., not logical or storage) functions, for example, well ties and/or decoupling capacitors.

One NC measurement technique, useful in connection with certain embodiments of the invention, involves measuring or inspecting the surface of a partially processed wafer (in-line) with a scanning electron microscope ("SEM") or other charged particle-based scanning/imaging device. As the measuring/inspecting proceeds, the SEM (or other device) induces charge on all electrically floating elements, whereas any grounded elements remain at zero potential. This voltage contrast becomes visible to the scanning/imaging device as a NCEM.

This NC measurement technique, commonly known as "voltage contrast inspection," has been used in the semiconductor industry for many years, see, e.g., U.S. Pat. No. 6,344,750 B1 ("Voltage contrast method for semiconductor inspection using low voltage particle beam"), and exists in many different flavors—as demonstrated by the dozens of subsequent patents that cite the '750 patent as prior art.

U.S. patent application Ser. No. 14/612,841 ("Opportunistic placement of IC test structures and/or e-beam target pads in areas otherwise used for filler cells, tap cells, decap cells, scribe lines, and/or dummy fill, as well as product IC chips containing same"), filed Feb. 3, 2015, by inventors De et al., incorporated by reference herein, and owned by the assignee of the present application, discloses a number of highly efficient—and herein preferred—methods for obtaining NCEMs from the NCEM-enabled test structures utilized in the present invention. While these '841 methods represent the applicant's preferred NC measurement methods, it is applicant's intent that usage of the terms "NC measurement" or "NCEM" in this application should not be limited to these preferred methods in the absence of specific language (e.g., "selectively targeting . . . ", " . . . fewer than 10 pixels") that indicates an intent to so limit a claim.

In general usage, the term Design of Experiments (DOE) or Experimental Design refers to the design of any information-gathering exercise where variation is present, whether under the full control of the experimenter or not.

Experimental Design is an established field, well known to persons skilled in the art. See NIST/SEMATECH e-Handbook of Statistical Methods, http://www.itl.nist.gov/div898/handbook/, updated Oct. 30, 2013, incorporated by reference herein.

As will be apparent to the skilled reader, the typical DOE herein relates to an experiment involving one or more semiconductor die(s) and/or wafer(s), wherein said one or more die(s) and/or wafer(s) contain multiple instances of a substantially similar test structure, at least some of which vary in terms of one or more layout-related parameters (including, but not limited to, size, spacing, offset, overlap, width, extension, run length, periodicity, density, neighborhood patterning, including underlayers) or process related parameters (including, but not limited to, dose, rate, exposure, processing time, temperature, or any tool-specifiable setting). As the person skilled in the art knows, the selection of specific parameter(s) to vary, the amount/distribution of their variation, and the number and location of test structures that express such variation will be selected based upon the goals of the experiment, the involved process, and the availability of appropriate places (e.g., fill cell locations, tap cell locations, decap cell locations, scribe line areas, etc.) to instantiate the test structures.

Preferred embodiments of the invention utilize DOEs constructed from NCEM-enabled fill cells. In accordance with certain preferred embodiments of the invention, NCEM-enabled fill cells all have some common elements (e.g., height, supply rail configuration, and gate patterning that is consistent with standard cells in the library), then vary according to the measurement type (e.g., short, open, leakage, or resistance), layer(s) involved, and/or structure(s) to be evaluated/tested. Such NCEM-enabled fill cells also generally include a pad, configured to accelerate targeted NC evaluation by, for example, determining an associated NCEM from a small number of enlarged pixels (e.g., 10 or fewer), or without creating any image at all. Such pads can be formed from a variety of low-resistance materials and configured in a variety of shapes.

In certain preferred embodiments, such NCEM-enabled fill cells may additionally include two or more mask-patterned features that define a rectangular test area, such test area being characterized by two parameters (e.g., X/Y or r/θ dimensions). Additionally, for such NCEM-enabled fill cells, an expanded test area surrounds the cell's test area, the expanded test area being defined by a predetermined expansion of each boundary of the test area, or by predetermined proportionate expansion of the test area's area. Alternatively, in the case of cells designed to measure or characterize inter-layer effects, such test areas may be characterized as "test volumes," with one or more additional parameter(s) characterizing the layers of the defining, mask-patterned features.

For fill cells designed to measure, detect, or characterize electrical short circuit behavior (so-called, "short-configured, NCEM-enabled fill cells"), the test area may represent an intended gap between two pattern-defined features that, in the absence of a manufacturing anomaly, would be electrically isolated. Alternatively, in such short-configured, NCEM-enabled fill cells, the test area may represent an overlap between two pattern-defined features that, in the absence of a manufacturing anomaly, would be electrically isolated. A single short-configured, NCEM-enabled fill cell may contain one or multiple test areas. In the case of a NCEM-enabled fill cell with multiple test areas, each of the cell's test areas is preferably wired in parallel, and each of the cell's test areas (and preferably each of its extended test areas, too) is identically or nearly identically configured.

Fill cells designed to measure, detect, or characterize electrical leakage behavior (so-called, "leakage-configured, NCEM-enabled fill cells") typically resemble short-configured cells. Like the short-configured cells, such leakage-configured cells may include a test area that represents an intended gap between two pattern-defined features that, in ideality, should be electrically isolated, but in reality, inevitably exhibit some amount of leakage. Alternatively, in such leakage-configured, NCEM-enabled fill cells, the test area may represent an overlap between two pattern-defined features that, in ideality, would be electrically isolated, but in reality, inevitably exhibit some amount of leakage. A single leakage-configured, NCEM-enabled fill cell may contain one, but preferably contains multiple test areas. In the case of a cell with multiple test areas, each of the cell's test areas is preferably wired in parallel, and each of the cell's test areas (and preferably each of its extended test areas, too) is identically or nearly identically configured.

For fill cells designed to measure, detect, or characterize electrical open circuit behavior (so-called, "open-configured, NCEM-enabled fill cells"), the test area typically represents an intended overlap, or extension, between two pattern-defined features that, in the absence of a manufacturing anomaly, would be electrically connected. (It may also represent a single-layer pattern, such as a snake.) A single open-configured, NCEM-enabled fill cell may contain one or multiple test areas. In the case of multiple test areas, each of the cell's test areas is preferably connected in series, and each of the cell's test areas (and preferably each of the extended test areas, too) is identically or nearly identically configured.

Fill cells designed to measure, detect, or characterize electrical resistance behavior (so-called, "resistance-configured, NCEM-enabled fill cells") typically resemble open-configured cells. Like the open-configured cells, such resistance-configured cells may include a test area that represents an intended overlap, or extension, between two pattern-defined features that, in ideality, would be connected by a nearly zero-resistance path, but in reality, inevitably produce a measurable level of resistance. (Such test area may also represent a single-layer pattern, such as a snake.) A single resistance-configured, NCEM-enabled fill cell may contain one, but preferably contains multiple test areas. In the case of multiple test areas, each of the cell's test areas is preferably connected in series, and each of the cell's test areas (and preferably each of the extended test areas, too) is identically or nearly identically configured.

DOEs, in accordance with such preferred embodiments, comprise a collection of substantially similarly configured NCEM-enabled fill cells, in a plurality of variants. Within a given DOE, such similarly configured fill cells would typically all be configured to measure, detect, or characterize the same behavior (e.g., gate-to-gate, or control-element-to-control-element, shorts, for example), in the same structural configuration (e.g., tip-to-tip, as per FIG. 14, for example). In single-parameter DOEs, the differences between variants may be limited to differences in the size, shape, or position of one of the features that defines the cells' test area. In multi-parameter DOEs, the differences between variants may involve differences in two or more such parameters. And in more complex DOEs, the differences may involve other non-incremental changes (e.g., the presence or absence of certain features, or changes in nearby or underlying patterning), either alone or in combination with additional to single- or multi-parameter variations.

In the case of DOEs involving complex changes to nearby patterning, changes that lie within an expanded test area (an area that encompasses a predetermined expansion of the test area by, for example 50-200%, or more) and involve either the test area-defining layer(s) or any layers that overlap or lie immediately above or below the test area-defining layers, are preferably limited in number. Limiting the number of such changes to fewer than three, five, ten, twenty, or thirty "background pattern variants" facilitates analysis of data that the experiment produces.

Another way to characterize the degree of relevant patterning variation between DOE variants—in certain embodiments of the invention—involves the concept of a pattern similarity ratio ("PSR"), whose computation is pictorially depicted in FIGS. 37-40 (and described later herein). In accordance with this aspect of the invention, for each variant in a DOE, there should exist another variant in the DOE that has a PSR of at least 0.90 (or preferably 0.95, or more preferably 0.97) for every test-area defining layer, and at least 0.75 (or preferably 0.85, or more preferably 0.90) for each layer that lies immediately below any of the test-area defining layer(s), when the expanded test areas are defined to be at least 150-200% of the corresponding test area sizes.

Another aspect of DOEs, in accordance with the preferred embodiments, is that they include multiple instances (e.g., 3, 5, 10, 20, 500, 100, 200, or 500+) of each NCEM-enabled fill cell variant. Furthermore, such variants are preferably distributed, either regularly or irregularly, throughout the space available for instantiation of fill cells.

Accordingly, generally speaking, and without intending to be limiting, one aspect of the invention relates to ICs that include, for example: a standard cell area that includes a mix of at least one thousand logic cells and fill cells of different widths and uniform heights, placed into at least twenty adjacent rows, with at least twenty cells placed side-by-side in each row; wherein the integrated circuit includes at least a first DOE, the first DOE comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the first DOE is configured to render a first selected manufacturing failure observable as an abnormal pad-to-ground leakage or conductance, detected by voltage contrast (VC) inspection of the pad; and, wherein the similarly-configured, NCEM-enabled fill cells of the first DOE include a plurality of variants, where the variants differ in terms of their respective probability of presenting an abnormal pad-to-ground leakage or resistance as a result of the first selected manufacturing failure. Such ICs may further include: a second DOE, comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the second DOE is configured to render a second selected manufacturing failure observable as an abnormal pad-to-ground leakage or conductance, detected by VC inspection of the pad, and wherein the second selected manufacturing failure is different than the first selected manufacturing failure; and, wherein the similarly-configured, NCEM-enabled fill cells of the second DOE include a plurality of variants, where the variants differ in terms of their respective probability of presenting an abnormal pad-to-ground leakage or conductance as a result of the second selected manufacturing failure. The first selected manufacturing failure may involve short or leakage defects that present as abnormally high pad-to-ground conductance or leakage, and the second selected manufacturing failure may involve open or resistance defects that present as abnormally low pad-to-ground conductance or abnormally high pad-to-ground resistance. Both the first and second selected manufacturing failures may involve layers in a connector stack region of the IC. Such ICs may further include: a third DOE, comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured NCEM-enabled fill cells in the third DOE is configured to render a third selected manufacturing failure observable as an abnormal pad-to-ground leakage, conductance or resistance, detected by VC inspection of the pad, and wherein the third selected manufacturing failure is different than the first selected manufacturing failure, and is different than the second selected manufacturing failure; and, wherein the similarly-configured NCEM-enabled fill cells of the third DOE include a plurality of variants, where the variants differ in terms of their respective probability of presenting an abnormal pad-to-ground leakage, conductance or resistance as a result of the third selected manufacturing failure. Each of the first, second, and third DOEs preferably include NCEM-enabled fill cells in at least three, five, seven, or ten variants. The NCEM-enabled fill cells of the first, second, and third DOEs are preferably irregularly distributed within the standard cell area of the IC. Each variant may differ from the other(s) only in the position, size, or shape of its first or second mask-patterned feature, or only by a single dimensional parameter that characterizes their respective test areas.

Again, generally speaking, and without intending to be limiting, another aspect of the invention relates to ICs that include, for example: a standard cell area that includes a mix of at least one thousand logic cells and fill cells of different widths and uniform heights, placed into at least twenty adjacent rows, with at least twenty cells placed side-by-side in each row; wherein the IC includes at least a first DOE, the first DOE comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of first and second distinct, mask-patterned features, the test area characterized by two dimensional parameters, the test area configured to provide electrical isolation between the first and second mask-patterned features in the absence of a first selected manufacturing failure; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the first DOE is configured to render a first selected manufacturing failure observable as an abnormally high pad-to-ground conductance or leakage, detected by VC inspection of the pad; and, wherein the similarly-configured, NCEM-enabled fill cells of the first DOE include a plurality of variants, where the variants differ in terms of their respective probability of presenting an abnormally high pad-to-ground conductance or leakage as a result of the first selected manufacturing failure. In each of the NCEM-enabled fill cells of the first DOE, the first and/or second distinct, mask-patterned features may each represent either a control element, or a portion thereof, and/or a portion of a control element connector or a substrate connector, and/or a portion of a control element jumper, substrate jumper, or interconnect jumper. In each of the NCEM-enabled fill cells of the first and/or second DOE(s), the first and second distinct, mask-patterned features may appear in a tip-to-tip configuration, a tip-to-side configuration, a side-to-side configuration, a diagonal configuration, or an interlayer overlap configuration.

Again, generally speaking, and without intending to be limiting, another aspect of the invention relates to ICs that include, for example: a standard cell area that includes a mix of at least one thousand logic cells and fill cells of different widths and uniform heights, placed into at least twenty adjacent rows, with at least twenty cells placed side-by-side in each row; wherein the IC includes at least a first DOE, the first DOE comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in one or more conductive layer(s), the pad being at least two times larger, in at least one dimension, than a minimum size permitted by design rules; a rectangular test area defined by selected boundaries of a plurality of mask-patterned features, the test area characterized by two dimensional parameters, the plurality of mask-patterned features including at least first and second features that are electrically connected in the absence of a first manufacturing failure; a first conductive pathway that electrically connects the first mask-patterned feature to the pad; and, a second conductive pathway that electrically connects the second mask-patterned feature to a permanently or virtually grounded structure; wherein each of the similarly-configured NCEM-enabled fill cells in the first DOE is configured to render a first selected manufacturing failure observable as an abnormally high pad-to-ground conductance or leakage, detected by VC inspection of the pad; wherein the similarly-configured NCEM-enabled fill cells of the first DOE include a plurality of variants, where the variants differ in terms of their respective probability of presenting an abnormally high pad-to-ground conductance or leakage as a result of the first selected manufacturing failure; and, wherein the similarly-configured NCEM-enabled fill cells of the first DOE are selected from the list consisting of: source/drain (AA)-tip-to-tip-short-configured, NCEM-enabled fill cells; source/drain contact (AACNT)-tip-to-tip-short-configured, NCEM-enabled fill cells; AACNT-AA-tip-to-tip-short-configured, NCEM-enabled fill cells; source/drain silicide (TS)-tip-to-tip-short-configured, NCEM-enabled fill cells; gate (GATE)-tip-to-tip-short-configured, NCEM-enabled fill cells; gate contact (GATECNT)-GATE-tip-to-tip-short-configured, NCEM-enabled fill cells; GATECNT-tip-to-tip-short-configured, NCEM-enabled fill cells; GATECNT-AACNT-tip-to-tip-short-configured, NCEM-enabled fill cells; first wiring layer (M1)-tip-to-tip-short-configured, NCEM-enabled fill cells; via to interconnect stack (V0)-tip-to-tip-short-configured, NCEM-enabled fill cells; M1-V0-tip-to-tip-short-configured, NCEM-enabled fill cells; V1-M1-tip-to-tip-short-configured, NCEM-enabled fill cells; first interconnect via layer (V1)-tip-to-tip-short-configured, NCEM-enabled fill cells; second wiring layer (M2)-tip-to-tip-short-configured, NCEM-enabled fill cells; M2-V1-tip-to-tip-short-configured, NCEM-enabled fill cells; second interconnect via layer (V2)-M2-tip-to-tip-short-configured, NCEM-enabled fill cells; third wiring layer (M3)-tip-to-tip-short-configured, NCEM-enabled fill cells; V2-tip-to-tip-short-configured, NCEM-enabled fill cells; M3-V2-tip-to-tip-short-configured, NCEM-enabled fill cells; AA-tip-to-side-short-configured, NCEM-enabled fill cells; AACNT-tip-to-side-short-configured, NCEM-enabled fill cells; AACNT-AA-tip-to-side-short-configured, NCEM-enabled fill cells; GATE-AA-tip-to-side-short-configured, NCEM-enabled fill cells; GATECNT-GATE-tip-to-side-short-configured, NCEM-enabled fill cells; GATECNT-tip-to-side-short-configured, NCEM-enabled fill cells; TS-GATECNT-tip-to-side-short-configured, NCEM-enabled fill cells; GATECNT-AACNT-tip-to-side-short-configured, NCEM-enabled fill cells; M1-tip-to-side-short-configured, NCEM-enabled fill cells; V0-tip-to-side-short-configured, NCEM-enabled fill cells; M1-V0-tip-to-side-short-configured, NCEM-enabled fill cells; V1-M1-tip-to-side-short-configured, NCEM-enabled fill cells; V1-tip-to-side-short-configured, NCEM-enabled fill cells; M2-tip-to-side-short-configured, NCEM-enabled fill cells; M2-V1-tip-to-side-short-configured, NCEM-enabled fill cells; V2-M2-tip-to-side-short-configured, NCEM-enabled fill cells; M3-tip-to-side-short-configured, NCEM-enabled fill cells; V2-tip-to-side-short-configured, NCEM-enabled fill cells; M3-V2-tip-to-side-short-configured, NCEM-enabled fill cells; AA-side-to-side-short-configured, NCEM-enabled fill cells; AACNT-side-to-side-short-configured, NCEM-enabled fill cells; AACNT-AA-side-to-side-short-configured, NCEM-enabled fill cells; AACNT-GATE-side-to-side-short-configured, NCEM-enabled fill cells; GATE-side-to-side-short-configured, NCEM-enabled fill cells; GATECNT-GATE-side-to-side-short-configured, NCEM-enabled fill cells; TS-GATE-side-to-side-short-configured, NCEM-enabled fill cells; GATECNT-side-to-side-short-configured, NCEM-enabled fill cells; GATECNT-AACNT-side-to-side-short-configured, NCEM-enabled fill cells; M1-side-to-side-short-configured, NCEM-enabled fill cells; V0-side-to-side-short-configured, NCEM-enabled fill cells; M1-V0-side-to-side-short-configured, NCEM-enabled fill cells; V1-M1-side-to-side-short-configured, NCEM-enabled fill cells; V1-side-to-side-short-configured, NCEM-enabled fill cells; M2-side-to-side-short-configured, NCEM-enabled fill cells; M2-V1-side-to-side-short-configured, NCEM-enabled fill cells; V2-M2-side-to-side-short-configured, NCEM-enabled fill cells; M3-side-to-side-short-configured, NCEM-enabled fill cells; V2-side-to-side-short-configured, NCEM-enabled fill cells; M3-V2-side-to-side-short-configured, NCEM-enabled fill cells; AA-L-shape-interlayer-short-configured, NCEM-enabled fill cells; AACNT-L-shape-interlayer-short-configured, NCEM-enabled fill cells; AACNT-AA-L-shape-interlayer-short-configured, NCEM-enabled fill cells; GATE-AA-L-shape-interlayer-short-configured, NCEM-enabled fill cells; GATE-TS-L-shape-interlayer-short-configured, NCEM-enabled fill cells; GATECNT-GATE-L-shape-interlayer-short-configured, NCEM-enabled fill cells; GATECNT-AA-L-shape-interlayer-short-configured, NCEM-enabled fill cells; GATECNT-TS-L-shape-interlayer-short-configured, NCEM-enabled fill cells; GATECNT-AACNT-L-shape-interlayer-short-configured, NCEM-enabled fill cells; V0-AA-L-shape-interlayer-short-configured, NCEM-enabled fill cells; V0-TS-L-shape-interlayer-short-configured, NCEM-enabled fill cells; V0-AACNT-L-shape-interlayer-short-configured, NCEM-enabled fill cells; V0-GATE-L-shape-interlayer-short-configured, NCEM-enabled fill cells; V0-GATECNT-L-shape-interlayer-short-configured, NCEM-enabled fill cells; M1-AACNT-L-shape-interlayer-short-configured, NCEM-enabled fill cells; M1-GATECNT-L-shape-interlayer-short-configured, NCEM-enabled fill cells; M1-V0-L-shape-interlayer-short-configured, NCEM-enabled fill cells; V1-M1-L-shape-interlayer-short-configured, NCEM-enabled fill cells; V1-V0-L-shape-interlayer-short-configured, NCEM-enabled fill cells; M2-M1-L-shape-interlayer-short-configured, NCEM-enabled fill cells; M2-V1-L-shape-interlayer-short-configured, NCEM-enabled fill cells; V2-V1-L-shape-interlayer-short-configured, NCEM-enabled fill cells; V2-M2-L-shape-interlayer-short-configured, NCEM-enabled fill cells; M3-M2-L-shape-interlayer-short-configured, NCEM-enabled fill cells; M3-V2-L-shape-interlayer-short-configured, NCEM-enabled fill cells; AA-diagonal-short-configured, NCEM-enabled fill cells; TS-diagonal-short-configured, NCEM-enabled fill cells; AACNT-diagonal-short-configured, NCEM-enabled fill cells; AACNT-AA-diagonal-short-configured, NCEM-enabled fill cells; GATE-diagonal-short-configured, NCEM-enabled fill cells; GATE-AACNT-diagonal-short-configured, NCEM-enabled fill cells; GATECNT-GATE-diagonal-short-configured, NCEM-enabled fill cells; GATECNT-diagonal-short-configured, NCEM-enabled fill cells; GATECNT-AACNT-diagonal-short-configured, NCEM-enabled fill cells; M1-diagonal-short-configured, NCEM-enabled fill cells; V0-diagonal-short-configured, NCEM-enabled fill cells; M1-V0-diagonal-short-configured, NCEM-enabled fill cells; V1-M1-diagonal-short-configured, NCEM-enabled fill cells; V1-diagonal-short-configured, NCEM-enabled fill cells; M2-diagonal-short-configured, NCEM-enabled fill cells; M2-V1-diagonal-short-configured, NCEM-enabled fill cells; M3-diagonal-short-configured, NCEM-enabled fill cells; V2-M2-diagonal-short-configured, NCEM-enabled fill cells; V2-diagonal-short-configured, NCEM-enabled fill cells; M3-V2-diagonal-short-configured, NCEM-enabled fill cells; AA-corner-short-configured, NCEM-enabled fill cells; AACNT-corner-short-configured, NCEM-enabled fill cells; AACNT-AA-corner-short-configured, NCEM-enabled fill cells; GATE-corner-short-configured, NCEM-enabled fill cells; GATECNT-GATE-corner-short-configured, NCEM-enabled fill cells; GATECNT-TS-corner-short-configured, NCEM-enabled fill cells; GATECNT-corner-short-configured, NCEM-enabled fill cells; GATECNT-AACNT-corner-short-configured, NCEM-enabled fill cells; M1-corner-short-configured, NCEM-enabled fill cells;

V0-corner-short-configured, NCEM-enabled fill cells; M1-V0-corner-short-configured, NCEM-enabled fill cells; V1-M1-corner-short-configured, NCEM-enabled fill cells; V1-corner-short-configured, NCEM-enabled fill cells; M2-corner-short-configured, NCEM-enabled fill cells; M2-V1-corner-short-configured, NCEM-enabled fill cells; M3-corner-short-configured, NCEM-enabled fill cells; V2-M2-corner-short-configured, NCEM-enabled fill cells; V2-corner-short-configured, NCEM-enabled fill cells; M3-V2-corner-short-configured, NCEM-enabled fill cells; GATE-AA-interlayer-overlap-short-configured, NCEM-enabled fill cells; GATE-TS-interlayer-overlap-short-configured, NCEM-enabled fill cells; GATE-AACNT-interlayer-overlap-short-configured, NCEM-enabled fill cells; GATECNT-TS-interlayer-overlap-short-configured, NCEM-enabled fill cells; GATECNT-AA-interlayer-overlap-short-configured, NCEM-enabled fill cells; V0-AA-interlayer-overlap-short-configured, NCEM-enabled fill cells; V0-AACNT-interlayer-overlap-short-configured, NCEM-enabled fill cells; V0-TS-interlayer-overlap-short-configured, NCEM-enabled fill cells; V0-GATE-interlayer-overlap-short-configured, NCEM-enabled fill cells; M1-GATECNT-interlayer-overlap-short-configured, NCEM-enabled fill cells; M1-AACNT-interlayer-overlap-short-configured, NCEM-enabled fill cells; V1-V0-interlayer-overlap-short-configured, NCEM-enabled fill cells; M2-M1-interlayer-overlap-short-configured, NCEM-enabled fill cells; V2-V1-interlayer-overlap-short-configured, NCEM-enabled fill cells; M3-M2-interlayer-overlap-short-configured, NCEM-enabled fill cells; V0-GATECNT-via-chamfer-short-configured, NCEM-enabled fill cells; V0-AACNT-via-chamfer-short-configured, NCEM-enabled fill cells; V1-M1-via-chamfer-short-configured, NCEM-enabled fill cells; V2-M2-via-chamfer-short-configured, NCEM-enabled fill cells; V0-merged-via-short-configured, NCEM-enabled fill cells; V1-merged-via-short-configured, NCEM-enabled fill cells; and, V2-merged-via-short-configured, NCEM-enabled fill cells; a second DOE, comprising a plurality of similarly-configured, NCEM-enabled fill cells, wherein each NCEM-enabled fill cell comprises at least: first and second elongated conductive supply rails, formed in a connector or interconnect stack, extending across the entire width of the cell, and configured for compatibility with corresponding supply rails contained in the logic cells of the standard cell region; a NCEM pad, formed in a conductive layer, the pad being at least two times larger, in at least one dimension, than a minimum size permitted by design rules; a rectangular test area defined by selected boundaries of at least first and second distinct, mask-patterned features, the test area being characterized by two dimensional parameters; a first conductive pathway that electrically connects the first mask-patterned feature to the pad; and, a second conductive pathway that electrically connects the second mask-patterned feature to a permanently or virtually grounded structure; wherein each of the similarly-configured, NCEM-enabled fill cells in the second DOE is configured to render a second selected manufacturing failure observable as an abnormally low pad-to-ground conductance or abnormally high pad-to-ground resistance, detected by VC inspection of the pad; and, wherein the similarly-configured, NCEM-enabled fill cells of the second DOE include a plurality of variants, where the variants differ in terms of their respective probability of presenting an abnormally low pad-to-ground conductance or abnormally high pad-to-ground resistance as a result of the second selected manufacturing failure; and, wherein the similarly-configured NCEM-enabled fill cells of the second DOE are selected from the list consisting of: AA-snake-open-configured, NCEM-enabled fill cells; TS-snake-open-configured, NCEM-enabled fill cells; AACNT-snake-open-configured, NCEM-enabled fill cells; GATE-snake-open-configured, NCEM-enabled fill cells; GATECNT-snake-open-configured, NCEM-enabled fill cells; V0-snake-open-configured, NCEM-enabled fill cells; M1-snake-open-configured, NCEM-enabled fill cells; V1-snake-open-configured, NCEM-enabled fill cells; M2-snake-open-configured, NCEM-enabled fill cells; V2-snake-open-configured, NCEM-enabled fill cells; M3-snake-open-configured, NCEM-enabled fill cells; AA-stitch-open-configured, NCEM-enabled fill cells; TS-stitch-open-configured, NCEM-enabled fill cells; AACNT-stitch-open-configured, NCEM-enabled fill cells; GATECNT-stitch-open-configured, NCEM-enabled fill cells; V0-stitch-open-configured, NCEM-enabled fill cells; M1-stitch-open-configured, NCEM-enabled fill cells; V1-stitch-open-configured, NCEM-enabled fill cells; M2-stitch-open-configured, NCEM-enabled fill cells; V2-stitch-open-configured, NCEM-enabled fill cells; M3-stitch-open-configured, NCEM-enabled fill cells; AACNT-TS-via-open-configured, NCEM-enabled fill cells; AACNT-AA-via-open-configured, NCEM-enabled fill cells; TS-AA-via-open-configured, NCEM-enabled fill cells; GATECNT-GATE-via-open, NCEM-enabled fill cells; V0-GATECNT-via-open-configured, NCEM-enabled fill cells; V0-AA-via-open-configured, NCEM-enabled fill cells; V0-TS-via-open-configured, NCEM-enabled fill cells; V0-AACNT-via-open-configured, NCEM-enabled fill cells; V0-GATE-via-open-configured, NCEM-enabled fill cells; V0-via-open-configured, NCEM-enabled fill cells; M1-V0-via-open-configured, NCEM-enabled fill cells; V1-M1-via-open-configured, NCEM-enabled fill cells; V1-M2-via-open-configured, NCEM-enabled fill cells; M1-GATECNT-via-open-configured, NCEM-enabled fill cells; M1-AANCT-via-open-configured, NCEM-enabled fill cells; V2-M2-via-open-configured, NCEM-enabled fill cells; V2-M3-via-open-configured, NCEM-enabled fill cells; M1-metal-island-open-configured, NCEM-enabled fill cells; M2-metal-island-open-configured, NCEM-enabled fill cells; M3-metal-island-open-configured, NCEM-enabled fill cells; V0-merged-via-open-configured, NCEM-enabled fill cells; V0-AACNT-merged-via-open-configured, NCEM-enabled fill cells; V0-GATECNT-merged-via-open-configured, NCEM-enabled fill cells; V1-merged-via-open-configured, NCEM-enabled fill cells; V2-merged-via-open-configured, NCEM-enabled fill cells; V1-M1-merged-via-open-configured, NCEM-enabled fill cells; V2-M2-merged-via-open-configured, NCEM-enabled fill cells.

Again, generally speaking, and without intending to be limiting, another aspect of the invention relates methods for making ICs that include, for example: (a) performing initial processing steps on a semiconductor wafer, the initial processing steps including: patterning a standard cell area that includes a mix of at least one thousand logic cells and fill cells of different widths and uniform heights, placed into at least twenty adjacent rows, with at least twenty cells placed side-by-side in each row; and, patterning a first DOE by instantiating a plurality of similarly-configured, NCEM-enabled fill cells in at least two variants, the NCEM-enabled fill cells configured for compatibility with logic cells in the standard cell area, each of the cells in the first DOE configured to enable evaluation of a first manufacturing failure by voltage contrast examination of a NCEM of a pad contained in the cell, the variants exhibiting different NCEM sensitivity to the first manufacturing failure; (b) determining a presence or absence of the first manufacturing failure by: performing a voltage contrast examination of NCEM-enabled fill cells in the first DOE; and, determining whether NCEMs of pads contained in the NCEM-enabled fill cells of the first DOE represent instance(s) of the first manufacturing failure and, if so, determining whether different cell variants exhibit a different prevalence of the first manufacturing failure; and, (c) based, at least in part, on results from step (b), selectively performing additional processing, metrology or inspection steps on the wafer, and/or on other wafer(s) currently being manufactured using a process flow(s) relevant to the observed first manufacturing failure. Step (a) may further involve: patterning a second DOE by instantiating a plurality of similarly-configured NCEM-enabled fill cells in at least two variants, the NCEM-enabled fill cells configured for compatibility with logic cells in the standard cell area and fill cells in the first DOE, each of the cells in the second DOE configured to enable evaluation of a second manufacturing failure, different from the first manufacturing failure, by voltage contrast examination of a NCEM of a pad contained in the cell, the variants exhibiting different NCEM sensitivity to the second manufacturing failure; and wherein step (b) further comprises: performing a voltage contrast examination of NCEM-enabled fill cells in the second DOE; and, determining whether NCEMs of pads contained in the NCEM-enabled fill cells of the second DOE represent instance(s) of the second manufacturing failure and, if so, determining whether different cell variants exhibit a different prevalence of the second manufacturing failure. Step (a) may further involve: patterning a third DOE by instantiating a plurality of similarly-configured NCEM-enabled fill cells in at least two variants, the NCEM-enabled fill cells configured for compatibility with logic cells in the standard cell area and fill cells in the first and second DOEs, each of the cells in the third DOE configured to enable evaluation of a third manufacturing failure, different from the first and second manufacturing failures, by voltage contrast examination of a NCEM of a pad contained in the cell, the variants exhibiting different NCEM sensitivity to the third manufacturing failure; and wherein step (b) further comprises: performing a voltage contrast examination of NCEM-enabled fill cells in the third DOE; and, determining whether NCEMs of pads contained in the NCEM-enabled fill cells of the third DOE represent instance(s) of the third manufacturing failure and, if so, determining whether different cell variants exhibit a different prevalence of the third manufacturing failure. At least one of the first, second, or third manufacturing failures preferably involves unintended shorts or leakages, and at least one of the first, second, or third manufacturing failures preferably involves unintended opens or excessive resistances. Instantiating the NCEM-enabled fill cells preferably comprises distributing the cells irregularly within the standard cell area. Within each of the DOEs, each variant may differ from the other(s) only in the position, size, or shape of a single mask-patterned feature. At least one of the first, second, or third manufacturing failures may involve unintended shorts between structures in a tip-to-tip configuration, or unintended shorts between structures in a tip-to-side configuration, or unintended shorts between structures in a side-to-side configuration, or unintended shorts between structures in a diagonal configuration, or unintended shorts between structures in an interlayer overlap configuration, or unintended interlayer shorts or leakages between structures in a corner configuration, unintended opens in snake-shaped structures, unintended opens in stitched structures, unintended opens in via-connected structures. Each of the first, second, and third DOEs preferably includes NCEM-enabled fill cells in at least three, five, seven, 11, 21, or more variants.

Each of the first, second, and third DOEs may consist of cells selected from the list of: AA-tip-to-tip-short-configured, NCEM-enabled fill cells; AACNT-tip-to-tip-short-configured, NCEM-enabled fill cells; AACNT-AA-tip-to-tip-short-configured, NCEM-enabled fill cells; TS-tip-to-tip-short-configured, NCEM-enabled fill cells; GATE-tip-to-tip-short-configured, NCEM-enabled fill cells; GATECNT-GATE-tip-to-tip-short-configured, NCEM-enabled fill cells; GATECNT-tip-to-tip-short-configured, NCEM-enabled fill cells; GATECNT-AACNT-tip-to-tip-short-configured, NCEM-enabled fill cells; M1-tip-to-tip-short-configured, NCEM-enabled fill cells; V0-tip-to-tip-short-configured, NCEM-enabled fill cells; M1-V0-tip-to-tip-short-configured, NCEM-enabled fill cells; V1-M1-tip-to-tip-short-configured, NCEM-enabled fill cells; V1-tip-to-tip-short-configured, NCEM-enabled fill cells; M2-tip-to-tip-short-configured, NCEM-enabled fill cells; M2-V1-tip-to-tip-short-configured, NCEM-enabled fill cells; V2-M2-tip-to-tip-short-configured, NCEM-enabled fill cells; M3-tip-to-tip-short-configured, NCEM-enabled fill cells; V2-tip-to-tip-short-configured, NCEM-enabled fill cells; M3-V2-tip-to-tip-short-configured, NCEM-enabled fill cells; AA-tip-to-side-short-configured, NCEM-enabled fill cells; AACNT-tip-to-side-short-configured, NCEM-enabled fill cells; AACNT-AA-tip-to-side-short-configured, NCEM-enabled fill cells; GATE-AA-tip-to-side-short-configured, NCEM-enabled fill cells; GATECNT-GATE-tip-to-side-short-configured, NCEM-enabled fill cells; GATECNT-tip-to-side-short-configured, NCEM-enabled fill cells; TS-GATECNT-tip-to-side-short-configured, NCEM-enabled fill cells; GATECNT-AACNT-tip-to-side-short-configured, NCEM-enabled fill cells; M1-tip-to-side-short-configured, NCEM-enabled fill cells; V0-tip-to-side-short-configured, NCEM-enabled fill cells; M1-V0-tip-to-side-short-configured, NCEM-enabled fill cells; V1-M1-tip-to-side-short-configured, NCEM-enabled fill cells; V1-tip-to-side-short-configured, NCEM-enabled fill cells; M2-tip-to-side-short-configured, NCEM-enabled fill cells; M2-V1-tip-to-side-short-configured, NCEM-enabled fill cells; V2-M2-tip-to-side-short-configured, NCEM-enabled fill cells; M3-tip-to-side-short-configured, NCEM-enabled fill cells; V2-tip-to-side-short-configured, NCEM-enabled fill cells; M3-V2-tip-to-side-short-configured, NCEM-enabled fill cells; AA-side-to-side-short-configured, NCEM-enabled fill cells; AACNT-side-to-side-short-configured, NCEM-enabled fill cells; AACNT-AA-side-to-side-short-configured, NCEM-enabled fill cells; AACNT-GATE-side-to-side-short-configured, NCEM-enabled fill cells; GATE-side-to-side-short-configured, NCEM-enabled fill cells; GATECNT-GATE-side-to-side-short-configured, NCEM-enabled fill cells; TS-GATE-side-to-side-short-configured, NCEM-enabled fill cells; GATECNT-side-to-side-short-configured, NCEM-enabled fill cells; GATECNT-AACNT-side-to-side-short-configured, NCEM-enabled fill cells; M1-side-to-side-short-configured, NCEM-enabled fill cells; V0-side-to-side-short-configured, NCEM-enabled fill cells; M1-V0-side-to-side-short-configured, NCEM-enabled fill cells; V1-M1-side-to-side-short-configured, NCEM-enabled fill cells; V1-side-to-side-short-configured, NCEM-enabled fill cells; M2-side-to-side-short-configured, NCEM-enabled fill cells; M2-V1-side-to-side-short-configured, NCEM-enabled fill cells; V2-M2-side-to-side-short-configured, NCEM-enabled fill cells; M3-side-to-side-short-configured, NCEM-enabled fill cells; V2-side-to-side-short-configured, NCEM-enabled fill cells; M3-V2-side-to-side-short-configured, NCEM-enabled fill cells; AA-L-shape-interlayer-short-configured, NCEM-enabled fill cells; AACNT-L-shape-interlayer-short-configured, NCEM-enabled fill cells; AACNT-AA-L-shape-interlayer-short-configured, NCEM-enabled fill cells; GATE-AA-L-shape-interlayer-short-configured, NCEM-enabled fill cells; GATE-TS-L-shape-interlayer-short-configured, NCEM-enabled fill cells; GATECNT-GATE-L-shape-interlayer-short-configured, NCEM-enabled fill cells; GATECNT-AA-L-shape-interlayer-short-configured, NCEM-enabled fill cells; GATECNT-TS-L-shape-interlayer-short-configured, NCEM-enabled fill cells; GATECNT-AACNT-L-shape-interlayer-short-configured, NCEM-enabled fill cells; V0-AA-L-shape-interlayer-short-configured, NCEM-enabled fill cells; V0-TS-L-shape-interlayer-short-configured, NCEM-enabled fill cells; V0-AACNT-L-shape-interlayer-short-configured, NCEM-enabled fill cells; V0-GATE-L-shape-interlayer-short-configured, NCEM-enabled fill cells; V0-GATECNT-L-shape-interlayer-short-configured, NCEM-enabled fill cells; M1-AACNT-L-shape-interlayer-short-configured, NCEM-enabled fill cells; M1-GATECNT-L-shape-interlayer-short-configured, NCEM-enabled fill cells; M1-V0-L-shape-interlayer-short-configured, NCEM-enabled fill cells; V1-M1-L-shape-interlayer-short-configured, NCEM-enabled fill cells; V1-V0-L-shape-interlayer-short-configured, NCEM-enabled fill cells; M2-M1-L-shape-interlayer-short-configured, NCEM-enabled fill cells; M2-V1-L-shape-interlayer-short-configured, NCEM-enabled fill cells; V2-V1-L-shape-interlayer-short-configured, NCEM-enabled fill cells; V2-M2-L-shape-interlayer-short-configured, NCEM-enabled fill cells; M3-M2-L-shape-interlayer-short-configured, NCEM-enabled fill cells; M3-V2-L-shape-interlayer-short-configured, NCEM-enabled fill cells; AA-diagonal-short-configured, NCEM-enabled fill cells; TS-diagonal-short-configured, NCEM-enabled fill cells; AACNT-diagonal-short-configured, NCEM-enabled fill cells; AACNT-AA-diagonal-short-configured, NCEM-enabled fill cells; GATE-diagonal-short-configured, NCEM-enabled fill cells; GATE-AACNT-diagonal-short-configured, NCEM-enabled fill cells; GATECNT-GATE-diagonal-short-configured, NCEM-enabled fill cells; GATECNT-diagonal-short-configured, NCEM-enabled fill cells; GATECNT-AACNT-diagonal-short-configured, NCEM-enabled fill cells; M1-diagonal-short-configured, NCEM-enabled fill cells; V0-diagonal-short-configured, NCEM-enabled fill cells; M1-V0-diagonal-short-configured, NCEM-enabled fill cells; V1-M1-diagonal-short-configured, NCEM-enabled fill cells; V1-diagonal-short-configured, NCEM-enabled fill cells; M2-diagonal-short-configured, NCEM-enabled fill cells; M2-V1-diagonal-short-configured, NCEM-enabled fill cells; M3-diagonal-short-configured, NCEM-enabled fill cells; V2-M2-diagonal-short-configured, NCEM-enabled fill cells; V2-diagonal-short-configured, NCEM-enabled fill cells; M3-V2-diagonal-short-configured, NCEM-enabled fill cells; AA-corner-short-configured, NCEM-enabled fill cells; AACNT-corner-short-configured, NCEM-enabled fill cells; AACNT-AA-corner-short-configured, NCEM-enabled fill cells; GATE-corner-short-configured, NCEM-enabled fill cells; GATECNT-GATE-corner-short-configured, NCEM-enabled fill cells; GATECNT-TS-corner-short-configured, NCEM-enabled fill cells; GATECNT-corner-short-configured, NCEM-enabled fill cells; GATECNT-AACNT-corner-short-configured, NCEM-enabled fill cells; M1-corner-short-configured, NCEM-enabled fill cells; V0-corner-short-configured, NCEM-enabled fill cells; M1-V0-corner-short-configured, NCEM-enabled fill cells; V1-M1-corner-short-configured, NCEM-enabled fill cells; V1-corner-short-configured, NCEM-enabled fill cells; M2-corner-short-configured, NCEM-enabled fill cells; M2-V1-corner-short-configured, NCEM-enabled fill cells; M3-corner-short-configured, NCEM-enabled fill cells; V2-M2-corner-short-configured, NCEM-enabled fill cells; V2-corner-short-configured, NCEM-enabled fill cells; M3-V2-corner-short-configured, NCEM-enabled fill cells; GATE-AA-interlayer-overlap-short-configured, NCEM-enabled fill cells; GATE-AACNT-interlayer-overlap-short-configured, NCEM-enabled fill cells; GATE-TS-interlayer-overlap-short-configured, NCEM-enabled fill cells; GATECNT-TS-interlayer-overlap-short-configured, NCEM-enabled fill cells; GATECNT-AA-interlayer-overlap-short-configured, NCEM-enabled fill cells; V0-AA-interlayer-overlap-short-configured, NCEM-enabled fill cells; V0-AACNT-interlayer-overlap-short-configured, NCEM-enabled fill cells; V0-TS-interlayer-overlap-short-configured, NCEM-enabled fill cells; V0-GATE-interlayer-overlap-short-configured, NCEM-enabled fill cells; M1-GATECNT-interlayer-overlap-short-configured, NCEM-enabled fill cells; M1-AACNT-interlayer-overlap-short-configured, NCEM-enabled fill cells; V1-V0-interlayer-overlap-short-configured, NCEM-enabled fill cells; M2-M1-interlayer-overlap-short-configured, NCEM-enabled fill cells; V2-V1-interlayer-overlap-short-configured, NCEM-enabled fill cells; M3-M2-interlayer-overlap-short-configured, NCEM-enabled fill cells; V0-GATECNT-via-chamfer-short-configured, NCEM-enabled fill cells; V0-AACNT-via-chamfer-short-configured, NCEM-enabled fill cells; V1-M1-via-chamfer-short-configured, NCEM-enabled fill cells; V2-M2-via-chamfer-short-configured, NCEM-enabled fill cells; V0-merged-via-short-configured, NCEM-enabled fill cells; V1-merged-via-short-configured, NCEM-enabled fill cells; V2-merged-via-short-configured, NCEM-enabled fill cells; AA-snake-open-configured, NCEM-enabled fill cells; TS-snake-open-configured, NCEM-enabled fill cells; AACNT-snake-open-configured, NCEM-enabled fill cells; GATE-snake-open-configured, NCEM-enabled fill cells; GATECNT-snake-open-configured, NCEM-enabled fill cells; V0-snake-open-configured, NCEM-enabled fill cells; M1-snake-open-configured, NCEM-enabled fill cells; V1-snake-open-configured, NCEM-enabled fill cells; M2-snake-open-configured, NCEM-enabled fill cells; V2-snake-open-configured, NCEM-enabled fill cells; M3-snake-open-configured, NCEM-enabled fill cells; AA-stitch-open-configured, NCEM-enabled fill cells; TS-stitch-open-configured, NCEM-enabled fill cells; AACNT-stitch-open-configured, NCEM-enabled fill cells; GATECNT-stitch-open-configured, NCEM-enabled fill cells; V0-stitch-open-configured, NCEM-enabled fill cells; M1-stitch-open-configured, NCEM-enabled fill cells; V1-stitch-open-configured, NCEM-enabled fill cells; M2-stitch-open-configured, NCEM-enabled fill cells; V2-stitch-open-configured, NCEM-enabled fill cells; M3-stitch-open-configured, NCEM-enabled fill cells; AACNT-TS-via-open-configured, NCEM-enabled fill cells; AACNT-AA-via-open-configured, NCEM-enabled fill cells; TS-AA-via-open-configured, NCEM-enabled fill cells; GATECNT-GATE-via-open, NCEM-enabled fill cells; V0-GATECNT-via-open-configured, NCEM-enabled fill cells; V0-AA-via-open-configured, NCEM-enabled fill cells; V0-TS-via-open-configured, NCEM-enabled fill cells; V0-AACNT-via-open-configured, NCEM-enabled fill cells; V0-GATE-via-open-configured, NCEM-enabled fill cells; V0-via-open-configured, NCEM-enabled fill cells; M1-V0-via-open-configured, NCEM-enabled fill cells; V1-M1-via-open-configured, NCEM-enabled fill cells; V1-M2-via-open-configured, NCEM-enabled fill cells; M1-GATECNT-viaopen-configured, NCEM-enabled fill cells; M1-AANCT-via-open-configured, NCEM-enabled fill cells; V2-M2-via-open-configured, NCEM-enabled fill cells; V2-M3-via-open-configured, NCEM-enabled fill cells; M1-metal-island-open-configured, NCEM-enabled fill cells; M2-metal-island-open-configured, NCEM-enabled fill cells; M3-metal-island-open-configured, NCEM-enabled fill cells; V0-merged-via-open-configured, NCEM-enabled fill cells; V0-AACNT-merged-via-open-configured, NCEM-enabled fill cells; V0-GATECNT-merged-via-open-configured, NCEM-enabled fill cells; V1-merged-via-open-configured, NCEM-enabled fill cells; V2-merged-via-open-configured, NCEM-enabled fill cells; V1-M1-merged-via-open-configured, NCEM-enabled fill cells; V2-M2-merged-via-open-configured, NCEM-enabled fill cells.

Again, generally speaking, and without intending to be limiting, another aspect of the invention relates to methods for making ICs that include, for example: (a) performing initial processing steps on a first semiconductor wafer, the initial processing steps including, at least: patterning a first DOE by instantiating a plurality of similarly-configured NCEM-enabled fill cells in at least two variants, the NCEM-enabled fill cells configured for compatibility with logic cells in the standard cell library, each of the cells in the first DOE configured to enable evaluation of a first manufacturing failure by voltage contrast examination of a NCEM of a pad contained in the cell, the variants exhibiting different NCEM sensitivity to the first manufacturing failure; patterning a second DOE by instantiating a plurality of similarly-configured NCEM-enabled fill cells in at least two variants, the NCEM-enabled fill cells configured for compatibility with logic cells in the standard cell library and fill cells in the first DOE, each of the cells in the second DOE configured to enable evaluation of a second manufacturing failure, different from the first manufacturing failure, by voltage contrast examination of a NCEM of a pad contained in the cell, the variants exhibiting different NCEM sensitivity to the second manufacturing failure; and, patterning a third DOE by instantiating a plurality of similarly-configured NCEM-enabled fill cells in at least two variants, the NCEM-enabled fill cells configured for compatibility with logic cells in the standard cell library and fill cells in the first and second DOEs, each of the cells in the third DOE configured to enable evaluation of a third manufacturing failure, different from the first and second manufacturing failures, by voltage contrast examination of a NCEM of a pad contained in the cell, the variants exhibiting different NCEM sensitivity to the third manufacturing failure; and, (b) determining a presence or absence of the first, second, and third manufacturing failures by: performing a voltage contrast examination of NCEM-enabled fill cells in the first DOE; determining whether NCEMs of pads contained in the NCEM-enabled fill cells of the first DOE represent instance(s) of the first manufacturing failure and, if so, determining whether different cell variants exhibit a different prevalence of the first manufacturing failure; performing a voltage contrast examination of NCEM-enabled fill cells in the second DOE; determining whether NCEMs of pads contained in the NCEM-enabled fill cells of the second DOE represent instance(s) of the second manufacturing failure and, if so, determining whether different cell variants exhibit a different prevalence of the second manufacturing failure; performing a voltage contrast examination of NCEM-enabled fill cells in the third DOE; and, determining whether NCEMs of pads contained in the NCEM-enabled fill cells of the third DOE represent instance(s) of the third manufacturing failure and, if so, determining whether different cell variants exhibit a different prevalence of the third manufacturing failure; and, (c) based, at least in part, on results from step (b), fabricating product masks that include: a standard cell area that includes a mix of at least one thousand logic cells, from the standard cell library, and fill cells of different widths and uniform heights, placed into at least twenty adjacent rows, with at least twenty cells placed side-by-side in each row; and, a fourth DOE that includes a plurality of similarly-configured NCEM-enabled fill cells in at least two variants, the NCEM-enabled fill cells configured for compatibility with logic cells in the standard cell area, each of the cells in the fourth DOE configured to enable evaluation of the first manufacturing failure by voltage contrast examination of a NCEM of a pad contained in the cell, the variants exhibiting different NCEM sensitivity to the first manufacturing failure; and, the product masks not including any DOEs configured to enable evaluation of the second or third manufacturing failures; and, (d) using the product masks, performing initial processing steps on a product wafer, the initial processing steps including: patterning the standard cell area; and, patterning the fourth DOE; (e) determining a presence or absence of the first manufacturing failure on the product wafer by: performing a voltage contrast examination of NCEM-enabled fill cells in the fourth DOE; and, determining whether NCEMs of pads contained in the NCEM-enabled fill cells of the fourth DOE represent instance(s) of the first manufacturing failure and, if so, determining whether different cell variants exhibit a different prevalence of the first manufacturing failure; and, (f) based, at least in part, on results from step (e), selectively performing additional processing, metrology or inspection steps on the product wafer, and/or on other product wafer(s) currently being manufactured using a process flow(s) relevant to the observed first manufacturing failure.

Again, generally speaking, and without intending to be limiting, another aspect of the invention relates to methods for making ICs that include, for example: (a) performing initial processing steps on an initial product wafer, the initial processing steps including, at least: patterning a standard cell area that includes a mix of at least one thousand logic cells and fill cells of different widths and uniform heights, placed into at least twenty adjacent rows, with at least twenty cells placed side-by-side in each row; and, patterning, within the standard cell area, a first DOE by instantiating a plurality of similarly-configured NCEM-enabled fill cells in at least two variants, the NCEM-enabled fill cells configured for compatibility with logic cells in the standard cell area, each of the cells in the first DOE configured to enable evaluation of a first manufacturing failure by voltage contrast examination of a NCEM of a pad contained in the cell, the variants exhibiting different NCEM sensitivity to the first manufacturing failure; patterning a second DOE by instantiating a plurality of similarly-configured NCEM-enabled fill cells in at least two variants, the NCEM-enabled fill cells configured for compatibility with logic cells in the standard cell area and fill cells in the first DOE, each of the cells in the second DOE configured to enable evaluation of a second manufacturing failure, different from the first manufacturing failure, by voltage contrast examination of a NCEM of a pad contained in the cell, the variants exhibiting different NCEM sensitivity to the second manufacturing failure; and, (b) determining a presence or absence of the first and second manufacturing failures on the initial product wafer by: performing a voltage contrast examination of NCEM-enabled fill cells in the first DOE; determining whether NCEMs of pads contained in the NCEM-enabled fill cells of the first DOE represent instance(s) of the first manufacturing failure and, if so, determining whether different cell variants exhibit a different prevalence of the first manufacturing failure; performing a voltage contrast examination of NCEM-enabled fill cells in the second DOE; and, determining whether NCEMs of pads contained in the NCEM-enabled fill cells of the second DOE represent instance(s) of the second manufacturing failure and, if so, determining whether different cell variants exhibit a different prevalence of the second manufacturing failure; and, (c) based, at least in part, on results from step (b), fabricating final product masks that include: a standard cell area that includes a mix of at least one thousand logic cells and fill cells of different widths and uniform heights, placed into at least twenty adjacent rows, with at least twenty cells placed side-by-side in each row; and, a third DOE that includes a plurality of similarly-configured NCEM-enabled fill cells in at least two variants, the NCEM-enabled fill cells configured for compatibility with logic cells in the standard cell area, each of the cells in the third DOE configured to enable evaluation of the first manufacturing failure by voltage contrast examination of a NCEM of a pad contained in the cell, the variants exhibiting different NCEM sensitivity to the first manufacturing failure; the final product masks not including any DOEs configured to enable evaluation of the second manufacturing failure; and, (d) using the final product masks, performing initial processing steps on a final product wafer, the initial processing steps including: patterning the standard cell area; and, patterning the third DOE; and, (e) determining a presence or absence of the first manufacturing failure on the final product wafer by: performing a voltage contrast examination of NCEM-enabled fill cells in the third DOE; and, determining whether NCEMs of pads contained in the NCEM-enabled fill cells of the third DOE represent instance(s) of the first manufacturing failure and, if so, determining whether different cell variants exhibit a different prevalence of the first manufacturing failure; and, (f) based, at least in part, on results from step (e), selectively performing additional processing, metrology or inspection steps on the final product wafer, and/or on other product wafer(s) currently being manufactured using a process flow(s) relevant to the observed first manufacturing failure.

Still further aspects of the invention relate to wafers, chips, and processes for making them that include/utilize DOEs based on means/steps for enabling NC detection of tip-to-tip shorts, including but not limited to:

means/steps for enabling NC detection of AA tip-to-tip shorts [see FIGS. 10-11, 14-15, 41, 43, and 1298-1326 for corresponding § 112(f) structure/acts];

means/steps for enabling NC detection of AACNT tip-to-tip shorts [see FIGS. 10-11, 14-15, 41, 43, and 1327-1405 for corresponding § 112(f) structure/acts];

means/steps for enabling NC detection of TS tip-to-tip shorts [see FIGS. 10-11, 14-15, 41, and 43 for corresponding § 112(f) structure/acts];

means/steps for enabling NC detection of AACNT-AA tip-to-tip shorts [see FIGS. 10-11, 14-15, 41, and 43 for corresponding § 112(f) structure/acts];

means/steps for enabling NC detection of GATE tip-to-tip shorts [see FIGS. 10-11, 14-15, 41, 43, and 1413-1461 for corresponding § 112(f) structure/acts];

means/steps for enabling NC detection of GATECNT-GATE tip-to-tip shorts [see FIGS. 10-11, 14-15, 41, and 43 for corresponding § 112(f) structure/acts];

means/steps for enabling NC detection of GATECNT tip-to-tip shorts [see FIGS. 10-11, 14-15, 41, 43, and 1462-1548 for corresponding § 112(f) structure/acts];

means/steps for enabling NC detection of GATECNT-AACNT tip-to-tip shorts [see FIGS. 10-11, 14-15, 41, and 43 for corresponding § 112(f) structure/acts];

means/steps for enabling NC detection of M1 tip-to-tip shorts [see FIGS. 10-11, 14-15, 41, 43, and 1549-1556 for corresponding § 112(f) structure/acts];

means/steps for enabling NC detection of V0 tip-to-tip shorts [see FIGS. 10-11, 14-15, 41, and 43 for corresponding § 112(f) structure/acts];

means/steps for enabling NC detection of M1-V0 tip-to-tip shorts [see FIGS. 10-11, 14-15, 41, and 43 for corresponding § 112(f) structure/acts];

means/steps for enabling NC detection of V1-M1 tip-to-tip shorts [see FIGS. 10-11, 14-15, 41, and 43 for corresponding § 112(f) structure/acts];

means/steps for enabling NC detection of V1 tip-to-tip shorts [see FIGS. 10-11, 14-15, 41, and 43 for corresponding § 112(f) structure/acts];

means/steps for enabling NC detection of M2 tip-to-tip shorts [see FIGS. 10-11, 14-15, 41, and 43 for corresponding § 112(f) structure/acts];

means/steps for enabling NC detection of V2-M2 tip-to-tip shorts [see FIGS. 10-11, 14-15, 41, and 43 for corresponding § 112(f) structure/acts];

means/steps for enabling NC detection of M2-V1 tip-to-tip shorts [see FIGS. 10-11, 14-15, 41, and 43 for corresponding § 112(f) structure/acts];

means/steps for enabling NC detection of M3 tip-to-tip shorts [see FIGS. 10-11, 14-15, 41, and 43 for corresponding § 112(f) structure/acts];

means/steps for enabling NC detection of V2 tip-to-tip shorts [see FIGS. 10-11, 14-15, 41, and 43 for corresponding § 112(f) structure/acts]; and, means/steps for enabling NC detection of M3-V2 tip-to-tip shorts [see FIGS. 10-11, 14-15, 41, and 43 for corresponding § 112(f) structure/acts].

Still further aspects of the invention relate to wafers, chips, and processes for making them that include/utilize DOEs based on means/steps for enabling NC detection of tip-to-side shorts, including but not limited to:

means/steps for enabling NC detection of AA tip-to-side shorts [see FIGS. 10-11, 16, 41, and 43 for corresponding § 112(f) structure/acts];

means/steps for enabling NC detection of AACNT tip-to-side shorts [see FIGS. 10-11, 16, 41, 43, and 45 for corresponding § 112(f) structure/acts];

means/steps for enabling NC detection of AACNT-AA tip-to-side shorts [see FIGS. 10-11, 16, 41, and 43 for corresponding § 112(f) structure/acts];

means/steps for enabling NC detection of GATE-AA tip-to-side shorts [see FIGS. 10-11, 16, 41, 43, 49, 50, and 1084-1119 for corresponding § 112(f) structure/acts];

means/steps for enabling NC detection of TS-GATECNT tip-to-side shorts [see FIGS. 10-11, 16, 41, 43, and 1239-1263 for corresponding § 112(f) structure/acts];

means/steps for enabling NC detection of GATECNT-GATE tip-to-side shorts [see FIGS. 10-11, 16, 41, 43, and 1201-1238 for corresponding § 112(f) structure/acts];

means/steps for enabling NC detection of GATECNT tip-to-side shorts [see FIGS. 10-11, 16, 41, 43, and 1120-1149 for corresponding § 112(f) structure/acts];

means/steps for enabling NC detection of GATECNT-AACNT tip-to-side shorts [see FIGS. 10-11, 16, 41, 43, 1150-1188 for corresponding § 112(f) structure/acts];

means/steps for enabling NC detection of M1 tip-to-side shorts [see FIGS. 10-11, 16, 41, 43, and 1264-1297 for corresponding § 112(f) structure/acts];

means/steps for enabling NC detection of V0 tip-to-side shorts [see FIGS. 10-11, 16, 41, and 43 for corresponding § 112(f) structure/acts];

means/steps for enabling NC detection of M1-V0 tip-to-side shorts [see FIGS. 10-11, 16, 41, and 43 for corresponding § 112(f) structure/acts];

means/steps for enabling NC detection of V1-M1 tip-to-side shorts [see FIGS. 10-11, 16, 41, and 43 for corresponding § 112(f) structure/acts];

means/steps for enabling NC detection of V1 tip-to-side shorts [see FIGS. 10-11, 16, 41, and 43 for corresponding § 112(f) structure/acts];

means/steps for enabling NC detection of M2-V1 tip-to-side shorts [see FIGS. 10-11, 16, 41, and 43 for corresponding § 112(f) structure/acts];

means/steps for enabling NC detection of M2 tip-to-side shorts [see FIGS. 10-11, 16, 41, and 43 for corresponding § 112(f) structure/acts];

means/steps for enabling NC detection of V2-M2 tip-to-side shorts [see FIGS. 10-11, 16, 41, and 43 for corresponding § 112(f) structure/acts];

means/steps for enabling NC detection of M3 tip-to-side shorts [see FIGS. 10-11, 16, 41, and 43 for corresponding § 112(f) structure/acts];

means/steps for enabling NC detection of V2 tip-to-side shorts [see FIGS. 10-11, 16, 41, and 43 for corresponding § 112(f) structure/acts]; and, means/steps for enabling NC detection of M3-V2 tip-to-side shorts [see FIGS. 10-11, 16, 41, and 43 for corresponding § 112(f) structure/acts].

Still further aspects of the invention relate to wafers, chips, and processes for making them that include/utilize DOEs based on means/steps for enabling NC detection of side-to-side shorts, including but not limited to:

means/steps for enabling NC detection of AA side-to-side shorts [see FIGS. 10-11, 17, 41, and 43 for corresponding § 112(f) structure/acts];

means/steps for enabling NC detection of AACNT side-to-side shorts [see FIGS. 10-11, 17, 41, 43, and 786-804 for corresponding § 112(f) structure/acts];

means/steps for enabling NC detection of AACNT-AA side-to-side shorts [see FIGS. 10-11, 17, 41, and 43 for corresponding § 112(f) structure/acts];

means/steps for enabling NC detection of GATE side-to-side shorts [see FIGS. 10-11, 17, 41, 43, and 833-859 for corresponding § 112(f) structure/acts];

means/steps for enabling NC detection of GATECNT-GATE side-to-side shorts [see FIGS. 10-11, 17, 41, 43, and 886-903 for corresponding § 112(f) structure/acts];

means/steps for enabling NC detection of GATECNT side-to-side shorts [see FIGS. 10-11, 17, 41, 43, and 860-872 for corresponding § 112(f) structure/acts];

means/steps for enabling NC detection of GATECNT-AACNT side-to-side shorts [see FIGS. 10-11, 17, 41, 43, 47A-C, and 873-885 for corresponding § 112(f) structure/acts];

means/steps for enabling NC detection of M1 side-to-side shorts [see FIGS. 10-11, 17, 41, 43, and 904-928 for corresponding § 112(f) structure/acts];

means/steps for enabling NC detection of V0 side-to-side shorts [see FIGS. 10-11, 17, 41, and 43 for corresponding § 112(f) structure/acts];

means/steps for enabling NC detection of M1-V0 side-to-side shorts [see FIGS. 10-11, 17, 41, 43, and 929-936 for corresponding § 112(f) structure/acts];

means/steps for enabling NC detection of V1-M1 side-to-side shorts [see FIGS. 10-11, 17, 41, and 43 for corresponding § 112(f) structure/acts];

means/steps for enabling NC detection of V1 side-to-side shorts [see FIGS. 10-11, 17, 41, and 43 for corresponding § 112(f) structure/acts];

means/steps for enabling NC detection of M2-V1 side-to-side shorts [see FIGS. 10-11, 17, 41, and 43 for corresponding § 112(f) structure/acts];

means/steps for enabling NC detection of M2 side-to-side shorts [see FIGS. 10-11, 17, 41, and 43 for corresponding § 112(f) structure/acts];

means/steps for enabling NC detection of V2-M2 side-to-side shorts [see FIGS. 10-11, 17, 41, and 43 for corresponding § 112(f) structure/acts];

means/steps for enabling NC detection of M3 side-to-side shorts [see FIGS. 10-11, 17, 41, and 43 for corresponding § 112(f) structure/acts];

means/steps for enabling NC detection of V2 side-to-side shorts [see FIGS. 10-11, 17, 41, and 43 for corresponding § 112(f) structure/acts]; and, means/steps for enabling NC detection of M3-V2 side-to-side shorts [see FIGS. 10-11, 17, 41, and 43 for corresponding § 112(f) structure/acts].

Still further aspects of the invention relate to wafers, chips, and processes for making them that include/utilize DOEs based on means/steps for enabling NC detection of L-shape interlayer shorts, including but not limited to:

means/steps for enabling NC detection of AA L-shape interlayer shorts [see FIGS. 10-11, 18-22, 41, and 43 for corresponding § 112(f) structure/acts];

means/steps for enabling NC detection of AACNT-L-shape interlayer shorts [see FIGS. 10-11, 18-22, 41, and 43 for corresponding § 112(f) structure/acts];

means/steps for enabling NC detection of AACNT-AA-L-shape interlayer shorts [see FIGS. 10-11, 18-22, 41, and 43 for corresponding § 112(f) structure/acts];

means/steps for enabling NC detection of GATE-AA-L-shape interlayer shorts [see FIGS. 10-11, 18-22, 41, and 43 for corresponding § 112(f) structure/acts];

means/steps for enabling NC detection of GATE-TS L-shape interlayer shorts [see FIGS. 10-11, 18-22, 41, and 43 for corresponding § 112(f) structure/acts];

means/steps for enabling NC detection of GATECNT-GATE-L-shape interlayer shorts [see FIGS. 10-11, 18-22, 41, and 43 for corresponding § 112(f) structure/acts];

means/steps for enabling NC detection of GATECNT-AA L-shape interlayer shorts [see FIGS. 10-11, 18-22, 41, and 43 for corresponding § 112(f) structure/acts];

means/steps for enabling NC detection of GATE-TS L-shape interlayer shorts [see FIGS. 10-11, 18-22, 41, and 43 for corresponding § 112(f) structure/acts];

means/steps for enabling NC detection of GATECNT-AACNT-L-shape interlayer shorts [see FIGS. 10-11, 18-22, 41, and 43 for corresponding § 112(f) structure/acts];

means/steps for enabling NC detection of V0-AA L-shape interlayer shorts [see FIGS. 10-11, 18-22, 41, and 43 for corresponding § 112(f) structure/acts];

means/steps for enabling NC detection of V0-TS L-shape interlayer shorts [see FIGS. 10-11, 18-22, 41, and 43 for corresponding § 112(f) structure/acts];

means/steps for enabling NC detection of V0-AACNT L-shape interlayer shorts [see FIGS. 10-11, 18-22, 41, and 43 for corresponding § 112(f) structure/acts];

means/steps for enabling NC detection of V0-GATE L-shape interlayer shorts [see FIGS. 10-11, 18-22, 41, and 43 for corresponding § 112(f) structure/acts];

means/steps for enabling NC detection of V0-GATECNT L-shape interlayer shorts [see FIGS. 10-11, 18-22, 41, and 43 for corresponding § 112(f) structure/acts];

means/steps for enabling NC detection of M1-AACNT L-shape interlayer shorts [see FIGS. 10-11, 18-22, 41, and 43 for corresponding § 112(f) structure/acts];

means/steps for enabling NC detection of M1-GATECNT L-shape interlayer shorts [see FIGS. 10-11, 18-22, 41, and 43 for corresponding § 112(f) structure/acts];

means/steps for enabling NC detection of M1-V0-L-shape interlayer shorts [see FIGS. 10-11, 18-22, 41, and 43 for corresponding § 112(f) structure/acts];

means/steps for enabling NC detection of V1-M1-L-shape interlayer shorts [see FIGS. 10-11, 18-22, 41, and 43 for corresponding § 112(f) structure/acts];

means/steps for enabling NC detection of V1-V0 L-shape interlayer shorts [see FIGS. 10-11, 18-22, 41, and 43 for corresponding § 112(f) structure/acts];

means/steps for enabling NC detection of M2-V1-L-shape interlayer shorts [see FIGS. 10-11, 18-22, 41, and 43 for corresponding § 112(f) structure/acts];

means/steps for enabling NC detection of V2-V1 L-shape interlayer shorts [see FIGS. 10-11, 18-22, 41, and 43 for corresponding § 112(f) structure/acts];

means/steps for enabling NC detection of V2-M2 L-shape interlayer shorts [see FIGS. 10-11, 18-22, 41, and 43 for corresponding § 112(f) structure/acts];

means/steps for enabling NC detection of M3-M2 L-shape interlayer shorts [see FIGS. 10-11, 18-22, 41, and 43 for corresponding § 112(f) structure/acts];

means/steps for enabling NC detection of M3-V2 L-shape interlayer shorts [see FIGS. 10-11, 18-22, 41, and 43 for corresponding § 112(f) structure/acts].

Still further aspects of the invention relate to wafers, chips, and processes for making them that include/utilize DOEs based on means/steps for enabling NC detection of diagonal shorts, including but not limited to:

means/steps for enabling NC detection of AA diagonal shorts [see FIGS. 10-11, 23, 41, and 43 for corresponding § 112(f) structure/acts];

means/steps for enabling NC detection of TS diagonal shorts [see FIGS. 10-11, 23, 41, and 43 for corresponding § 112(f) structure/acts];

means/steps for enabling NC detection of AACNT diagonal shorts [see FIGS. 10-11, 23, 41, and 43 for corresponding § 112(f) structure/acts];

means/steps for enabling NC detection of AACNT-AA diagonal shorts [see FIGS. 10-11, 23, 41, and 43 for corresponding § 112(f) structure/acts];

means/steps for enabling NC detection of GATE diagonal shorts [see FIGS. 10-11, 23, 41, and 43 for corresponding § 112(f) structure/acts];

means/steps for enabling NC detection of GATE-AACNT diagonal shorts [see FIGS. 10-11, 23, 41, and 43 for corresponding § 112(f) structure/acts];

means/steps for enabling NC detection of GATECNT-GATE diagonal shorts [see FIGS. 10-11, 23, 41, and 43 for corresponding § 112(f) structure/acts];

means/steps for enabling NC detection of GATECNT diagonal shorts [see FIGS. 10-11, 23, 41, 43, and 495-554 for corresponding § 112(f) structure/acts];

means/steps for enabling NC detection of GATECNT-AACNT diagonal shorts [see FIGS. 10-11, 23, 41, 43, and 555-632 for corresponding § 112(f) structure/acts];

means/steps for enabling NC detection of M1 diagonal shorts [see FIGS. 10-11, 23, 41, and 43 for corresponding § 112(f) structure/acts];

means/steps for enabling NC detection of V0 diagonal shorts [see FIGS. 10-11, 23, 41, and 43 for corresponding § 112(f) structure/acts];

means/steps for enabling NC detection of M1-V0 diagonal shorts [see FIGS. 10-11, 23, 41, and 43 for corresponding § 112(f) structure/acts];

means/steps for enabling NC detection of V1-M1 diagonal shorts [see FIGS. 10-11, 23, 41, and 43 for corresponding § 112(f) structure/acts];

means/steps for enabling NC detection of V1 diagonal shorts [see FIGS. 10-11, 23, 41, and 43 for corresponding § 112(f) structure/acts];

means/steps for enabling NC detection of M2 diagonal shorts [see FIGS. 10-11, 23, 41, and 43 for corresponding § 112(f) structure/acts];

means/steps for enabling NC detection of M2-V1 diagonal shorts [see FIGS. 10-11, 23, 41, and 43 for corresponding § 112(f) structure/acts];

means/steps for enabling NC detection of M3 diagonal shorts [see FIGS. 10-11, 23, 41, and 43 for corresponding § 112(f) structure/acts];

means/steps for enabling NC detection of V2-M2 diagonal shorts [see FIGS. 10-11, 23, 41, and 43 for corresponding § 112(f) structure/acts];

means/steps for enabling NC detection of V2 diagonal shorts [see FIGS. 10-11, 23, 41, and 43 for corresponding § 112(f) structure/acts]; and, means/steps for enabling NC detection of M3-V2 diagonal shorts [see FIGS. 10-11, 23, 41, and 43 for corresponding § 112(f) structure/acts].

Still further aspects of the invention relate to wafers, chips, and processes for making them that include/utilize DOEs based on means/steps for enabling NC detection of corner shorts, including but not limited to:

means/steps for enabling NC detection of AA corner shorts [see FIGS. 10-11, 24-26, 41, and 43 for corresponding § 112(f) structure/acts];

means/steps for enabling NC detection of AACNT corner shorts [see FIGS. 10-11, 24-26, 41, and 43 for corresponding § 112(f) structure/acts];

means/steps for enabling NC detection of AACNT-AA corner shorts [see FIGS. 10-11, 24-26, 41, and 43 for corresponding § 112(f) structure/acts];

means/steps for enabling NC detection of GATE corner shorts [see FIGS. 10-11, 24-26, 41, and 43 for corresponding § 112(f) structure/acts];

means/steps for enabling NC detection of GATECNT-GATE corner shorts [see FIGS. 10-11, 24-26, 41, and 43 for corresponding § 112(f) structure/acts];

means/steps for enabling NC detection of GATECNT-TS corner shorts [see FIGS. 10-11, 24-26, 41, and 43 for corresponding § 112(f) structure/acts];

means/steps for enabling NC detection of GATECNT corner shorts [see FIGS. 10-11, 24-26, 41, and 43 for corresponding § 112(f) structure/acts];

means/steps for enabling NC detection of GATECNT-AA corner shorts [see FIGS. 10-11, 24-26, 41, 43, and 263-286 for corresponding § 112(f) structure/acts];

means/steps for enabling NC detection of GATECNT-AACNT corner shorts [see FIGS. 10-11, 24-26, 41, and 43 for corresponding § 112(f) structure/acts];

means/steps for enabling NC detection of M1 corner shorts [see FIGS. 10-11, 24-26, 41, 43, and 416-494 for corresponding § 112(f) structure/acts];

means/steps for enabling NC detection of V0 corner shorts [see FIGS. 10-11, 24-26, 41, and 43 for corresponding § 112(f) structure/acts];

means/steps for enabling NC detection of M1-V0 corner shorts [see FIGS. 10-11, 24-26, 41, and 43 for corresponding § 112(f) structure/acts];

means/steps for enabling NC detection of V1-M1 corner shorts [see FIGS. 10-11, 24-26, 41, and 43 for corresponding § 112(f) structure/acts];

means/steps for enabling NC detection of V1 corner shorts [see FIGS. 10-11, 24-26, 41, and 43 for corresponding § 112(f) structure/acts];

means/steps for enabling NC detection of M2 corner shorts [see FIGS. 10-11, 24-26, 41, and 43 for corresponding § 112(f) structure/acts];

means/steps for enabling NC detection of M2-V1 corner shorts [see FIGS. 10-11, 24-26, 41, and 43 for corresponding § 112(f) structure/acts];

means/steps for enabling NC detection of M3 corner shorts [see FIGS. 10-11, 24-26, 41, and 43 for corresponding § 112(f) structure/acts];

means/steps for enabling NC detection of V2-M2 corner shorts [see FIGS. 10-11, 24-26, 41, and 43 for corresponding § 112(f) structure/acts];

means/steps for enabling NC detection of V2 corner shorts [see FIGS. 10-11, 24-26, 41, and 43 for corresponding § 112(f) structure/acts]; and, means/steps for enabling NC detection of M3-V2 corner shorts [see FIGS. 10-11, 24-26, 41, and 43 for corresponding § 112(f) structure/acts].

Still further aspects of the invention relate to wafers, chips, and processes for making them that include/utilize DOEs based on means/steps for enabling NC detection of interlayer-overlap shorts, including but not limited to:

means/steps for enabling NC detection of GATE-AA interlayer overlap shorts [see FIGS. 10-11, 27, 41, 43, and 692-734 for corresponding § 112(f) structure/acts];

means/steps for enabling NC detection of GATE-AACNT interlayer overlap shorts [see FIGS. 10-11, 27, 41, 43, and 633-691 for corresponding § 112(f) structure/acts];

means/steps for enabling NC detection of GATE-TS interlayer overlap shorts [see FIGS. 10-11, 27, 41, and 43 for corresponding § 112(f) structure/acts];

means/steps for enabling NC detection of GATECNT-TS interlayer overlap shorts [see FIGS. 10-11, 27, 41, and 43 for corresponding § 112(f) structure/acts];

means/steps for enabling NC detection of GATECNT-AA interlayer overlap shorts [see FIGS. 10-11, 27, 41, and 43 for corresponding § 112(f) structure/acts];

means/steps for enabling NC detection of V0-AA interlayer overlap shorts [see FIGS. 10-11, 27, 41, and 43 for corresponding § 112(f) structure/acts];

means/steps for enabling NC detection of V0-AACNT interlayer overlap shorts [see FIGS. 10-11, 27, 41, and 43 for corresponding § 112(f) structure/acts];

means/steps for enabling NC detection of V0-TS interlayer overlap shorts [see FIGS. 10-11, 27, 41, and 43 for corresponding § 112(f) structure/acts];

means/steps for enabling NC detection of V0-GATE interlayer overlap shorts [see FIGS. 10-11, 27, 41, and 43 for corresponding § 112(f) structure/acts];

means/steps for enabling NC detection of M1-GATECNT interlayer overlap shorts [see FIGS. 10-11, 27, 41, and 43 for corresponding § 112(f) structure/acts];

means/steps for enabling NC detection of M1-AACNT interlayer overlap shorts [see FIGS. 10-11, 27, 41, and 43 for corresponding § 112(f) structure/acts];

means/steps for enabling NC detection of V1-V0 interlayer overlap shorts [see FIGS. 10-11, 27, 41, and 43 for corresponding § 112(f) structure/acts];

means/steps for enabling NC detection of M2-M1-interlayer-overlap shorts [see FIGS. 10-11, 27, 41, and 43 for corresponding § 112(f) structure/acts];

means/steps for enabling NC detection of V2-V1-interlayer-overlap shorts [see FIGS. 10-11, 27, 41, and 43 for corresponding § 112(f) structure/acts]; and, means/steps for enabling NC detection of M3-M2-interlayer-overlap shorts [see FIGS. 10-11, 27, 41, and 43 for corresponding § 112(f) structure/acts].

Still further aspects of the invention relate to wafers, chips, and processes for making them that include/utilize DOEs based on means/steps for enabling NC detection of via-chamfer shorts, including but not limited to:

means/steps for enabling NC detection of V0-GATECNT via chamfer shorts [see FIGS. 10-11, 28, 41, and 43 for corresponding § 112(f) structure/acts];

means/steps for enabling NC detection of V0-AACNT via chamfer shorts [see FIGS. 10-11, 28, 41, 43, and 52-256 for corresponding § 112(f) structure/acts];

means/steps for enabling NC detection of V1-M1 via chamfer shorts [see FIGS. 10-11, 28, 41, and 43 for corresponding § 112(f) structure/acts];

means/steps for enabling NC detection of V2-M2 via chamfer shorts [see FIGS. 10-11, 28, 41, and 43 for corresponding § 112(f) structure/acts]; and, means/step for enabling NC detection of V3-M3 via chamfer shorts [see FIGS. 10-11, 28, 41, 43, and 257-262 for corresponding § 112(f) structure/acts].

Still further aspects of the invention relate to wafers, chips, and processes for making them that include/utilize DOEs based on means/steps for enabling NC detection of merged-via shorts, including but not limited to:

means/steps for enabling NC detection of V0 merged via shorts [see FIGS. 10-11, 29, 41, and 43 for corresponding § 112(f) structure/acts];

means/steps for enabling NC detection of V1 merged via shorts [see FIGS. 10-11, 29, 41, and 43 for corresponding § 112(f) structure/acts]; and, means/steps for enabling NC detection of V2 merged via shorts [see FIGS. 10-11, 29, 41, and 43 for corresponding § 112(f) structure/acts].

Still further aspects of the invention relate to wafers, chips, and processes for making them that include/utilize DOEs based on means/steps for enabling NC detection of snake opens, including but not limited to:

means/steps for enabling NC detection of AA snake opens [see FIGS. 12-13, 30, 41, and 43 for corresponding § 112(f) structure/acts];

means/steps for enabling NC detection of TS snake opens [see FIGS. 12-13, 30, 41, and 43 for corresponding § 112(f) structure/acts];

means/steps for enabling NC detection of AACNT snake opens [see FIGS. 12-13, 30, 41, and 43 for corresponding § 112(f) structure/acts];

means/steps for enabling NC detection of GATE snake opens [see FIGS. 12-13, 30, 41, 43, and 1041-1048 for corresponding § 112(f) structure/acts];

means/steps for enabling NC detection of GATECNT snake opens [see FIGS. 12-13, 30, 41, and 43 for corresponding § 112(f) structure/acts];

means/steps for enabling NC detection of V0 snake opens [see FIGS. 12-13, 30, 41, and 43 for corresponding § 112(f) structure/acts];

means/steps for enabling NC detection of M1 snake opens [see FIGS. 12-13, 30, 41, 43, 44, and 1049-1066 for corresponding § 112(f) structure/acts];

means/steps for enabling NC detection of M1-V0-AACNT snake opens [see FIGS. 12-13, 30, 41, 43, and 1067-1071 for corresponding § 112(f) structure/acts];

means/steps for enabling NC detection of V1 snake opens [see FIGS. 12-13, 30, 41, and 43 for corresponding § 112(f) structure/acts];

means/steps for enabling NC detection of M2 snake opens [see FIGS. 12-13, 30, 41, and 43 for corresponding § 112(f) structure/acts];

means/steps for enabling NC detection of V2 snake opens [see FIGS. 12-13, 30, 41, and 43 for corresponding § 112(f) structure/acts]; and, means/steps for enabling NC detection of M3 snake opens [see FIGS. 12-13, 30, 41, and 43 for corresponding § 112(f) structure/acts].

Still further aspects of the invention relate to wafers, chips, and processes for making them that include/utilize DOEs based on means/steps for enabling NC detection of stitch opens, including but not limited to:

means/steps for enabling NC detection of AA stitch opens [see FIGS. 12-13, 31-32, 41, and 43 for corresponding § 112(f) structure/acts];

means/steps for enabling NC detection of TS stitch opens [see FIGS. 12-13, 31-32, 41, and 43 for corresponding § 112(f) structure/acts];

means/steps for enabling NC detection of AACNT stitch opens [see FIGS. 12-13, 31-32, 41, and 43 for corresponding § 112(f) structure/acts];

means/steps for enabling NC detection of GATECNT stitch opens [see FIGS. 12-13, 31-32, 41, and 43 for corresponding § 112(f) structure/acts];

means/steps for enabling NC detection of V0 stitch opens [see FIGS. 12-13, 31-32, 41, and 43 for corresponding § 112(f) structure/acts];

means/steps for enabling NC detection of M1 stitch opens [see FIGS. 12-13, 31-32, 41, 43, and 1072-1083 for corresponding § 112(f) structure/acts];

means/steps for enabling NC detection of V1 stitch opens [see FIGS. 12-13, 31-32, 41, and 43 for corresponding § 112(f) structure/acts];

means/steps for enabling NC detection of M2 stitch opens [see FIGS. 12-13, 31-32, 41, and 43 for corresponding § 112(f) structure/acts];

means/steps for enabling NC detection of V2 stitch opens [see FIGS. 12-13, 31-32, 41, and 43 for corresponding § 112(f) structure/acts]; and, means/steps for enabling NC detection of M3 stitch opens [see FIGS. 12-13, 31-32, 41, and 43 for corresponding § 112(f) structure/acts].

Still further aspects of the invention relate to wafers, chips, and processes for making them that include/utilize DOEs based on means/steps for enabling NC detection of via opens, including but not limited to:

means/steps for enabling NC detection of AACNT-TS via opens [see FIGS. 12-13, 33, 41, 43, and 1629-1673 for corresponding § 112(f) structure/acts];

means/steps for enabling NC detection of AACNT-AA via opens [see FIGS. 12-13, 33, 41, 43, and 1557-1628 for corresponding § 112(f) structure/acts];

means/steps for enabling NC detection of TS-AA via opens [see FIGS. 12-13, 33, 41, 43, and 2315-2330 for corresponding § 112(f) structure/acts];

means/steps for enabling NC detection of GATECNT-GATE via opens [see FIGS. 12-13, 33, 41, 43, 48, and 1699-2005 for corresponding § 112(f) structure/acts];

means/steps for enabling NC detection of GATECNT-AACNT via opens [see FIGS. 12-13, 33, 41, 43, and 1674-1682 for corresponding § 112(f) structure/acts];

means/steps for enabling NC detection of GATECNT-AACNT-GATE via opens [see FIGS. 12-13, 33, 41, 43, and 1683-1698 for corresponding § 112(f) structure/acts];

means/steps for enabling NC detection of V0-GATECNT via opens [see FIGS. 12-13, 33, 41, 43, and 2375-2439 for corresponding § 112(f) structure/acts];

means/steps for enabling NC detection of V0-AA via opens [see FIGS. 12-13, 33, 41, and 43 for corresponding § 112(f) structure/acts];

means/steps for enabling NC detection of V0 via opens [see FIGS. 12-13, 33, 41, 43, and 2331-2344 for corresponding § 112(f) structure/acts];

means/steps for enabling NC detection of V0-TS via opens [see FIGS. 12-13, 33, 41, and 43 for corresponding § 112(f) structure/acts];

means/steps for enabling NC detection of V0-AACNT via opens [see FIGS. 12-13, 33, 41, 43, and 2345-2374 for corresponding § 112(f) structure/acts];

means/steps for enabling NC detection of V0-GATE via opens [see FIGS. 12-13, 33, 41, and 43 for corresponding § 112(f) structure/acts];

means/steps for enabling NC detection of V1 via opens [see FIGS. 12-13, 33, 41, 43, and 2440-2441 for corresponding § 112(f) structure/acts];

means/steps for enabling NC detection of M1-V0 via opens [see FIGS. 12-13, 33, 41, 43, and 2006-2220 for corresponding § 112(f) structure/acts];

means/steps for enabling NC detection of V1-M1 via opens [see FIGS. 12-13, 33, 41, 43, and 2442-2459 for corresponding § 112(f) structure/acts];

means/steps for enabling NC detection of V1-M2 via opens [see FIGS. 12-13, 33, 41, 43, and 2221-2256 for corresponding § 112(f) structure/acts];

means/steps for enabling NC detection of M1-GATECNT via opens [see FIGS. 12-13, 33, 41, and 43 for corresponding § 112(f) structure/acts];

means/steps for enabling NC detection of V2-M3 via opens [see FIGS. 12-13, 33, 41, 43, and 2257-2274 for corresponding § 112(f) structure/acts];

means/steps for enabling NC detection of M1-AANCT via opens [see FIGS. 12-13, 33, 41, and 43 for corresponding § 112(f) structure/acts];

means/steps for enabling NC detection of V2-M2 via opens [see FIGS. 12-13, 33, 41, and 43 for corresponding § 112(f) structure/acts];

means/steps for enabling NC detection V3 via opens [see FIGS. 12-13, 33, 41, 43, and 2460-2461 for corresponding § 112(f) structure/acts];

means/steps for enabling NC detection of M4-V3 via opens [see FIGS. 12-13, 33, 41, 43, and 2275-2296 for corresponding § 112(f) structure/acts]; and, means/steps for enabling NC detection of M5-V4 via opens [see FIGS. 12-13, 33, 41, 43, and 2297-2314 for corresponding § 112(f) structure/acts].

Still further aspects of the invention relate to wafers, chips, and processes for making them that include/utilize DOEs based on means/steps for enabling NC detection of metal island opens, including but not limited to:

means/steps for enabling NC detection of M1 metal island opens [see FIGS. 12-13, 34-35, 41, and 43 for corresponding § 112(f) structure/acts];

means/steps for enabling NC detection of M2 metal island opens [see FIGS. 12-13, 34-35, 41, and 43 for corresponding § 112(f) structure/acts];

means/steps for enabling NC detection of M3 metal island opens [see FIGS. 12-13, 34-35, 41, and 43 for corresponding § 112(f) structure/acts];

Still further aspects of the invention relate to wafers, chips, and processes for making them that include/utilize DOEs based on means/steps for enabling NC detection of merged-via opens, including but not limited to:

means/steps for enabling NC detection of V0-GATECNT merged via opens [see FIGS. 12-13, 36, 41, and 43 for corresponding § 112(f) structure/acts];

means/steps for enabling NC detection of V0 merged via opens [see FIGS. 12-13, 36, 41, 43, and 735-785 for corresponding § 112(f) structure/acts];

means/steps for enabling NC detection of V0-AACNT merged via opens [see FIGS. 12-13, 36, 41, and 43 for corresponding § 112(f) structure/acts];

means/steps for enabling NC detection of V1 merged via opens [see FIGS. 12-13, 36, 41, and 43 for corresponding § 112(f) structure/acts];

means/steps for enabling NC detection of V2 merged via opens [see FIGS. 12-13, 36, 41, and 43 for corresponding § 112(f) structure/acts];

means/steps for enabling NC detection of V1-M1 merged via opens [see FIGS. 12-13, 36, 41, and 43 for corresponding § 112(f) structure/acts]; and, means/steps for enabling NC detection of V2-M2 merged via opens [see FIGS. 12-13, 36, 41, and 43 for corresponding § 112(f) structure/acts].

Still further aspects of the invention relate to wafers, chips, and processes for making them that include/utilize DOEs based on means/steps for enabling NC detection of tip-to-tip leakages, including but not limited to:

means/steps for enabling NC detection of AA tip-to-tip leakages [see FIGS. 10-11, 14-15, 41, 43, and 1298-1326 for corresponding § 112(f) structure/acts];

means/steps for enabling NC detection of AACNT tip-to-tip leakages [see FIGS. 10-11, 14-15, 41, 43, and 1327-1405 for corresponding § 112(f) structure/acts];

means/steps for enabling NC detection of TS tip-to-tip leakages [see FIGS. 10-11, 14-15, 41, and 43 for corresponding § 112(f) structure/acts];

means/steps for enabling NC detection of AACNT-AA tip-to-tip leakages [see FIGS. 10-11, 14-15, 41, and 43 for corresponding § 112(f) structure/acts];

means/steps for enabling NC detection of GATE tip-to-tip leakages [see FIGS. 10-11, 14-15, 41, 43, and 1413-1461 for corresponding § 112(f) structure/acts];

means/steps for enabling NC detection of GATECNT-GATE tip-to-tip leakages [see FIGS. 10-11, 14-15, 41, and 43 for corresponding § 112(f) structure/acts];

means/steps for enabling NC detection of GATECNT tip-to-tip leakages [see FIGS. 10-11, 14-15, 41, 43, and 1462-1548 for corresponding § 112(f) structure/acts];

means/steps for enabling NC detection of GATECNT-AACNT tip-to-tip leakages [see FIGS. 10-11, 14-15, 41, and 43 for corresponding § 112(f) structure/acts];

means/steps for enabling NC detection of M1 tip-to-tip leakages [see FIGS. 10-11, 14-15, 41, 43, and 1549-1556 for corresponding § 112(f) structure/acts];

means/steps for enabling NC detection of V0 tip-to-tip leakages [see FIGS. 10-11, 14-15, 41, and 43 for corresponding § 112(f) structure/acts];

means/steps for enabling NC detection of M1-V0 tip-to-tip leakages [see FIGS. 10-11, 14-15, 41, and 43 for corresponding § 112(f) structure/acts];

means/steps for enabling NC detection of V1-M1 tip-to-tip leakages [see FIGS. 10-11, 14-15, 41, and 43 for corresponding § 112(f) structure/acts];

means/steps for enabling NC detection of V1 tip-to-tip leakages [see FIGS. 10-11, 14-15, 41, and 43 for corresponding § 112(f) structure/acts];

means/steps for enabling NC detection of M2 tip-to-tip leakages [see FIGS. 10-11, 14-15, 41, and 43 for corresponding § 112(f) structure/acts];

means/steps for enabling NC detection of V2-M2 tip-to-tip leakages [see FIGS. 10-11, 14-15, 41, and 43 for corresponding § 112(f) structure/acts];

means/steps for enabling NC detection of M2-V1 tip-to-tip leakages [see FIGS. 10-11, 14-15, 41, and 43 for corresponding § 112(f) structure/acts];

means/steps for enabling NC detection of M3 tip-to-tip leakages [see FIGS. 10-11, 14-15, 41, and 43 for corresponding § 112(f) structure/acts];

means/steps for enabling NC detection of V2 tip-to-tip leakages [see FIGS. 10-11, 14-15, 41, and 43 for corresponding § 112(f) structure/acts]; and, means/steps for enabling NC detection of M3-V2 tip-to-tip leakages [see FIGS. 10-11, 14-15, 41, and 43 for corresponding § 112(f) structure/acts].

Still further aspects of the invention relate to wafers, chips, and processes for making them that include/utilize DOEs based on means/steps for enabling NC detection of tip-to-side leakages, including but not limited to:

means/steps for enabling NC detection of AA tip-to-side leakages [see FIGS. 10-11, 16, 41, and 43 for corresponding § 112(f) structure/acts];

means/steps for enabling NC detection of AACNT tip-to-side leakages [see FIGS. 10-11, 16, 41, 43, and 45 for corresponding § 112(f) structure/acts];

means/steps for enabling NC detection of AACNT-AA tip-to-side leakages [see FIGS. 10-11, 16, 41, and 43 for corresponding § 112(f) structure/acts];

means/steps for enabling NC detection of GATE-AA tip-to-side leakages [see FIGS. 10-11, 16, 41, 43, 49, 50, and 1084-1119 for corresponding § 112(f) structure/acts];

means/steps for enabling NC detection of TS-GATECNT tip-to-side leakages [see FIGS. 10-11, 16, 41, 43, and 1239-1263 for corresponding § 112(f) structure/acts];

means/steps for enabling NC detection of GATECNT-GATE tip-to-side leakages [see FIGS. 10-11, 16, 41, 43, and 1201-1238 for corresponding § 112(f) structure/acts];

means/steps for enabling NC detection of GATECNT tip-to-side leakages [see FIGS. 10-11, 16, 41, 43, and 1120-1149 for corresponding § 112(f) structure/acts];

means/steps for enabling NC detection of GATECNT-AACNT tip-to-side leakages [see FIGS. 10-11, 16, 41, 43, 1150-1188 for corresponding § 112(f) structure/acts];

means/steps for enabling NC detection of M1 tip-to-side leakages [see FIGS. 10-11, 16, 41, 43, and 1264-1297 for corresponding § 112(f) structure/acts];

means/steps for enabling NC detection of V0 tip-to-side leakages [see FIGS. 10-11, 16, 41, and 43 for corresponding § 112(f) structure/acts];

means/steps for enabling NC detection of M1-V0 tip-to-side leakages [see FIGS. 10-11, 16, 41, and 43 for corresponding § 112(f) structure/acts];

means/steps for enabling NC detection of V1-M1 tip-to-side leakages [see FIGS. 10-11, 16, 41, and 43 for corresponding § 112(f) structure/acts];

means/steps for enabling NC detection of V1 tip-to-side leakages [see FIGS. 10-11, 16, 41, and 43 for corresponding § 112(f) structure/acts];

means/steps for enabling NC detection of M2-V1 tip-to-side leakages [see FIGS. 10-11, 16, 41, and 43 for corresponding § 112(f) structure/acts];

means/steps for enabling NC detection of M2 tip-to-side leakages [see FIGS. 10-11, 16, 41, and 43 for corresponding § 112(f) structure/acts];

means/steps for enabling NC detection of V2-M2 tip-to-side leakages [see FIGS. 10-11, 16, 41, and 43 for corresponding § 112(f) structure/acts];

means/steps for enabling NC detection of M3 tip-to-side leakages [see FIGS. 10-11, 16, 41, and 43 for corresponding § 112(f) structure/acts];

means/steps for enabling NC detection of V2 tip-to-side leakages [see FIGS. 10-11, 16, 41, and 43 for corresponding § 112(f) structure/acts]; and, means/steps for enabling NC detection of M3-V2 tip-to-side leakages [see FIGS. 10-11, 16, 41, and 43 for corresponding § 112(f) structure/acts].

Still further aspects of the invention relate to wafers, chips, and processes for making them that include/utilize DOEs based on means/steps for enabling NC detection of side-to-side leakages, including but not limited to:

means/steps for enabling NC detection of AA side-to-side leakages [see FIGS. 10-11, 17, 41, and 43 for corresponding § 112(f) structure/acts];

means/steps for enabling NC detection of AACNT side-to-side leakages [see FIGS. 10-11, 17, 41, 43, and 786-804 for corresponding § 112(f) structure/acts];

means/steps for enabling NC detection of AACNT-AA side-to-side leakages [see FIGS. 10-11, 17, 41, and 43 for corresponding § 112(f) structure/acts];

means/steps for enabling NC detection of GATE side-to-side leakages [see FIGS. 10-11, 17, 41, 43, and 833-859 for corresponding § 112(f) structure/acts];

means/steps for enabling NC detection of GATECNT-GATE side-to-side leakages [see FIGS. 10-11, 17, 41, 43, and 886-903 for corresponding § 112(f) structure/acts];

means/steps for enabling NC detection of GATECNT side-to-side leakages [see FIGS. 10-11, 17, 41, 43, and 860-872 for corresponding § 112(f) structure/acts];

means/steps for enabling NC detection of GATECNT-AACNT side-to-side leakages [see FIGS. 10-11, 17, 41, 43, 47A-C, and 873-885 for corresponding § 112(f) structure/acts];

means/steps for enabling NC detection of M1 side-to-side leakages [see FIGS. 10-11, 17, 41, 43, and 904-928 for corresponding § 112(f) structure/acts];

means/steps for enabling NC detection of V0 side-to-side leakages [see FIGS. 10-11, 17, 41, and 43 for corresponding § 112(f) structure/acts];

means/steps for enabling NC detection of M1-V0 side-to-side leakages [see FIGS. 10-11, 17, 41, 43, and 929-936 for corresponding § 112(f) structure/acts];

means/steps for enabling NC detection of V1-M1 side-to-side leakages [see FIGS. 10-11, 17, 41, and 43 for corresponding § 112(f) structure/acts];

means/steps for enabling NC detection of V1 side-to-side leakages [see FIGS. 10-11, 17, 41, and 43 for corresponding § 112(f) structure/acts];

means/steps for enabling NC detection of M2-V1 side-to-side leakages [see FIGS. 10-11, 17, 41, and 43 for corresponding § 112(f) structure/acts];

means/steps for enabling NC detection of M2 side-to-side leakages [see FIGS. 10-11, 17, 41, and 43 for corresponding § 112(f) structure/acts];

means/steps for enabling NC detection of V2-M2 side-to-side leakages [see FIGS. 10-11, 17, 41, and 43 for corresponding § 112(f) structure/acts];

means/steps for enabling NC detection of M3 side-to-side leakages [see FIGS. 10-11, 17, 41, and 43 for corresponding § 112(f) structure/acts];

means/steps for enabling NC detection of V2 side-to-side leakages [see FIGS. 10-11, 17, 41, and 43 for corresponding § 112(f) structure/acts]; and, means/steps for enabling NC detection of M3-V2 side-to-side leakages [see FIGS. 10-11, 17, 41, and 43 for corresponding § 112(f) structure/acts].

Still further aspects of the invention relate to wafers, chips, and processes for making them that include/utilize DOEs based on means/steps for enabling NC detection of L-shape interlayer leakages, including but not limited to:

means/steps for enabling NC detection of AA L-shape interlayer leakages [see FIGS. 10-11, 18-22, 41, and 43 for corresponding § 112(f) structure/acts];

means/steps for enabling NC detection of AACNT-L-shape interlayer leakages [see FIGS. 10-11, 18-22, 41, and 43 for corresponding § 112(f) structure/acts];

means/steps for enabling NC detection of AACNT-AA-L-shape interlayer leakages [see FIGS. 10-11, 18-22, 41, and 43 for corresponding § 112(f) structure/acts];

means/steps for enabling NC detection of GATE-AA-L-shape interlayer leakages [see FIGS. 10-11, 18-22, 41, and 43 for corresponding § 112(f) structure/acts];

means/steps for enabling NC detection of GATE-TS L-shape interlayer leakages [see FIGS. 10-11, 18-22, 41, and 43 for corresponding § 112(f) structure/acts];

means/steps for enabling NC detection of GATECNT-GATE-L-shape interlayer leakages [see FIGS. 10-11, 18-22, 41, and 43 for corresponding § 112(f) structure/acts];

means/steps for enabling NC detection of GATECNT-AA L-shape interlayer leakages [see FIGS. 10-11, 18-22, 41, and 43 for corresponding § 112(f) structure/acts];

means/steps for enabling NC detection of GATE-TS L-shape interlayer leakages [see FIGS. 10-11, 18-22, 41, and 43 for corresponding § 112(f) structure/acts];

means/steps for enabling NC detection of GATECNT-AACNT-L-shape interlayer leakages [see FIGS. 10-11, 18-22, 41, and 43 for corresponding § 112(f) structure/acts];

means/steps for enabling NC detection of V0-AA L-shape interlayer leakages [see FIGS. 10-11, 18-22, 41, and 43 for corresponding § 112(f) structure/acts];

means/steps for enabling NC detection of V0-TS L-shape interlayer leakages [see FIGS. 10-11, 18-22, 41, and 43 for corresponding § 112(f) structure/acts];

means/steps for enabling NC detection of V0-AACNT L-shape interlayer leakages [see FIGS. 10-11, 18-22, 41, and 43 for corresponding § 112(f) structure/acts];

means/steps for enabling NC detection of V0-GATE L-shape interlayer leakages [see FIGS. 10-11, 18-22, 41, and 43 for corresponding § 112(f) structure/acts];

means/steps for enabling NC detection of V0-GATECNT L-shape interlayer leakages [see FIGS. 10-11, 18-22, 41, and 43 for corresponding § 112(f) structure/acts];
means/steps for enabling NC detection of M1-AACNT L-shape interlayer leakages [see FIGS. 10-11, 18-22, 41, and 43 for corresponding § 112(f) structure/acts];
means/steps for enabling NC detection of M1-GATECNT L-shape interlayer leakages [see FIGS. 10-11, 18-22, 41, and 43 for corresponding § 112(f) structure/acts];
means/steps for enabling NC detection of M1-V0-L-shape interlayer leakages [see FIGS. 10-11, 18-22, 41, and 43 for corresponding § 112(f) structure/acts];
means/steps for enabling NC detection of V1-M1-L-shape interlayer leakages [see FIGS. 10-11, 18-22, 41, and 43 for corresponding § 112(f) structure/acts];
means/steps for enabling NC detection of V1-V0 L-shape interlayer leakages [see FIGS. 10-11, 18-22, 41, and 43 for corresponding § 112(f) structure/acts];
means/steps for enabling NC detection of M2-V1-L-shape interlayer leakages [see FIGS. 10-11, 18-22, 41, and 43 for corresponding § 112(f) structure/acts];
means/steps for enabling NC detection of V2-V1 L-shape interlayer leakages [see FIGS. 10-11, 18-22, 41, and 43 for corresponding § 112(f) structure/acts];
means/steps for enabling NC detection of V2-M2 L-shape interlayer leakages [see FIGS. 10-11, 18-22, 41, and 43 for corresponding § 112(f) structure/acts];
means/steps for enabling NC detection of M3-M2 L-shape interlayer leakages [see FIGS. 10-11, 18-22, 41, and 43 for corresponding § 112(f) structure/acts];
means/steps for enabling NC detection of M3-V2 L-shape interlayer leakages [see FIGS. 10-11, 18-22, 41, and 43 for corresponding § 112(f) structure/acts].

Still further aspects of the invention relate to wafers, chips, and processes for making them that include/utilize DOEs based on means/steps for enabling NC detection of diagonal leakages, including but not limited to:
means/steps for enabling NC detection of AA diagonal leakages [see FIGS. 10-11, 23, 41, and 43 for corresponding § 112(f) structure/acts];
means/steps for enabling NC detection of TS diagonal leakages [see FIGS. 10-11, 23, 41, and 43 for corresponding § 112(f) structure/acts];
means/steps for enabling NC detection of AACNT diagonal leakages [see FIGS. 10-11, 23, 41, and 43 for corresponding § 112(f) structure/acts];
means/steps for enabling NC detection of AACNT-AA diagonal leakages [see FIGS. 10-11, 23, 41, and 43 for corresponding § 112(f) structure/acts];
means/steps for enabling NC detection of GATE diagonal leakages [see FIGS. 10-11, 23, 41, and 43 for corresponding § 112(f) structure/acts];
means/steps for enabling NC detection of GATE-AACNT diagonal leakages [see FIGS. 10-11, 23, 41, and 43 for corresponding § 112(f) structure/acts];
means/steps for enabling NC detection of GATECNT-GATE diagonal leakages [see FIGS. 10-11, 23, 41, and 43 for corresponding § 112(f) structure/acts];
means/steps for enabling NC detection of GATECNT diagonal leakages [see FIGS. 10-11, 23, 41, 43, and 495-554 for corresponding § 112(f) structure/acts];
means/steps for enabling NC detection of GATECNT-AACNT diagonal leakages [see FIGS. 10-11, 23, 41, 43, and 555-632 for corresponding § 112(f) structure/acts];
means/steps for enabling NC detection of M1 diagonal leakages [see FIGS. 10-11, 23, 41, and 43 for corresponding § 112(f) structure/acts];
means/steps for enabling NC detection of V0 diagonal leakages [see FIGS. 10-11, 23, 41, and 43 for corresponding § 112(f) structure/acts];
means/steps for enabling NC detection of M1-V0 diagonal leakages [see FIGS. 10-11, 23, 41, and 43 for corresponding § 112(f) structure/acts];
means/steps for enabling NC detection of V1-M1 diagonal leakages [see FIGS. 10-11, 23, 41, and 43 for corresponding § 112(f) structure/acts];
means/steps for enabling NC detection of V1 diagonal leakages [see FIGS. 10-11, 23, 41, and 43 for corresponding § 112(f) structure/acts];
means/steps for enabling NC detection of M2 diagonal leakages [see FIGS. 10-11, 23, 41, and 43 for corresponding § 112(f) structure/acts];
means/steps for enabling NC detection of M2-V1 diagonal leakages [see FIGS. 10-11, 23, 41, and 43 for corresponding § 112(f) structure/acts];
means/steps for enabling NC detection of M3 diagonal leakages [see FIGS. 10-11, 23, 41, and 43 for corresponding § 112(f) structure/acts];
means/steps for enabling NC detection of V2-M2 diagonal leakages [see FIGS. 10-11, 23, 41, and 43 for corresponding § 112(f) structure/acts];
means/steps for enabling NC detection of V2 diagonal leakages [see FIGS. 10-11, 23, 41, and 43 for corresponding § 112(f) structure/acts]; and,
means/steps for enabling NC detection of M3-V2 diagonal leakages [see FIGS. 10-11, 23, 41, and 43 for corresponding § 112(f) structure/acts].

Still further aspects of the invention relate to wafers, chips, and processes for making them that include/utilize DOEs based on means/steps for enabling NC detection of corner leakages, including but not limited to:
means/steps for enabling NC detection of AA corner leakages [see FIGS. 10-11, 24-26, 41, and 43 for corresponding § 112(f) structure/acts];
means/steps for enabling NC detection of AACNT corner leakages [see FIGS. 10-11, 24-26, 41, and 43 for corresponding § 112(f) structure/acts];
means/steps for enabling NC detection of AACNT-AA corner leakages [see FIGS. 10-11, 24-26, 41, and 43 for corresponding § 112(f) structure/acts];
means/steps for enabling NC detection of GATE corner leakages [see FIGS. 10-11, 24-26, 41, and 43 for corresponding § 112(f) structure/acts];
means/steps for enabling NC detection of GATECNT-GATE corner leakages [see FIGS. 10-11, 24-26, 41, and 43 for corresponding § 112(f) structure/acts];
means/steps for enabling NC detection of GATECNT-TS corner leakages [see FIGS. 10-11, 24-26, 41, and 43 for corresponding § 112(f) structure/acts];
means/steps for enabling NC detection of GATECNT corner leakages [see FIGS. 10-11, 24-26, 41, and 43 for corresponding § 112(f) structure/acts];
means/steps for enabling NC detection of GATECNT-AA corner leakages [see FIGS. 10-11, 24-26, 41, 43, and 263-286 for corresponding § 112(f) structure/acts];
means/steps for enabling NC detection of GATECNT-AACNT corner leakages [see FIGS. 10-11, 24-26, 41, and 43 for corresponding § 112(f) structure/acts];
means/steps for enabling NC detection of M1 corner leakages [see FIGS. 10-11, 24-26, 41, 43, and 416-494 for corresponding § 112(f) structure/acts];

means/steps for enabling NC detection of V0 corner leakages [see FIGS. 10-11, 24-26, 41, and 43 for corresponding § 112(f) structure/acts];

means/steps for enabling NC detection of M1-V0 corner leakages [see FIGS. 10-11, 24-26, 41, and 43 for corresponding § 112(f) structure/acts];

means/steps for enabling NC detection of V1-M1 corner leakages [see FIGS. 10-11, 24-26, 41, and 43 for corresponding § 112(f) structure/acts];

means/steps for enabling NC detection of V1 corner leakages [see FIGS. 10-11, 24-26, 41, and 43 for corresponding § 112(f) structure/acts];

means/steps for enabling NC detection of M2 corner leakages [see FIGS. 10-11, 24-26, 41, and 43 for corresponding § 112(f) structure/acts];

means/steps for enabling NC detection of M2-V1 corner leakages [see FIGS. 10-11, 24-26, 41, and 43 for corresponding § 112(f) structure/acts];

means/steps for enabling NC detection of M3 corner leakages [see FIGS. 10-11, 24-26, 41, and 43 for corresponding § 112(f) structure/acts];

means/steps for enabling NC detection of V2-M2 corner leakages [see FIGS. 10-11, 24-26, 41, and 43 for corresponding § 112(f) structure/acts];

means/steps for enabling NC detection of V2 corner leakages [see FIGS. 10-11, 24-26, 41, and 43 for corresponding § 112(f) structure/acts]; and, means/steps for enabling NC detection of M3-V2 corner leakages [see FIGS. 10-11, 24-26, 41, and 43 for corresponding § 112(f) structure/acts];

Still further aspects of the invention relate to wafers, chips, and processes for making them that include/utilize DOEs based on means/steps for enabling NC detection of interlayer-overlap leakages, including but not limited to:

means/steps for enabling NC detection of GATE-AA interlayer overlap leakages [see FIGS. 10-11, 27, 41, 43, and 692-734 for corresponding § 112(f) structure/acts];

means/steps for enabling NC detection of GATE-AACNT interlayer overlap leakages [see FIGS. 10-11, 27, 41, 43, and 633-691 for corresponding § 112(f) structure/acts];

means/steps for enabling NC detection of GATE-TS interlayer overlap leakages [see FIGS. 10-11, 27, 41, and 43 for corresponding § 112(f) structure/acts];

means/steps for enabling NC detection of GATECNT-TS interlayer overlap leakages [see FIGS. 10-11, 27, 41, and 43 for corresponding § 112(f) structure/acts];

means/steps for enabling NC detection of GATECNT-AA interlayer overlap leakages [see FIGS. 10-11, 27, 41, and 43 for corresponding § 112(f) structure/acts];

means/steps for enabling NC detection of V0-AA interlayer overlap leakages [see FIGS. 10-11, 27, 41, and 43 for corresponding § 112(f) structure/acts];

means/steps for enabling NC detection of V0-AACNT interlayer overlap leakages [see FIGS. 10-11, 27, 41, and 43 for corresponding § 112(f) structure/acts];

means/steps for enabling NC detection of V0-TS interlayer overlap leakages [see FIGS. 10-11, 27, 41, and 43 for corresponding § 112(f) structure/acts];

means/steps for enabling NC detection of V0-GATE interlayer overlap leakages [see FIGS. 10-11, 27, 41, and 43 for corresponding § 112(f) structure/acts];

means/steps for enabling NC detection of M1-GATECNT interlayer overlap leakages see FIGS. 10-11, 27, 41, and 43 for corresponding § 112(f) structure/acts];

means/steps for enabling NC detection of M1-AACNT interlayer overlap leakages [see FIGS. 10-11, 27, 41, and 43 for corresponding § 112(f) structure/acts];

means/steps for enabling NC detection of V1-V0 interlayer overlap leakages [see FIGS. 10-11, 27, 41, and 43 for corresponding § 112(f) structure/acts];

means/steps for enabling NC detection of M2-M1-interlayer-overlap leakages [see FIGS. 10-11, 27, 41, and 43 for corresponding § 112(f) structure/acts];

means/steps for enabling NC detection of V2-V1-interlayer-overlap leakages [see FIGS. 10-11, 27, 41, and 43 for corresponding § 112(f) structure/acts]; and, means/steps for enabling NC detection of M3-M2-interlayer-overlap leakages [see FIGS. 10-11, 27, 41, and 43 for corresponding § 112(f) structure/acts].

Still further aspects of the invention relate to wafers, chips, and processes for making them that include/utilize DOEs based on means/steps for enabling NC detection of via-chamfer leakages, including but not limited to:

means/steps for enabling NC detection of V0-GATECNT via chamfer leakages [see FIGS. 10-11, 28, 41, and 43 for corresponding § 112(f) structure/acts];

means/steps for enabling NC detection of V0-AACNT via chamfer leakages [see FIGS. 10-11, 28, 41, 43, and 52-256 for corresponding § 112(f) structure/acts];

means/steps for enabling NC detection of V1-M1 via chamfer leakages [see FIGS. 10-11, 28, 41, and 43 for corresponding § 112(f) structure/acts];

means/steps for enabling NC detection of V2-M2 via chamfer leakages [see FIGS. 10-11, 28, 41, and 43 for corresponding § 112(f) structure/acts]; and, means/steps for enabling NC detection of V3-M3 via chamfer leakages [see FIGS. 10-11, 28, 41, 43, and 257-262 for corresponding § 112(f) structure/acts].

Still further aspects of the invention relate to wafers, chips, and processes for making them that include/utilize DOEs based on means/steps for enabling NC detection of merged-via leakages, including but not limited to:

means/steps for enabling NC detection of V0 merged via leakages [see FIGS. 10-11, 29, 41, and 43 for corresponding § 112(f) structure/acts];

means/steps for enabling NC detection of V1 merged via leakages [see FIGS. 10-11, 29, 41, and 43 for corresponding § 112(f) structure/acts]; and, means/steps for enabling NC detection of V2 merged via leakages [see FIGS. 10-11, 29, 41, and 43 for corresponding § 112(f) structure/acts].

Still further aspects of the invention relate to wafers, chips, and processes for making them that include/utilize DOEs based on means/steps for enabling NC detection of snake resistances, including but not limited to:

means/steps for enabling NC detection of AA snake resistances [see FIGS. 12-13, 30, 41, and 43 for corresponding § 112(f) structure/acts];

means/steps for enabling NC detection of TS snake resistances [see FIGS. 12-13, 30, 41, and 43 for corresponding § 112(f) structure/acts];

means/steps for enabling NC detection of AACNT snake resistances [see FIGS. 12-13, 30, 41, and 43 for corresponding § 112(f) structure/acts];

means/steps for enabling NC detection of GATE snake resistances [see FIGS. 12-13, 30, 41, 43, and 1041-1048 for corresponding § 112(f) structure/acts];

means/steps for enabling NC detection of GATECNT snake resistances [see FIGS. 12-13, 30, 41, and 43 for corresponding § 112(f) structure/acts];

means/steps for enabling NC detection of V0 snake resistances [see FIGS. 12-13, 30, 41, and 43 for corresponding § 112(f) structure/acts];

means/steps for enabling NC detection of M1 snake resistances [see FIGS. 12-13, 30, 41, 43, 44, and 1049-1066 for corresponding § 112(f) structure/acts];

means/steps for enabling NC detection of M1-V0-AACNT snake resistances [see FIGS. 12-13, 30, 41, 43, and 1067-1071 for corresponding § 112(f) structure/acts];

means/steps for enabling NC detection of V1 snake resistances [see FIGS. 12-13, 30, 41, and 43 for corresponding § 112(f) structure/acts];

means/steps for enabling NC detection of M2 snake resistances [see FIGS. 12-13, 30, 41, and 43 for corresponding § 112(f) structure/acts];

means/steps for enabling NC detection of V2 snake resistances [see FIGS. 12-13, 30, 41, and 43 for corresponding § 112(f) structure/acts]; and, means/steps for enabling NC detection of M3 snake resistances [see FIGS. 12-13, 30, 41, and 43 for corresponding § 112(f) structure/acts].

Still further aspects of the invention relate to wafers, chips, and processes for making them that include/utilize DOEs based on means/steps for enabling NC detection of stitch resistances, including but not limited to:

means/steps for enabling NC detection of AA stitch resistances [see FIGS. 12-13, 31-32, 41, and 43 for corresponding § 112(f) structure/acts];

means/steps for enabling NC detection of TS stitch resistances [see FIGS. 12-13, 31-32, 41, and 43 for corresponding § 112(f) structure/acts];

means/steps for enabling NC detection of AACNT stitch resistances [see FIGS. 12-13, 31-32, 41, and 43 for corresponding § 112(f) structure/acts];

means/steps for enabling NC detection of GATECNT stitch resistances [see FIGS. 12-13, 31-32, 41, and 43 for corresponding § 112(f) structure/acts];

means/steps for enabling NC detection of V0 stitch resistances [see FIGS. 12-13, 31-32, 41, and 43 for corresponding § 112(f) structure/acts];

means/steps for enabling NC detection of M1 stitch resistances [see FIGS. 12-13, 31-32, 41, 43, and 1072-1083 for corresponding § 112(f) structure/acts];

means/steps for enabling NC detection of V1 stitch resistances [see FIGS. 12-13, 31-32, 41, and 43 for corresponding § 112(f) structure/acts];

means/steps for enabling NC detection of M2 stitch resistances [see FIGS. 12-13, 31-32, 41, and 43 for corresponding § 112(f) structure/acts];

means/steps for enabling NC detection of V2 stitch resistances [see FIGS. 12-13, 31-32, 41, and 43 for corresponding § 112(f) structure/acts]; and, means/steps for enabling NC detection of M3 stitch resistances [see FIGS. 12-13, 31-32, 41, and 43 for corresponding § 112(f) structure/acts].

Still further aspects of the invention relate to wafers, chips, and processes for making them that include/utilize DOEs based on means/steps for enabling NC detection of via resistances, including but not limited to:

means/steps for enabling NC detection of AACNT-TS via resistances [see FIGS. 12-13, 33, 41, 43, and 1629-1673 for corresponding § 112(f) structure/acts];

means/steps for enabling NC detection of AACNT-AA via resistances [see FIGS. 12-13, 33, 41, 43, and 1557-1628 for corresponding § 112(f) structure/acts];

means/steps for enabling NC detection of TS-AA via resistances [see FIGS. 12-13, 33, 41, 43, and 2315-2330 for corresponding § 112(f) structure/acts];

means/steps for enabling NC detection of GATECNT-GATE via resistances [see FIGS. 12-13, 33, 41, 43, 48, and 1699-2005 for corresponding § 112(f) structure/acts];

means/steps for enabling NC detection of GATECNT-AACNT via resistances [see FIGS. 12-13, 33, 41, 43, and 1674-1682 for corresponding § 112(f) structure/acts];

means/steps for enabling NC detection of GATECNT-AACNT-GATE via resistances [see FIGS. 12-13, 33, 41, 43, and 1683-1698 for corresponding § 112(f) structure/acts];

means/steps for enabling NC detection of V0-GATECNT via resistances [see FIGS. 12-13, 33, 41, 43, and 2375-2439 for corresponding § 112(f) structure/acts];

means/steps for enabling NC detection of V0-AA via resistances [see FIGS. 12-13, 33, 41, and 43 for corresponding § 112(f) structure/acts];

means/steps for enabling NC detection of V0 via resistances [see FIGS. 12-13, 33, 41, 43, and 2331-2344 for corresponding § 112(f) structure/acts];

means/steps for enabling NC detection of V0-TS via resistances [see FIGS. 12-13, 33, 41, and 43 for corresponding § 112(f) structure/acts];

means/steps for enabling NC detection of V0-AACNT via resistances [see FIGS. 12-13, 33, 41, 43, and 2345-2374 for corresponding § 112(f) structure/acts];

means/steps for enabling NC detection of V0-GATE via resistances [see FIGS. 12-13, 33, 41, and 43 for corresponding § 112(f) structure/acts];

means/steps for enabling NC detection of V1 via resistances [see FIGS. 12-13, 33, 41, 43, and 2440-2441 for corresponding § 112(f) structure/acts];

means/steps for enabling NC detection of M1-V0 resistances [see FIGS. 12-13, 33, 41, 43, and 2006-2220 for corresponding § 112(f) structure/acts];

means/steps for enabling NC detection of V1-M1 via resistances [see FIGS. 12-13, 33, 41, 43, and 2442-2459 for corresponding § 112(f) structure/acts];

means/steps for enabling NC detection of V1-M2 via resistances [see FIGS. 12-13, 33, 41, 43, and 2221-2256 for corresponding § 112(f) structure/acts];

means/steps for enabling NC detection of M1-GATECNT via resistances [see FIGS. 12-13, 33, 41, and 43 for corresponding § 112(f) structure/acts];

means/steps for enabling NC detection of V2-M3 via resistances [see FIGS. 12-13, 33, 41, 43, and 2257-2274 for corresponding § 112(f) structure/acts];

means/steps for enabling NC detection of M1-AANCT via resistances [see FIGS. 12-13, 33, 41, and 43 for corresponding § 112(f) structure/acts];

means/steps for enabling NC detection of V2-M2 via resistances [see FIGS. 12-13, 33, 41, and 43 for corresponding § 112(f) structure/acts];

means/steps for enabling NC detection V3 via resistances [see FIGS. 12-13, 33, 41, 43, and 2460-2461 for corresponding § 112(f) structure/acts];

means/steps for enabling NC detection of M4-V3 via resistances [see FIGS. 12-13, 33, 41, 43, and 2275-2296 for corresponding § 112(f) structure/acts]; and, means/steps for enabling NC detection of M5-V4 via resistances [see FIGS. 12-13, 33, 41, 43, and 2297-2314 for corresponding § 112(f) structure/acts].

Still further aspects of the invention relate to wafers, chips, and processes for making them that include/utilize DOEs based on means/steps for enabling NC detection of metal island resistances, including but not limited to:

means/steps for enabling NC detection of M1 metal island resistances [see FIGS. 12-13, 34-35, 41, and 43 for corresponding § 112(f) structure/acts];

means/steps for enabling NC detection of M2 metal island resistances [see FIGS. 12-13, 34-35, 41, and 43 for corresponding § 112(f) structure/acts];

means/steps for enabling NC detection of M3 metal island resistances [see FIGS. 12-13, 34-35, 41, and 43 for corresponding § 112(f) structure/acts];

Still further aspects of the invention relate to wafers, chips, and processes for making them that include/utilize DOEs based on means/steps for enabling NC detection of merged-via resistances, including but not limited to:

means/steps for enabling NC detection of V0-GATECNT merged via resistances [see FIGS. 12-13, 36, 41, and 43 for corresponding § 112(f) structure/acts];

means/steps for enabling NC detection of V0 merged via resistances [see FIGS. 12-13, 36, 41, 43, and 735-785 for corresponding § 112(f) structure/acts];

means/steps for enabling NC detection of V0-AACNT merged via resistances [see FIGS. 12-13, 36, 41, and 43 for corresponding § 112(f) structure/acts];

means/steps for enabling NC detection of V1 merged via resistances [see FIGS. 12-13, 36, 41, and 43 for corresponding § 112(f) structure/acts];

means/steps for enabling NC detection of V2 merged via resistances [see FIGS. 12-13, 36, 41, and 43 for corresponding § 112(f) structure/acts];

means/steps for enabling NC detection of V1-M1 merged via resistances [see FIGS. 12-13, 36, 41, and 43 for corresponding § 112(f) structure/acts]; and, means/steps for enabling NC detection of V2-M2 merged via resistances [see FIGS. 12-13, 36, 41, and 43 for corresponding § 112(f) structure/acts].

Still further aspects of the invention relate to mesh-style NCEM pads, and their use with in-line process control/optimization, such pads comprising, for example: at least two parallel, elongated AACNT features, extending longitudinally in a first direction; at least two parallel, elongated GATECNT features, extending longitudinally in a second direction, perpendicular to the first direction; wherein the features are positioned such that each of the AANCT features intersects each of the GATECNT features. Such pads may include at least three (or four, or five, or six, etc.) parallel, elongated AACNT features that extend longitudinally in the first direction, and/or at least three (or four, or five, or six, etc.) parallel, elongated GATECNT features that extend longitudinally in the second direction. Such pads may be part of an assembly that includes: a mesh-style NCEM pad; and, an upper layer NCEM pad, overlying the mesh-style NCEM pad, said upper layer NCEM pad comprising: one or more mask-patterned features, in a first wiring layer (M1), that substantially cover the mesh-style NCEM pad; and, one or more mask-patterned features, in a via to interconnect stack (V0) layer, that provide electrical connection(s) between the M1 feature(s) and the mesh-style NCEM pad. Such V0 features may be positioned at the intersections of the underlying AACNT and GATECNT features, or may be positioned to avoid intersections of the underlying AACNT and GATECNT features. The one or more M1 features may include multiple, parallel, elongated M1 features. Any of the aforesaid features may be single-patterned, double-patterned, triple-patterned, etc. Such mesh-style NCEM pads may be used in NCEM-enabled fill cells, including but not limited to: AA-tip-to-tip-short-configured, NCEM-enabled fill cells; AACNT-tip-to-tip-short-configured, NCEM-enabled fill cells; AACNT-AA-tip-to-tip-short-configured, NCEM-enabled fill cells; AACNT-TS-tip-to-tip-short-configured, NCEM-enabled fill cells; TS-tip-to-tip-short-configured, NCEM-enabled fill cells; GATE-tip-to-tip-short-configured, NCEM-enabled fill cells; GATECNT-GATE-tip-to-tip-short-configured, NCEM-enabled fill cells; GATECNT-tip-to-tip-short-configured, NCEM-enabled fill cells; GATECNT-AACNT-tip-to-tip-short-configured, NCEM-enabled fill cells; M1-tip-to-tip-short-configured, NCEM-enabled fill cells; V0-tip-to-tip-short-configured, NCEM-enabled fill cells; M1-V0-tip-to-tip-short-configured, NCEM-enabled fill cells; V1-M1-tip-to-tip-short-configured, NCEM-enabled fill cells; V1-tip-to-tip-short-configured, NCEM-enabled fill cells; M2-tip-to-tip-short-configured, NCEM-enabled fill cells; M2-V1-tip-to-tip-short-configured, NCEM-enabled fill cells; V2-M2-tip-to-tip-short-configured, NCEM-enabled fill cells; M3-tip-to-tip-short-configured, NCEM-enabled fill cells; V2-tip-to-tip-short-configured, NCEM-enabled fill cells; M3-V2-tip-to-tip-short-configured, NCEM-enabled fill cells; AA-tip-to-side-short-configured, NCEM-enabled fill cells; AACNT-tip-to-side-short-configured, NCEM-enabled fill cells; AACNT-AA-tip-to-side-short-configured, NCEM-enabled fill cells; GATE-AA-tip-to-side-short-configured, NCEM-enabled fill cells; GATECNT-GATE-tip-to-side-short-configured, NCEM-enabled fill cells; GATECNT-tip-to-side-short-configured, NCEM-enabled fill cells; TS-GATECNT-tip-to-side-short-configured, NCEM-enabled fill cells; GATECNT-AACNT-tip-to-side-short-configured, NCEM-enabled fill cells; GATECNT-AACNT-TS-tip-to-side-short-configured, NCEM-enabled fill cells; M1-tip-to-side-short-configured, NCEM-enabled fill cells; V0-tip-to-side-short-configured, NCEM-enabled fill cells; M1-V0-tip-to-side-short-configured, NCEM-enabled fill cells; V1-M1-tip-to-side-short-configured, NCEM-enabled fill cells; V1-tip-to-side-short-configured, NCEM-enabled fill cells; M2-tip-to-side-short-configured, NCEM-enabled fill cells; M2-V1-tip-to-side-short-configured, NCEM-enabled fill cells; V2-M2-tip-to-side-short-configured, NCEM-enabled fill cells; M3-tip-to-side-short-configured, NCEM-enabled fill cells; V2-tip-to-side-short-configured, NCEM-enabled fill cells; M3-V2-tip-to-side-short-configured, NCEM-enabled fill cells; AA-side-to-side-short-configured, NCEM-enabled fill cells; AACNT-side-to-side-short-configured, NCEM-enabled fill cells; AACNT-AA-side-to-side-short-configured, NCEM-enabled fill cells; AACNT-GATE-side-to-side-short-configured, NCEM-enabled fill cells; GATE-side-to-side-short-configured, NCEM-enabled fill cells; GATECNT-GATE-side-to-side-short-configured, NCEM-enabled fill cells; TS-GATE-side-to-side-short-configured, NCEM-enabled fill cells; GATECNT-side-to-side-short-configured, NCEM-enabled fill cells; GATECNT-AACNT-side-to-side-short-configured, NCEM-enabled fill cells; M1-side-to-side-short-configured, NCEM-enabled fill cells; V0-side-to-side-short-configured, NCEM-enabled fill cells; M1-V0-side-to-side-short-configured, NCEM-enabled fill cells; V1-M1-side-to-side-short-configured, NCEM-enabled fill cells; V1-side-to-side-short-configured, NCEM-enabled fill cells; M2-side-to-side-short-configured, NCEM-enabled fill cells; M2-V1-side-to-side-short-configured, NCEM-enabled fill cells; V2-M2-side-to-side-short-configured, NCEM-enabled fill cells; M3-side-to-side-short-configured, NCEM-enabled fill cells; V2-side-to-side-short-configured, NCEM-enabled fill cells; M3-V2-side-to-sideshort-configured, NCEM-enabled fill cells; AA-L-shape-interlayer-short-configured, NCEM-enabled fill cells; AACNT-L-shape-interlayer-short-configured, NCEM-enabled fill cells; AACNT-AA-L-shape-interlayer-short-configured, NCEM-enabled fill cells; GATE-AA-L-shape-interlayer-short-configured, NCEM-enabled fill cells; GATE-TS-L-shape-interlayer-short-configured, NCEM-enabled fill cells; GATECNT-GATE-L-shape-interlayer-short-configured, NCEM-enabled fill cells; GATECNT-AA-L-shape-interlayer-short-configured, NCEM-enabled fill cells; GATECNT-TS-L-shape-interlayer-short-configured, NCEM-enabled fill cells; GATECNT-AACNT-L-shape-interlayer-short-configured, NCEM-enabled fill cells; V0-AA-L-shape-interlayer-short-configured, NCEM-enabled fill cells; V0-TS-L-shape-interlayer-short-configured, NCEM-enabled fill cells; V0-AACNT-L-shape-interlayer-short-configured, NCEM-enabled fill cells; V0-GATE-L-shape-interlayer-short-configured, NCEM-enabled fill cells; V0-GATECNT-L-shape-interlayer-short-configured, NCEM-enabled fill cells; M1-AACNT-L-shape-interlayer-short-configured, NCEM-enabled fill cells; M1-GATECNT-L-shape-interlayer-short-configured, NCEM-enabled fill cells; M1-V0-L-shape-interlayer-short-configured, NCEM-enabled fill cells; V1-M1-L-shape-interlayer-short-configured, NCEM-enabled fill cells; V1-V0-L-shape-interlayer-short-configured, NCEM-enabled fill cells; M2-M1-L-shape-interlayer-short-configured, NCEM-enabled fill cells; M2-V1-L-shape-interlayer-short-configured, NCEM-enabled fill cells; V2-V1-L-shape-interlayer-short-configured, NCEM-enabled fill cells; V2-M2-L-shape-interlayer-short-configured, NCEM-enabled fill cells; M3-M2-L-shape-interlayer-short-configured, NCEM-enabled fill cells; M3-V2-L-shape-interlayer-short-configured, NCEM-enabled fill cells; AA-diagonal-short-configured, NCEM-enabled fill cells; TS-diagonal-short-configured, NCEM-enabled fill cells; AACNT-diagonal-short-configured, NCEM-enabled fill cells; AACNT-AA-diagonal-short-configured, NCEM-enabled fill cells; GATE-diagonal-short-configured, NCEM-enabled fill cells; GATE-AACNT-diagonal-short-configured, NCEM-enabled fill cells; GATECNT-GATE-diagonal-short-configured, NCEM-enabled fill cells; GATECNT-diagonal-short-configured, NCEM-enabled fill cells; GATECNT-AACNT-diagonal-short-configured, NCEM-enabled fill cells; M1-diagonal-short-configured, NCEM-enabled fill cells; V0-diagonal-short-configured, NCEM-enabled fill cells; M1-V0-diagonal-short-configured, NCEM-enabled fill cells; V1-M1-diagonal-short-configured, NCEM-enabled fill cells; V1-diagonal-short-configured, NCEM-enabled fill cells; M2-diagonal-short-configured, NCEM-enabled fill cells; M2-V1-diagonal-short-configured, NCEM-enabled fill cells; M3-diagonal-short-configured, NCEM-enabled fill cells; V2-M2-diagonal-short-configured, NCEM-enabled fill cells; V2-diagonal-short-configured, NCEM-enabled fill cells; M3-V2-diagonal-short-configured, NCEM-enabled fill cells; AA-corner-short-configured, NCEM-enabled fill cells; AACNT-corner-short-configured, NCEM-enabled fill cells; AACNT-AA-corner-short-configured, NCEM-enabled fill cells; GATE-corner-short-configured, NCEM-enabled fill cells; GATECNT-GATE-corner-short-configured, NCEM-enabled fill cells; GATECNT-TS-corner-short-configured, NCEM-enabled fill cells; GATECNT-corner-short-configured, NCEM-enabled fill cells; GATECNT-AA-corner-short-configured, NCEM-enabled fill cells; GATECNT-AACNT-corner-short-configured, NCEM-enabled fill cells; M1-corner-short-configured, NCEM-enabled fill cells; V0-corner-short-configured, NCEM-enabled fill cells; M1-V0-corner-short-configured, NCEM-enabled fill cells; V1-M1-corner-short-configured, NCEM-enabled fill cells; V1-corner-short-configured, NCEM-enabled fill cells; M2-corner-short-configured, NCEM-enabled fill cells; M2-V1-corner-short-configured, NCEM-enabled fill cells; M3-corner-short-configured, NCEM-enabled fill cells; V2-M2-corner-short-configured, NCEM-enabled fill cells; V2-corner-short-configured, NCEM-enabled fill cells; M3-V2-corner-short-configured, NCEM-enabled fill cells; GATE-AA-interlayer-overlap-short-configured, NCEM-enabled fill cells; GATE-AACNT-interlayer-overlap-short-configured, NCEM-enabled fill cells; GATE-TS-interlayer-overlap-short-configured, NCEM-enabled fill cells; GATECNT-TS-interlayer-overlap-short-configured, NCEM-enabled fill cells; GATECNT-AA-interlayer-overlap-short-configured, NCEM-enabled fill cells; V0-AA-interlayer-overlap-short-configured, NCEM-enabled fill cells; V0-AACNT-interlayer-overlap-short-configured, NCEM-enabled fill cells; V0-TS-interlayer-overlap-short-configured, NCEM-enabled fill cells; V0-GATE-interlayer-overlap-short-configured, NCEM-enabled fill cells; M1-GATECNT-interlayer-overlap-short-configured, NCEM-enabled fill cells; M1-AACNT-interlayer-overlap-short-configured, NCEM-enabled fill cells; V1-V0-interlayer-overlap-short-configured, NCEM-enabled fill cells; M2-M1-interlayer-overlap-short-configured, NCEM-enabled fill cells; V2-V1-interlayer-overlap-short-configured, NCEM-enabled fill cells; M3-M2-interlayer-overlap-short-configured, NCEM-enabled fill cells; V0-GATECNT-via-chamfer-short-configured, NCEM-enabled fill cells; V0-AACNT-via-chamfer-short-configured, NCEM-enabled fill cells; V1-M1-via-chamfer-short-configured, NCEM-enabled fill cells; V2-M2-via-chamfer-short-configured, NCEM-enabled fill cells; V3-M3-via-chamfer-short-configured, NCEM-enabled fill cells; V0-merged-via-short-configured, NCEM-enabled fill cells; V1-merged-via-short-configured, NCEM-enabled fill cells; V2-merged-via-short-configured, NCEM-enabled fill cells; AA-snake-open-configured, NCEM-enabled fill cells; TS-snake-open-configured, NCEM-enabled fill cells; AACNT-snake-open-configured, NCEM-enabled fill cells; GATE-snake-open-configured, NCEM-enabled fill cells;

GATECNT-snake-open-configured, NCEM-enabled fill cells; V0-snake-open-configured, NCEM-enabled fill cells; M1-snake-open-configured, NCEM-enabled fill cells; M1-V0-AACNT-snake-open-configured, NCEM-enabled fill cells; V1-snake-open-configured, NCEM-enabled fill cells; M2-snake-open-configured, NCEM-enabled fill cells; V2-snake-open-configured, NCEM-enabled fill cells; M3-snake-open-configured, NCEM-enabled fill cells; AA-stitch-open-configured, NCEM-enabled fill cells; TS-stitch-open-configured, NCEM-enabled fill cells; AACNT-stitch-open-configured, NCEM-enabled fill cells; GATECNT-stitch-open-configured, NCEM-enabled fill cells; V0-stitch-open-configured, NCEM-enabled fill cells; M1-stitch-open-configured, NCEM-enabled fill cells; V1-stitch-open-configured, NCEM-enabled fill cells; M2-stitch-open-configured, NCEM-enabled fill cells; V2-stitch-open-configured, NCEM-enabled fill cells; M3-stitch-open-configured, NCEM-enabled fill cells; AACNT-TS-via-open-configured, NCEM-enabled fill cells; AACNT-AA-via-open-configured, NCEM-enabled fill cells; TS-AA-via-open-configured, NCEM-enabled fill cells; GATECNT-GATE-via-open-configured, NCEM-enabled fill cells; GATECNT-AACNT-via-open-configured, NCEM-enabled fill cells; GATECNT-AACNT-GATE-via-open-configured, NCEM-enabled fill cells; V0-GATECNT-via-open-configured, NCEM-enabled fill cells; V0-AA-via-open-configured, NCEM-enabled fill cells; V0-TS-via-open-configured, NCEM-enabled fill cells; V0-AACNT-via-open-configured, NCEM-enabled fill cells; V0-GATE-via-open-configured, NCEM-enabled fill cells; V0-via-open-configured, NCEM-enabled fill cells; M1-V0-via-open-configured, NCEM-enabled fill cells; V1-via-open-configured, NCEM-enabled fill cells; V1-M1-via-open-configured, NCEM-enabled fill cells; V1-M2-via-open-configured, NCEM-enabled fill cells; M1-GATECNT-via-open-configured, NCEM-enabled fill cells; M1-AANCT-via-open-configured, NCEM-enabled fill cells; V2-M2-via-open-configured, NCEM-enabled fill cells; V2-M3-via-open-configured, NCEM-enabled fill cells; V3-via-open-configured, NCEM-enabled fill cells; M4-V3-via-open-configured, NCEM-enabled fill cells; M5-V4-via-open-configured, NCEM-enabled fill cells; M1-metal-island-open-configured, NCEM-enabled fill cells; M2-metal-island-open-configured, NCEM-enabled fill cells; M3-metal-island-open-configured, NCEM-enabled fill cells; V0-merged-via-open-configured, NCEM-enabled fill cells; V0-AACNT-merged-via-open-configured, NCEM-enabled fill cells; V0-GATECNT-merged-via-open-configured, NCEM-enabled fill cells; V1-merged-via-open-configured, NCEM-enabled fill cells; V2-merged-via-open-configured, NCEM-enabled fill cells; V1-M1-merged-via-open-configured, NCEM-enabled fill cells; and/or V2-M2-merged-via-open-configured, NCEM-enabled fill cells. Using such mesh-style pads, a method for processing a semiconductor substrate may include: using a first mask to pattern a plurality of adjacent AACNT stripes on the substrate; using a second mask to pattern a plurality of adjacent GATECNT stripes on the substrate, where the GATECNT stripes perpendicularly overlap the AACNT stripes to form a mesh-style NCEM pad; and, obtaining in-line NCEM from the mesh-style NCEM pad. Such process may further include: using a third mask to pattern a plurality of V0 vias above at least some of the GATECNT and/or AACNT stripes of the mesh-style NCEM pad; and, using a fourth mask to pattern one or more M1 features above one or more of said V0 vias to form an M1 NCEM pad, and may further include: obtaining in-line NCEM from the M1 NCEM pad.

BRIEF DESCRIPTION OF THE FIGURES

To provide a more complete understanding of the present disclosure and features and advantages thereof, reference is made to the following set of figures, taken in conjunction with the accompanying description, in which:

FIG. 9AA depicts an exemplary mesh-style, NCEM-enabled pad, formed from a 10×9 grid of single-patterned GATECNT and double-patterned AACNT stripes, with an overlying, solid M1 pad, and a plurality of V0 vias positioned to avoid GATECNT-AACNT junction points;

FIG. 9BB depicts an exemplary mesh-style, NCEM-enabled pad, formed from a 10×9 grid of double-patterned GATECNT and double-patterned AACNT stripes, with an overlying, solid M1 pad, and a plurality of V0 vias positioned to avoid GATECNT-AACNT junction points;

FIG. 9CC depicts an exemplary mesh-style, NCEM-enabled pad, formed from a 10×9 grid of triple-patterned GATECNT and single-patterned AACNT stripes, with an overlying, solid M1 pad, and a plurality of V0 vias positioned to avoid GATECNT-AACNT junction points;

FIG. 9DD depicts an exemplary mesh-style, NCEM-enabled pad, formed from a 10×9 grid of triple-patterned GATECNT and double-patterned AACNT stripes, with an overlying, solid M1 pad, and a plurality of V0 vias positioned to avoid GATECNT-AACNT junction points;

FIG. 9EE depicts an exemplary mesh-style, NCEM-enabled pad, formed from a 10×9 grid of single-patterned GATECNT and triple-patterned AACNT stripes, with an overlying, solid M1 pad, and a plurality of V0 vias positioned to avoid GATECNT-AACNT junction points;

FIG. 9FF depicts an exemplary mesh-style, NCEM-enabled pad, formed from a 10×9 grid of double-patterned GATECNT and triple-patterned AACNT stripes, with an overlying, solid M1 pad, and a plurality of V0 vias positioned to avoid GATECNT-AACNT junction points, with an overlying, solid M1 pad, and a plurality of V0 vias positioned to avoid GATECNT-AACNT junction points;

FIG. 9GG depicts an exemplary mesh-style, NCEM-enabled pad, formed from a 10×9 grid of triple-patterned GATECNT and triple-patterned AACNT stripes, with an overlying, solid M1 pad, and a plurality of V0 vias positioned to avoid GATECNT-AACNT junction points;

FIG. 9HH depicts an exemplary mesh-style, NCEM-enabled pad, formed from a 10×9 grid of single-patterned GATECNT and single-patterned AACNT stripes, with an overlying, non-solid M1 pad, and a plurality of V0 vias positioned at GATECNT-AACNT junction points;

FIG. 9II depicts an exemplary mesh-style, NCEM-enabled pad, formed from a 10×9 grid of double-patterned GATECNT and single-patterned AACNT stripes, with an overlying, non-solid M1 pad, and a plurality of V0 vias positioned at GATECNT-AACNT junction points;

FIG. 9JJ depicts an exemplary mesh-style, NCEM-enabled pad, formed from a 10×9 grid of single-patterned GATECNT and double-patterned AACNT stripes, with an overlying, non-solid M1 pad, and a plurality of V0 vias positioned at GATECNT-AACNT junction points;

FIG. 9KK depicts an exemplary mesh-style, NCEM-enabled pad, formed from a 10×9 grid of double-patterned GATECNT and double-patterned AACNT stripes, with an overlying, non-solid M1 pad, and a plurality of V0 vias positioned at GATECNT-AACNT junction points;

FIG. 9LL depicts an exemplary mesh-style, NCEM-enabled pad, formed from a 10×9 grid of triple-patterned GATECNT and single-patterned AACNT stripes, with an overlying, non-solid M1 pad, and a plurality of V0 vias positioned at GATECNT-AACNT junction points;

FIG. 9MM depicts an exemplary mesh-style, NCEM-enabled pad, formed from a 10×9 grid of triple-patterned GATECNT and double-patterned AACNT stripes, with an overlying, non-solid M1 pad, and a plurality of V0 vias positioned at GATECNT-AACNT junction points;

FIG. 9NN depicts an exemplary mesh-style, NCEM-enabled pad, formed from a 10×9 grid of single-patterned GATECNT and triple-patterned AACNT stripes, with an overlying, non-solid M1 pad, and a plurality of V0 vias positioned at GATECNT-AACNT junction points;

FIG. 9OO depicts an exemplary mesh-style, NCEM-enabled pad, formed from a 10×9 grid of double-patterned GATECNT and triple-patterned AACNT stripes, with an overlying, non-solid M1 pad, and a plurality of V0 vias positioned at GATECNT-AACNT junction points;

FIG. 9PP depicts an exemplary mesh-style, NCEM-enabled pad, formed from a 10×9 grid of triple-patterned GATECNT and triple-patterned AACNT stripes, with an overlying, non-solid M1 pad, and a plurality of V0 vias positioned at GATECNT-AACNT junction points;

FIG. 9QQ depicts an exemplary mesh-style, NCEM-enabled pad, formed from a 10×9 grid of single-patterned GATECNT and single-patterned AACNT stripes, with an overlying, non-solid M1 pad, and a plurality of V0 vias positioned to avoid GATECNT-AACNT junction points;

FIG. 9RR depicts an exemplary mesh-style, NCEM-enabled pad, formed from a 10×9 grid of double-patterned GATECNT and single-patterned AACNT stripes, with an overlying, non-solid M1 pad, and a plurality of V0 vias positioned to avoid GATECNT-AACNT junction points;

FIG. 9SS depicts an exemplary mesh-style, NCEM-enabled pad, formed from a 10×9 grid of single-patterned GATECNT and double-patterned AACNT stripes, with an overlying, non-solid M1 pad, and a plurality of V0 vias positioned to avoid GATECNT-AACNT junction points;

FIG. 9TT depicts an exemplary mesh-style, NCEM-enabled pad, formed from a 10×9 grid of double-patterned GATECNT and double-patterned AACNT stripes, with an overlying, non-solid M1 pad, and a plurality of V0 vias positioned to avoid GATECNT-AACNT junction points;

FIG. 9UU depicts an exemplary mesh-style, NCEM-enabled pad, formed from a 10×9 grid of triple-patterned GATECNT and single-patterned AACNT stripes, with an overlying, non-solid M1 pad, and a plurality of V0 vias positioned to avoid GATECNT-AACNT junction points;

FIG. 9VV depicts an exemplary mesh-style, NCEM-enabled pad, formed from a 10×9 grid of triple-patterned GATECNT and double-patterned AACNT stripes, with an overlying, non-solid M1 pad, and a plurality of V0 vias positioned to avoid GATECNT-AACNT junction points;

FIG. 9WW depicts an exemplary mesh-style, NCEM-enabled pad, formed from a 10×9 grid of single-patterned GATECNT and triple-patterned AACNT stripes, with an overlying, non-solid M1 pad, and a plurality of V0 vias positioned to avoid GATECNT-AACNT junction points;

FIG. 9XX depicts an exemplary mesh-style, NCEM-enabled pad, formed from a 10×9 grid of double-patterned GATECNT and triple-patterned AACNT stripes, with an overlying, non-solid M1 pad, and a plurality of V0 vias positioned to avoid GATECNT-AACNT junction points;

FIG. 9YY depicts an exemplary mesh-style, NCEM-enabled pad, formed from a 10×9 grid of triple-patterned GATECNT and triple-patterned AACNT stripes, with an overlying, non-solid M1 pad, and a plurality of V0 vias positioned to avoid GATECNT-AACNT junction points;

FIG. 9ZZ depicts an exemplary mesh-style, NCEM-enabled pad, formed from a 10×9 grid of single-patterned GATECNT and single-patterned AACNT stripes, with an overlying, non-solid, double-patterned M1 pad, and a plurality of V0 vias positioned at GATECNT-AACNT junction points;

FIG. 9AAA depicts an exemplary mesh-style, NCEM-enabled pad, formed from a 10×9 grid of double-patterned GATECNT and single-patterned AACNT stripes, with an overlying, non-solid, double-patterned M1 pad, and a plurality of V0 vias positioned at GATECNT-AACNT junction points;

FIG. 9BBB depicts an exemplary mesh-style, NCEM-enabled pad, formed from a 10×9 grid of single-patterned GATECNT and double-patterned AACNT stripes, with an overlying, non-solid, double-patterned M1 pad, and a plurality of V0 vias positioned at GATECNT-AACNT junction points;

FIG. 9CCC depicts an exemplary mesh-style, NCEM-enabled pad, formed from a 10×9 grid of double-patterned GATECNT and double-patterned AACNT stripes, with an overlying, non-solid, double-patterned M1 pad, and a plurality of V0 vias positioned at GATECNT-AACNT junction points;

FIG. 9DDD depicts an exemplary mesh-style, NCEM-enabled pad, formed from a 10×9 grid of triple-patterned GATECNT and single-patterned AACNT stripes, with an overlying, non-solid, double-patterned M1 pad, and a plurality of V0 vias positioned at GATECNT-AACNT junction points;

FIG. 9EEE depicts an exemplary mesh-style, NCEM-enabled pad, formed from a 10×9 grid of triple-patterned GATECNT and double-patterned AACNT stripes, with an overlying, non-solid, double-patterned M1 pad, and a plurality of V0 vias positioned at GATECNT-AACNT junction points;

FIG. 9FFF depicts an exemplary mesh-style, NCEM-enabled pad, formed from a 10×9 grid of single-patterned GATECNT and triple-patterned AACNT stripes, with an overlying, non-solid, double-patterned M1 pad, and a plurality of V0 vias positioned at GATECNT-AACNT junction points;

FIG. 9GGG depicts an exemplary mesh-style, NCEM-enabled pad, formed from a 10×9 grid of double-patterned GATECNT and triple-patterned AACNT stripes, with an overlying, non-solid, double-patterned M1 pad, and a plurality of V0 vias positioned at GATECNT-AACNT junction points;

FIG. 9HHH depicts an exemplary mesh-style, NCEM-enabled pad, formed from a 10×9 grid of triple-patterned GATECNT and triple-patterned AACNT stripes, with an overlying, non-solid, double-patterned M1 pad, and a plurality of V0 vias positioned at GATECNT-AACNT junction points;

FIG. 9III depicts an exemplary mesh-style, NCEM-enabled pad, formed from a 10×9 grid of single-patterned GATECNT and single-patterned AACNT stripes, with an overlying, non-solid, double-patterned M1 pad, and a plurality of V0 vias positioned to avoid GATECNT-AACNT junction points;

FIG. 9JJJ depicts an exemplary mesh-style, NCEM-enabled pad, formed from a 10×9 grid of double-patterned GATECNT and single-patterned AACNT stripes, with an overlying, non-solid, double-patterned M1 pad, and a plurality of V0 vias positioned to avoid GATECNT-AACNT junction points;

FIG. 9KKK depicts an exemplary mesh-style, NCEM-enabled pad, formed from a 10×9 grid of single-patterned GATECNT and double-patterned AACNT stripes, with an overlying, non-solid, double-patterned M1 pad, and a plurality of V0 vias positioned to avoid GATECNT-AACNT junction points;

FIG. 9LLL depicts an exemplary mesh-style, NCEM-enabled pad, formed from a 10×9 grid of double-patterned GATECNT and double-patterned AACNT stripes, with an overlying, non-solid, double-patterned M1 pad, and a plurality of V0 vias positioned to avoid GATECNT-AACNT junction points;

FIG. 9MMM depicts an exemplary mesh-style, NCEM-enabled pad, formed from a 10×9 grid of triple-patterned GATECNT and single-patterned AACNT stripes, with an overlying, non-solid, double-patterned M1 pad, and a plurality of V0 vias positioned to avoid GATECNT-AACNT junction points;

FIG. 9NNN depicts an exemplary mesh-style, NCEM-enabled pad, formed from a 10×9 grid of triple-patterned GATECNT and double-patterned AACNT stripes, with an overlying, non-solid, double-patterned M1 pad, and a plurality of V0 vias positioned to avoid GATECNT-AACNT junction points;

FIG. 9OOO depicts an exemplary mesh-style, NCEM-enabled pad, formed from a 10×9 grid of single-patterned GATECNT and triple-patterned AACNT stripes, with an overlying, non-solid, double-patterned M1 pad, and a plurality of V0 vias positioned to avoid GATECNT-AACNT junction points;

FIG. 9PPP depicts an exemplary mesh-style, NCEM-enabled pad, formed from a 10×9 grid of double-patterned GATECNT and triple-patterned AACNT stripes, with an overlying, non-solid, double-patterned M1 pad, and a plurality of V0 vias positioned to avoid GATECNT-AACNT junction points;

FIG. 9QQQ depicts an exemplary mesh-style, NCEM-enabled pad, formed from a 10×9 grid of triple-patterned GATECNT and triple-patterned AACNT stripes, with an overlying, non-solid, double-patterned M1 pad, and a plurality of V0 vias positioned to avoid GATECNT-AACNT junction points;

FIG. 9RRR depicts an exemplary mesh-style, NCEM-enabled pad, formed from a 10×9 grid of single-patterned GATECNT and single-patterned AACNT stripes, with an overlying, non-solid, triple-patterned M1 pad, and a plurality of V0 vias positioned at GATECNT-AACNT junction points;

FIG. 9SSS depicts an exemplary mesh-style, NCEM-enabled pad, formed from a 10×9 grid of double-patterned GATECNT and single-patterned AACNT stripes, with an overlying, non-solid, triple-patterned M1 pad, and a plurality of V0 vias positioned at GATECNT-AACNT junction points;

FIG. 9TTT depicts an exemplary mesh-style, NCEM-enabled pad, formed from a 10×9 grid of single-patterned GATECNT and double-patterned AACNT stripes, with an overlying, non-solid, triple-patterned M1 pad, and a plurality of V0 vias positioned at GATECNT-AACNT junction points;

FIG. 9OOO depicts an exemplary mesh-style, NCEM-enabled pad, formed from a 10×9 grid of double-patterned GATECNT and double-patterned AACNT stripes, with an overlying, non-solid, triple-patterned M1 pad, and a plurality of V0 vias positioned at GATECNT-AACNT junction points;

FIG. 9VVV depicts an exemplary mesh-style, NCEM-enabled pad, formed from a 10×9 grid of triple-patterned GATECNT and single-patterned AACNT stripes, with an overlying, non-solid, triple-patterned M1 pad, and a plurality of V0 vias positioned at GATECNT-AACNT junction points;

FIG. 9WWW depicts an exemplary mesh-style, NCEM-enabled pad, formed from a 10×9 grid of triple-patterned GATECNT and double-patterned AACNT stripes, with an overlying, non-solid, triple-patterned M1 pad, and a plurality of V0 vias positioned at GATECNT-AACNT junction points;

FIG. 9XXX depicts an exemplary mesh-style, NCEM-enabled pad, formed from a 10×9 grid of single-patterned GATECNT and triple-patterned AACNT stripes, with an overlying, non-solid, triple-patterned M1 pad, and a plurality of V0 vias positioned at GATECNT-AACNT junction points;

FIG. 9YYY depicts an exemplary mesh-style, NCEM-enabled pad, formed from a 10×9 grid of double-patterned GATECNT and triple-patterned AACNT stripes, with an overlying, non-solid, triple-patterned M1 pad, and a plurality of V0 vias positioned at GATECNT-AACNT junction points;

FIG. 9ZZZ depicts an exemplary mesh-style, NCEM-enabled pad, formed from a 10×9 grid of triple-patterned GATECNT and triple-patterned AACNT stripes, with an overlying, non-solid, triple-patterned M1 pad, and a plurality of V0 vias positioned at GATECNT-AACNT junction points;

FIG. 9AAAA depicts an exemplary mesh-style, NCEM-enabled pad, formed from a 10×9 grid of single-patterned GATECNT and single-patterned AACNT stripes, with an overlying, non-solid, triple-patterned M1 pad, and a plurality of V0 vias positioned to avoid GATECNT-AACNT junction points;

FIG. 9BBBB depicts an exemplary mesh-style, NCEM-enabled pad, formed from a 10×9 grid of double-patterned GATECNT and single-patterned AACNT stripes, with an overlying, non-solid, triple-patterned M1 pad, and a plurality of V0 vias positioned to avoid GATECNT-AACNT junction points;

FIG. 9CCCC depicts an exemplary mesh-style, NCEM-enabled pad, formed from a 10×9 grid of single-patterned GATECNT and double-patterned AACNT stripes, with an overlying, non-solid, triple-patterned M1 pad, and a plurality of V0 vias positioned to avoid GATECNT-AACNT junction points;

FIG. 9DDDD depicts an exemplary mesh-style, NCEM-enabled pad, formed from a 10×9 grid of double-patterned GATECNT and double-patterned AACNT stripes, with an overlying, non-solid, triple-patterned M1 pad, and a plurality of V0 vias positioned to avoid GATECNT-AACNT junction points;

FIG. 9EEEE depicts an exemplary mesh-style, NCEM-enabled pad, formed from a 10×9 grid of triple-patterned GATECNT and single-patterned AACNT stripes, with an overlying, non-solid, triple-patterned M1 pad, and a plurality of V0 vias positioned to avoid GATECNT-AACNT junction points;

FIG. 9FFFF depicts an exemplary mesh-style, NCEM-enabled pad, formed from a 10×9 grid of triple-patterned GATECNT and double-patterned AACNT stripes, with an overlying, non-solid, triple-patterned M1 pad, and a plurality of V0 vias positioned to avoid GATECNT-AACNT junction points;

FIG. 9GGGG depicts an exemplary mesh-style, NCEM-enabled pad, formed from a 10×9 grid of single-patterned GATECNT and triple-patterned AACNT stripes, with an overlying, non-solid, triple-patterned M1 pad, and a plurality of V0 vias positioned to avoid GATECNT-AACNT junction points;

FIG. 9HHHH depicts an exemplary mesh-style, NCEM-enabled pad, formed from a 10×9 grid of double-patterned GATECNT and triple-patterned AACNT stripes, with an overlying, non-solid, triple-patterned M1 pad, and a plurality of V0 vias positioned to avoid GATECNT-AACNT junction points;

FIG. 9IIII depicts an exemplary mesh-style, NCEM-enabled pad, formed from a 10×9 grid of triple-patterned GATECNT and triple-patterned AACNT stripes, with an overlying, non-solid, triple-patterned M1 pad, and a plurality of V0 vias positioned to avoid GATECNT-AACNT junction points;

FIG. 40 shows the logical OR of patterning within both expanded test areas (of FIGS. 37 & 38);

FIG. 41 depicts an exemplary process flow, suitable for use in connection with certain embodiments of the invention;

FIG. 42 depicts an exemplary process flow for obtaining and (optionally) using measurements from mesh-style NCEM pads;

FIG. 43 depicts another exemplary process flow, suitable for use in accordance with certain embodiments of the invention;

FIG. 44 depicts a plan view of an exemplary M1-snake-open-configured, NCEM-enabled fill cell;

FIG. 45 depicts a plan view of an exemplary AACNT-tip-to-side-short-configured, NCEM-enabled fill cell;

Figure 47B:
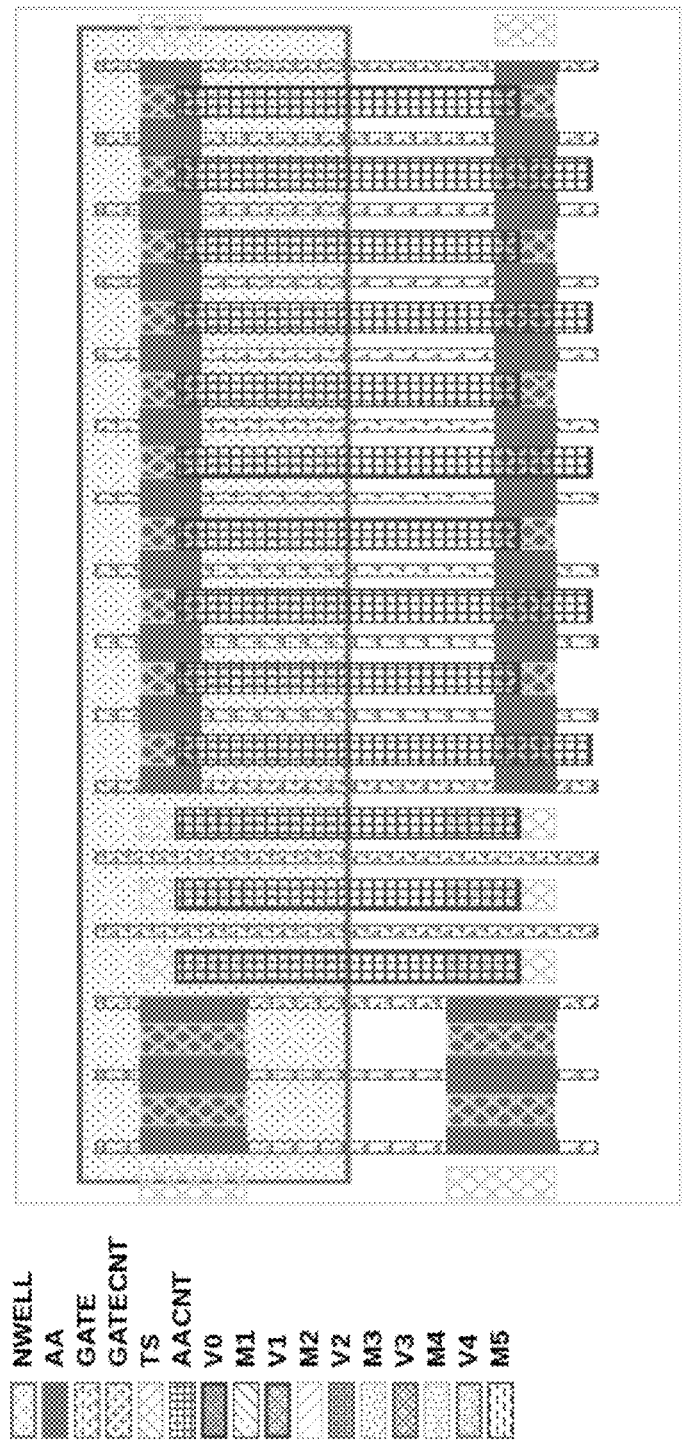
Figure 49B:
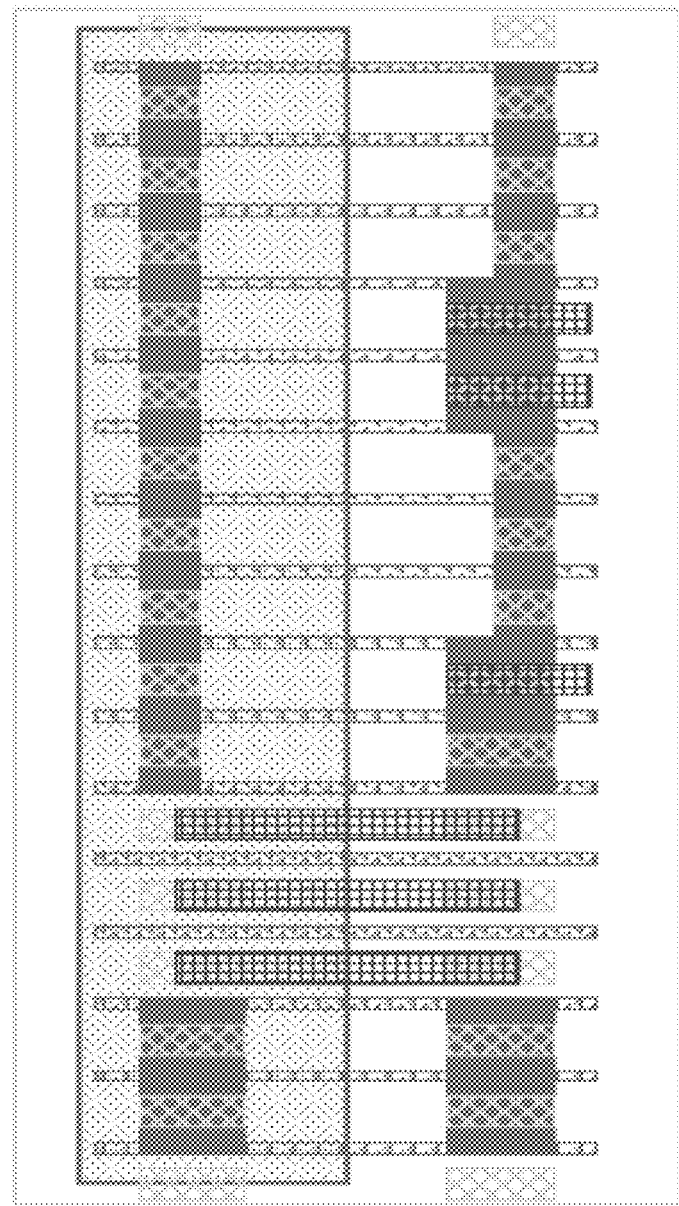
Figure 49C:
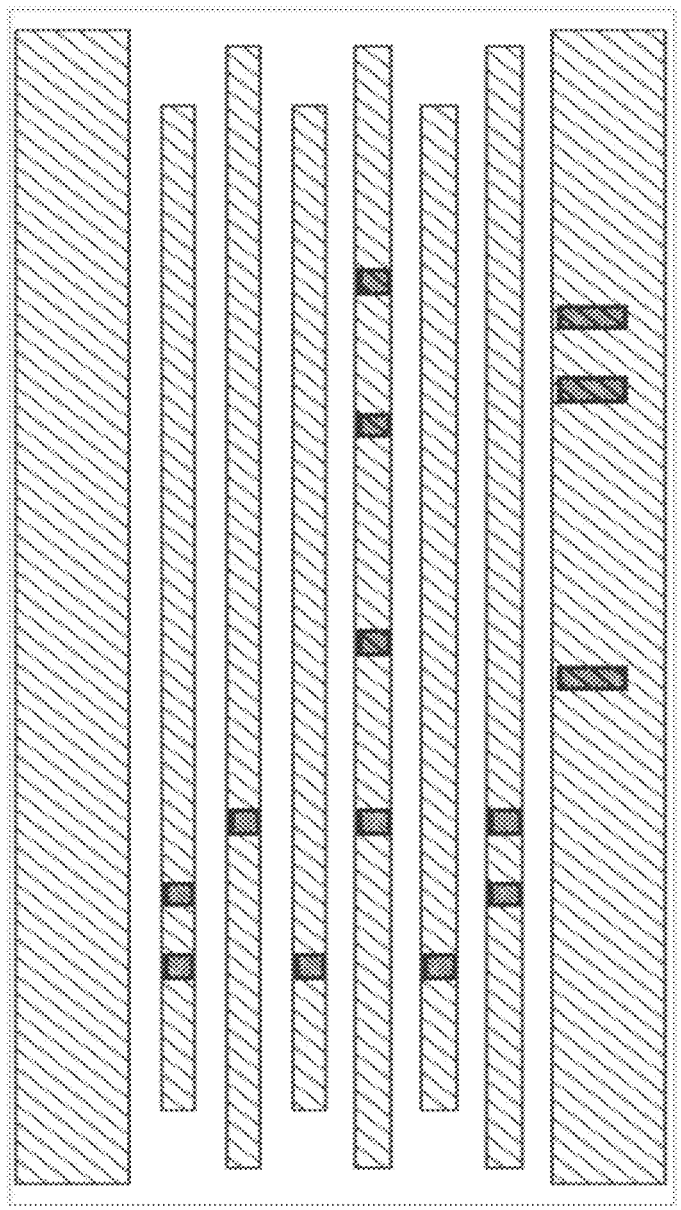

FIGS. 46A-C respectively depict plan views of—(A) all layers; (B) NWELL, AA, GATE, GATECNT, TS, and AACNT layers; (C) V0 and M1 layers—of an exemplary TS-GATE-side-to-side-short-configured, NCEM-enabled fill cell of type PDF_D_VCI_V16_14S1_01;

FIGS. 47A-C respectively depict plan views of—(A) all layers; (B) NWELL, AA, GATE, GATECNT, TS, and AACNT layers; (C) V0 and M1 layers—of an exemplary GATECNT-AACNT-side-to-side-short-configured, NCEM-enabled fill cell of type PDF_D_VCI_V16_14S1_05;

FIGS. 48A-C respectively depict plan views of—(A) all layers; (B) NWELL, AA, GATE, GATECNT, TS, and AACNT layers; (C) V0 and M1 layers—of an exemplary GATECNT-via-open-configured, NCEM-enabled fill cell of type PDF_D_VCI_V16_14S1_08;

FIGS. 49A-C respectively depict plan views of—(A) all layers; (B) NWELL, AA, GATE, GATECNT, TS, and AACNT layers; (C) V0 and M1 layers—of an exemplary GATE-AA-tip-to-side-short-configured, NCEM-enabled fill cell of type PDF_D_VCI_V16_14S1_11; and, FIGS. 50A-C respectively depict plan views of—(A) all layers; (B) NWELL, AA, GATE, GATECNT, TS, and AACNT layers; (C) V0 and M1 layers—of an exemplary GATE-AA-tip-to-side-short-configured, NCEM-enabled fill cell of type PDF_D_VCI_V16_14S1_12.

DESCRIPTION OF EXEMPLARY/PREFERRED EMBODIMENT(S)

Figure 1:
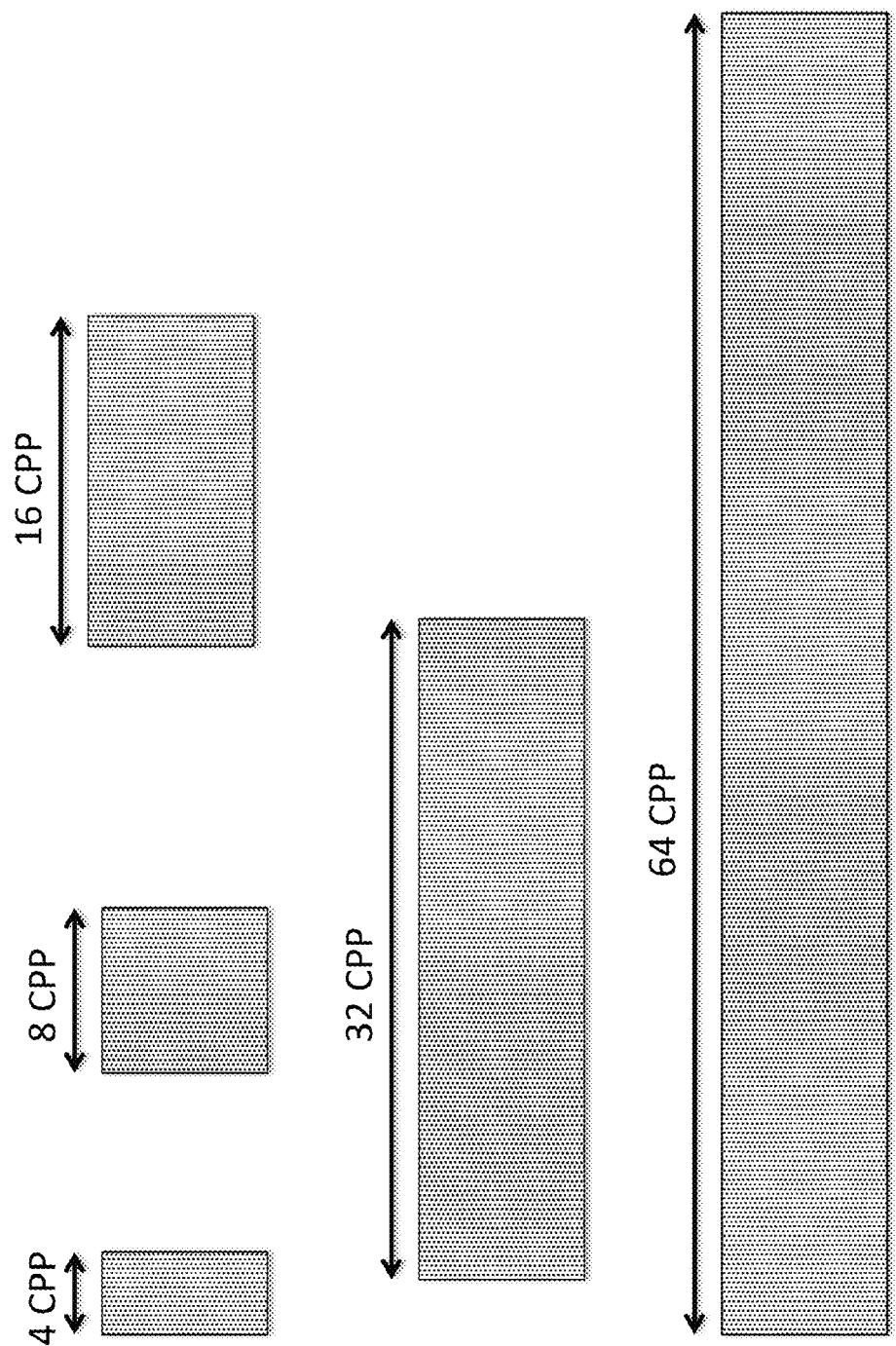
FIG. 1 depicts an outline of illustrative fill cells, suitable for use in connection certain embodiments of the invention.

Reference is now made to FIG. 1, which depicts an outline of illustrative fill cells suitable for use in connection certain embodiments of the invention, such fill cells are typically provided in a uniform height and various widths, traditionally multiples of the minimum contacted poly pitch (CPP) permitted by the fabrication process. FIG. 1 includes fill cells of width 4 CPP, 8 CPP, 16 CPP, 32 CPP, and 64 CPP, but any collection of widths—or just a single width—is possible. Furthermore, certain embodiments of the invention may include double or triple height fill cells, as well. As persons skilled in the art will appreciate, traditional fill cells include certain features necessary for compatibility with the logic cells used to form circuits on the chip. Such necessary features include a height that is consistent with logic cells in the library (or an integer multiple of that height), as well as power/ground rails that extend horizontally across the fill cells (traditionally, though not necessarily, at the top and bottom of each cell). Such necessary features are preferably maintained in the NCEM-enabled fill cells used in connection with the present invention.

Figure 2:
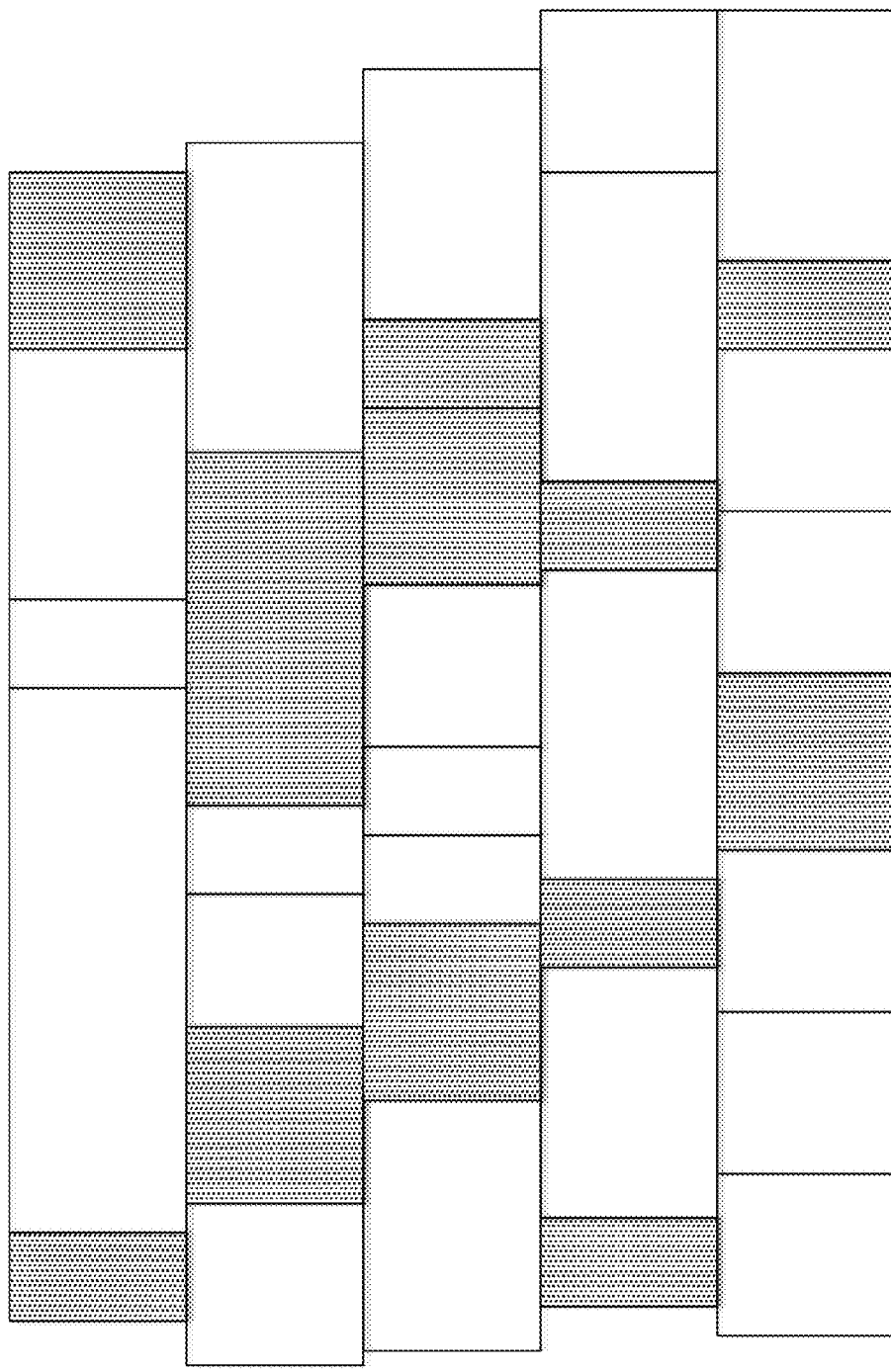
FIG. 2 depicts an exemplary standard cell logic section with (shaded) NCEM-enabled fill cells, of various widths.

Reference is now made to FIG. 2, which depicts an exemplary standard cell logic section with (shaded) NCEM-enabled fill cells, of various widths. As depicted, the NCEM-enabled fill cells are preferably instantiated wherever a traditional fill cell would otherwise be placed. However, the invention places no restriction on the distribution of such NCEM-enabled fill cells. While they would typically appear in each standard cell row, they need not. The fill cell placement can be regular, semi-regular (e.g., at least one fill cell every X nm, or every Y cells), or irregular. Two fill cells can be adjacent to each other. There may be some double height (or greater) fill cells. And the logic section may include both NCEM-enabled as well as other types of fill cells.

Figure 3:
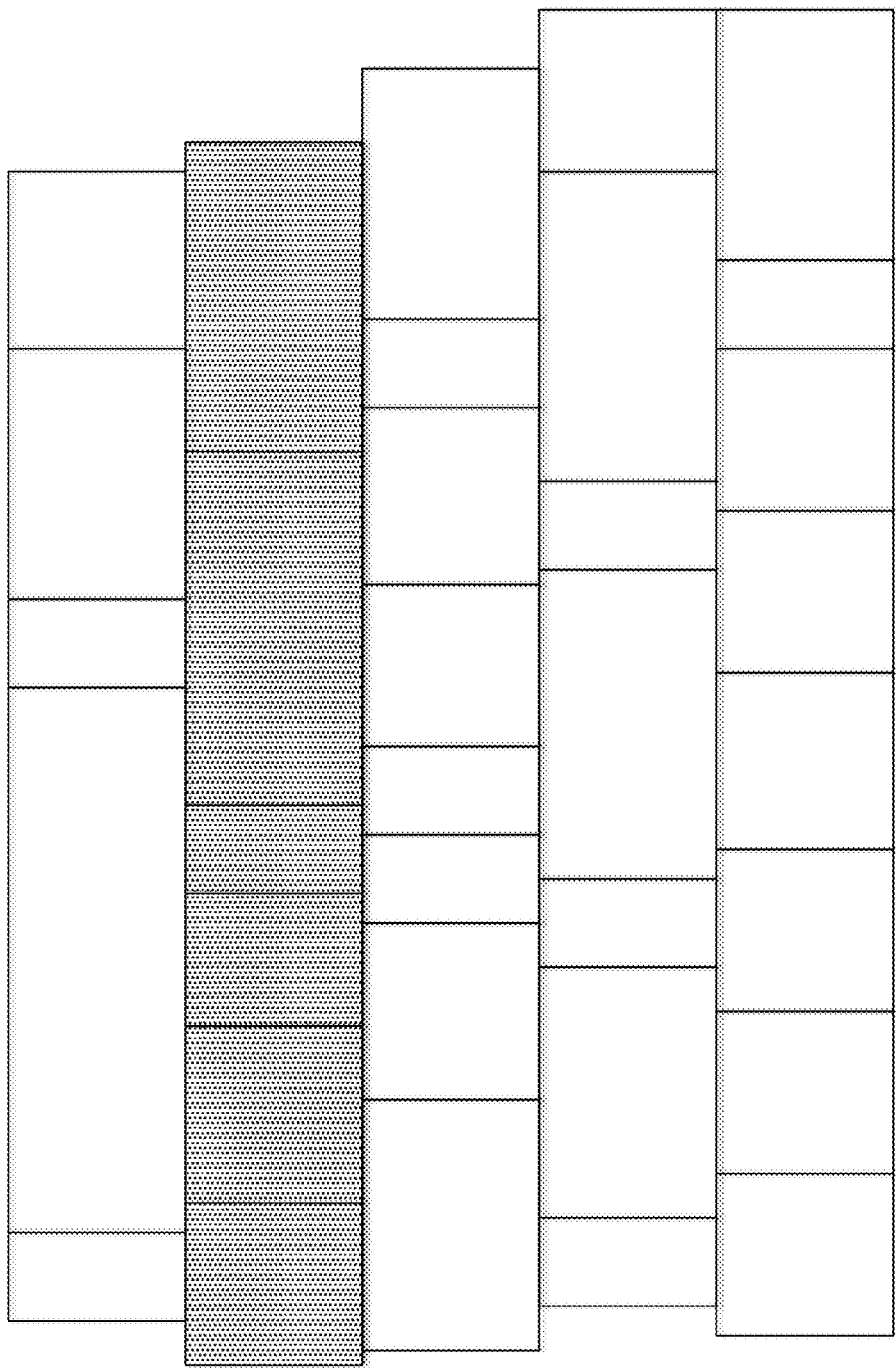
FIG. 3 depicts an exemplary standard cell logic section with a row (or portion thereof) that contains NCEM-enabled fill cells, of various widths.

Reference is now made to FIG. 3, which depicts an exemplary standard cell logic section with a row (or portion thereof) that contains NCEM-enabled fill cells, of various widths. As depicted, certain embodiments of the invention may include complete row(s), or contiguous portion(s) thereof, populated entirely with NCEM-enabled fill cells.

Such row(s) may include fill cells of varying or fixed widths, and such row(s) may be adjacent or separated, and may be distributed regularly, semi-regularly or irregularly throughout the logic section.

Figure 4:
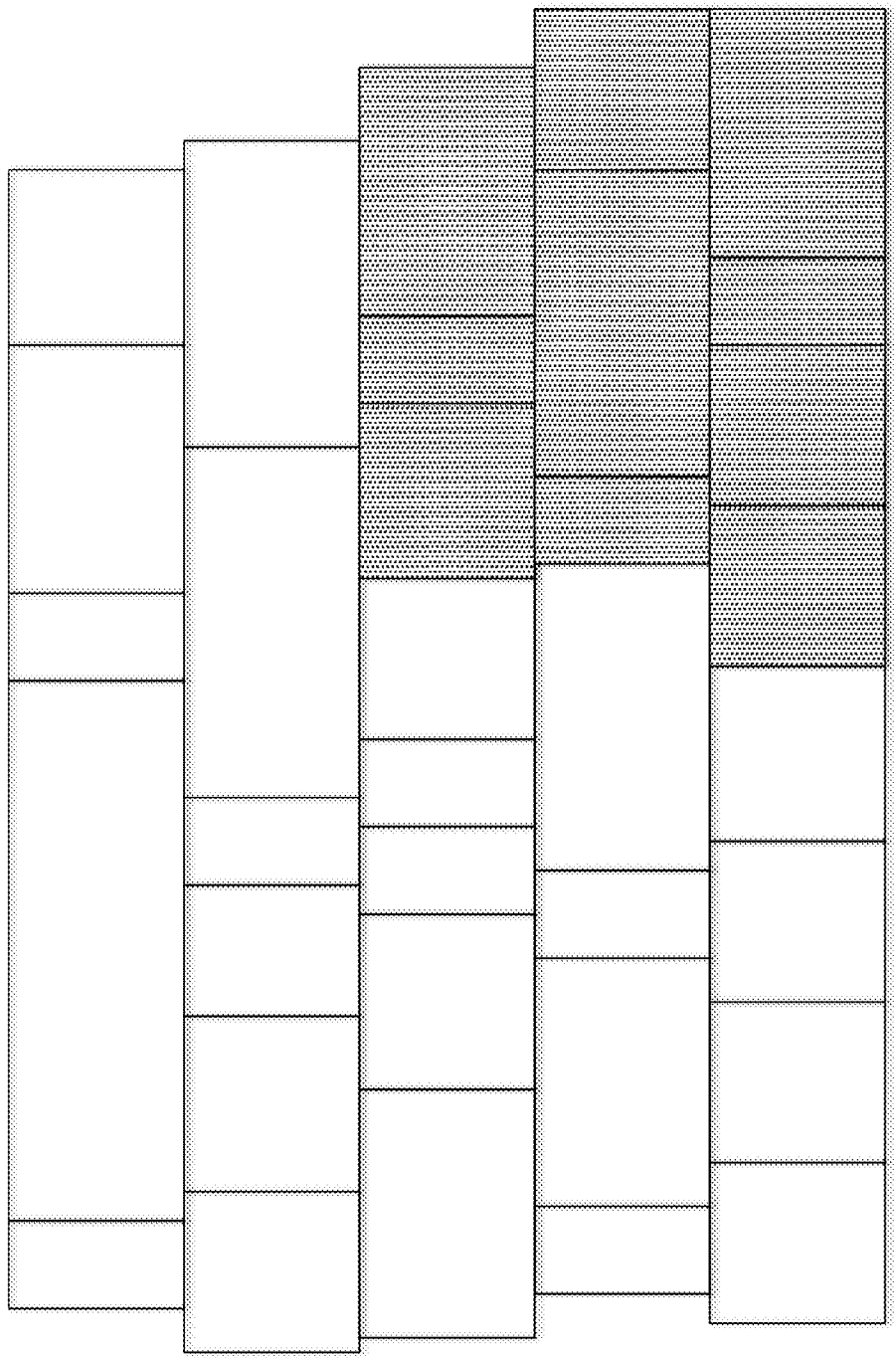
FIG. 4 depicts an exemplary standard cell logic section with a test block area (lower right portion) populated with NCEM-enabled fill cells, of various widths.

Reference is now made to FIG. 4, which depicts an exemplary standard cell logic section with a test block area (lower right portion) populated with NCEM-enabled fill cells, of various widths. Such test block section(s) need not be entirely contiguous, need not be generally rectangular or square, may include fill cells of a single width or multiple widths, and one or multiple heights.

Figure 5:
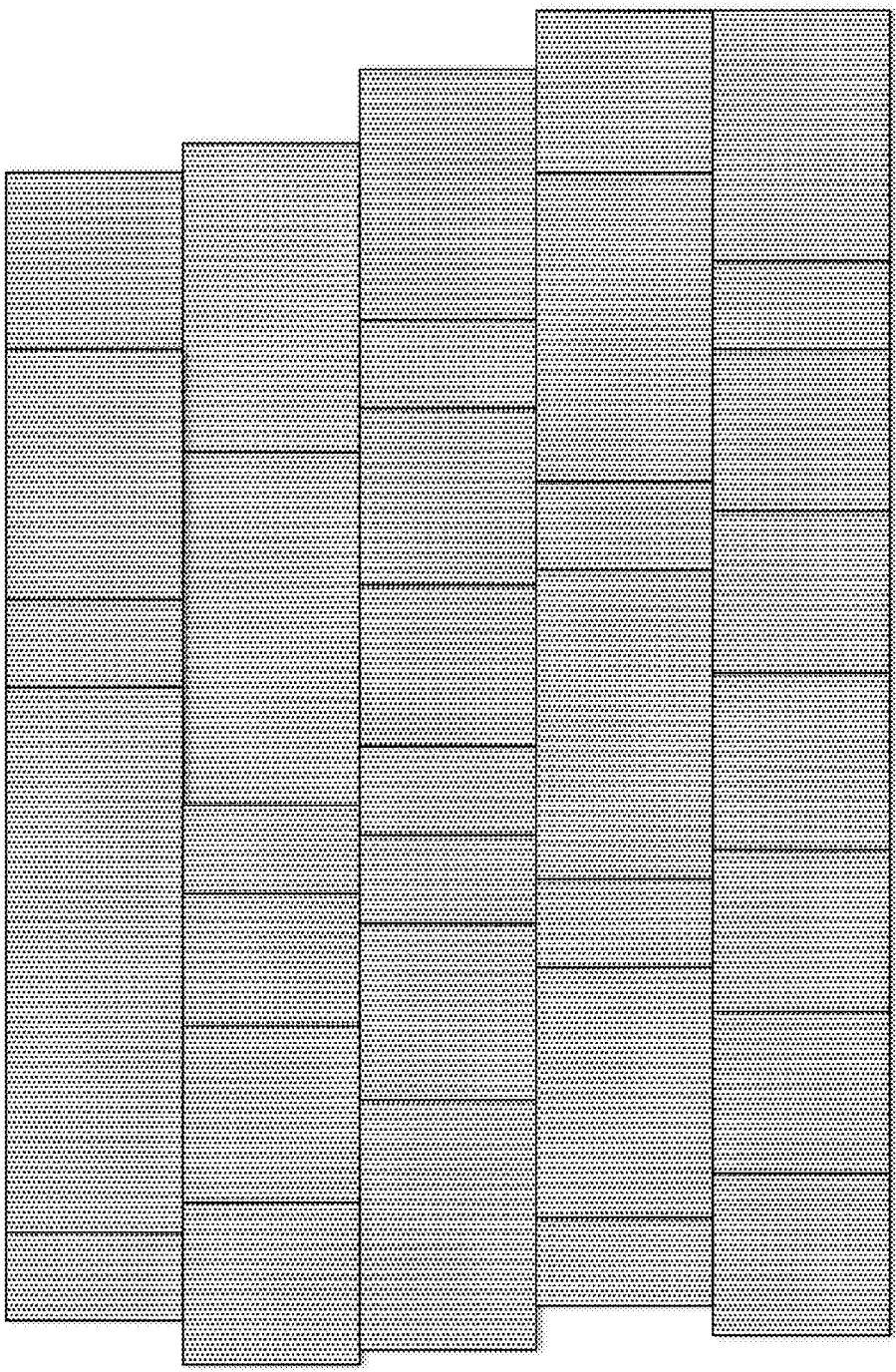
FIG. 5 depicts an exemplary portion of a test chip/wafer comprised of NCEM-enabled fill cells, of various widths.

Reference is now made to FIG. 5, which depicts an exemplary portion of a test chip/wafer comprised of NCEM-enabled fill cells, of various widths. Such test vehicles may comprise a die, a chip, a wafer, or a portion of any of these. Such test vehicles need not be entirely contiguous, may have any overall shape, and may include fill cells of a single width or multiple widths, and one or multiple heights.

Figure 6:
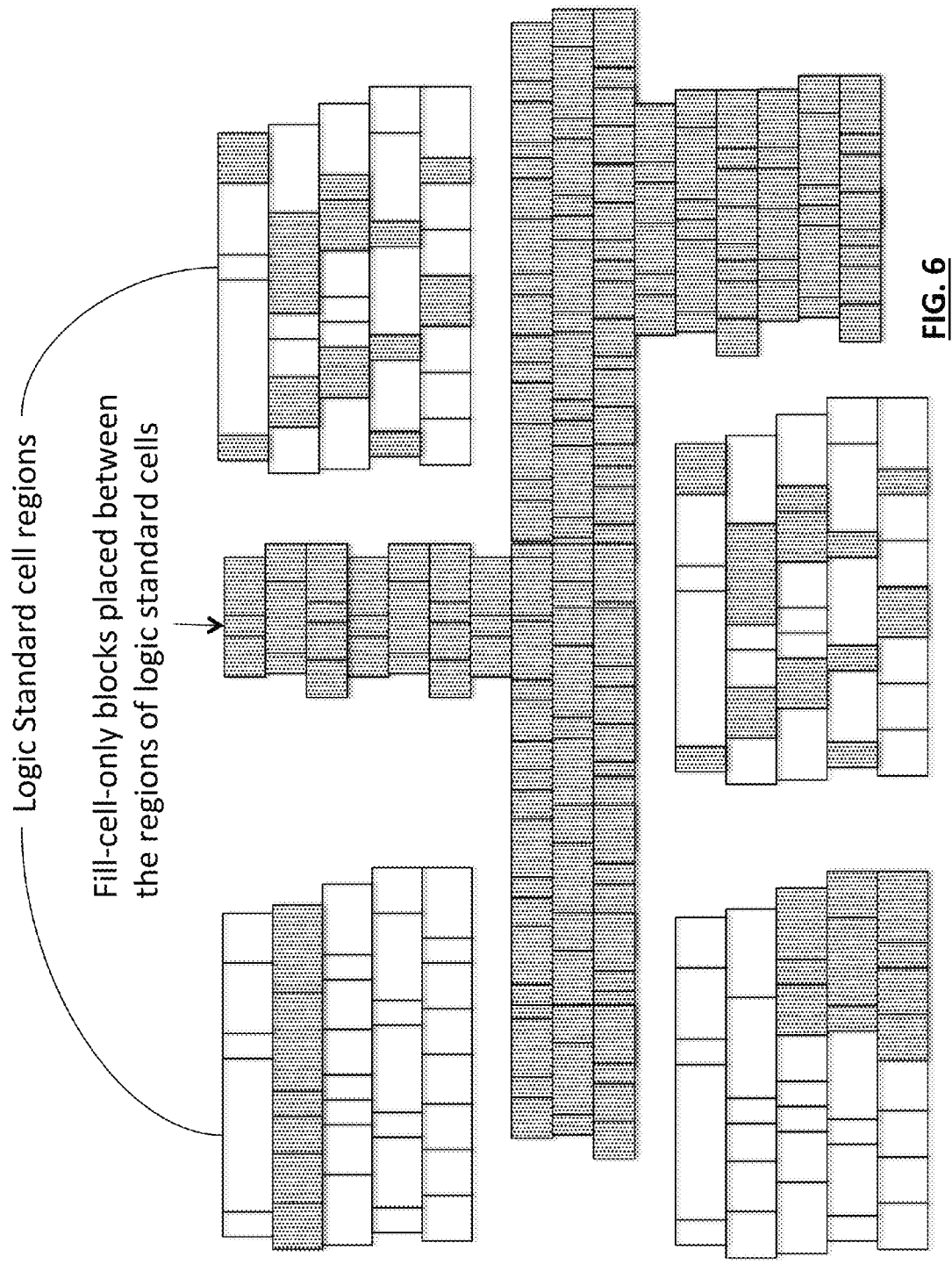
FIG. 6 conceptually depicts a portion of an exemplary chip/wafer in which a region comprised only (or almost only) of NCEM-enabled fill cells is positioned between two or more standard cell regions.

Reference is now made to FIG. 6, which conceptually depicts a portion of an exemplary chip/die/wafer with a region comprised only (or almost only) of NCEM-enabled fill cells positioned between two or more standard cell regions (such as those of FIGS. 2-5). As persons skilled in the art will appreciate, FIG. 6 illustrates how various embodiments of the invention may instantiate/distribute the inventive NCEM-enabled fill cells (and DOEs based on them) in any manner whatsoever, and that the distribution patterns—both regular and irregular—may vary throughout different regions of a chip or wafer.

As persons skilled in the art will appreciate, the configurations of FIGS. 2-5 and 6 are mere examples of many available possibilities, and are not intended to be limiting or exhaustive. Furthermore, such skilled persons will appreciate that any given die, chip or wafer may include a combination of these and/or other possible configurations.

Figure 7:
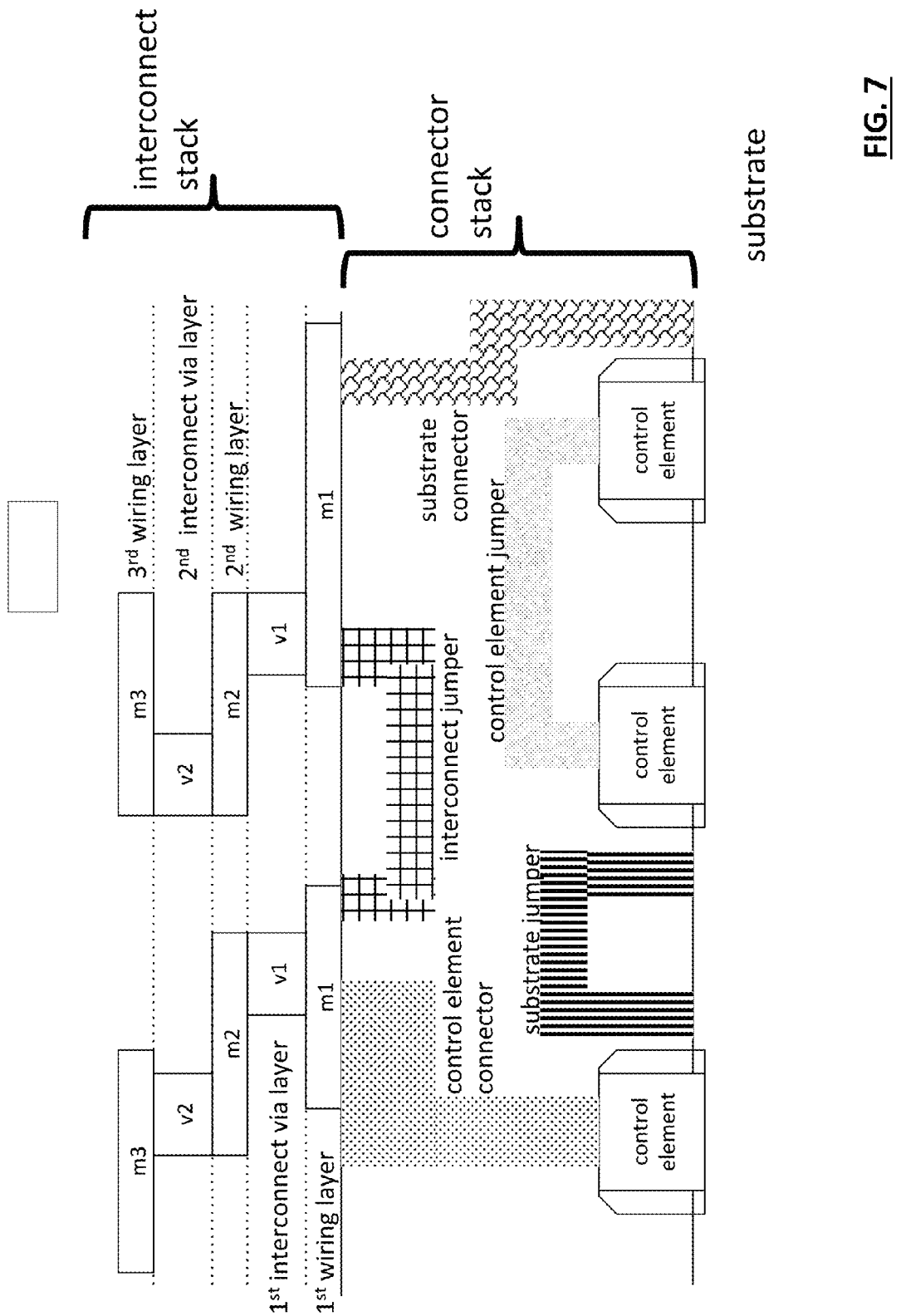
FIG. 7 depicts a cross-sectional, topological view of a monolithic IC structure.

Reference is now made to FIG. 7, which depicts cross-sectional, topological view of a monolithic IC structure to which the invention may be applied. This topological view depicts—from bottom to top—three vertically defined portions: (i) substrate; (ii) connector stack; and (iii) interconnect stack.

The substrate preferably comprises a wafer, die, or other portion of monocrystalline silicon, or another substrate suitable for forming semiconductor devices, such as silicon-on-insulator (SOI), Ge, C, GaAs, InP, GaInAs, AlAs, GaSb, (Ga,Mn)As, GaP, GaN, InAS, SiGe, SiSn, CdSe, CdTe, CdHgTe, ZnS, SiC, etc. Generally speaking, the substrate represents the object to which manufacturing steps (e.g., deposition, masking, etching, implantation) are initially applied, and is the object within which, or upon which, switching devices (e.g., FETs, bipolar transistors, photodiodes, magnetic devices, etc.) or storage devices (e.g., charged oxides, capacitors, phase change memories, etc.) are built.

Figure 8:
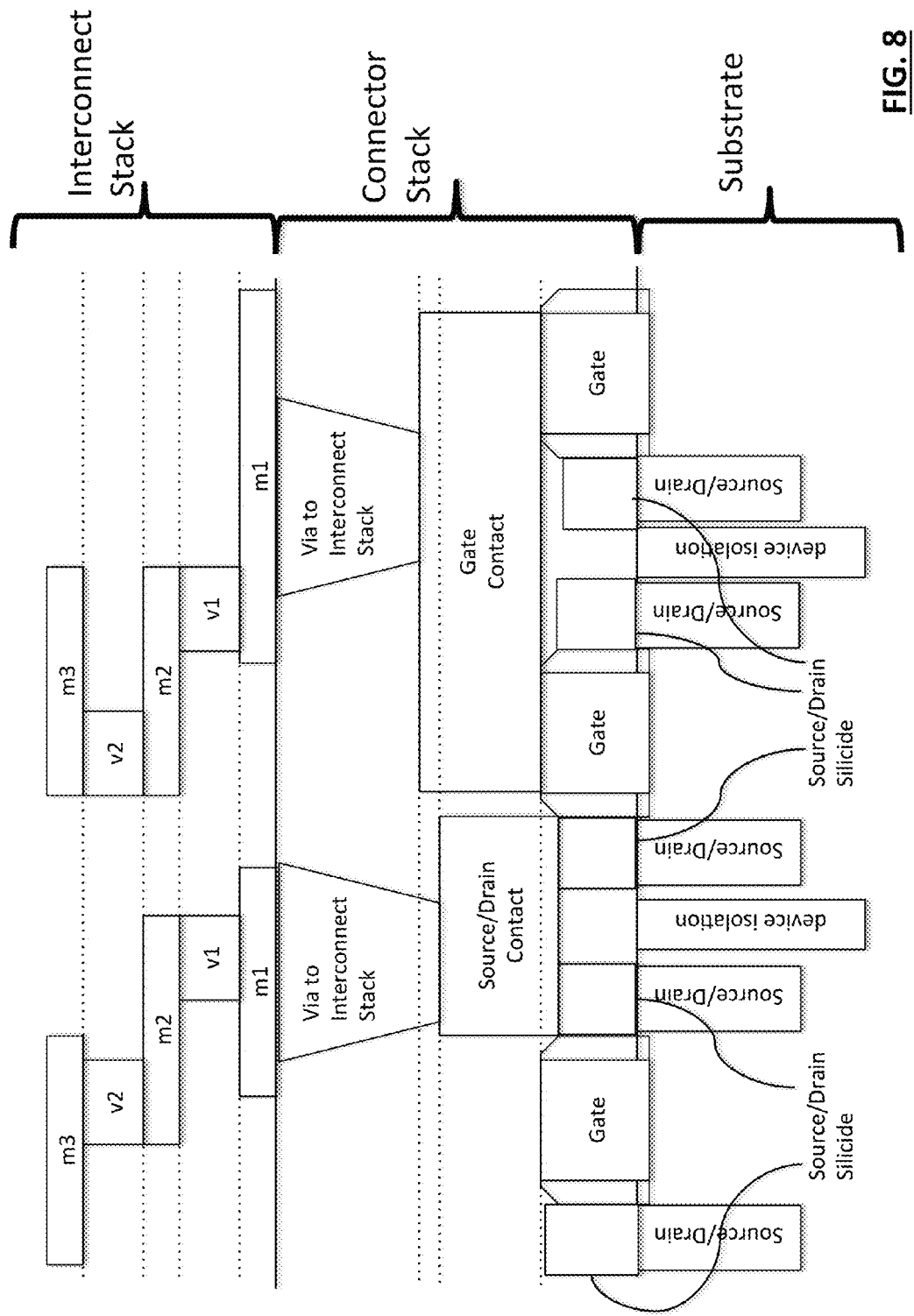
FIG. 8 depicts a physical layer stack for an exemplary CMOS process.

The connector stack is a collection of multiple layers, generally formed on top of the substrate, that supports localized connections between devices in, or on, the substrate, and/or connections to wires in an interconnect stack located above. The layers that make up the connector stack need not be strictly "stacked"; some can be partially or fully co-planar. For example, as illustrated in FIG. 8, which depicts a physical view of an exemplary CMOS layer stack, the source/drain contact and gate contact layers are partially co-planar because they share vertical extent, but on the bottom, the source/drain contact layer extends below the bottom of the gate contact layer, and on the top, the gate contact layer extends above the top of the source/drain contact layer. An example of full co-planarity would be where these two layers had identical vertical extent.

The connector stack supports various types of "connectors" and "jumpers," as illustrated in FIG. 7. These illustrative connectors and jumpers are not intended to represent individual physical layers, but rather conductive pathways that connect the identified elements. As persons skilled in the art will appreciate, each connector or jumper can be implemented using one or more manufactured "layers," where some layers may appear as parts of multiple types of connectors/jumpers.

FIG. 7. specifically illustrates the following connectors/jumpers:

Control element connector
    A conductive pathway between (i) one or more control elements and (ii) a wire in the first (e.g., m1) layer of the interconnect stack. Control element connectors will also contact any interconnect jumpers, substrate connectors, or control element jumpers that they cross.

Substrate connector
    A conductive pathway between (i) a portion of the substrate and (ii) a wire in the first layer of the interconnect stack. Substrate connectors will also contact any interconnect jumpers, substrate jumpers, control element connectors, or control element jumpers that they cross.

Substrate jumper
    A conductive pathway between two portions of the substrate that would not be connected without the substrate jumper. Substrate jumpers will also contact any substrate connectors—but not interconnect jumpers—that they cross.

Interconnect jumper
    A conductive pathway between two wires in the first interconnect layer that would not be connected without the interconnect jumper. Interconnect jumpers will also contact any substrate connectors or control element connectors that they cross.

Control element jumper
    A conductive pathway between two control elements. Control element jumpers will also contact any control elements, control element connectors, or substrate connectors that they cross.

Non-adjacent control element jumper, not depicted in FIG. 7, but defined as follows:
    A conductive pathway between two control elements. Non-adjacent control element jumpers can pass over other control elements without contacting them. Non-adjacent control element jumpers will contact any control element connectors or substrate connectors that they cross.

Above the connector stack lies the interconnect stack. The interconnect stack is comprised of conductive wiring layers (labeled "m1," "m2," etc.—that need only be conductive, not necessarily metallic) with conductive vias (labeled "v1," "v2," etc.) that connect adjacent wiring layers. While three wiring layers are shown in FIGS. 7-8, it is understood that this number could vary from one to ten or more. Furthermore, while the vias and wiring layers in FIGS. 7-8 are shown as non-overlapping, it is possible for vias to extend into one or both of the wiring layers that they connect, or traverse more than two wiring layers.

Reference is now made to FIG. 8, which depicts a (simplified) layer stack for an exemplary CMOS process, with the correspondence between major regions—substrate, connector stack, interconnect stack—and process layers indicated on the drawing. As depicted in FIG. 8, the substrate hosts the source(s)/drain(s) of the FETs, the device isolation trenches (STI), and a lower portion of the gate(s). The connector stack implements the upper portions of the gate(s), the source/drain silicide(s), source/drain contact(s), gate contact(s), and via(s) to the interconnect stack. The interconnect stack contains multiple wiring (m1, m2, . . . ) layers, with vias (v1, v2, . . . ) between adjacent wiring layers.

The vendor-independent layers of FIG. 8 can be readily mapped to those of commercial CMOS processes, such as GlobalFoundries ("GF") (see U.S. Pat. Pub. Nos. US2014/0302660A1 and US2015/0170735A1 re the "GF layers") or Taiwan Semiconductor Manufacturing Co. ("TSMC") (see U.S. Pat. Pub. No. US2014/0210014A1 re the "TSMC layers"). Below is an exemplary mapping:

| FIG. 8 layer | GF layer | TSMC layer |
| --- | --- | --- |
| gate (GATE) | PC | PO |
| source/drain (AA) | RX | OD |
| source/drain suicide (TS) | TS | M0_OD1 |
| gate contact (GATECNT) | CB | M0_PO |
| source/drain contact (AACNT) | CA | M0_OD2 |
| via to interconnect stack (V0) | V0 | Via0 |
| first wiring layer (M1) | M1 | M1 |

Figure 10:
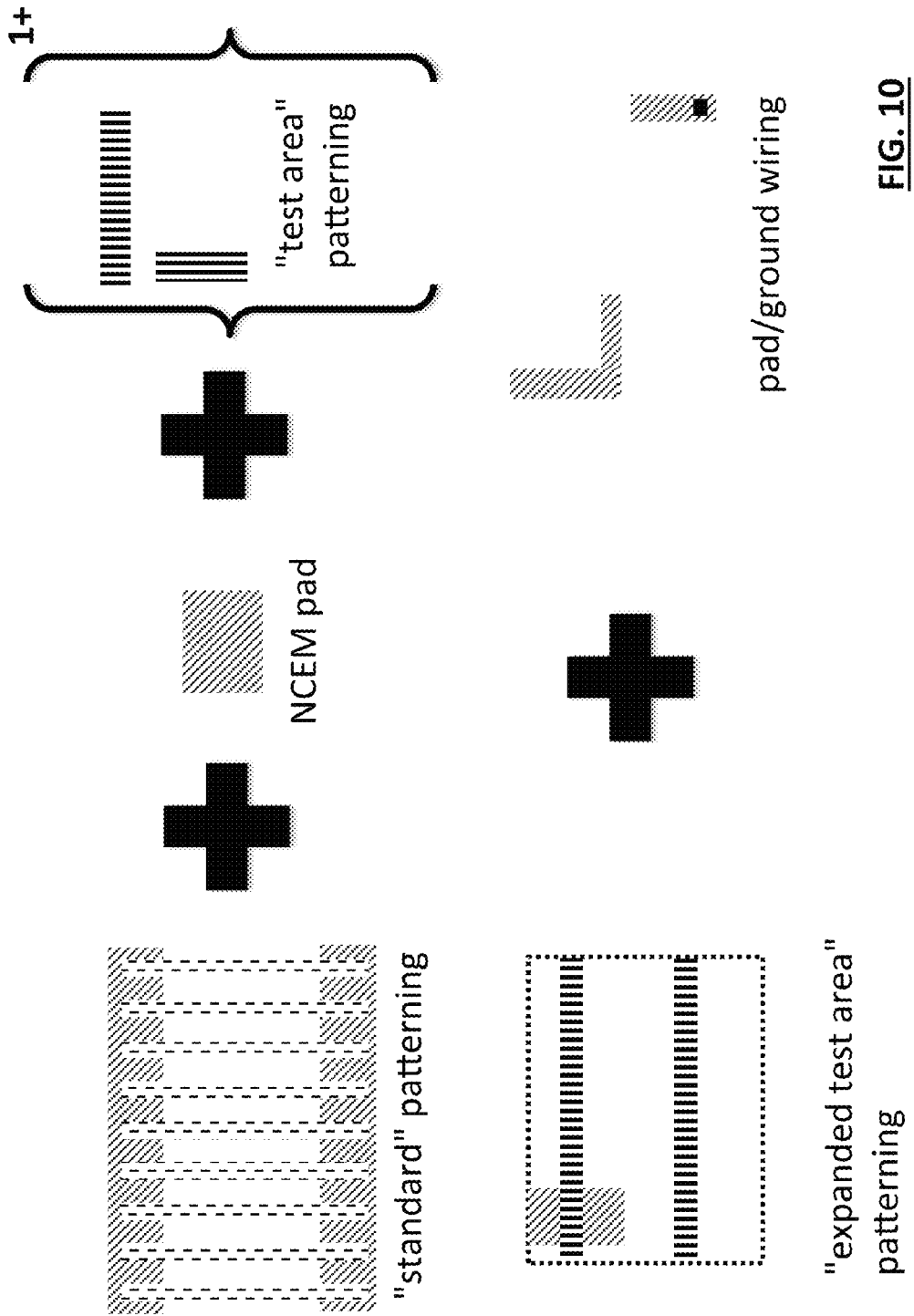
FIGS. 10-11, in conjunction with the description below, depict the overall physical structure and connectivity of short-configured (and/or leakage-configured), NCEM-enabled fill cells in accordance with certain aspects of the invention.
Figure 11:
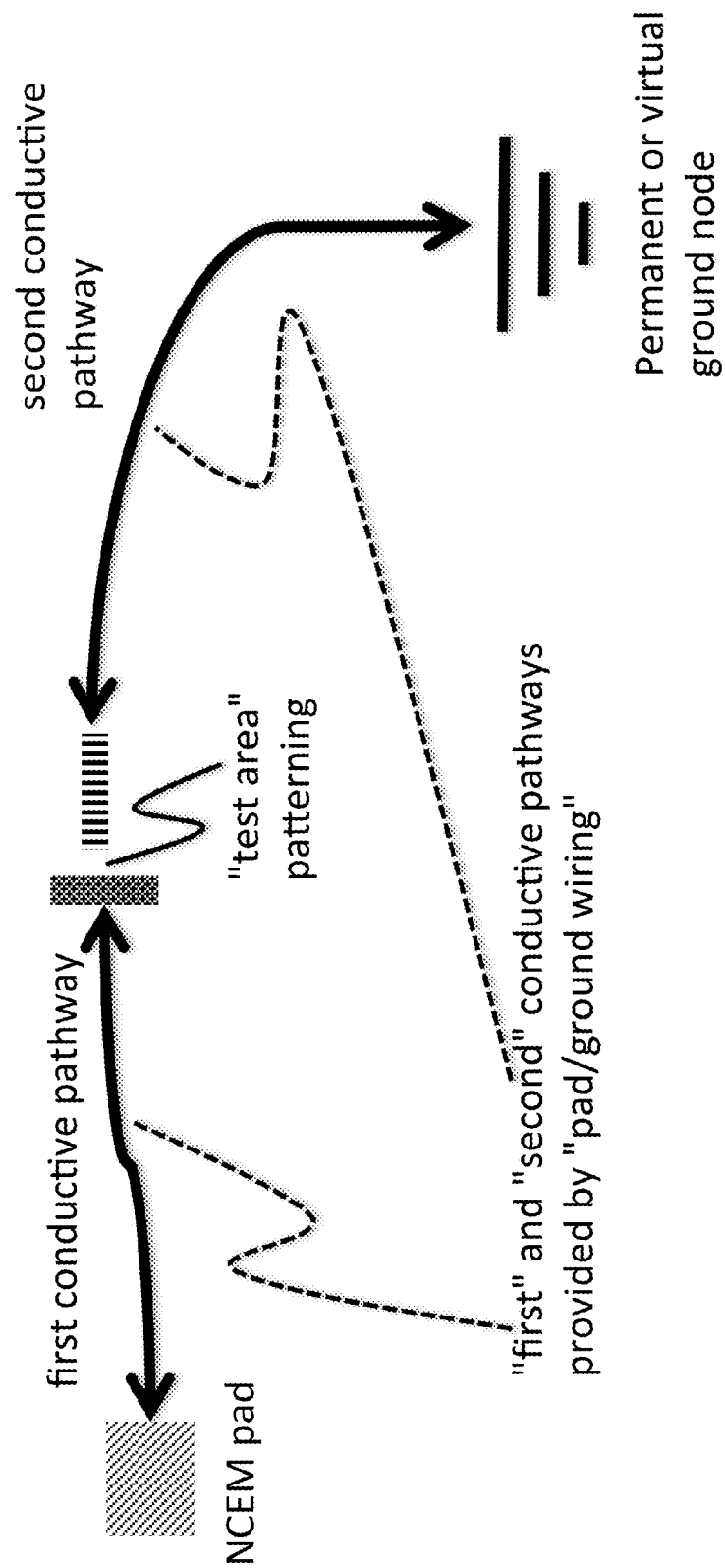

Indicated in parentheses are the names used to label these layers in FIGS. 10, 11, et seq. of this application. Persons skilled in the art will realize that these represent a minority of the many layers/masks/etc. used in the fabrication of modern devices. Nevertheless, these are believed to be the layers most relevant to enabling a skilled artisan to make and use the invention, and are the layers traditionally depicted in patent drawings of semiconductor structures (as shown, for example, by the cited GF and TSMC applications). In certain instances, additional layers may be added to depictions of selected NCEM-enabled fill cells.

Persons skilled in the art will also understand that most of the above layers can—and often are—rendered in multiple patterning steps. Typically, in this application, the drawings will combine all exposures into a single depicted layer (e.g., M1=M1E1+M1E2, or M1E1+M1E2+M1E3). In most cases, such details are irrelevant to the operation of the invention, and are determined largely by requirements of the fabrication process. In certain cases (e.g., an M1-M1-stitch-overlap-open-configured, NCEM-enabled fill cell), some potentially relevant detail(s) may be obscured by the exposure merging; however, such obscured detail(s) will nonetheless be readily apparent to the skilled artisan (by, for example, the fact that the named structure, e.g., M1-M1-stitch-overlap-open-configured, NCEM-enabled fill cell, must contain at least one overlap test region, as per FIG. 32, that is rendered in different exposures of M1, and located on the M1 path between the NCEM pad and ground).

Furthermore, short-configured cells can exist in both "same color" and "different color" varieties. For example, in a process that uses multi-patterned M1, the M1-tip-to-tip-configured, NCEM-enabled fill cells would come in two varieties: M1-tip-to-tip-same-color-short-configured cells, as well as M1-tip-to-tip-different-color-short-configured cells. The same applies to other short configurations, such as side-to-side, diagonal, etc.

Figure 9E:
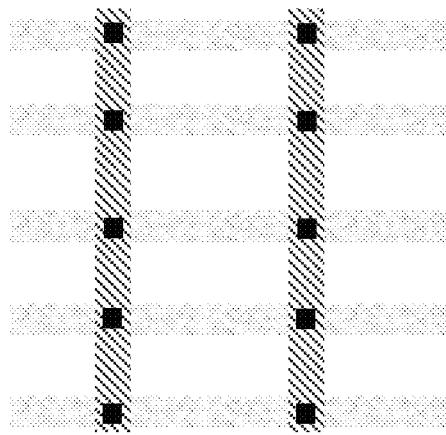
FIGS. 9A-9F depict several illustrative designs for a NCEM-enabled pad, suitable for use in connection with certain embodiments of the invention.
Figure 9F:
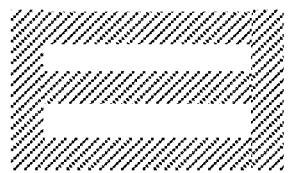
Figure 9B:
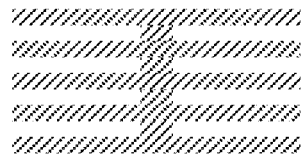
Figure 9D:
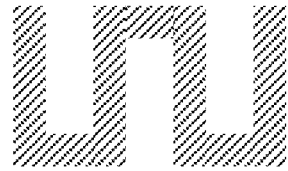
Figure 9A:
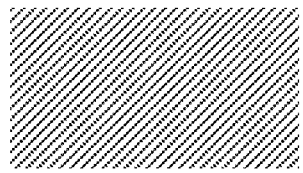
Figure 9C:
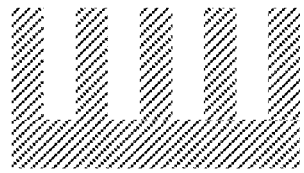
Figure 9G:
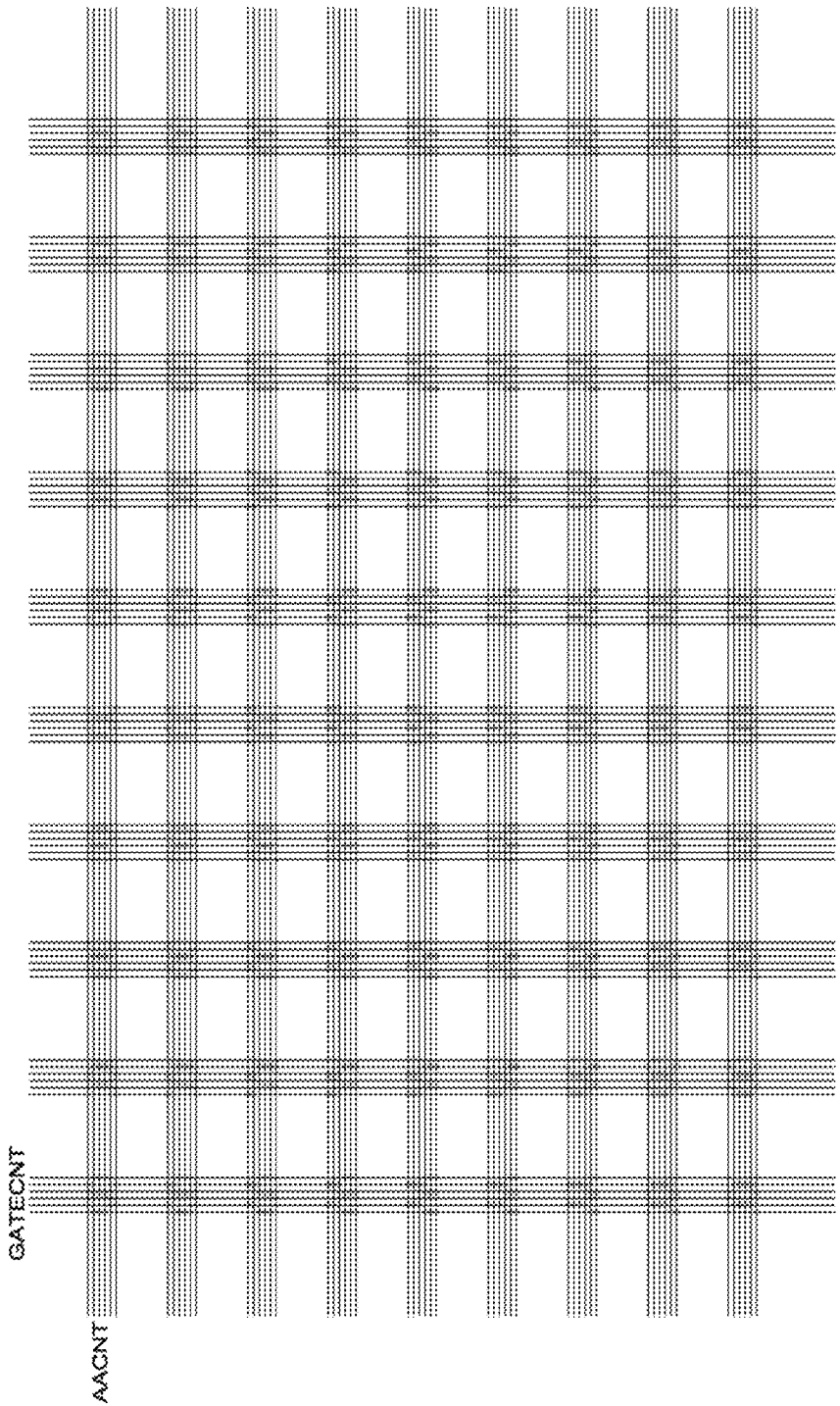
FIG. 9G depicts an exemplary mesh-style, NCEM-enabled pad, formed from a 10×9 grid of single-patterned GATECNT and single-patterned AACNT stripes.
Figure 9H:
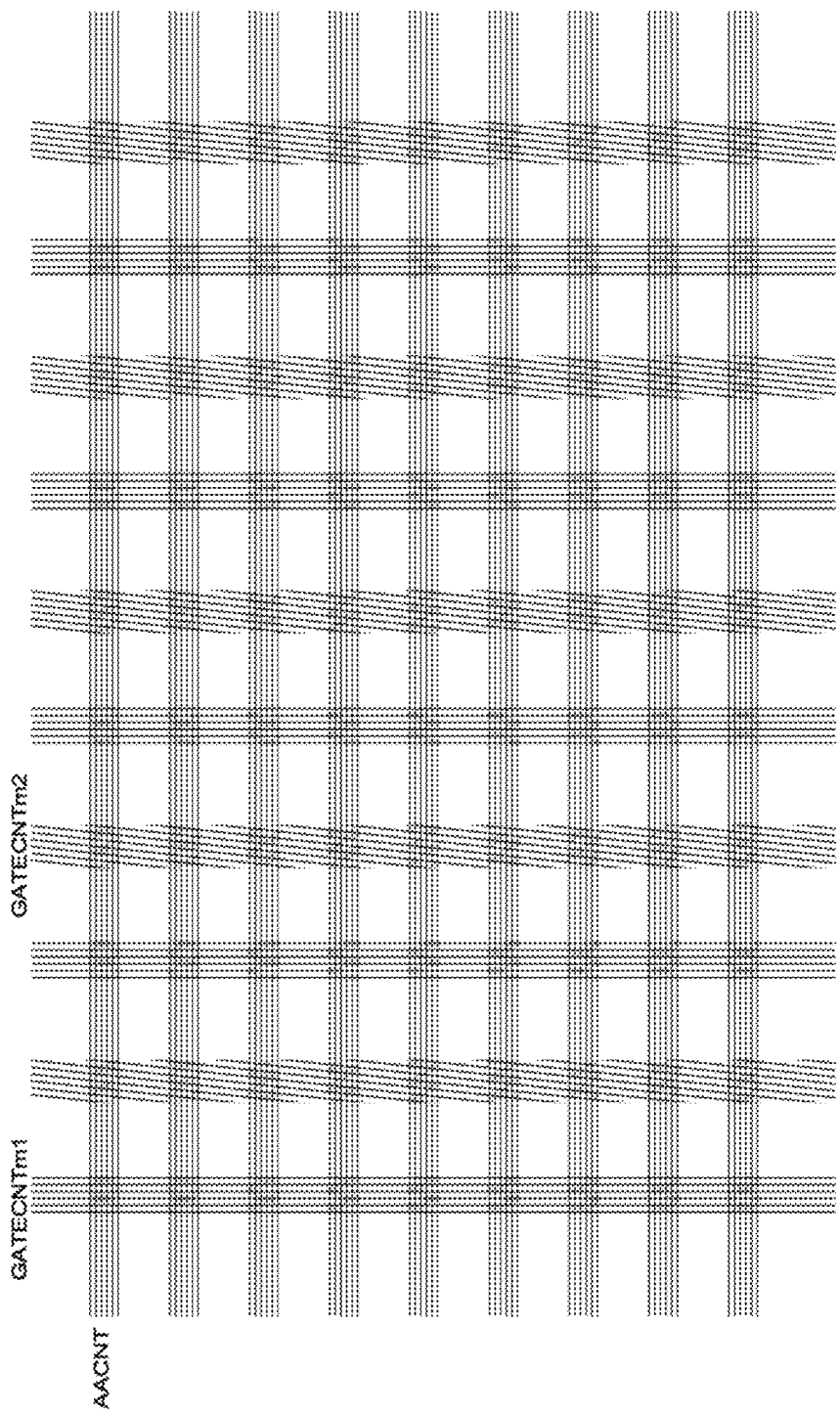
FIG. 9H depicts an exemplary mesh-style, NCEM-enabled pad, formed from a 10×9 grid of double-patterned GATECNT and single-patterned AACNT stripes.
Figure 91:
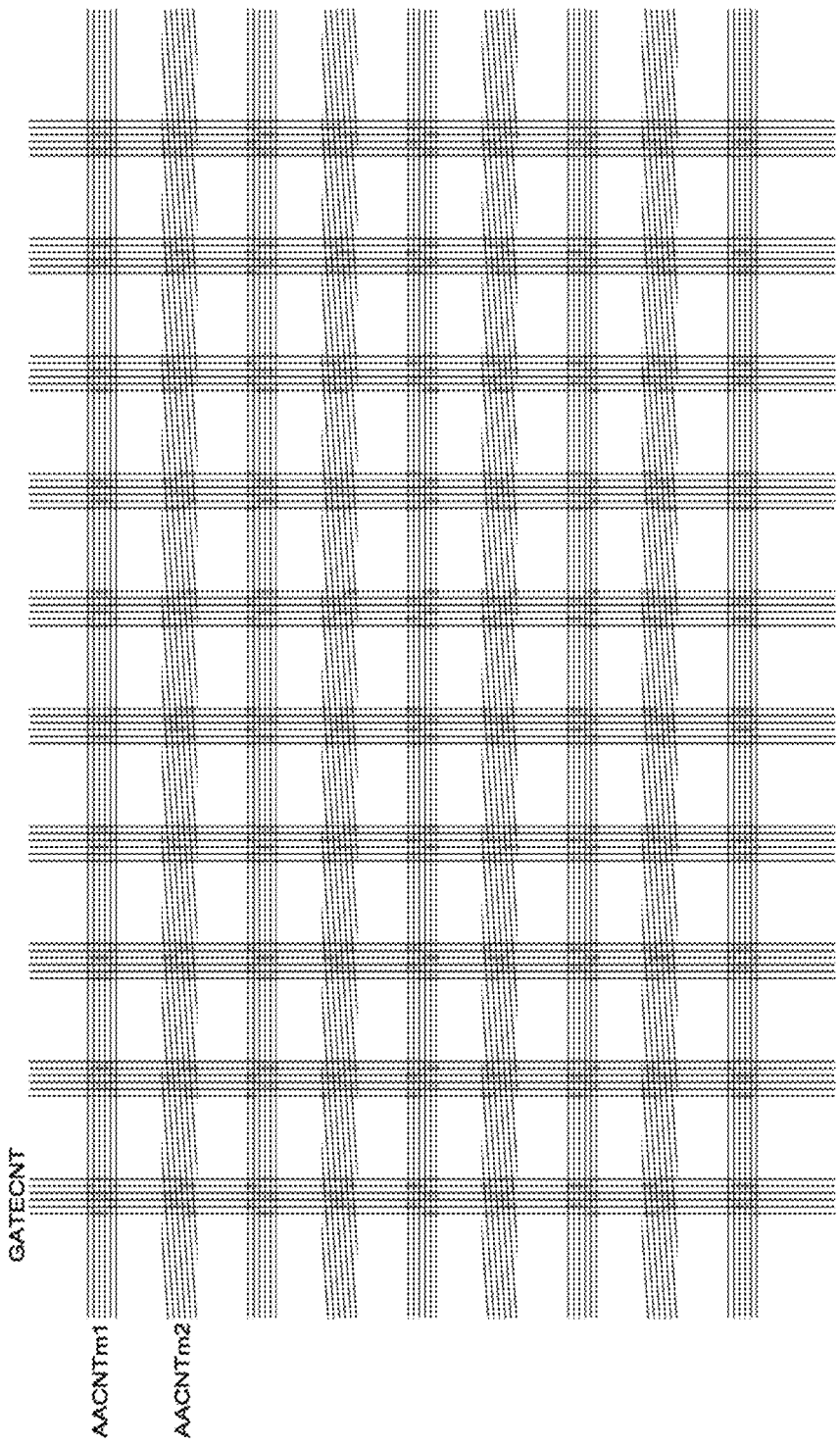
Figure 9J:
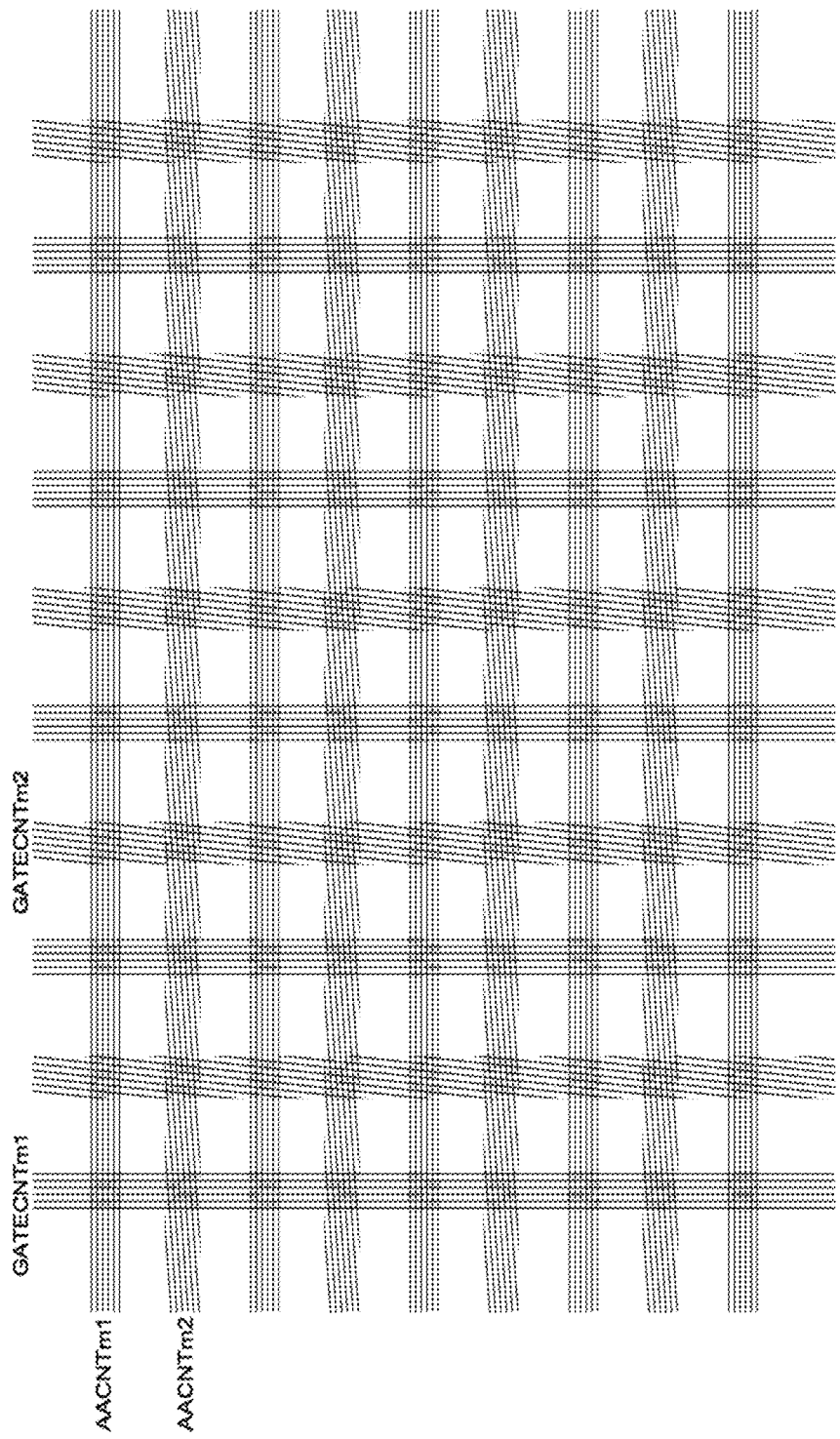
FIG. 9J depicts an exemplary mesh-style, NCEM-enabled pad, formed from a 10×9 grid of double-patterned GATECNT and double-patterned AACNT stripes.
Figure 9K:
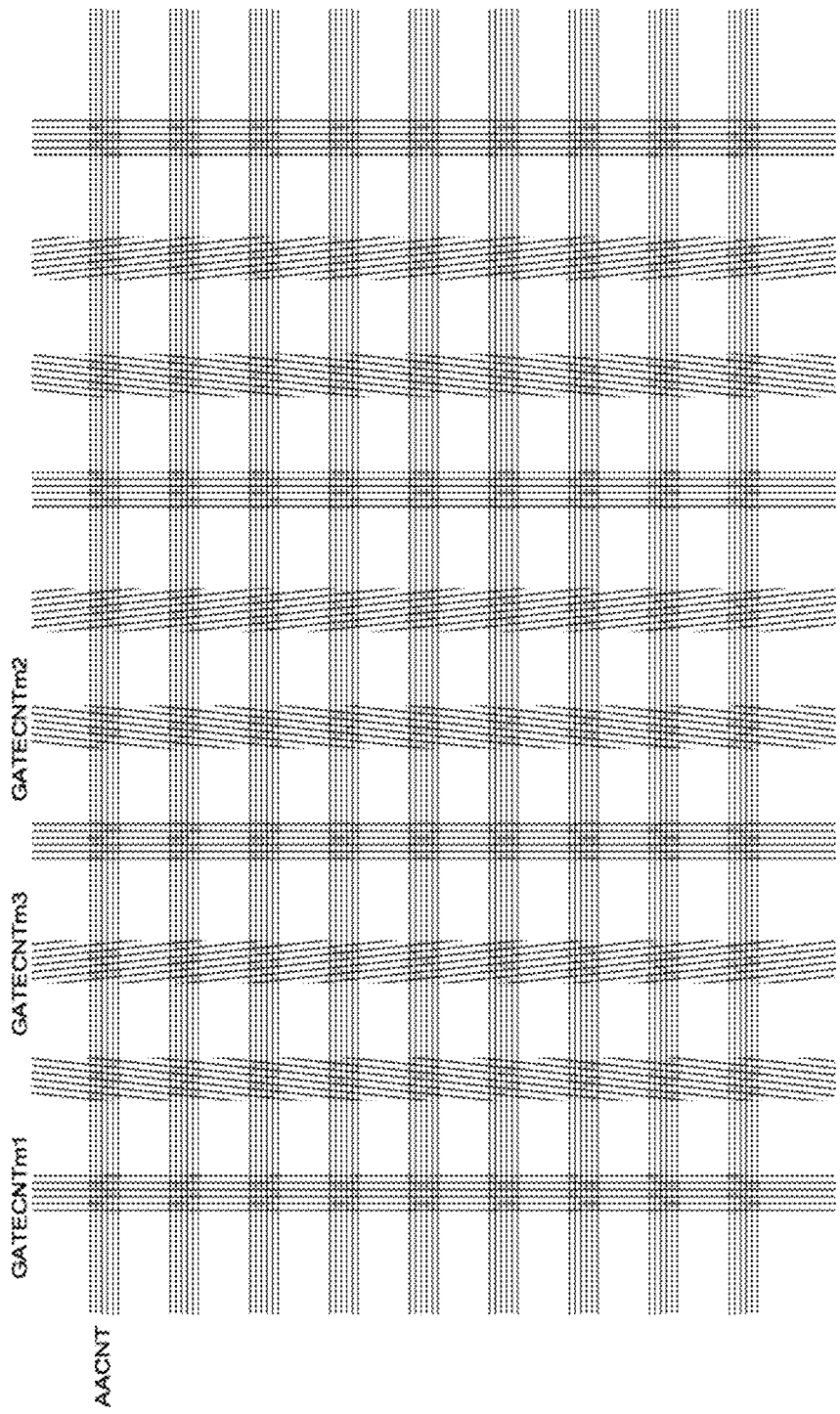
FIG. 9K depicts an exemplary mesh-style, NCEM-enabled pad, formed from a 10×9 grid of triple-patterned GATECNT and single-patterned AACNT stripes.
Figure 9L:
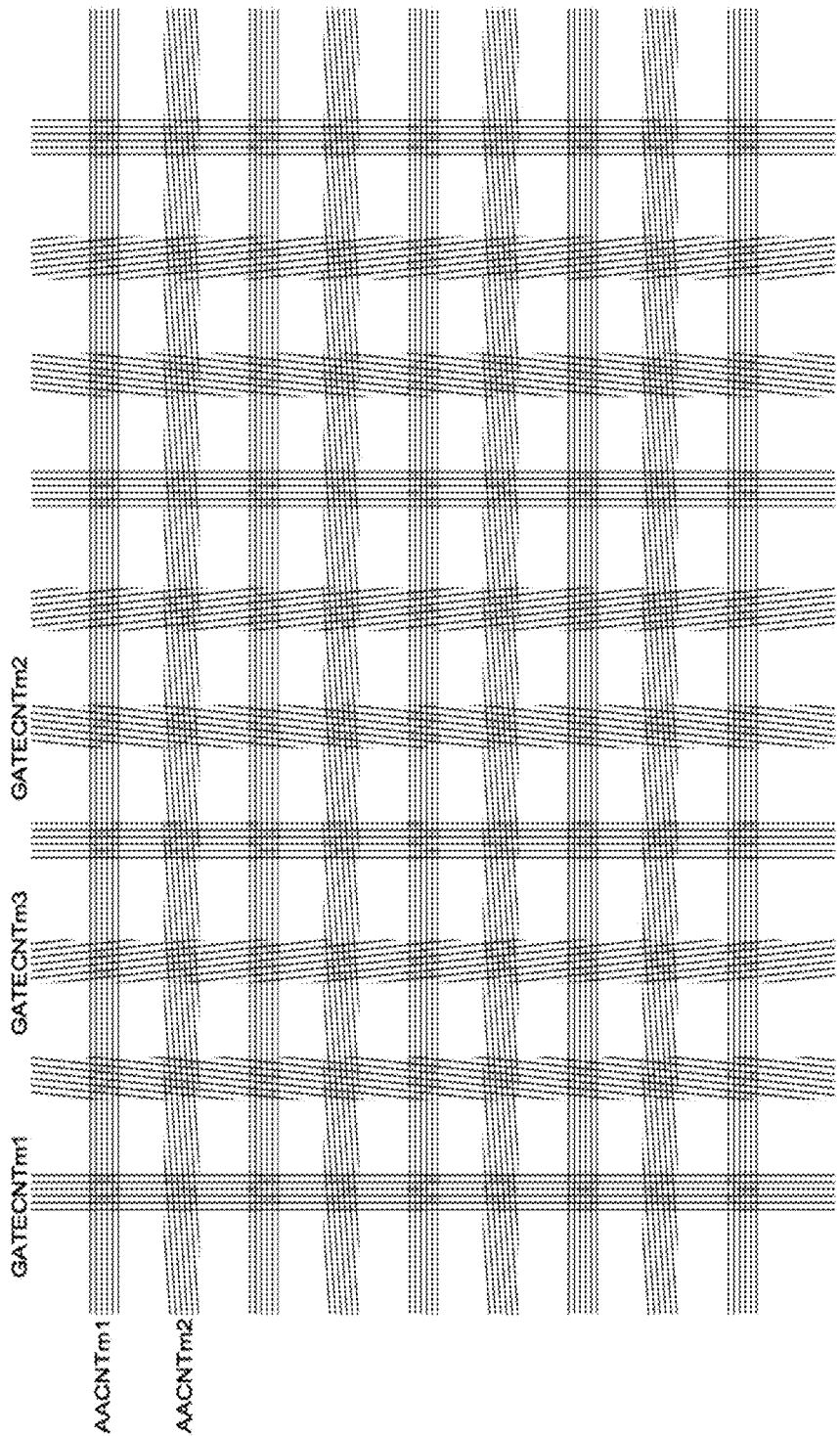
FIG. 9L depicts an exemplary mesh-style, NCEM-enabled pad, formed from a 10×9 grid of triple-patterned GATECNT and double-patterned AACNT stripes.
Figure 9M:
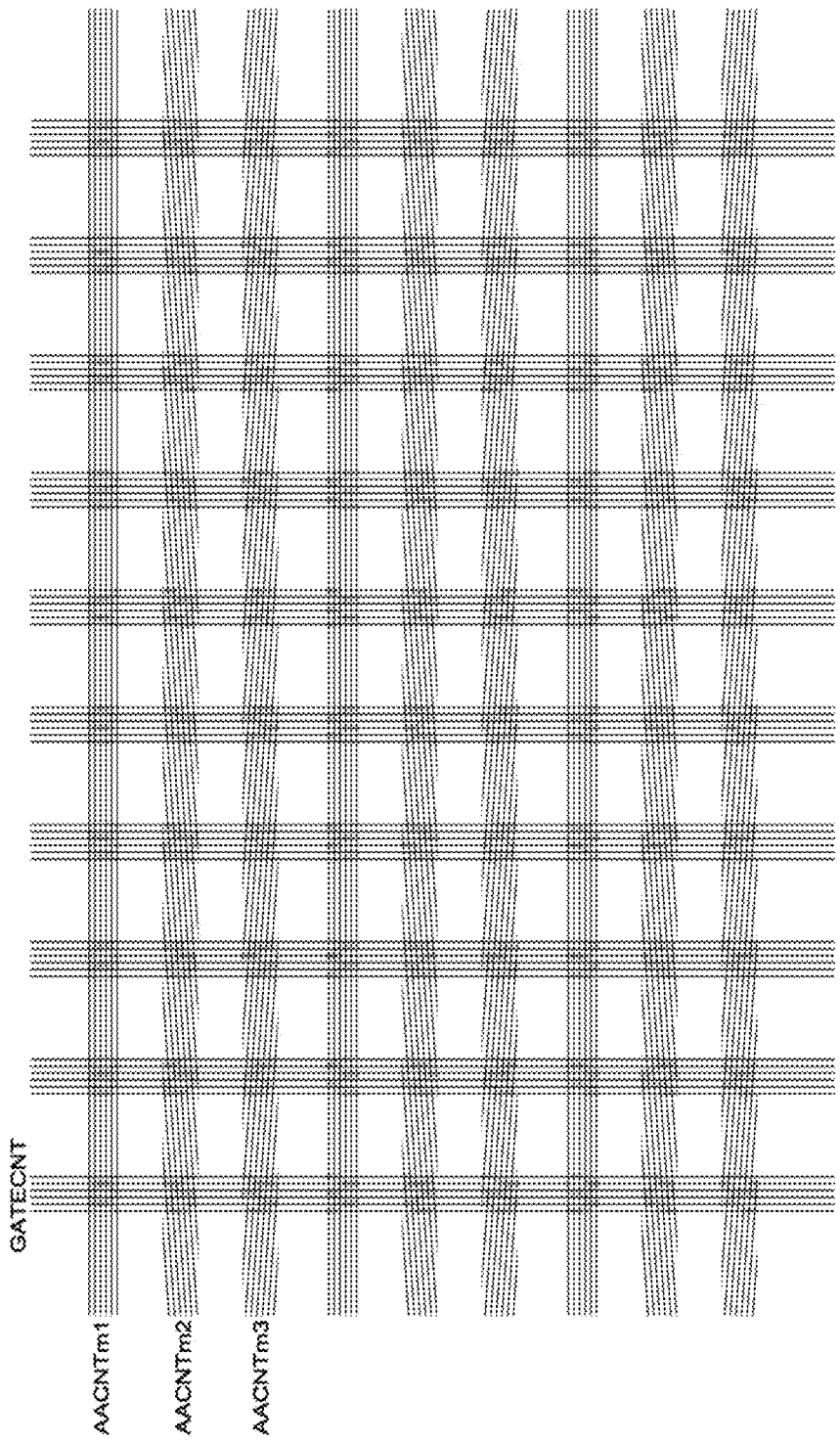
FIG. 9M depicts an exemplary mesh-style, NCEM-enabled pad, formed from a 10×9 grid of single-patterned GATECNT and triple-patterned AACNT stripes.
Figure 9O:
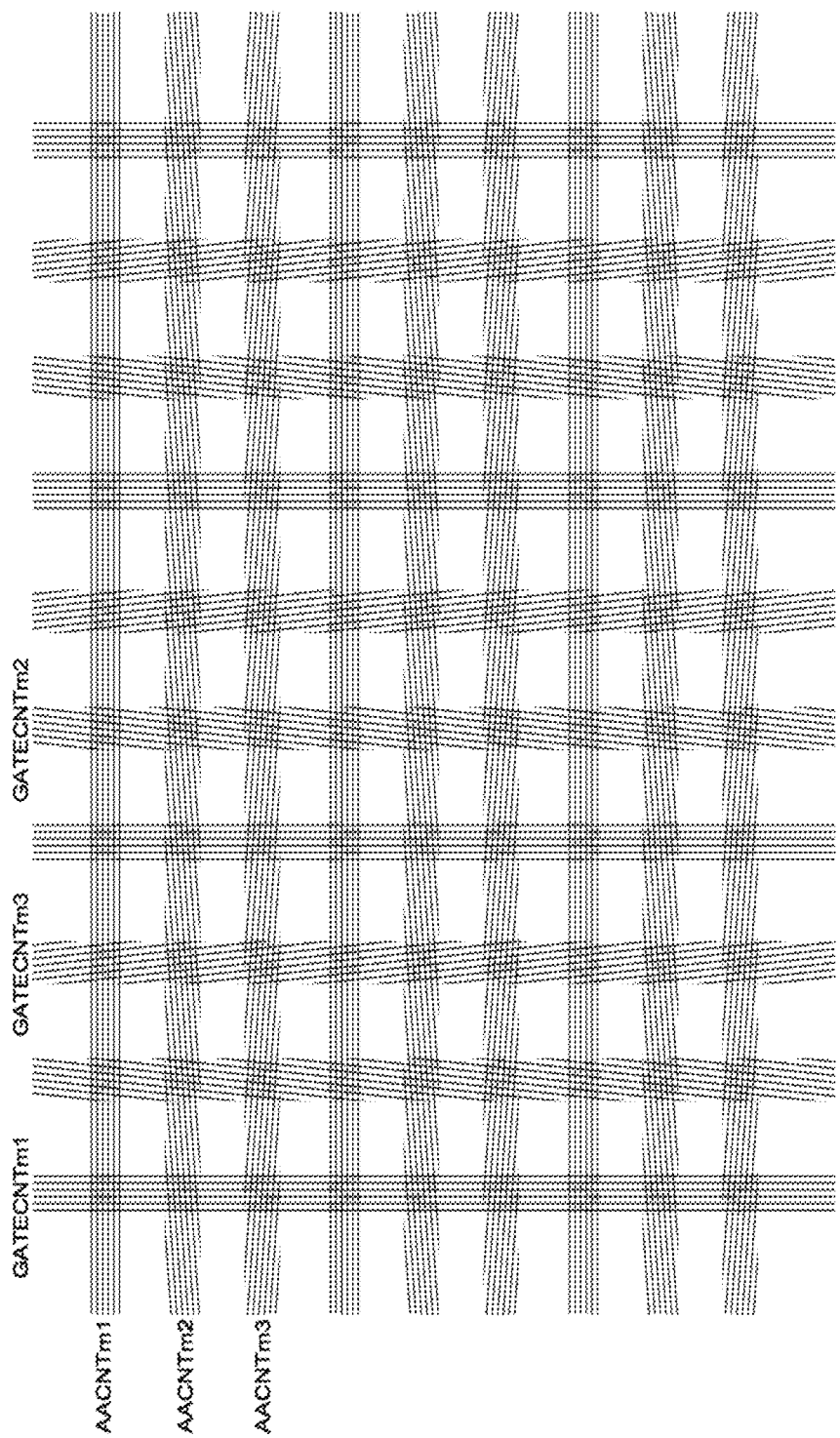
FIG. 9O depicts an exemplary mesh-style, NCEM-enabled pad, formed from a 10×9 grid of triple-patterned GATECNT and triple-patterned AACNT stripes.
Figure 9P:
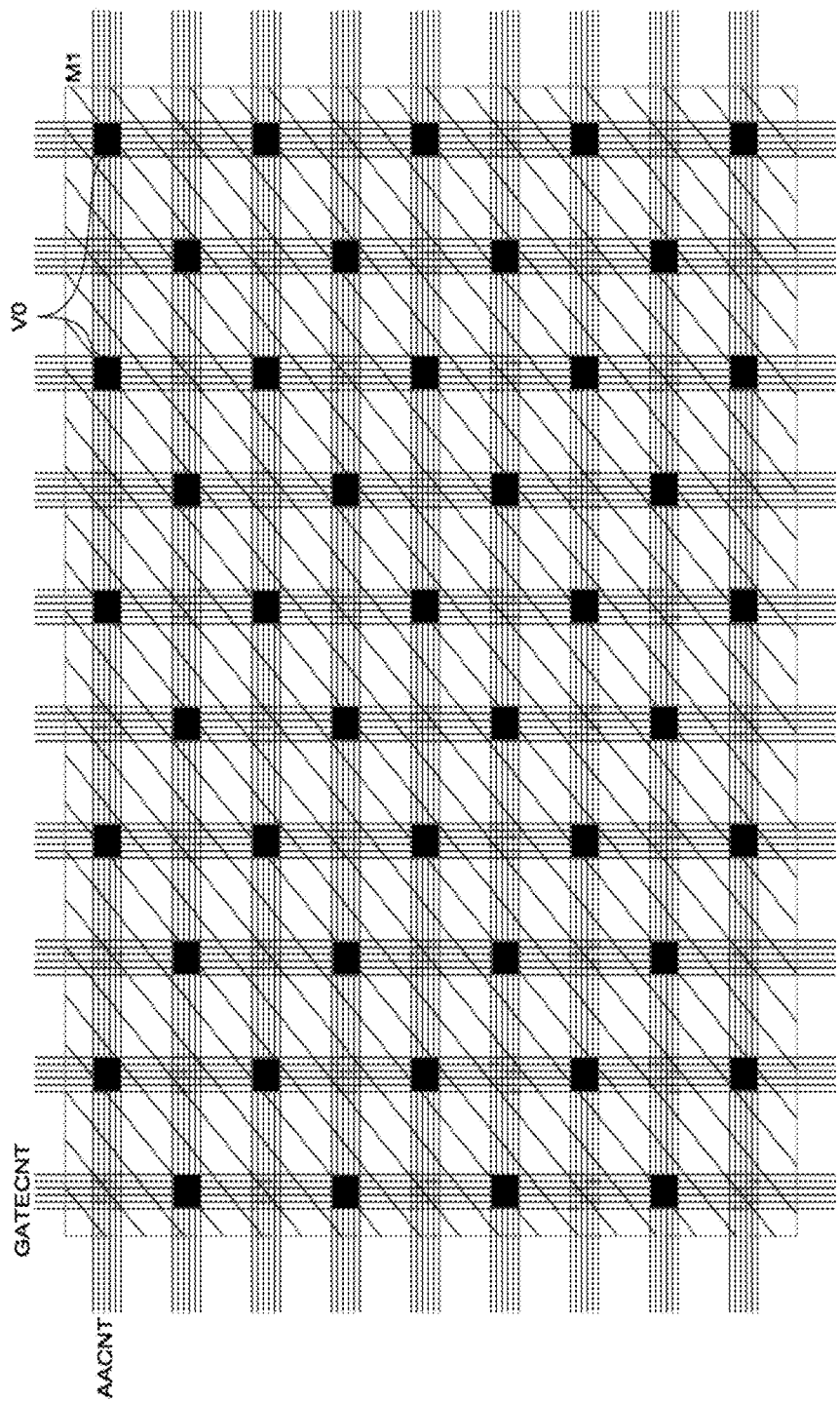
FIG. 9P depicts an exemplary mesh-style, NCEM-enabled pad, formed from a 10×9 grid of single-patterned GATECNT and single-patterned AACNT stripes, with an overlying, solid M1 pad, and a plurality of V0 vias positioned at GATECNT-AACNT junction points.
Figure 9Q:
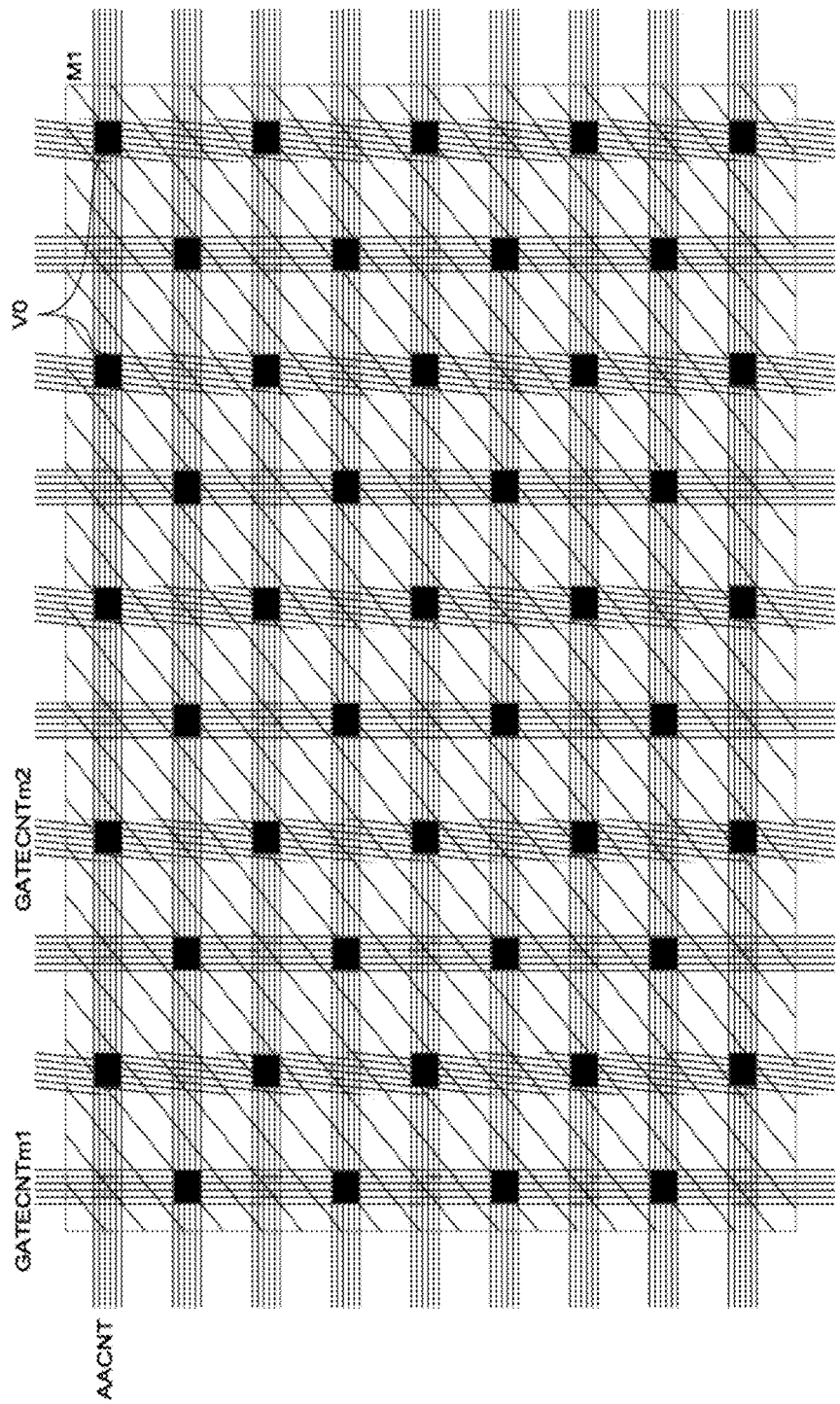
FIG. 9Q depicts an exemplary mesh-style, NCEM-enabled pad, formed from a 10×9 grid of double-patterned GATECNT and single-patterned AACNT stripes, with an overlying, solid M1 pad, and a plurality of V0 vias positioned at GATECNT-AACNT junction points.
Figure 9R:
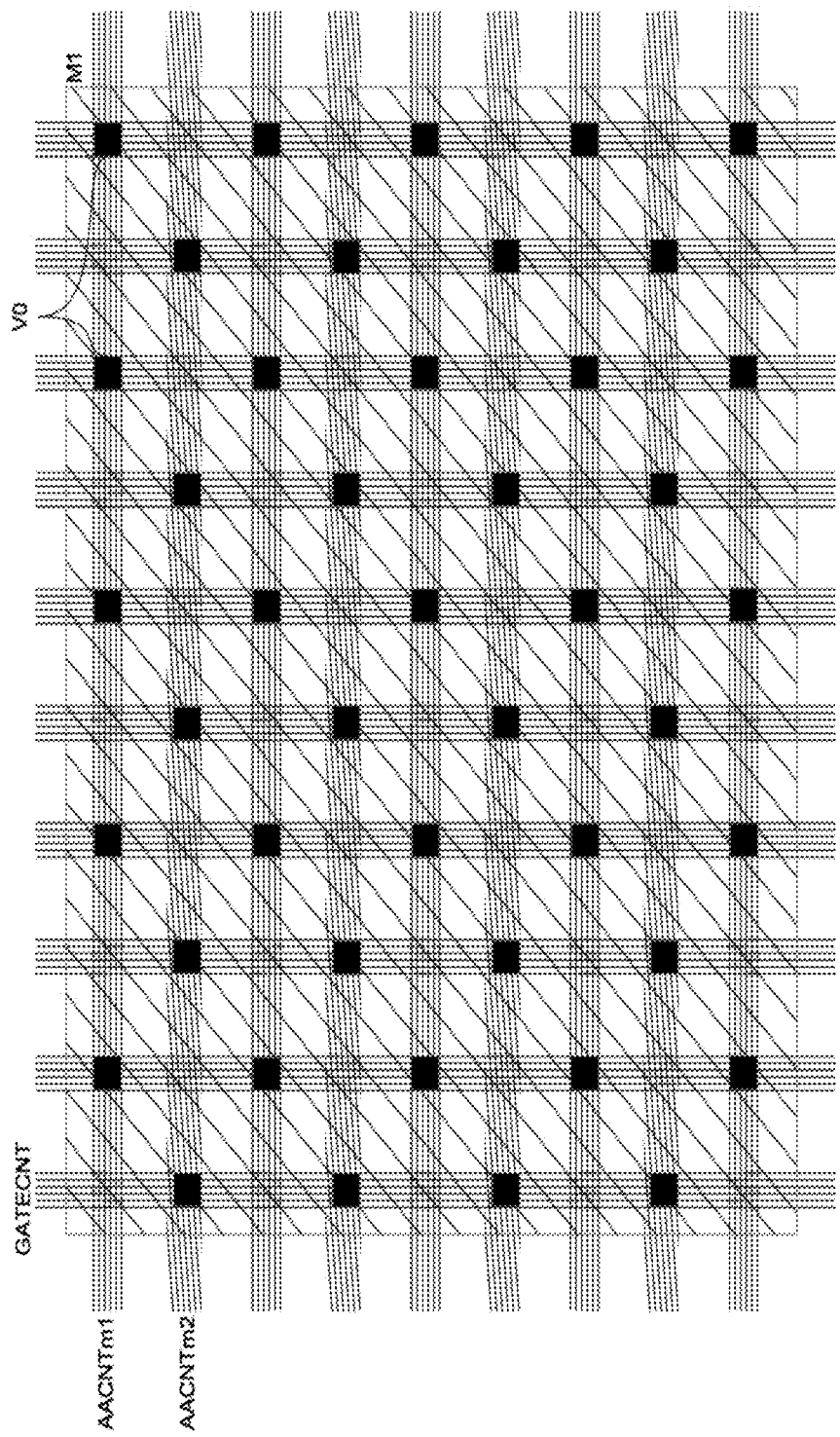
FIG. 9R depicts an exemplary mesh-style, NCEM-enabled pad, formed from a 10×9 grid of single-patterned GATECNT and double-patterned AACNT stripes, with an overlying, solid M1 pad, and a plurality of V0 vias positioned at GATECNT-AACNT junction points.
Figure 9S:
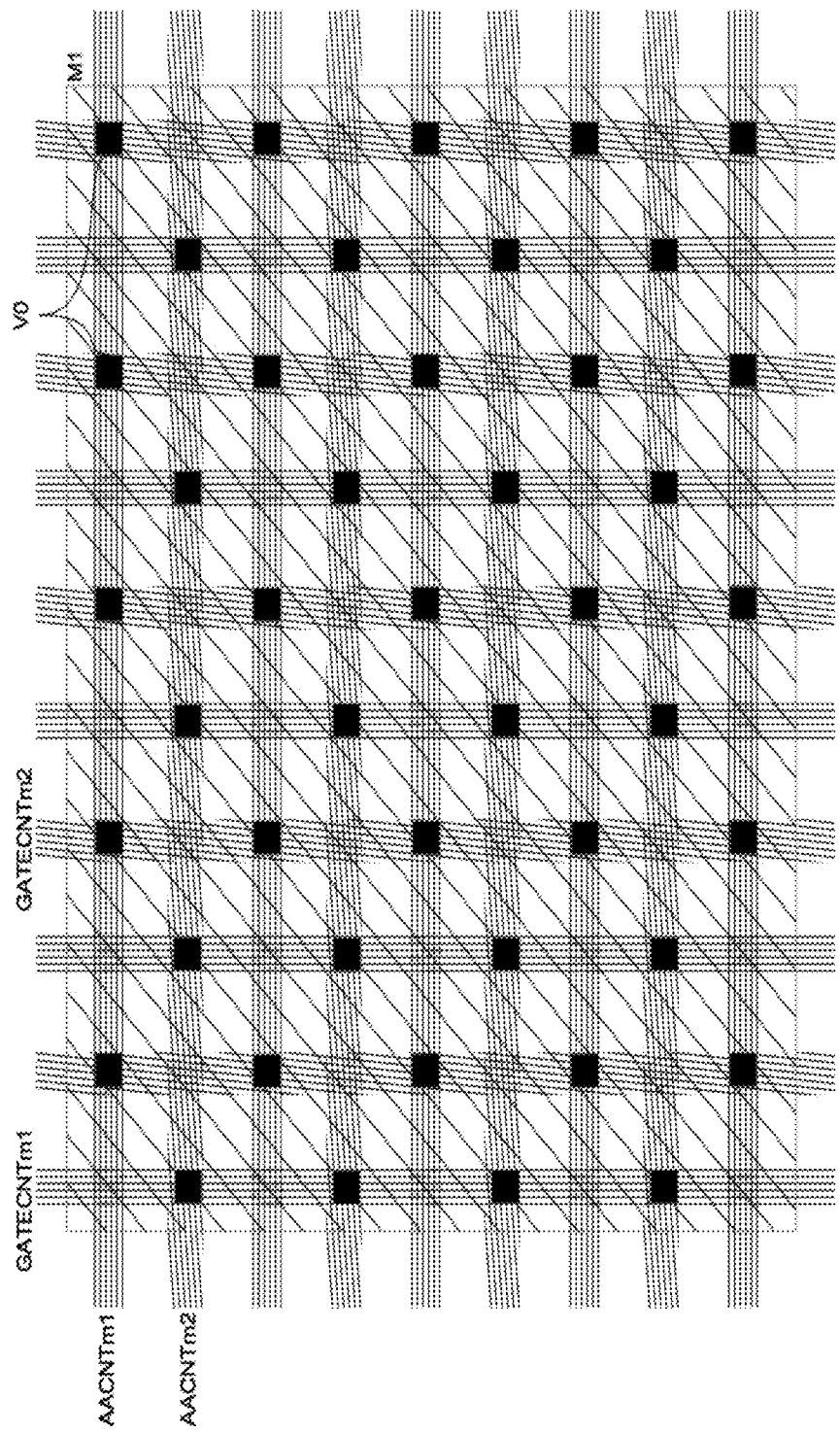
FIG. 9S depicts an exemplary mesh-style, NCEM-enabled pad, formed from a 10×9 grid of double-patterned GATECNT and double-patterned AACNT stripes, with an overlying, solid M1 pad, and a plurality of V0 vias positioned at GATECNT-AACNT junction points.
Figure 9T:
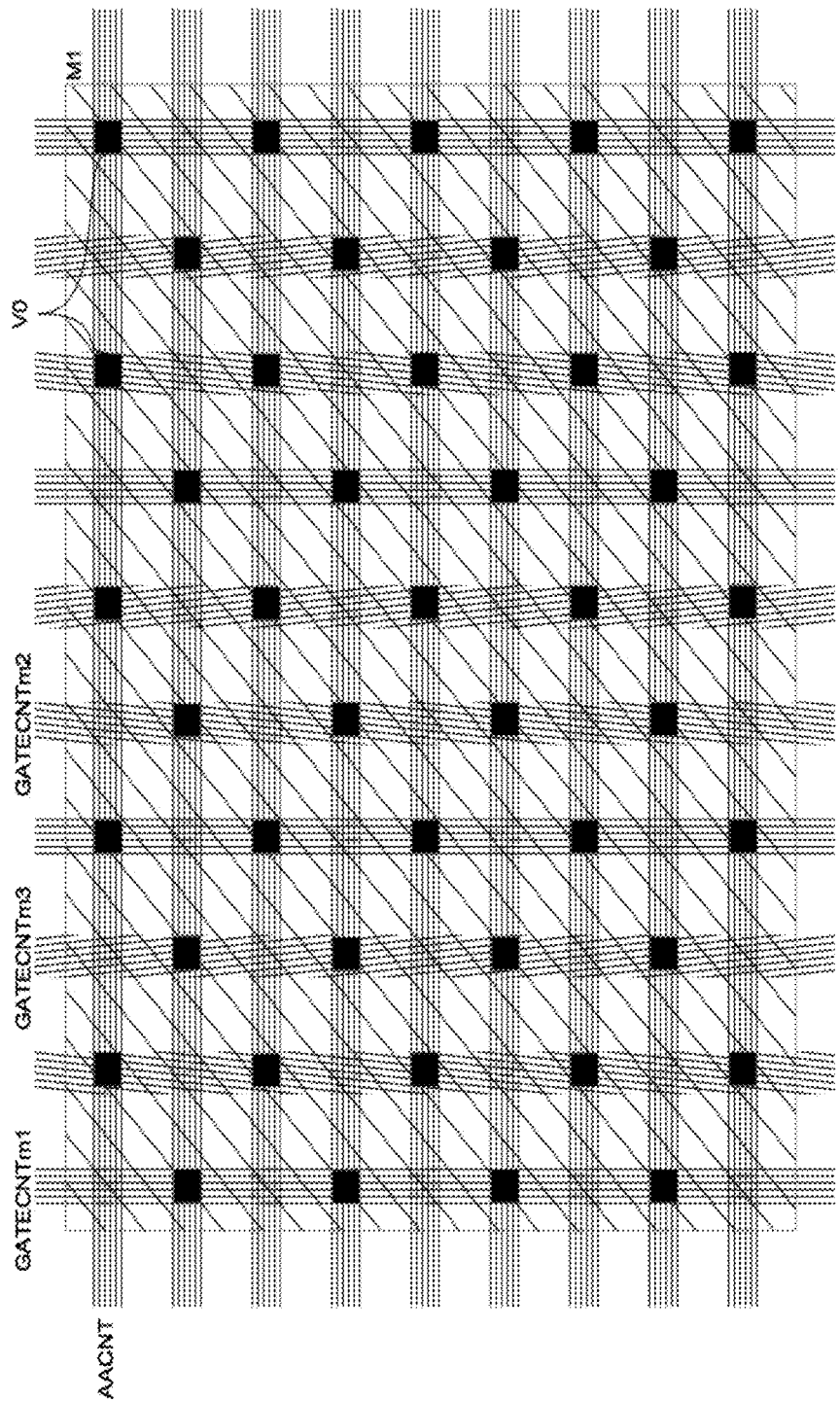
FIG. 9T depicts an exemplary mesh-style, NCEM-enabled pad, formed from a 10×9 grid of triple-patterned GATECNT and single-patterned AACNT stripes, with an overlying, solid M1 pad, and a plurality of V0 vias positioned at GATECNT-AACNT junction points.
Figure 9U:
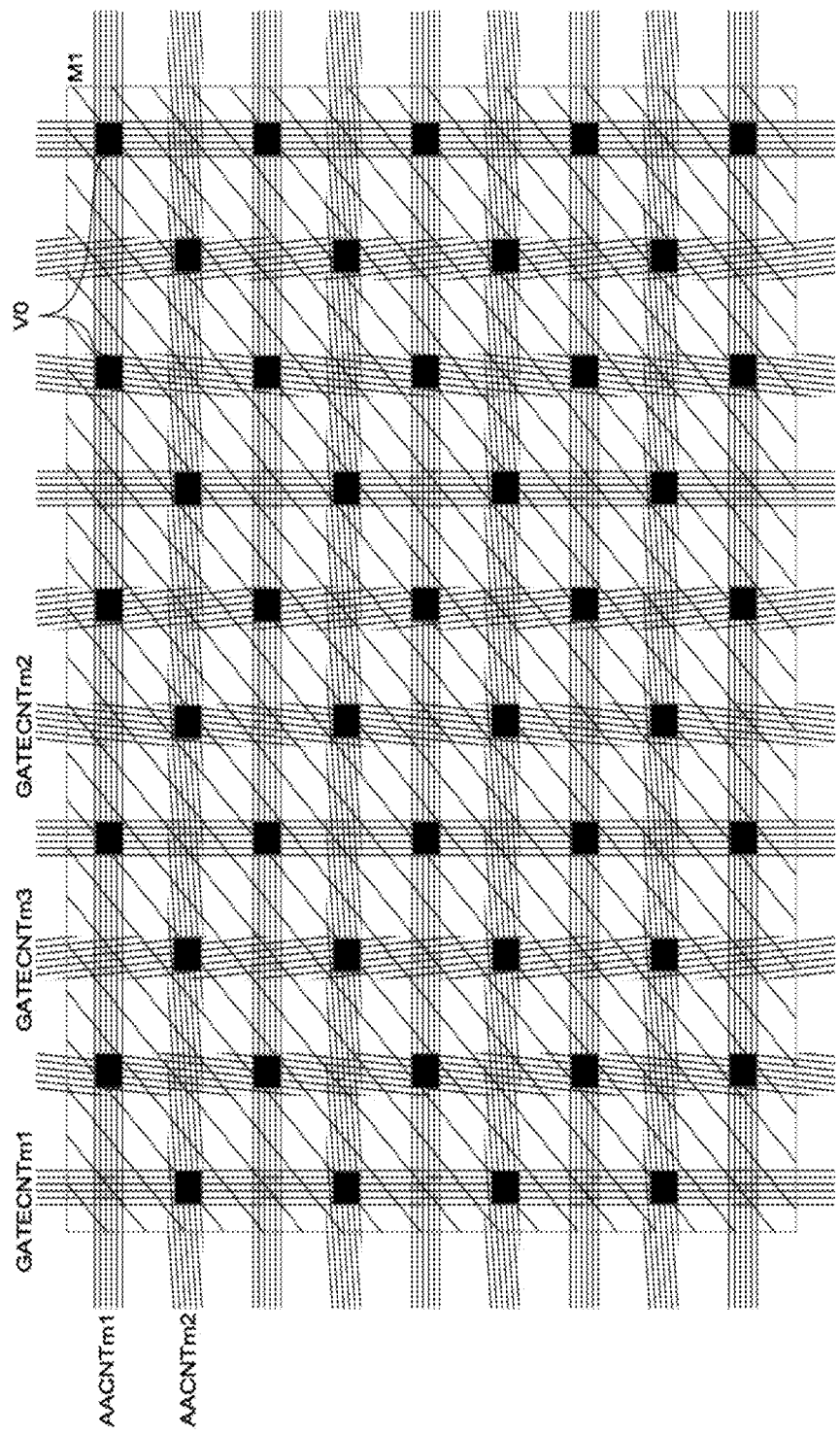
FIG. 9U depicts an exemplary mesh-style, NCEM-enabled pad, formed from a 10×9 grid of triple-patterned GATECNT and double-patterned AACNT stripes, with an overlying, solid M1 pad, and a plurality of V0 vias positioned at GATECNT-AACNT junction points.
Figure 9V:
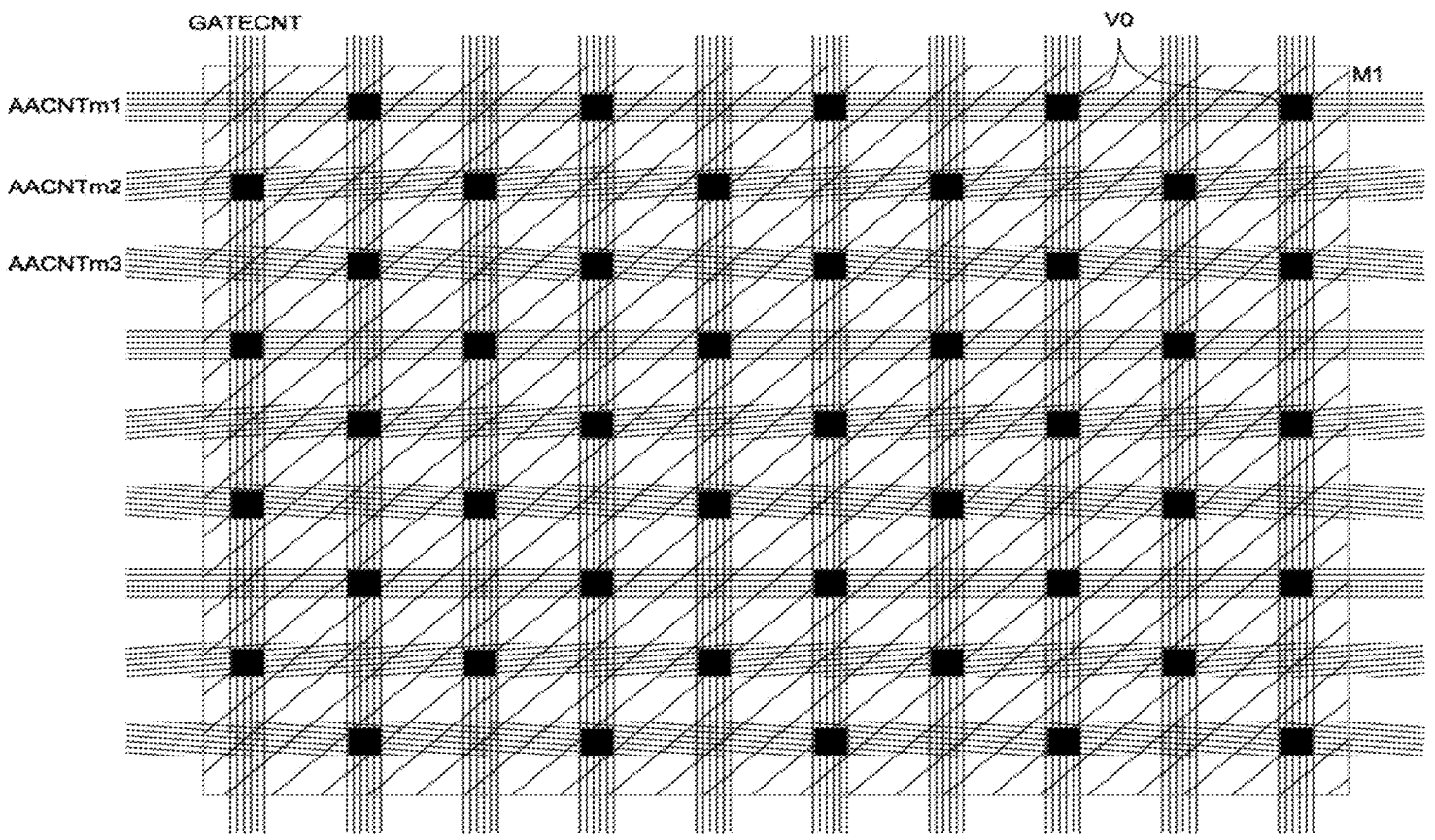
FIG. 9V depicts an exemplary mesh-style, NCEM-enabled pad, formed from a 10×9 grid of single-patterned GATECNT and triple-patterned AACNT stripes, with an overlying, solid M1 pad, and a plurality of V0 vias positioned at GATECNT-AACNT junction points.
Figure 9W:
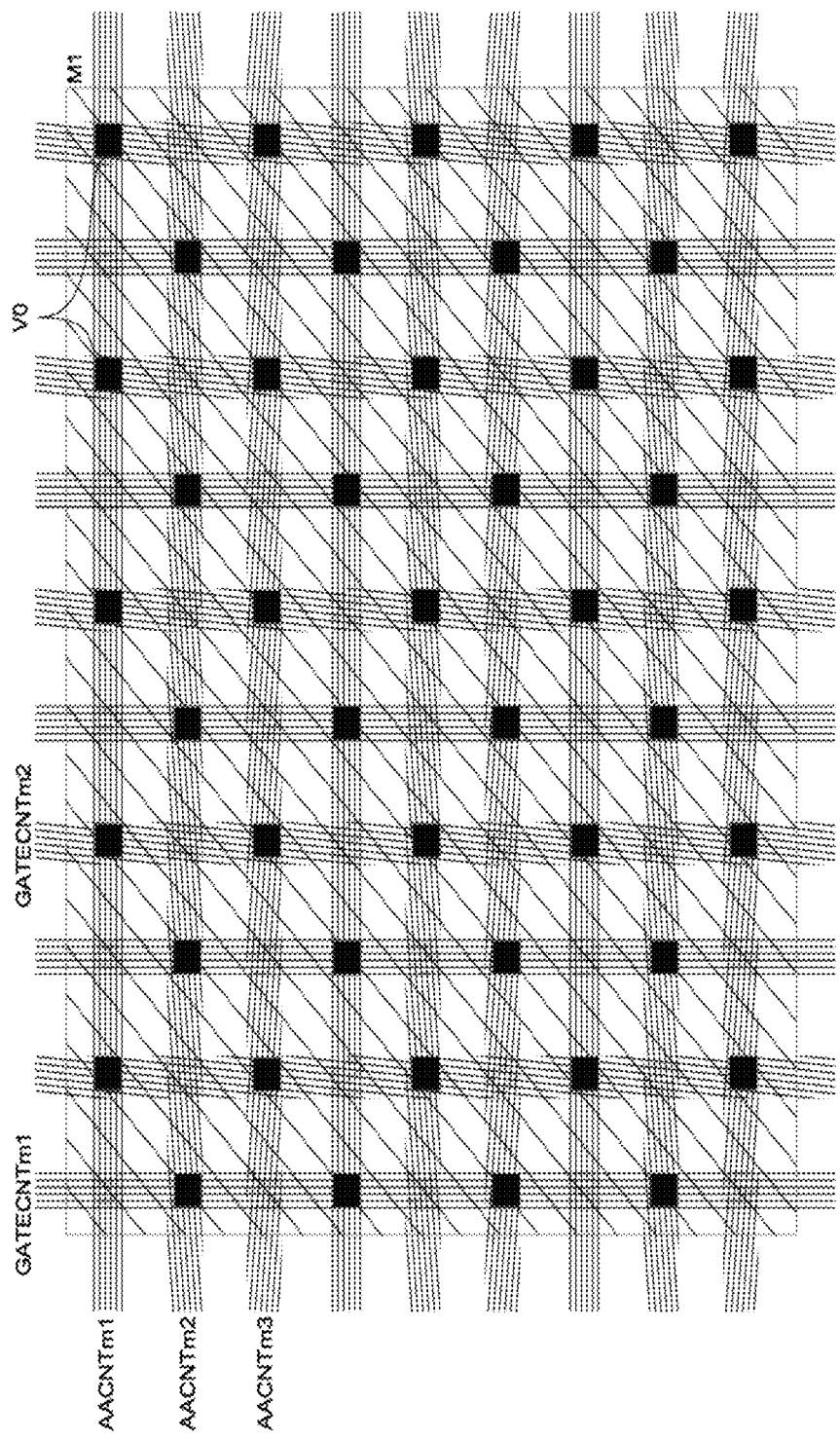
FIG. 9W depicts an exemplary mesh-style, NCEM-enabled pad, formed from a 10×9 grid of double-patterned GATECNT and triple-patterned AACNT stripes, with an overlying, solid M1 pad, and a plurality of V0 vias positioned at GATECNT-AACNT junction points.
Figure 9X:
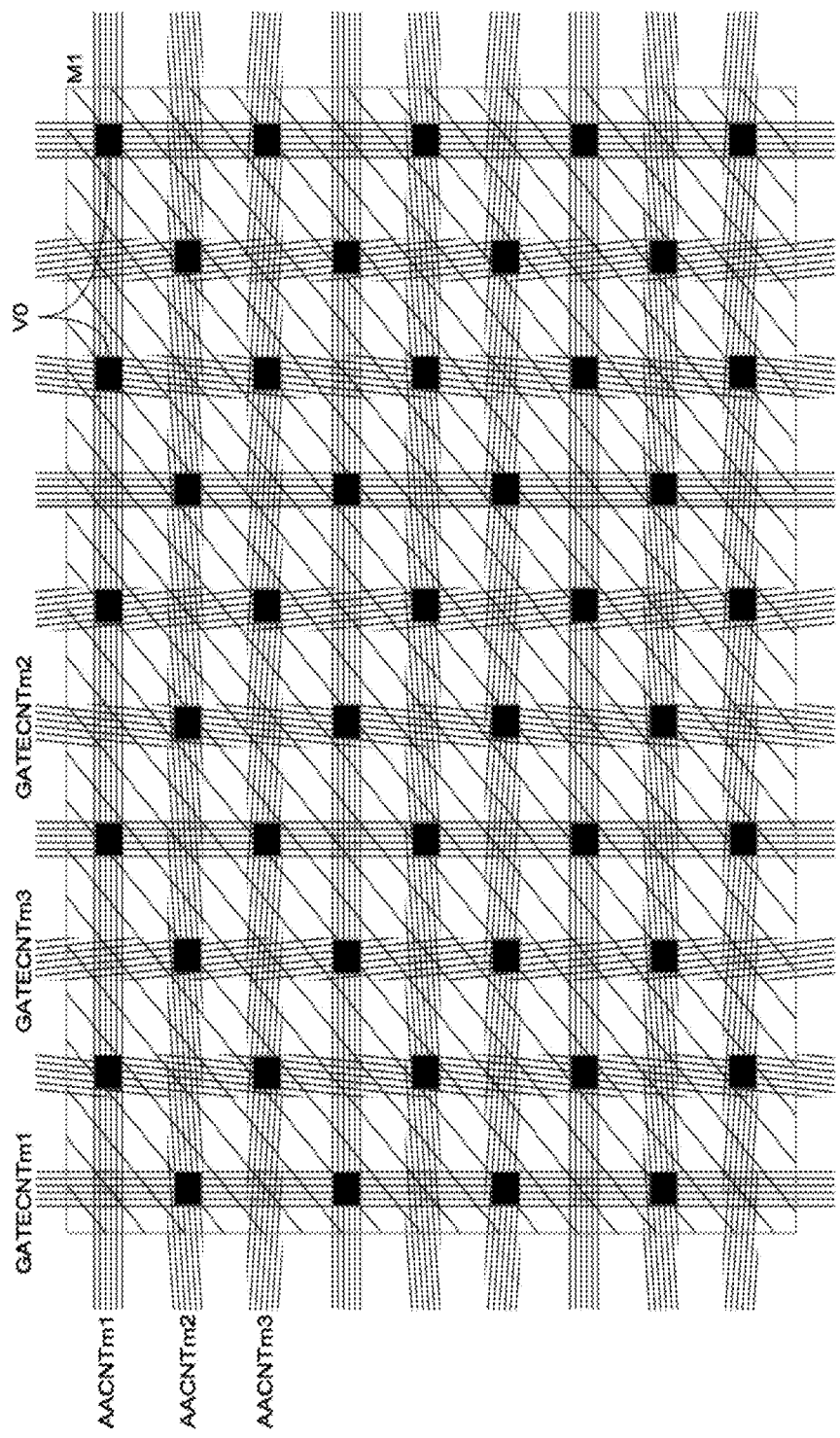
FIG. 9X depicts an exemplary mesh-style, NCEM-enabled pad, formed from a 10×9 grid of triple-patterned GATECNT and triple-patterned AACNT stripes, with an overlying, solid M1 pad, and a plurality of V0 vias positioned at GATECNT-AACNT junction points.
Figure 9Y:
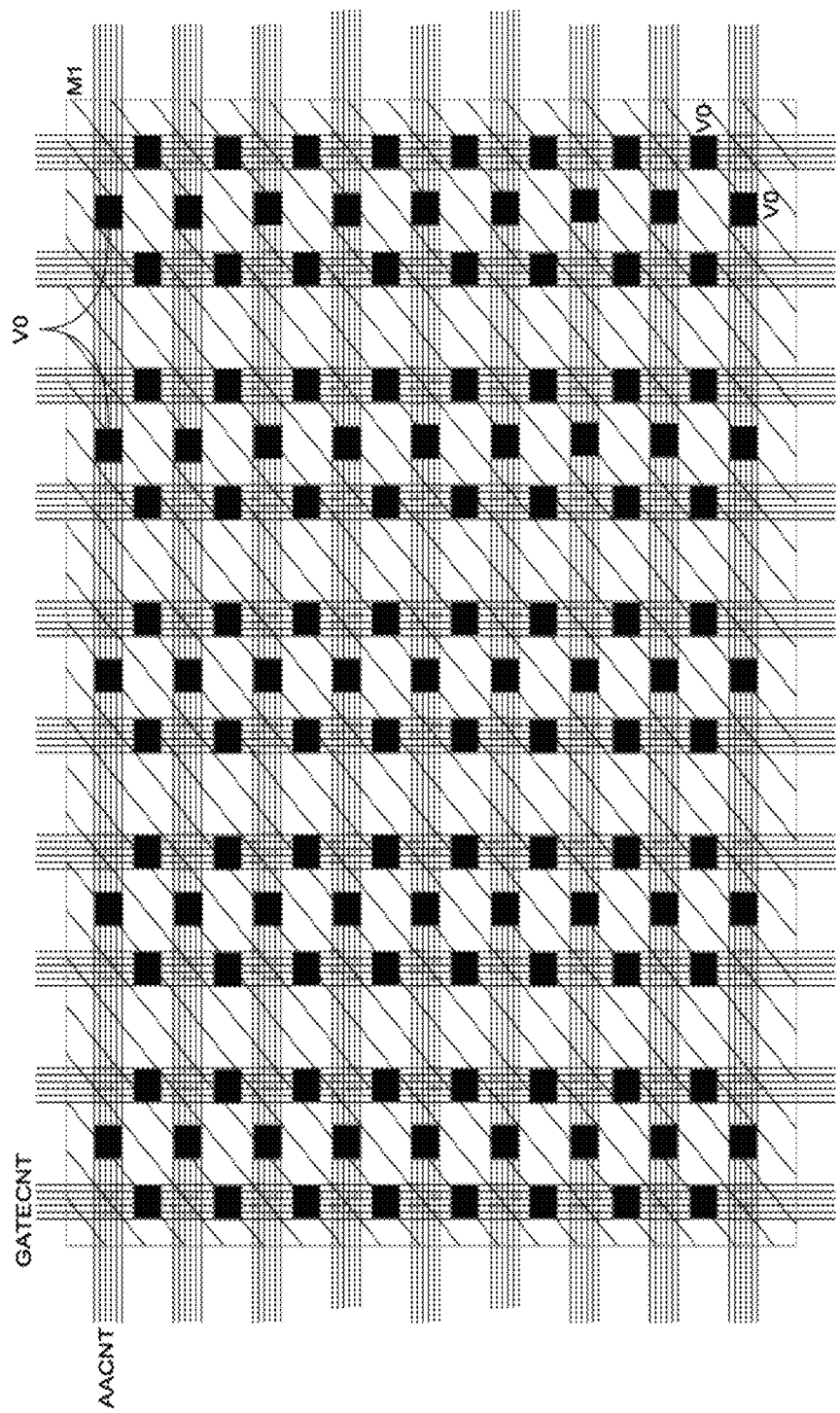
FIG. 9Y depicts an exemplary mesh-style, NCEM-enabled pad, formed from a 10×9 grid of single-patterned GATECNT and single-patterned AACNT stripes, with an overlying, solid M1 pad, and a plurality of V0 vias positioned to avoid GATECNT-AACNT junction points.
Figure 9Z:
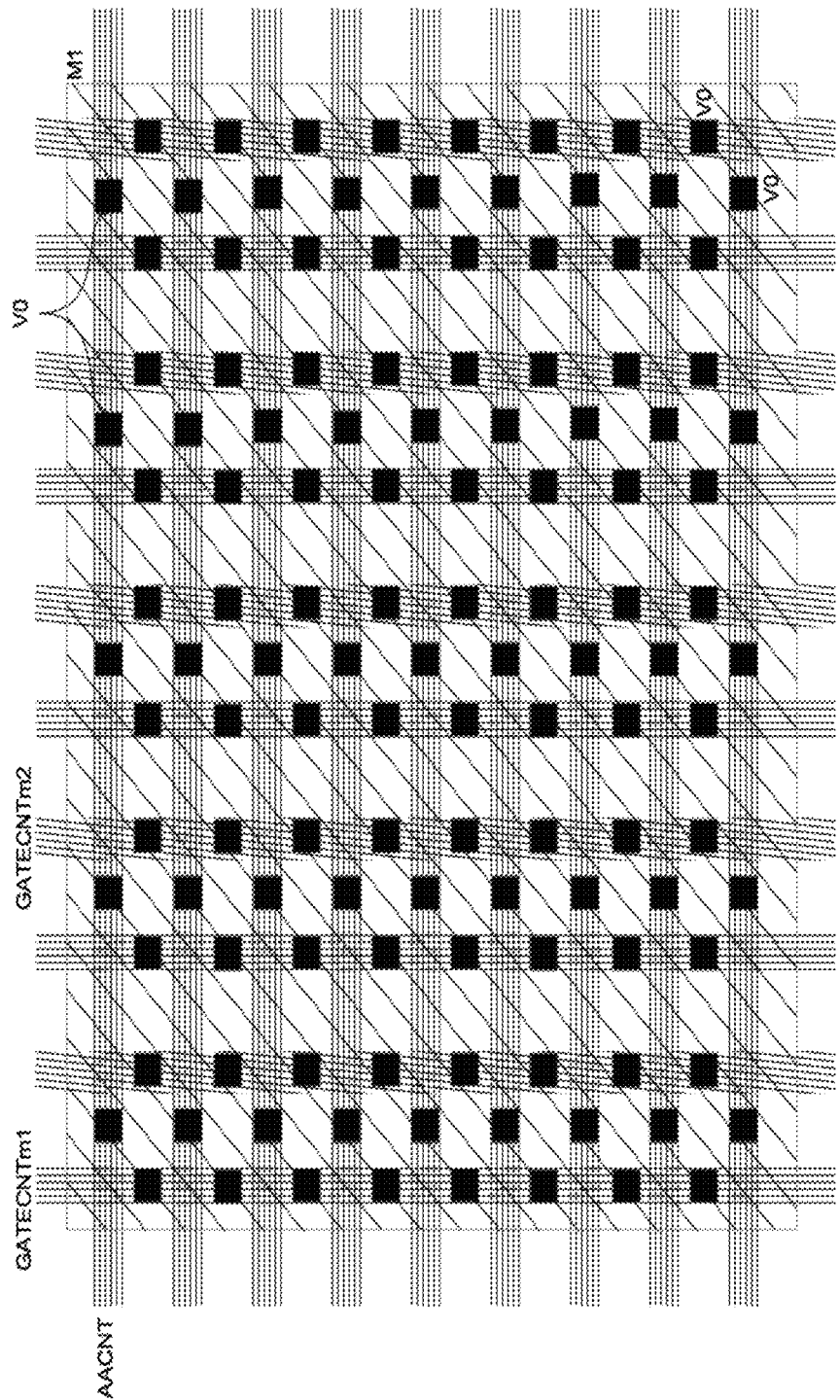
FIG. 9Z depicts an exemplary mesh-style, NCEM-enabled pad, formed from a 10×9 grid of double-patterned GATECNT and single-patterned AACNT stripes, with an overlying, solid M1 pad, and a plurality of V0 vias positioned to avoid GATECNT-AACNT junction points.
Figure 9A:
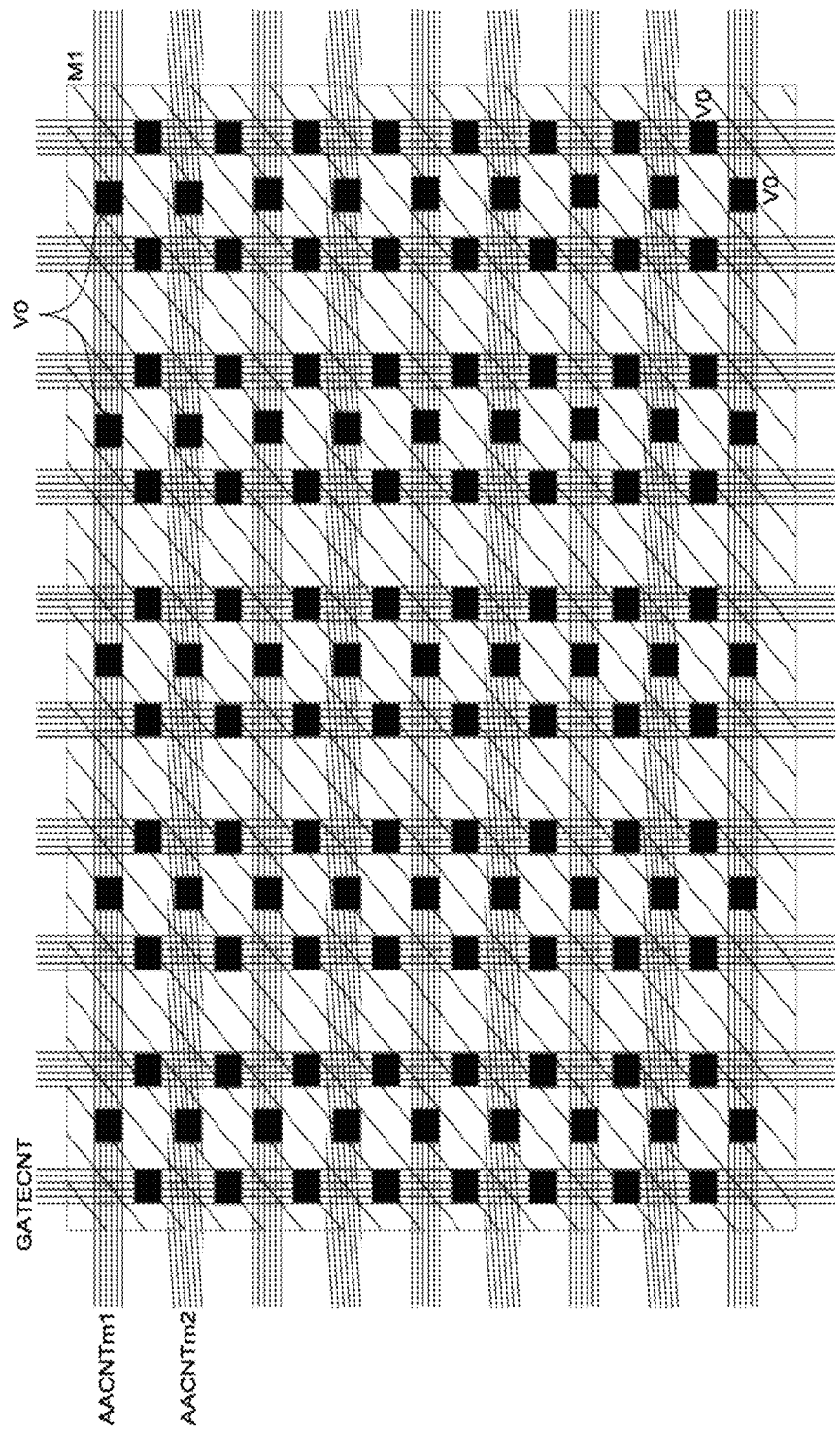
Figure 9B:
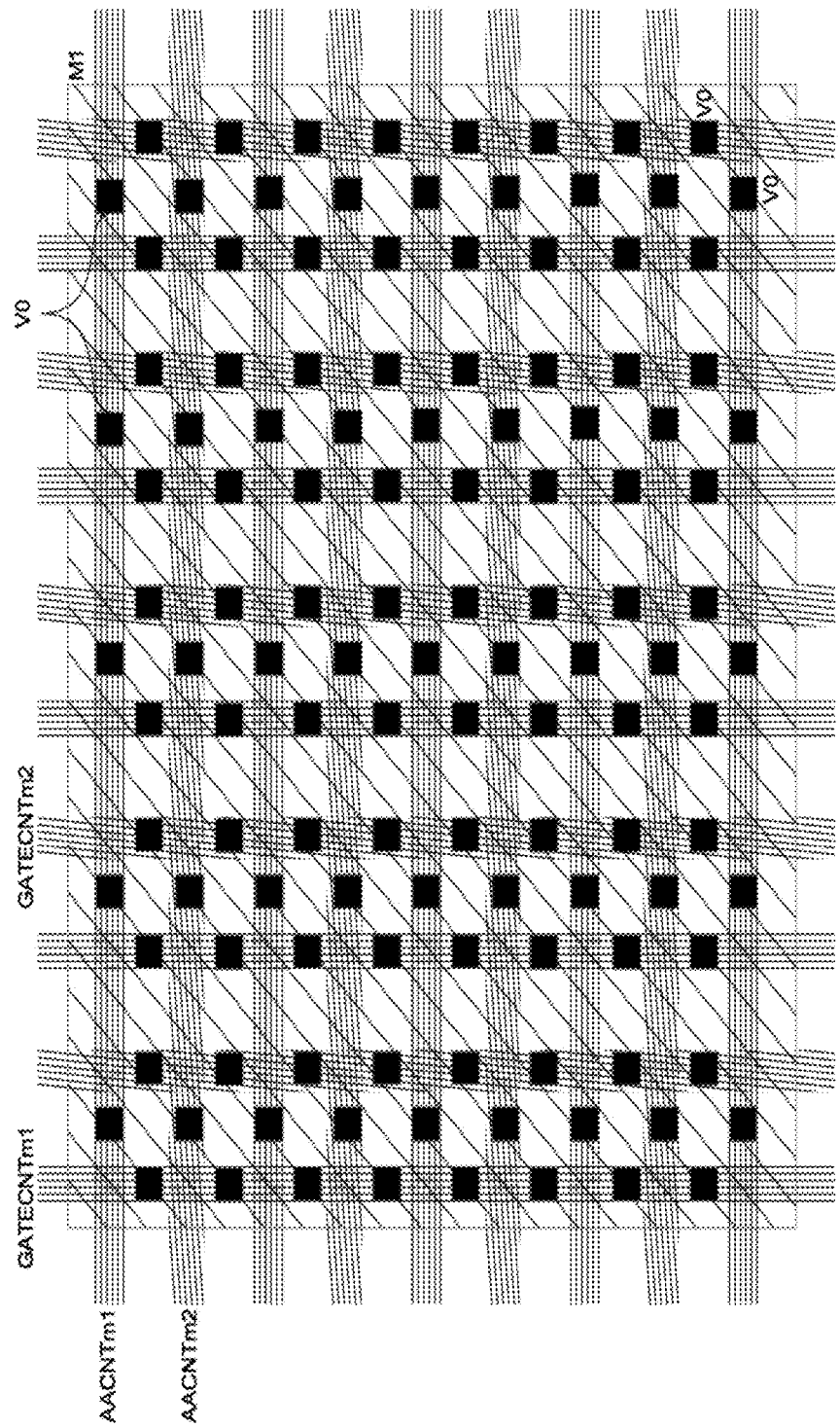
Figure 9C:
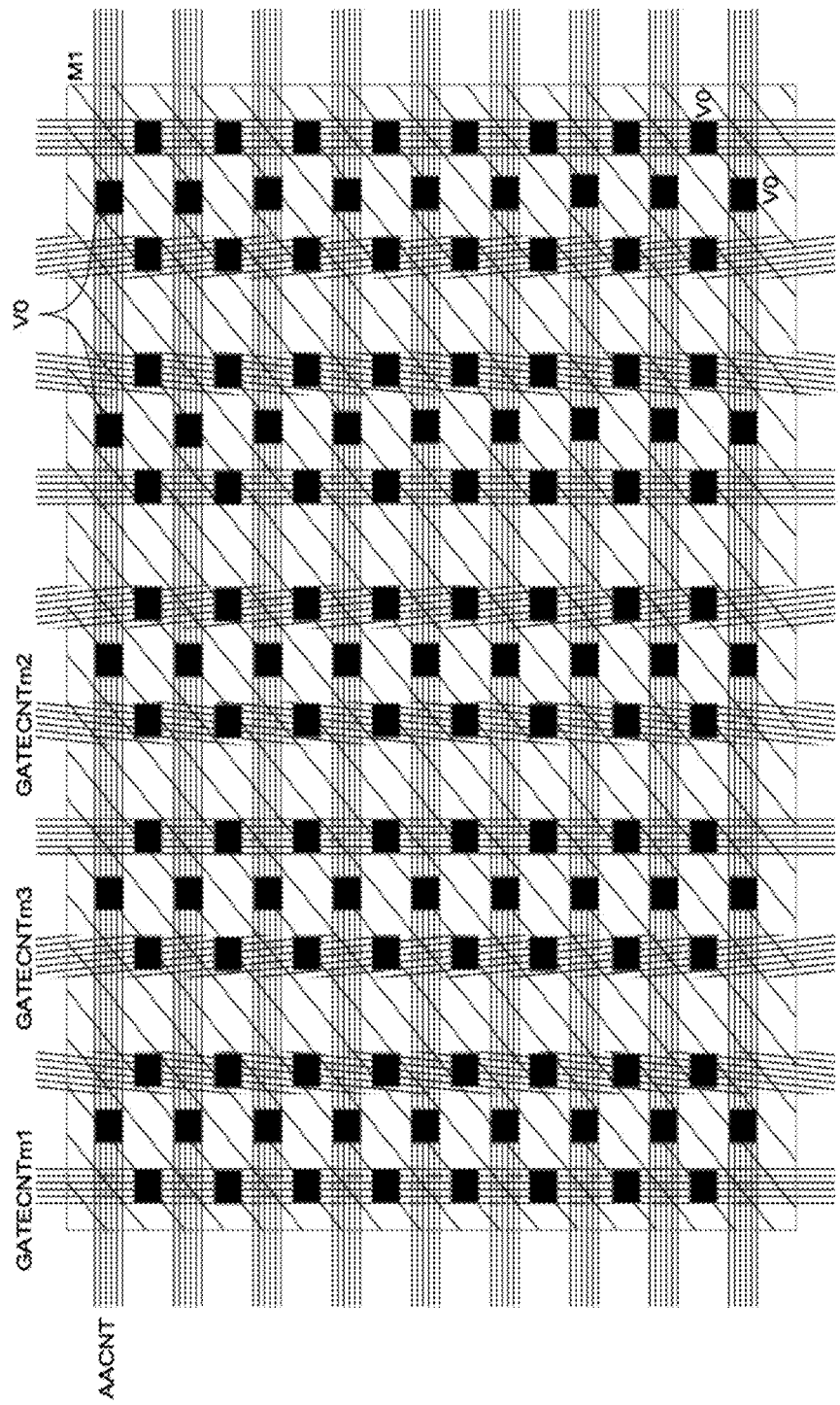
Figure 9D:
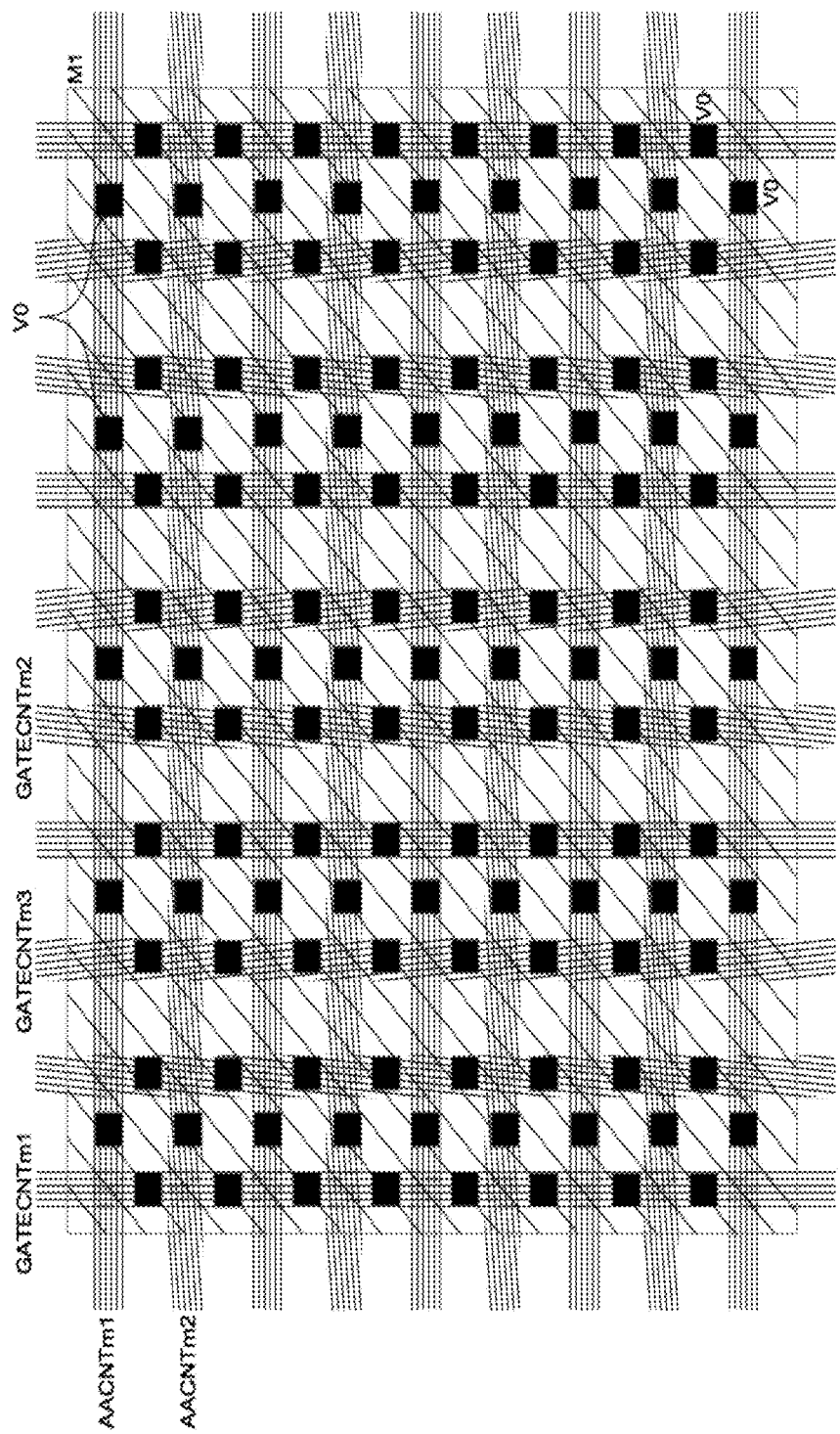
Figure 9E:
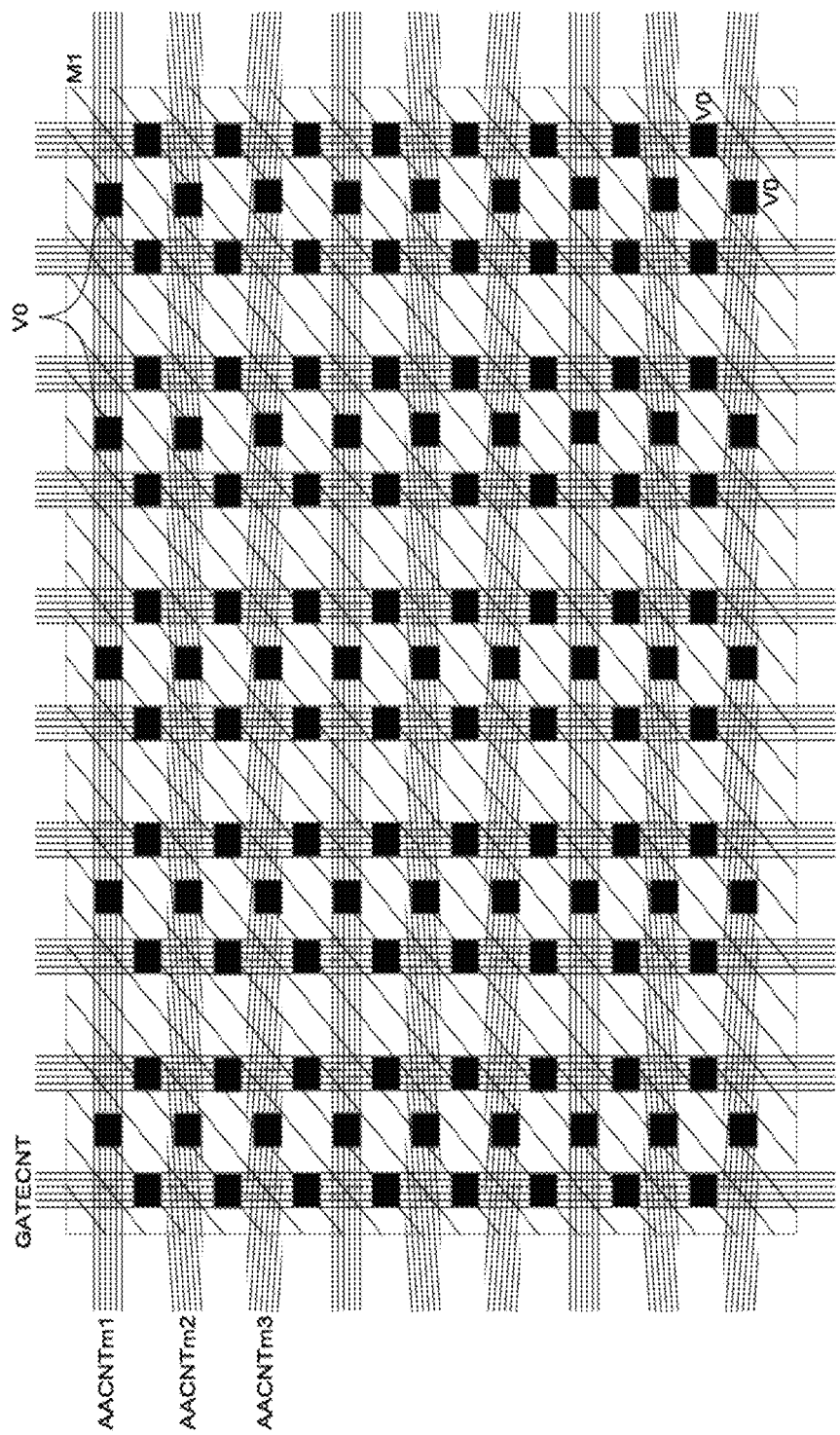
Figure 9F:
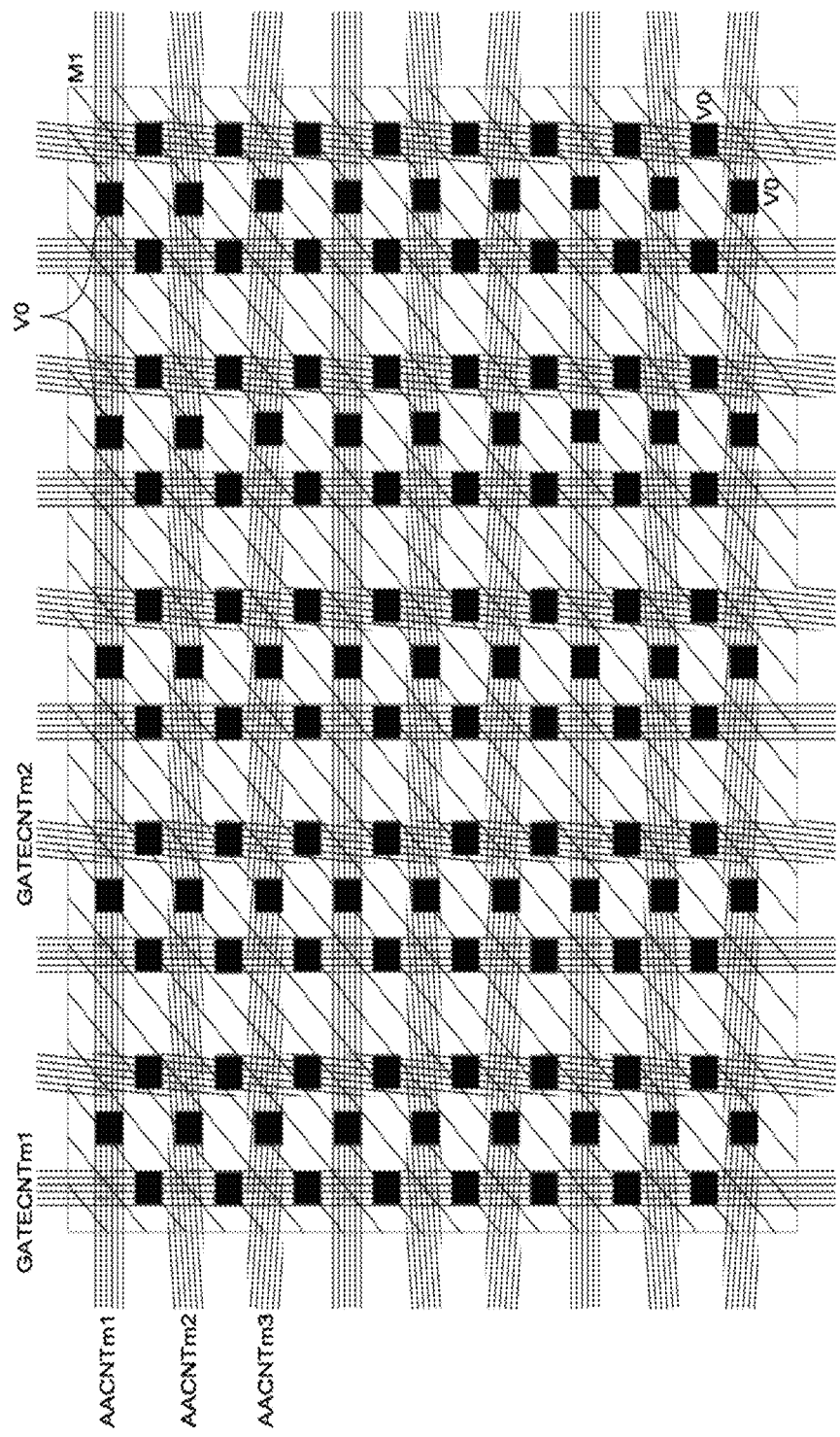
Figure 9G:
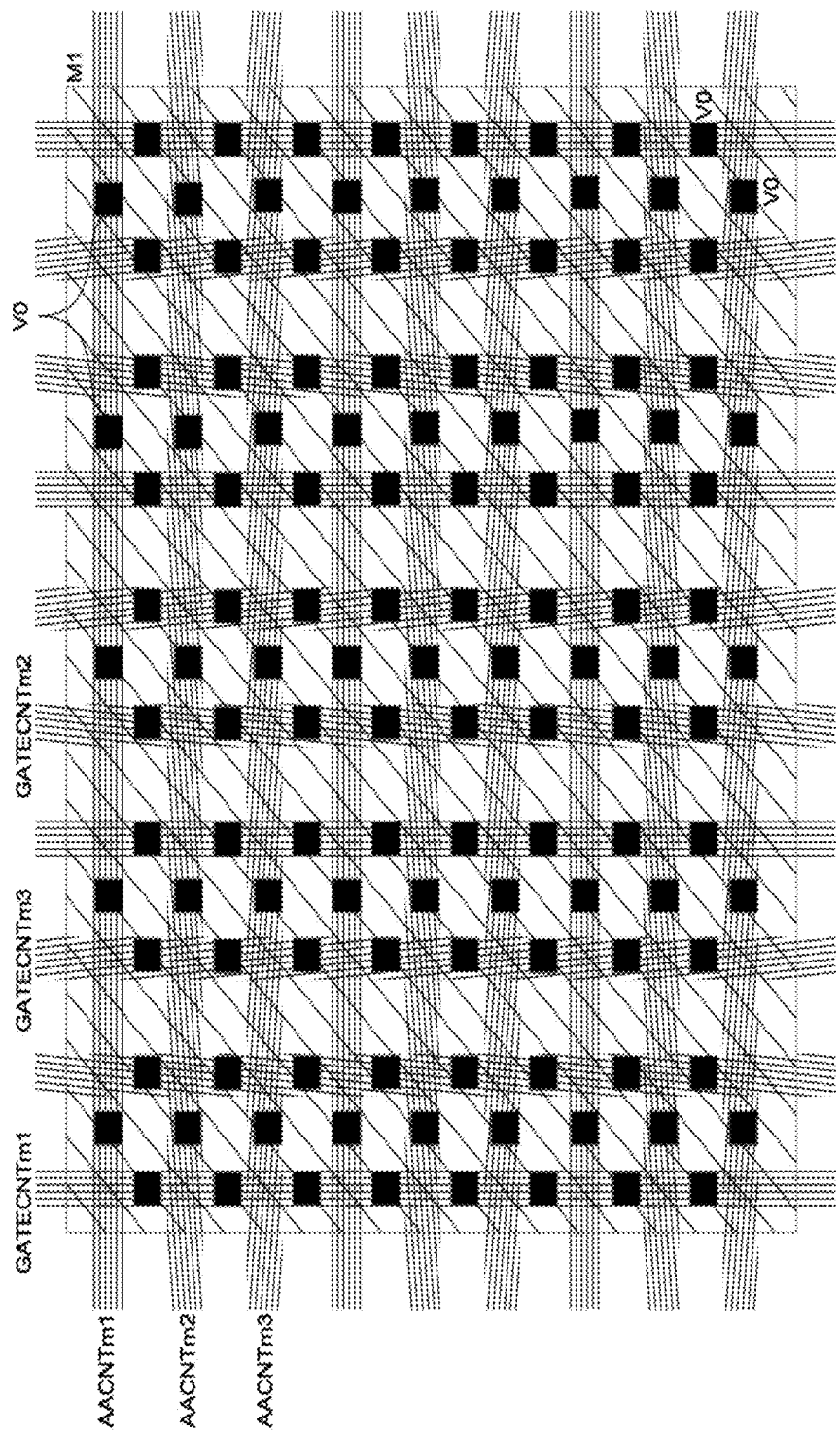
Figure 9H:
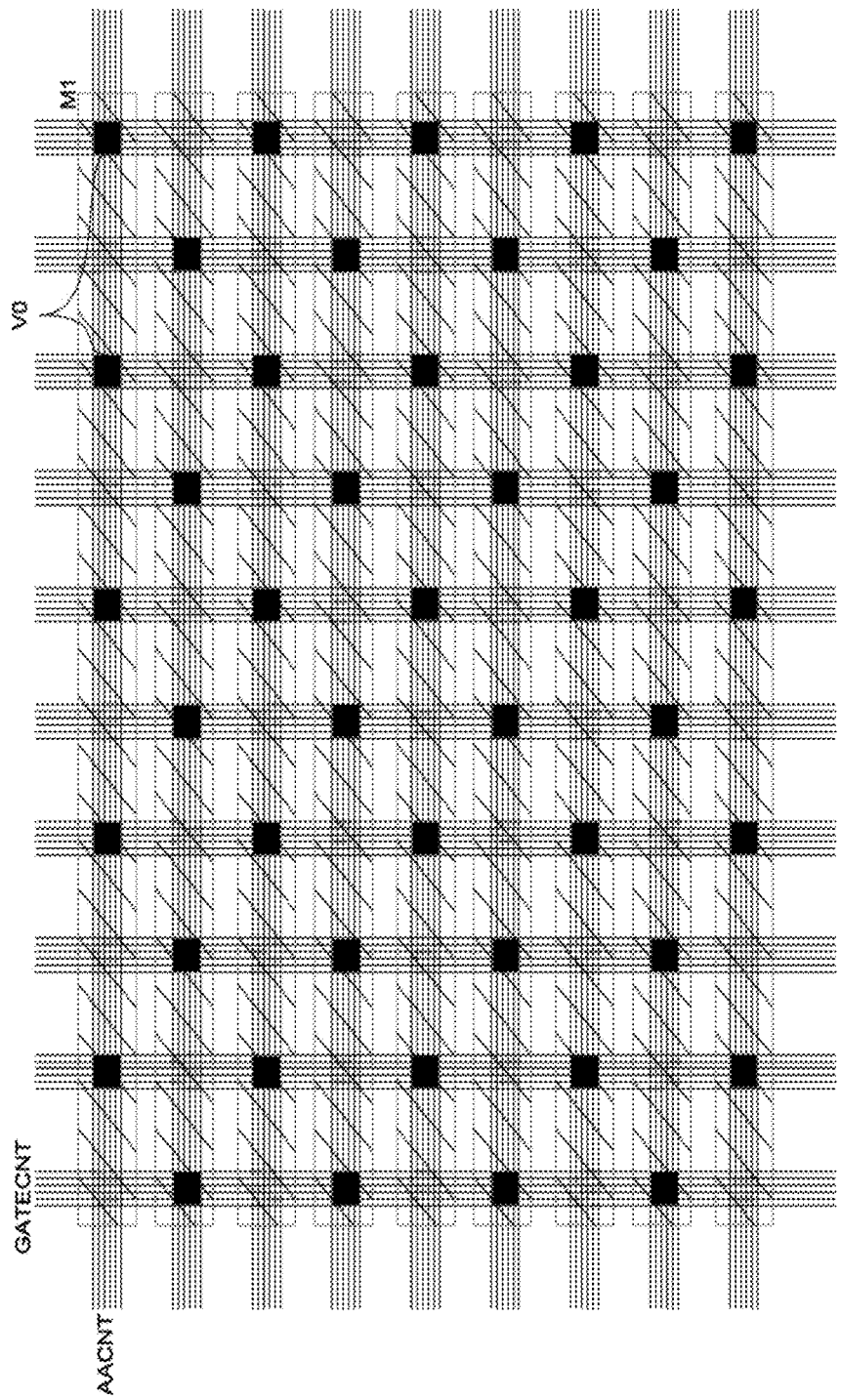
Figure 9I:
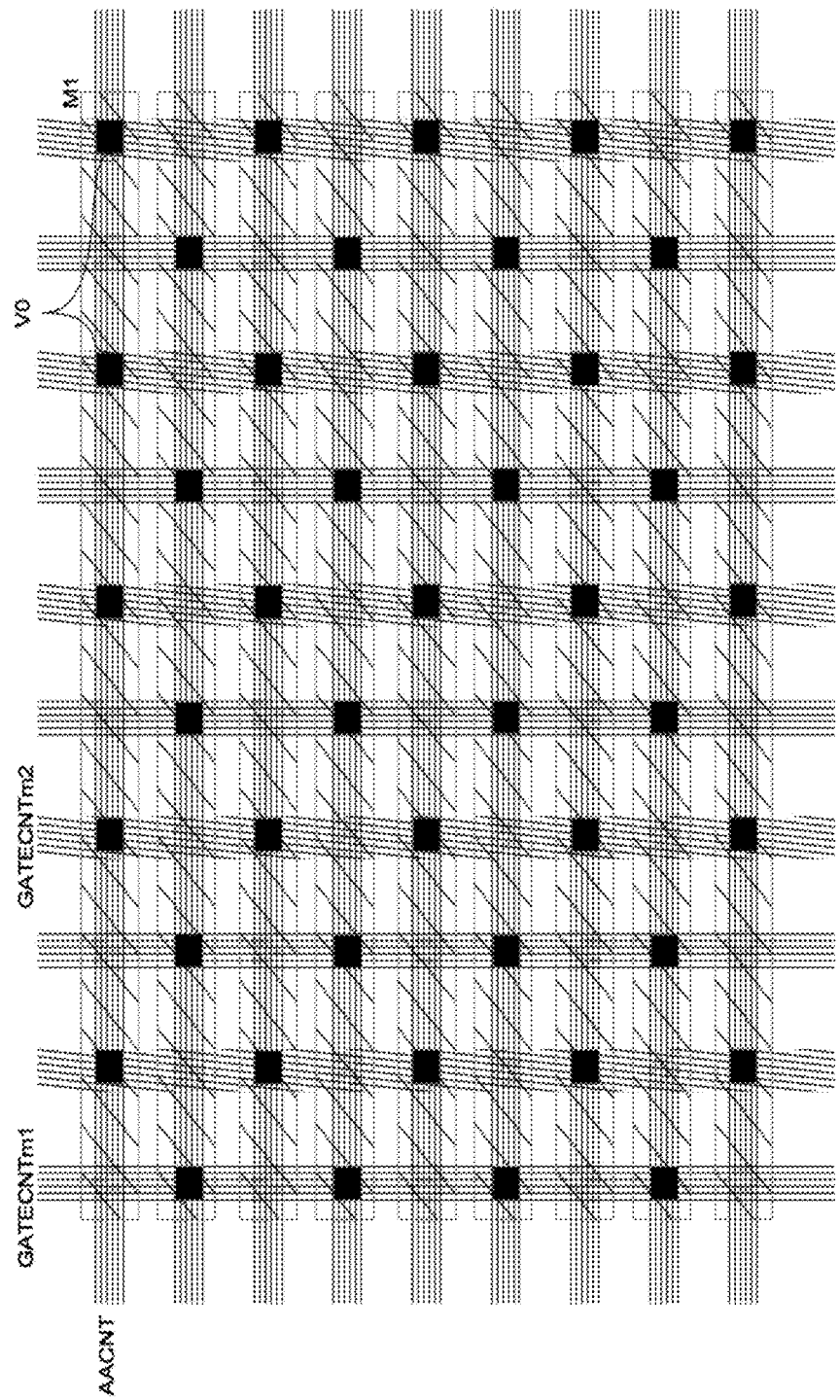
FIG. 9I depicts an exemplary mesh-style, NCEM-enabled pad, formed from a 10×9 grid of single-patterned GATECNT and double-patterned AACNT stripes.
Figure 9J:
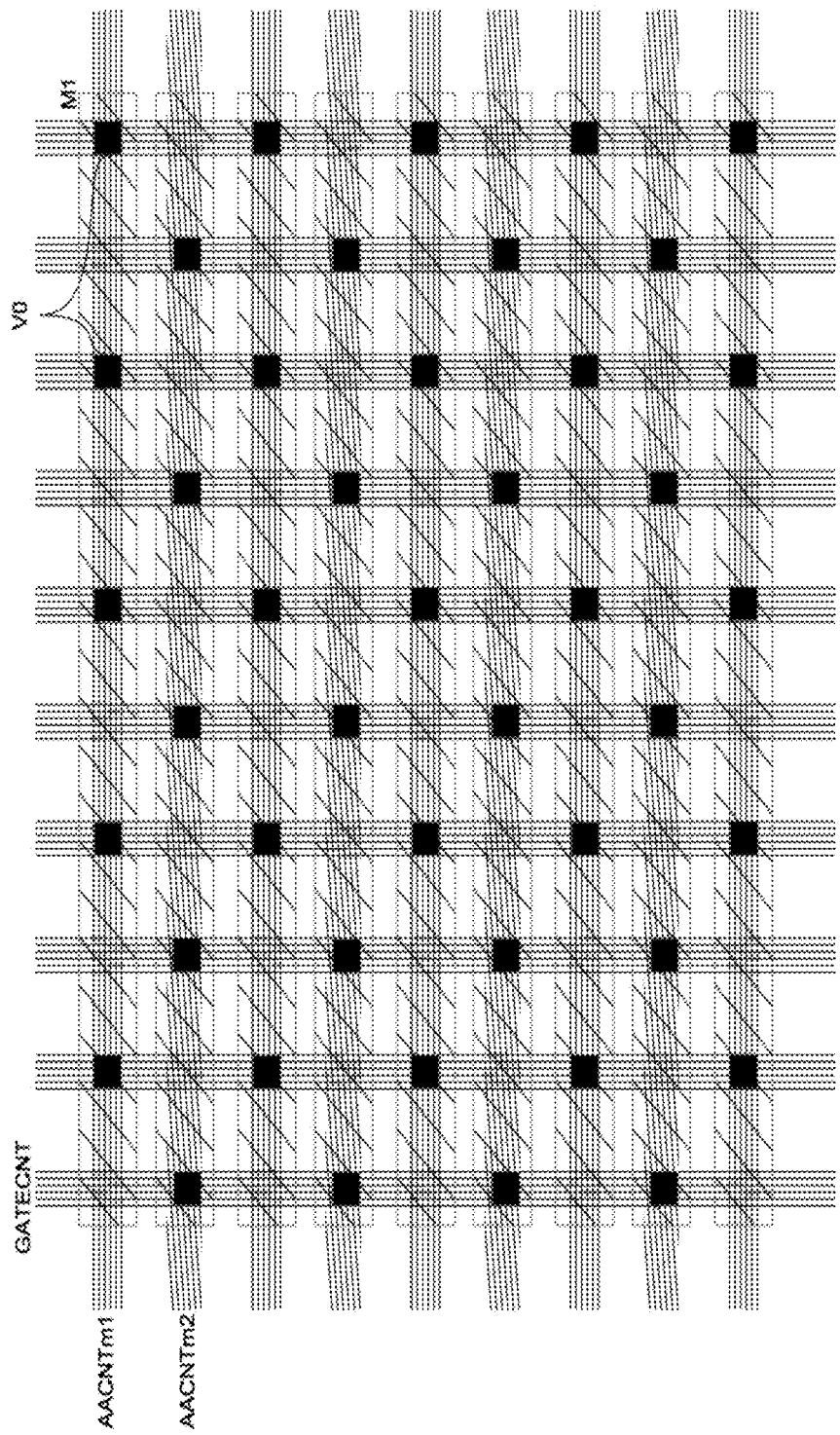
Figure 9K:
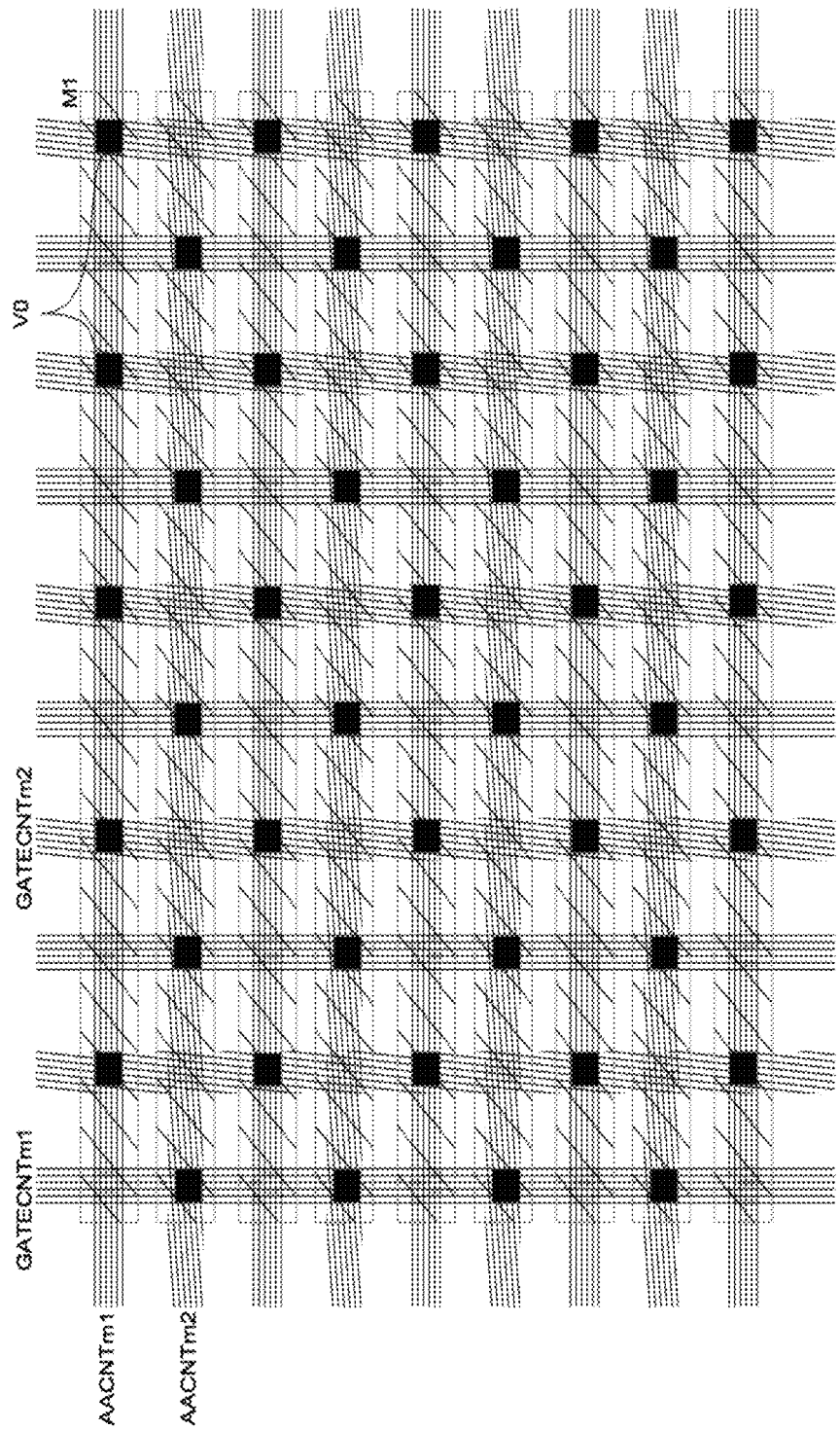
Figure 9L:
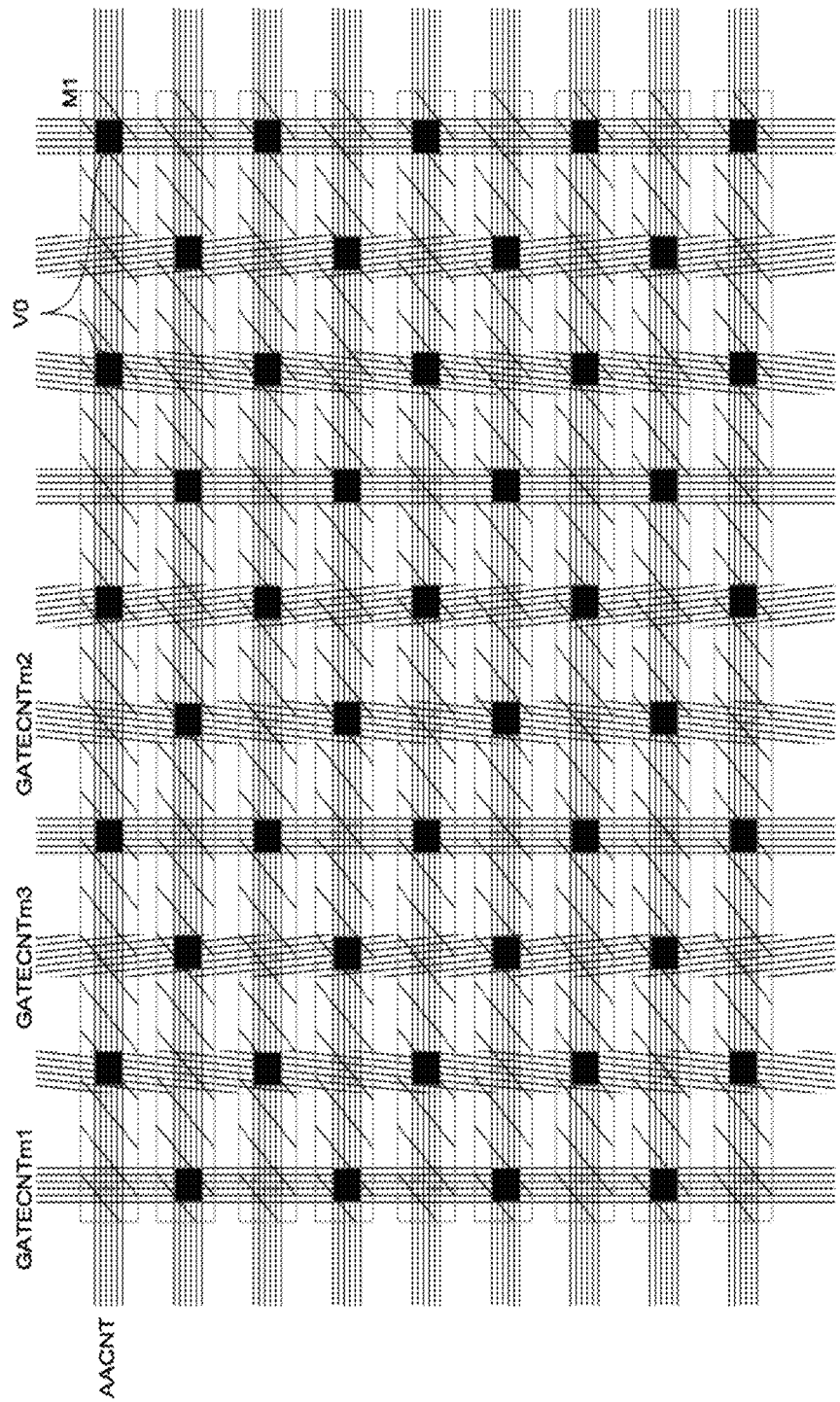
Figure 9M:
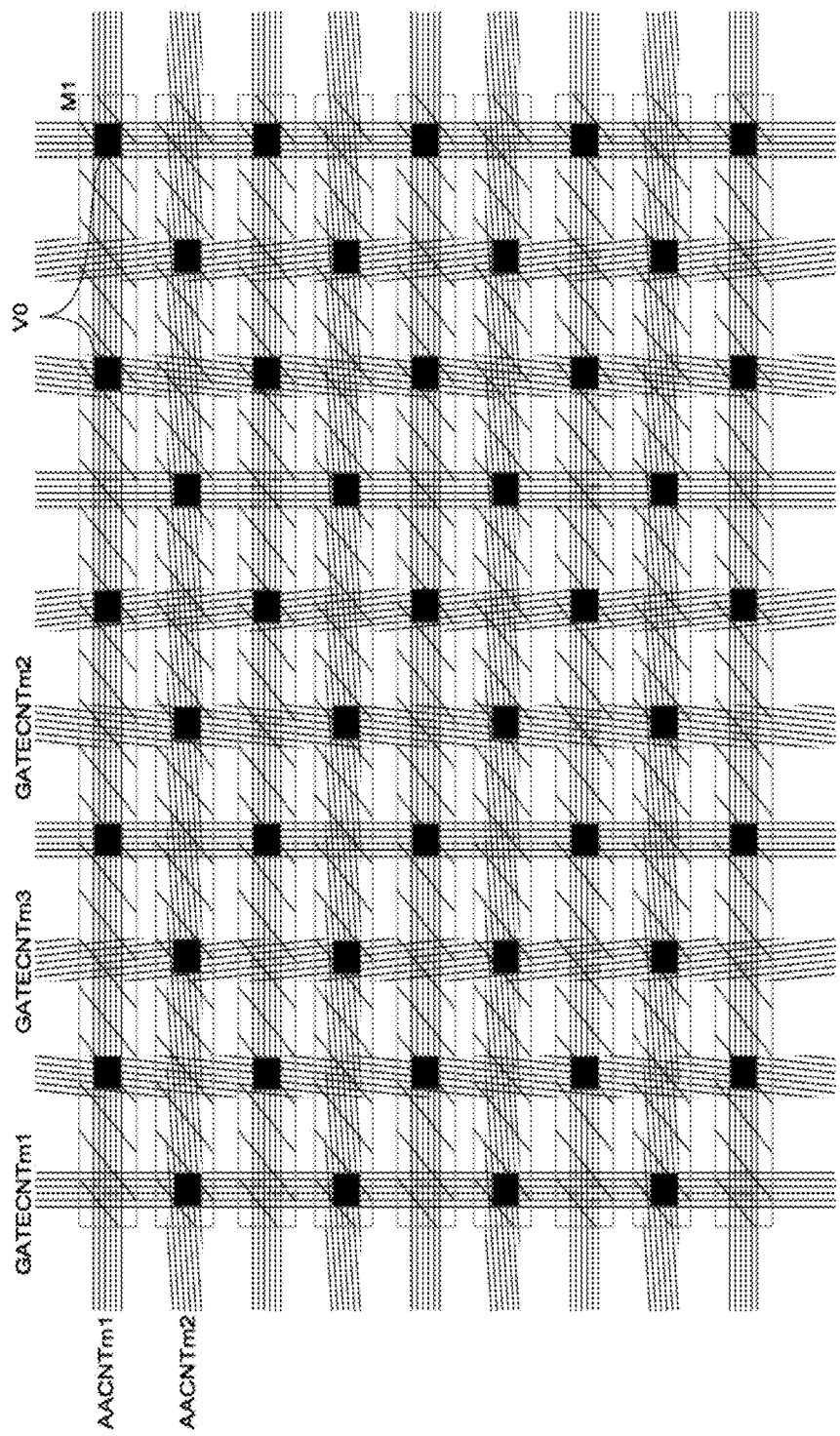
Figure 9N:
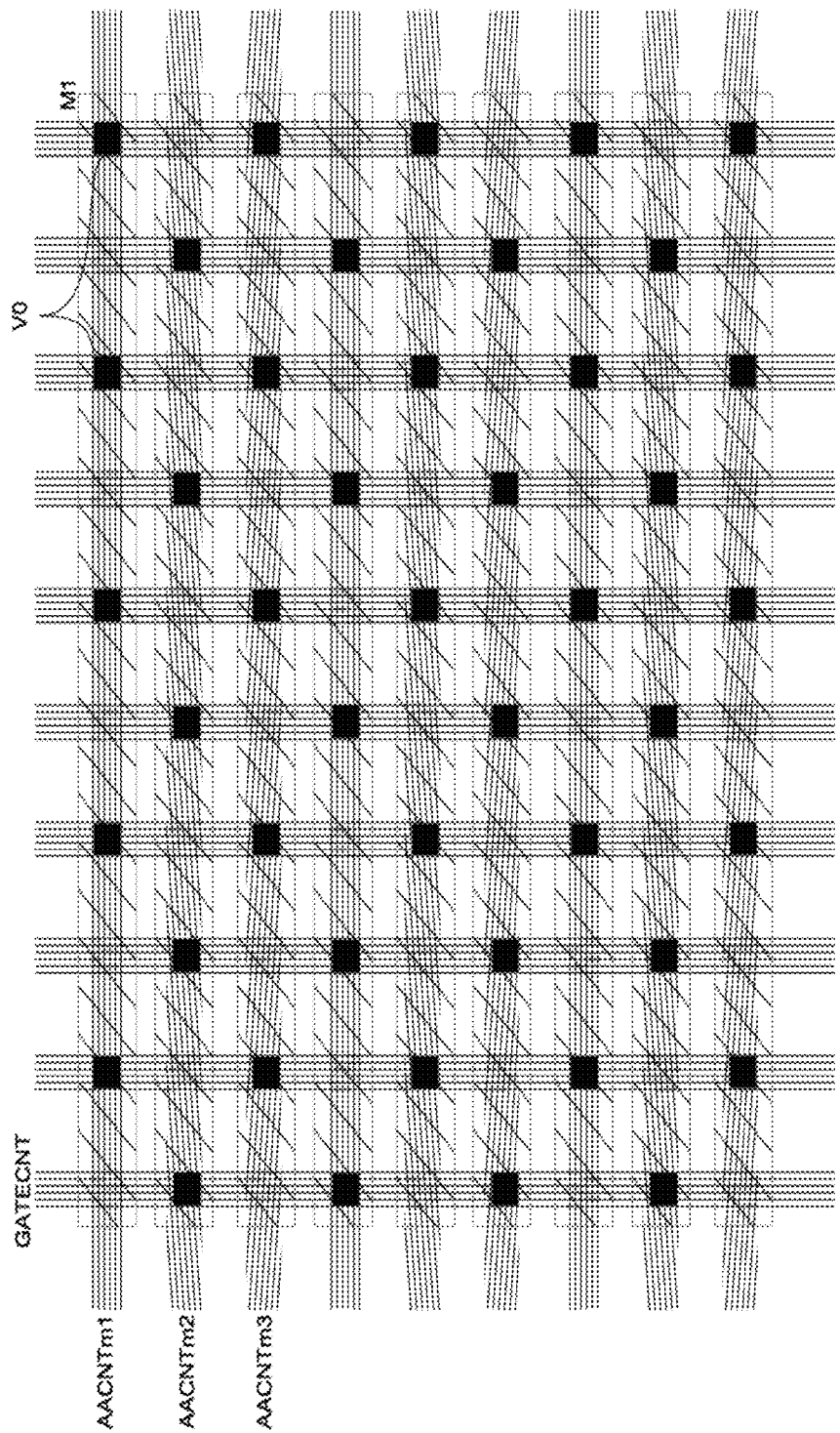
FIG. 9N depicts an exemplary mesh-style, NCEM-enabled pad, formed from a 10×9 grid of double-patterned GATECNT and triple-patterned AACNT stripes.
Figure 900:
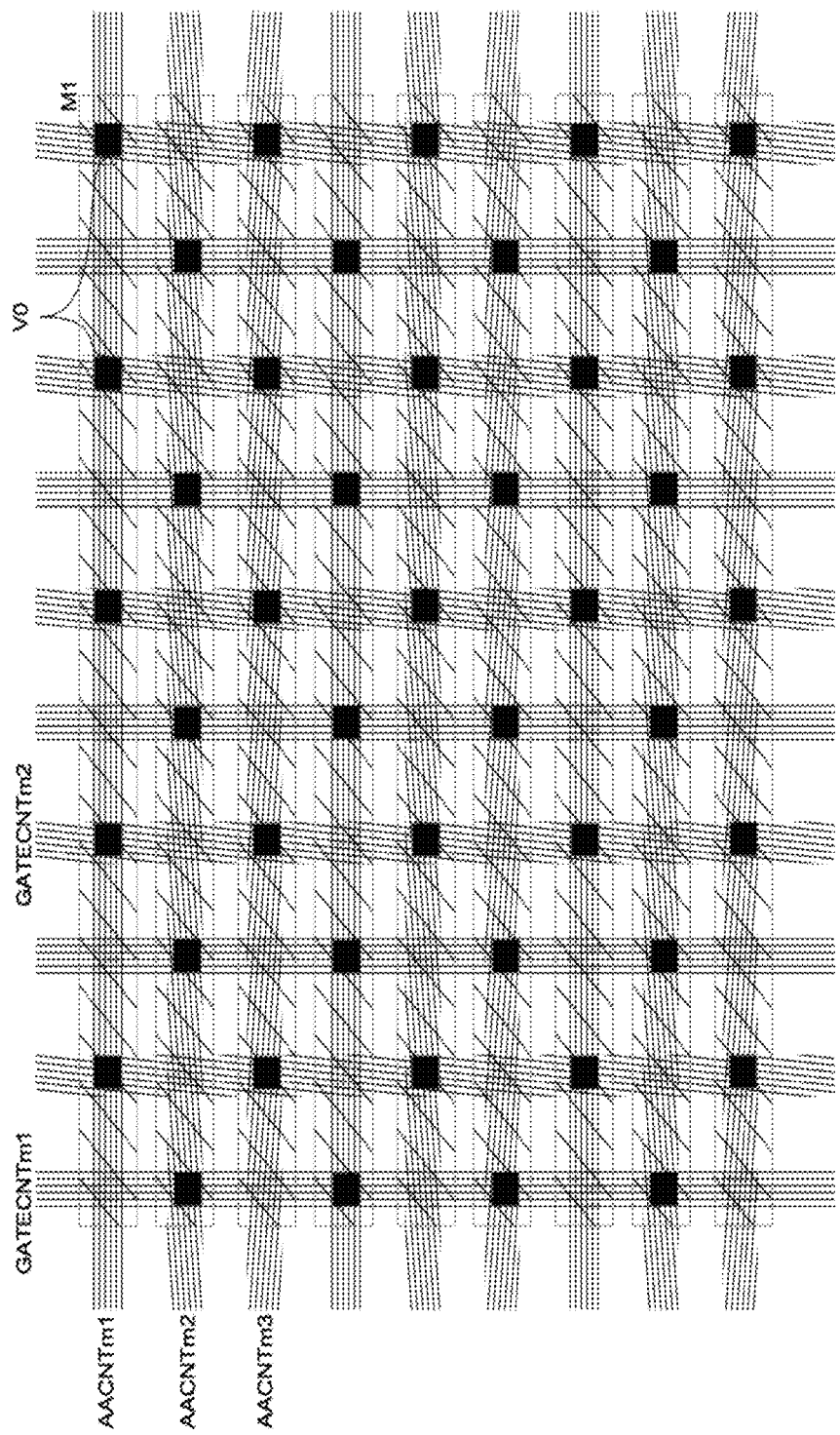
Figure 9P:
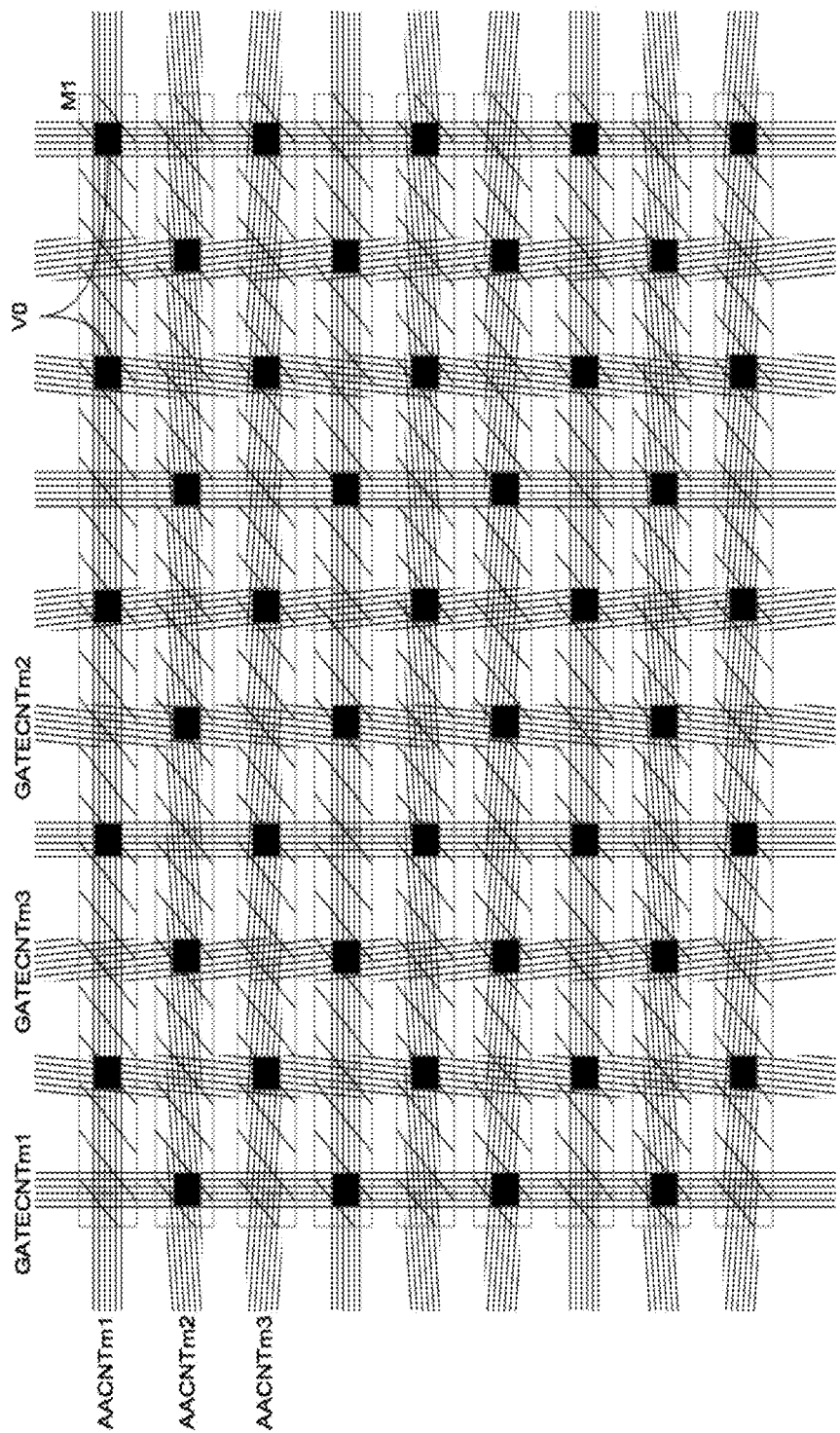
Figure 9Q:
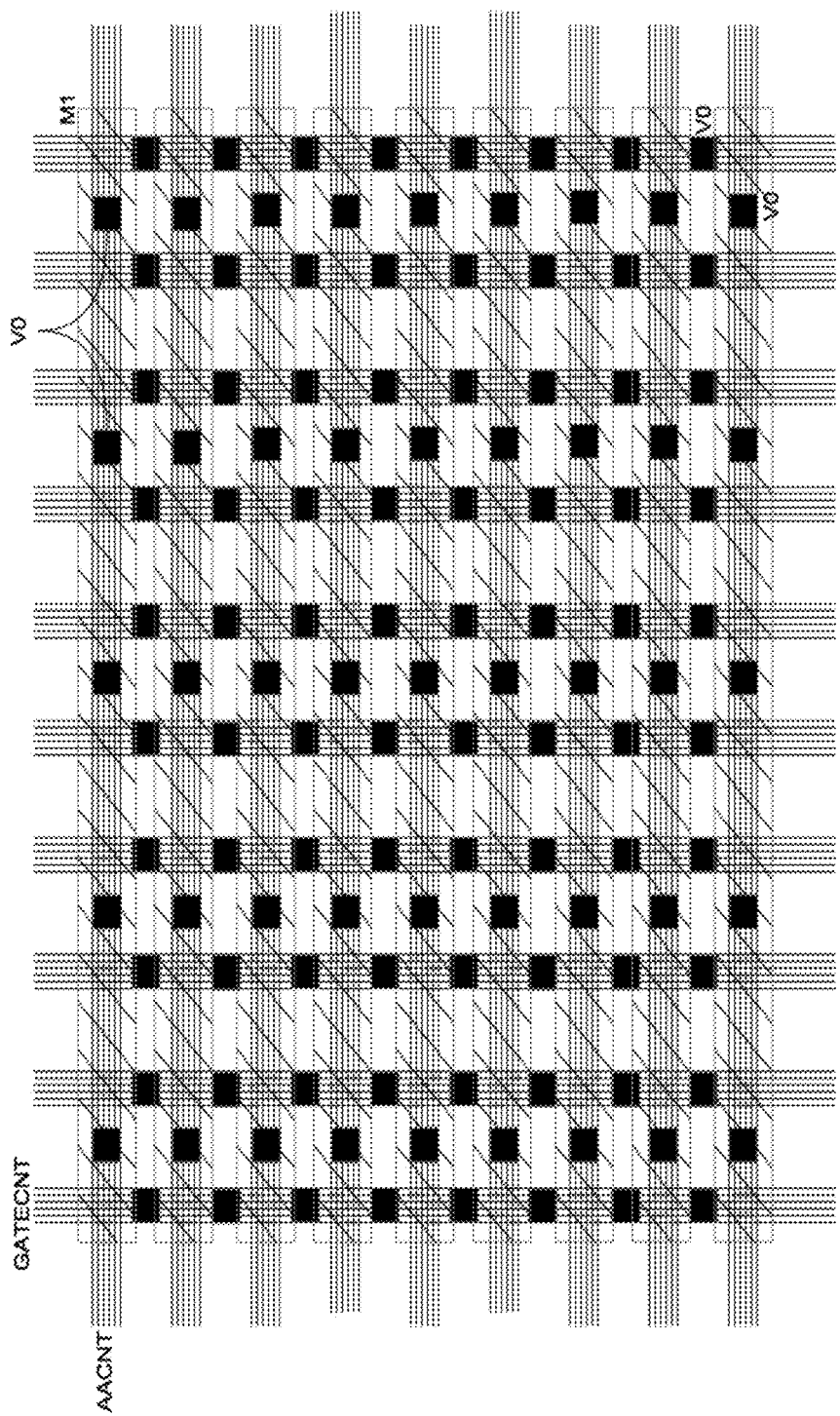
Figure 9R:
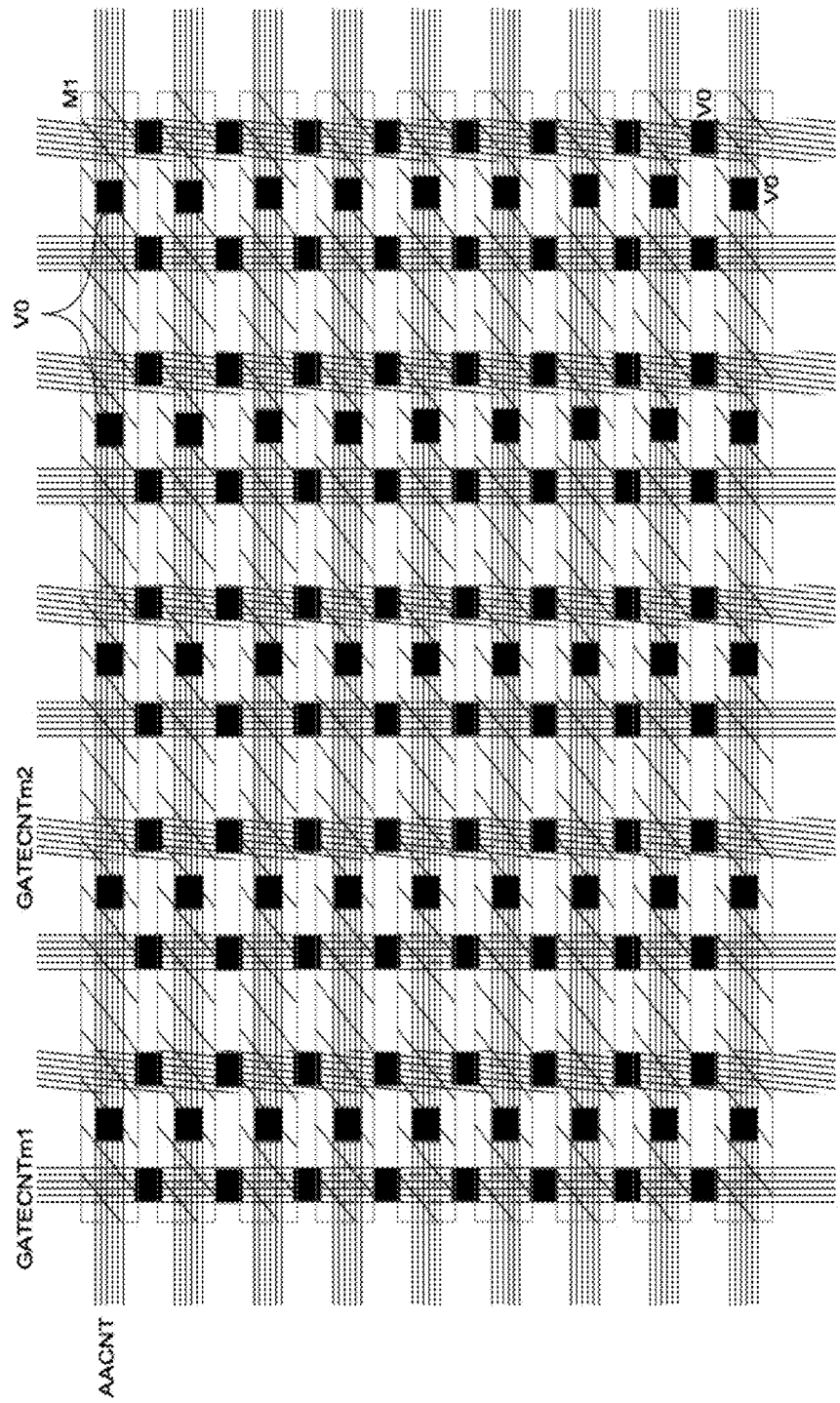
Figure 9S:
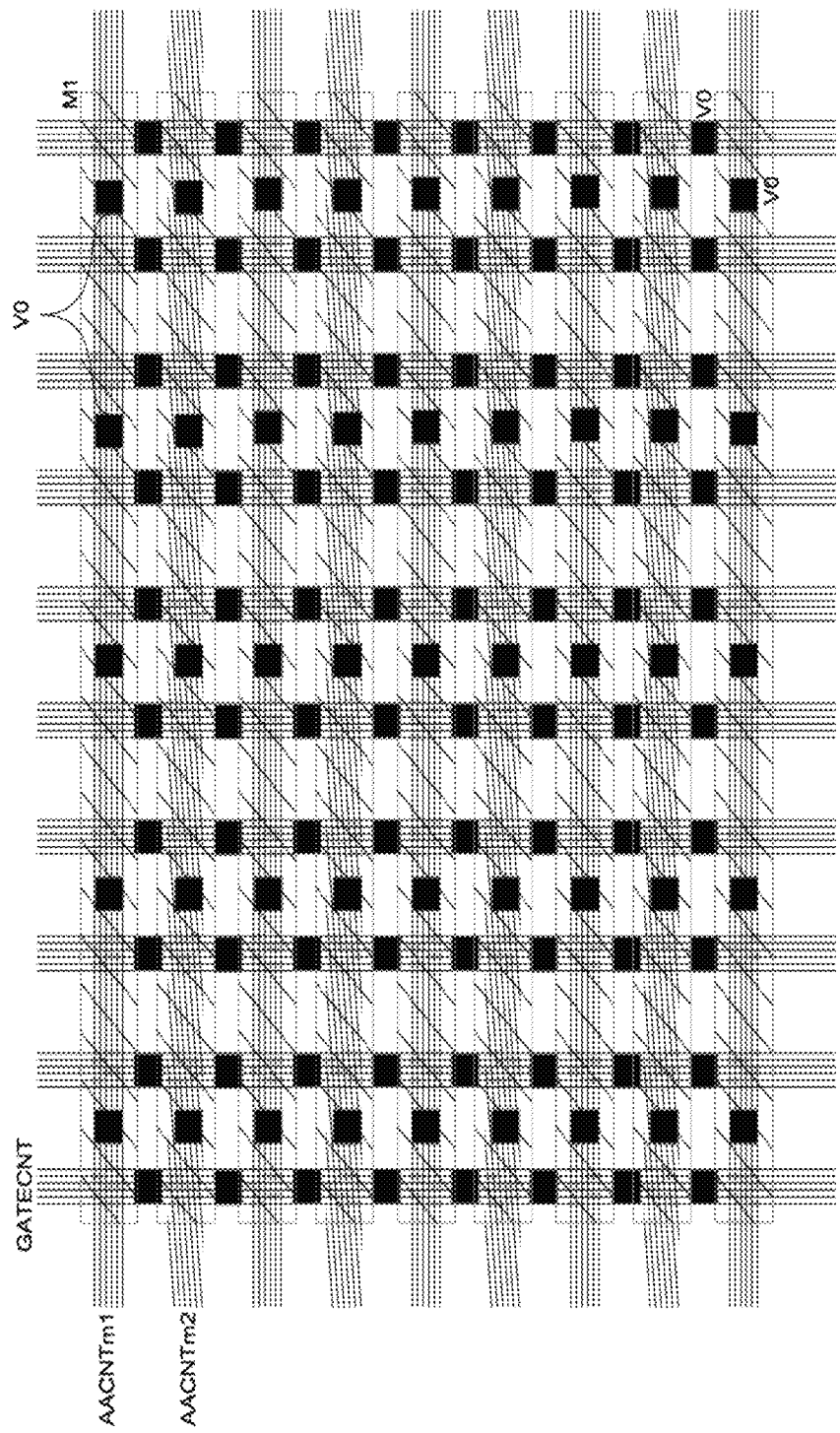
Figure 9T:
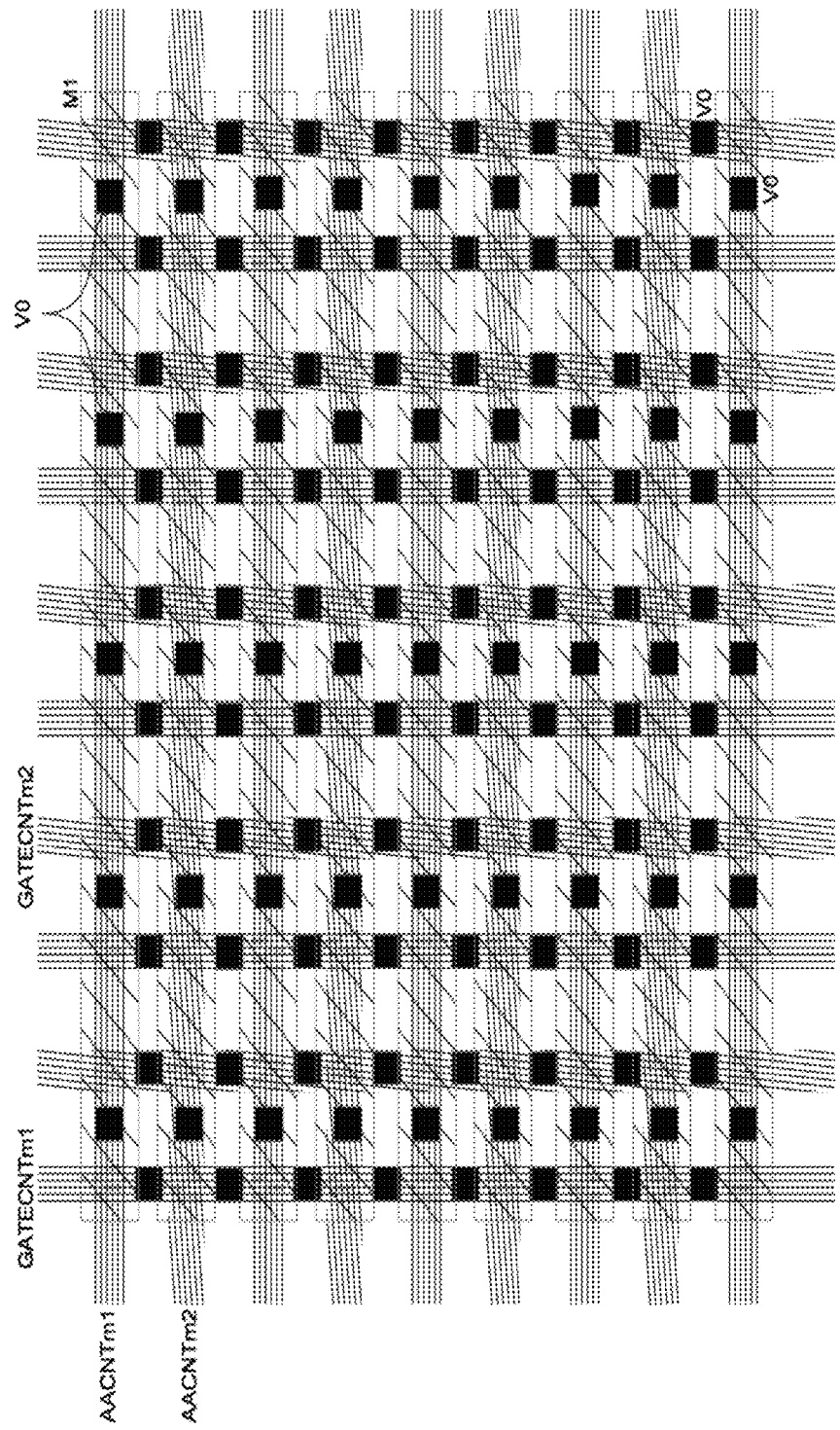
Figure 9U:
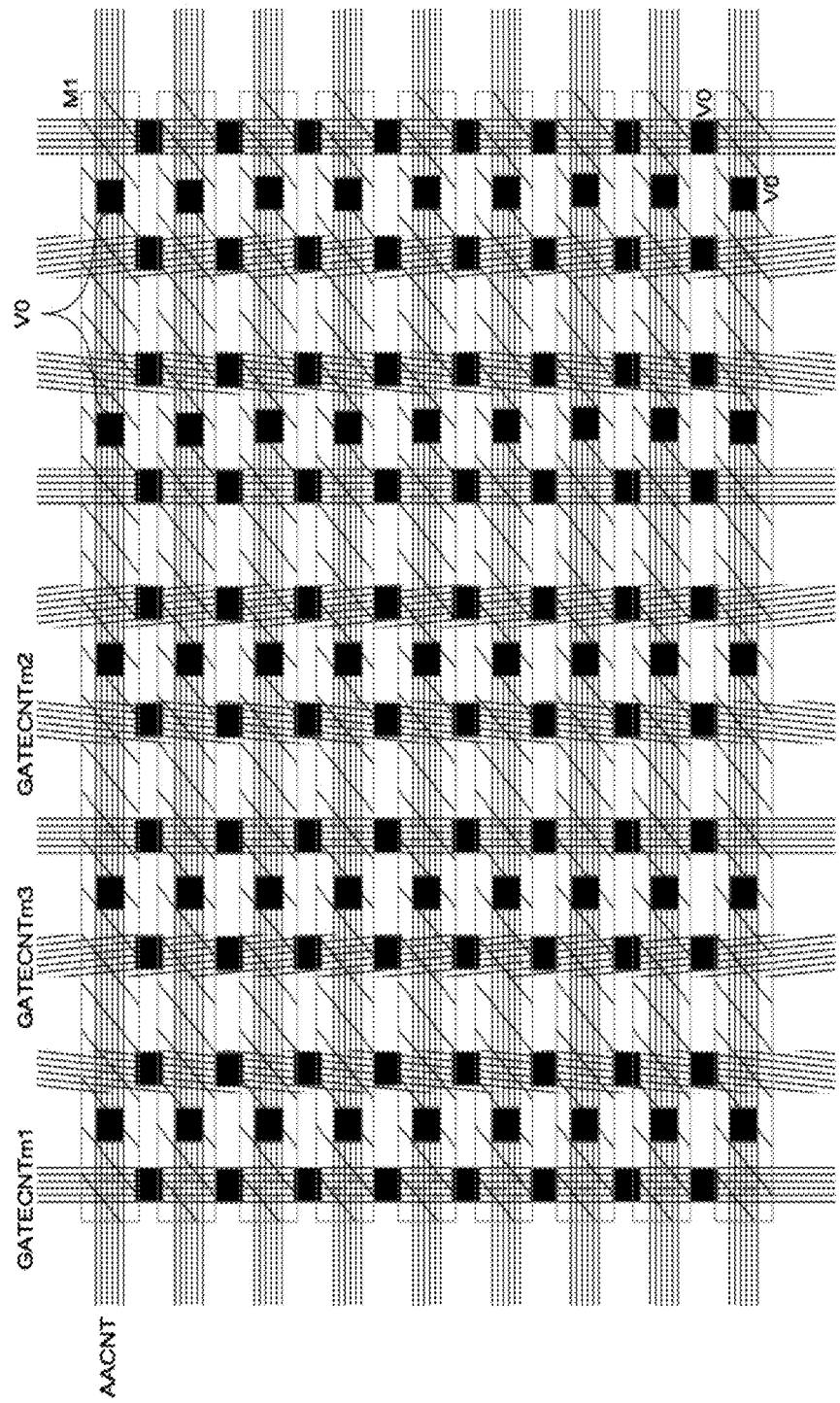
Figure 9V:
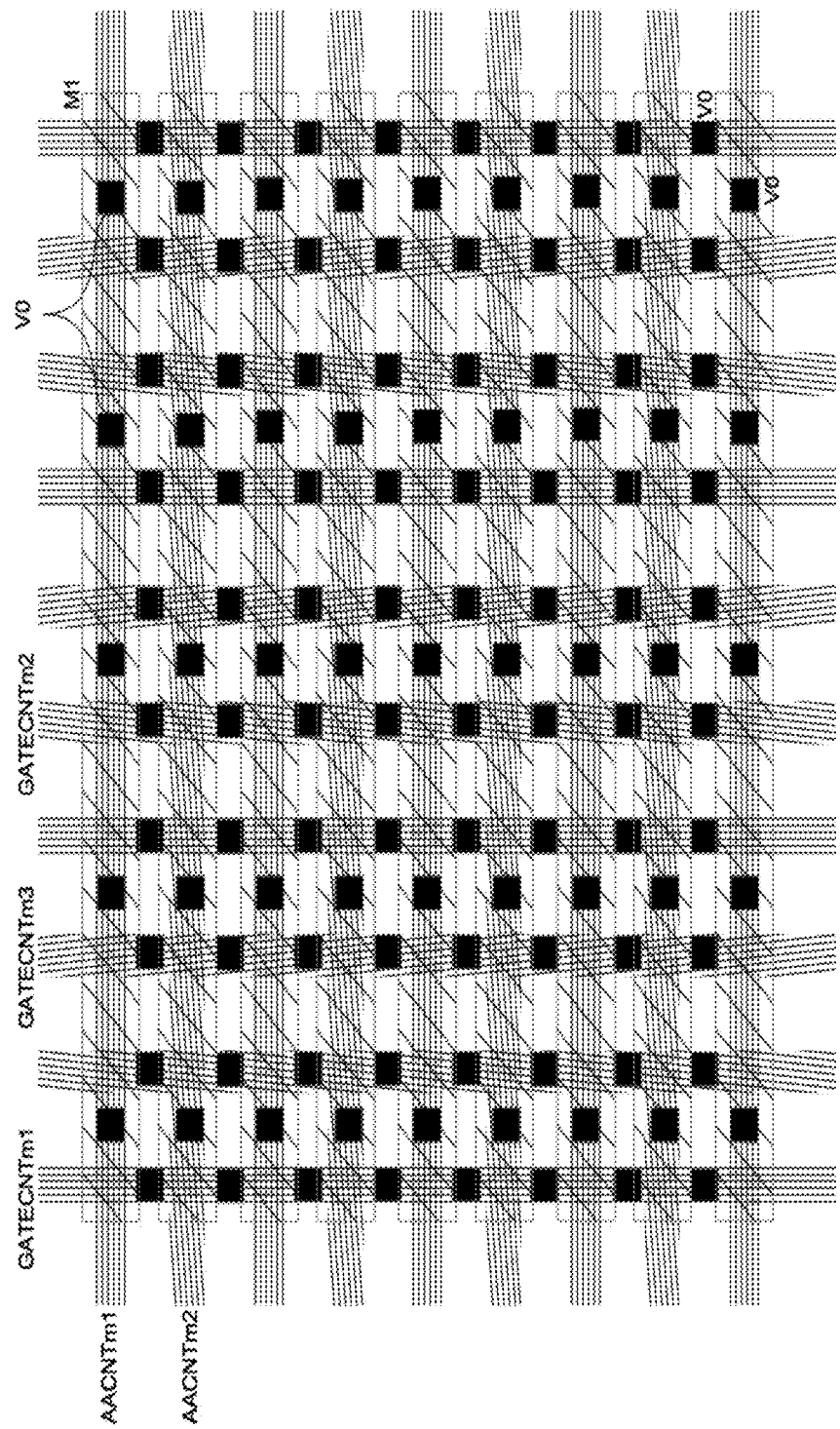
Figure 9W:
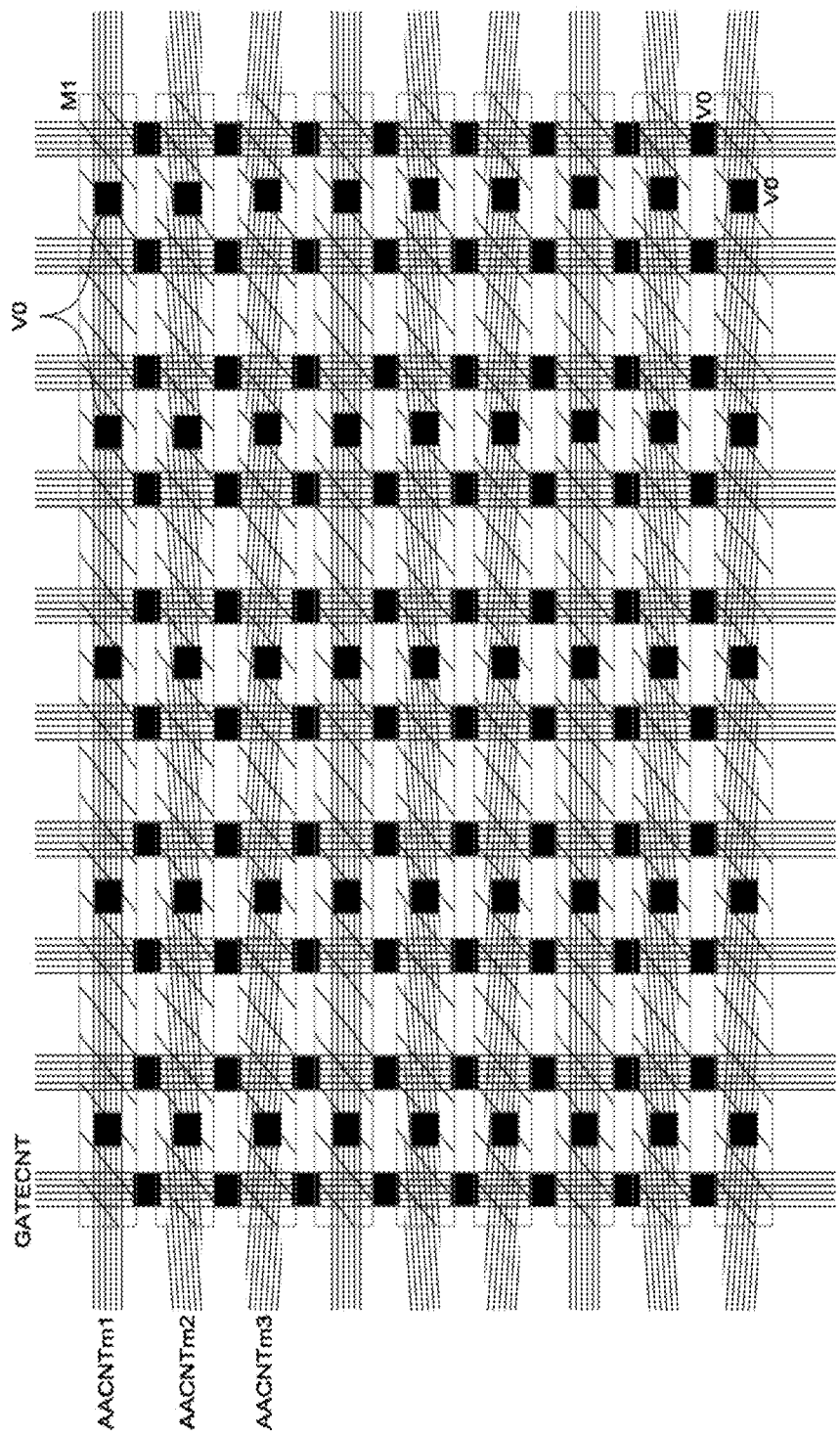
Figure 9X:
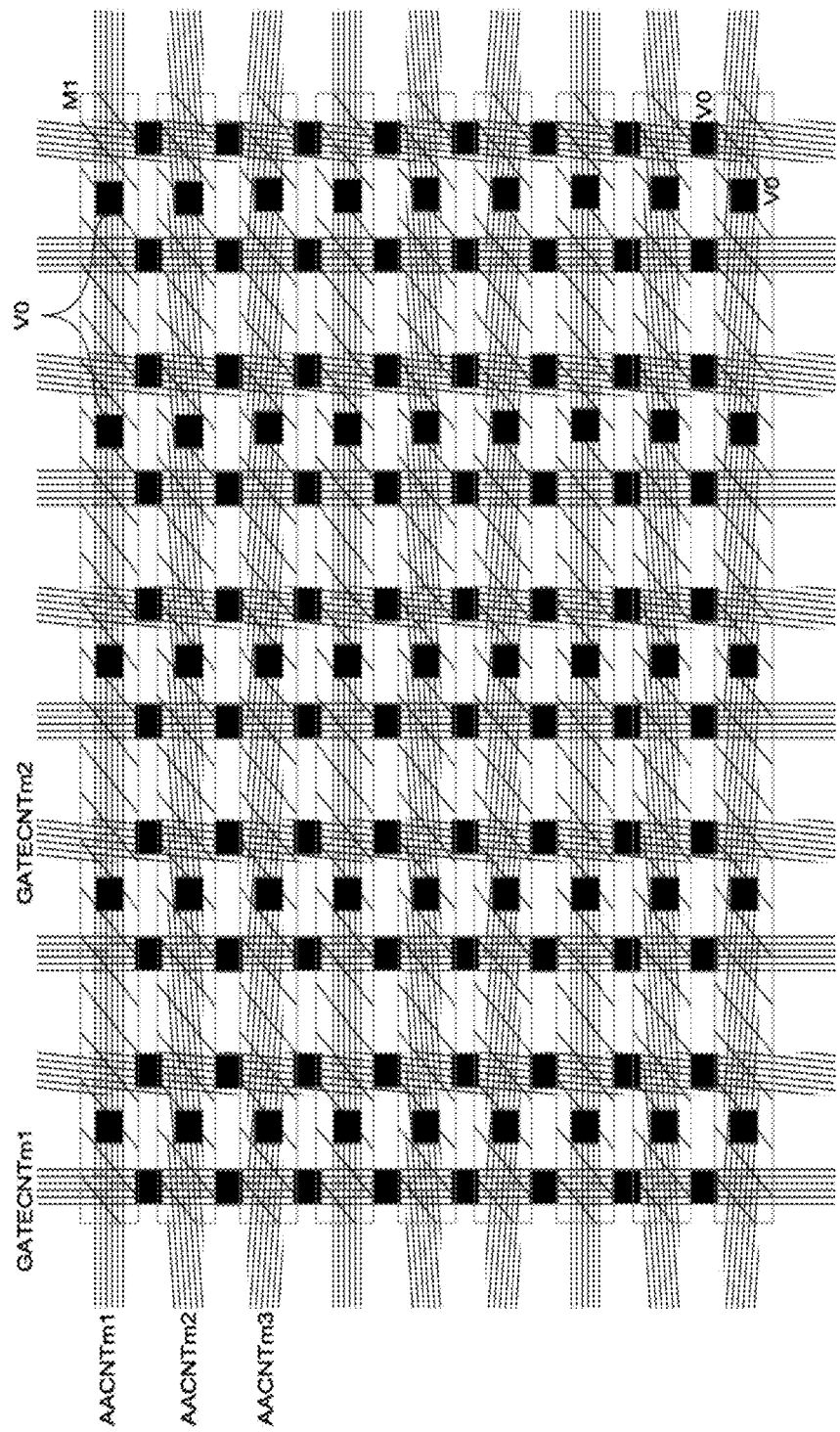
Figure 9Y:
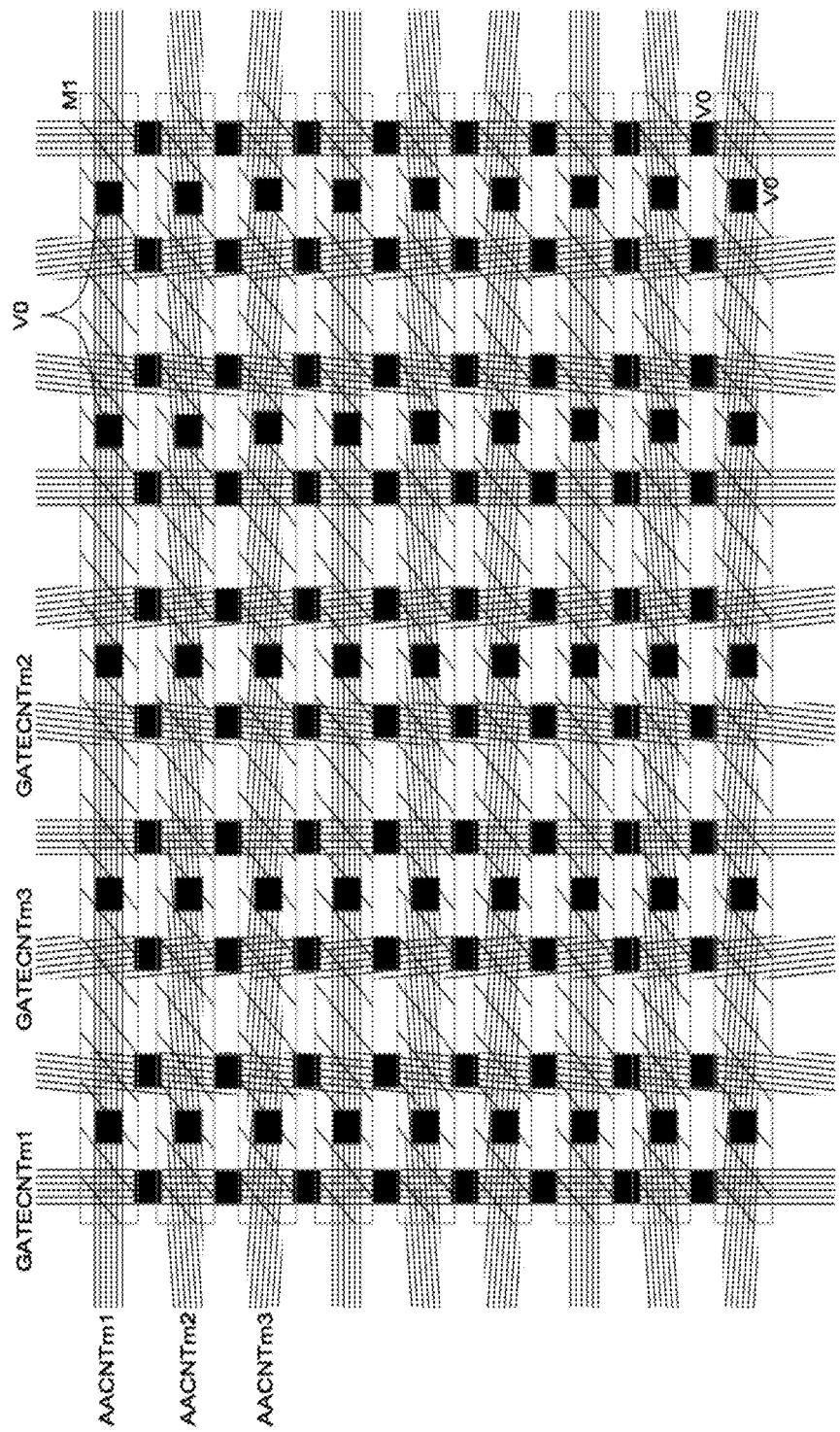
Figure 9Z:
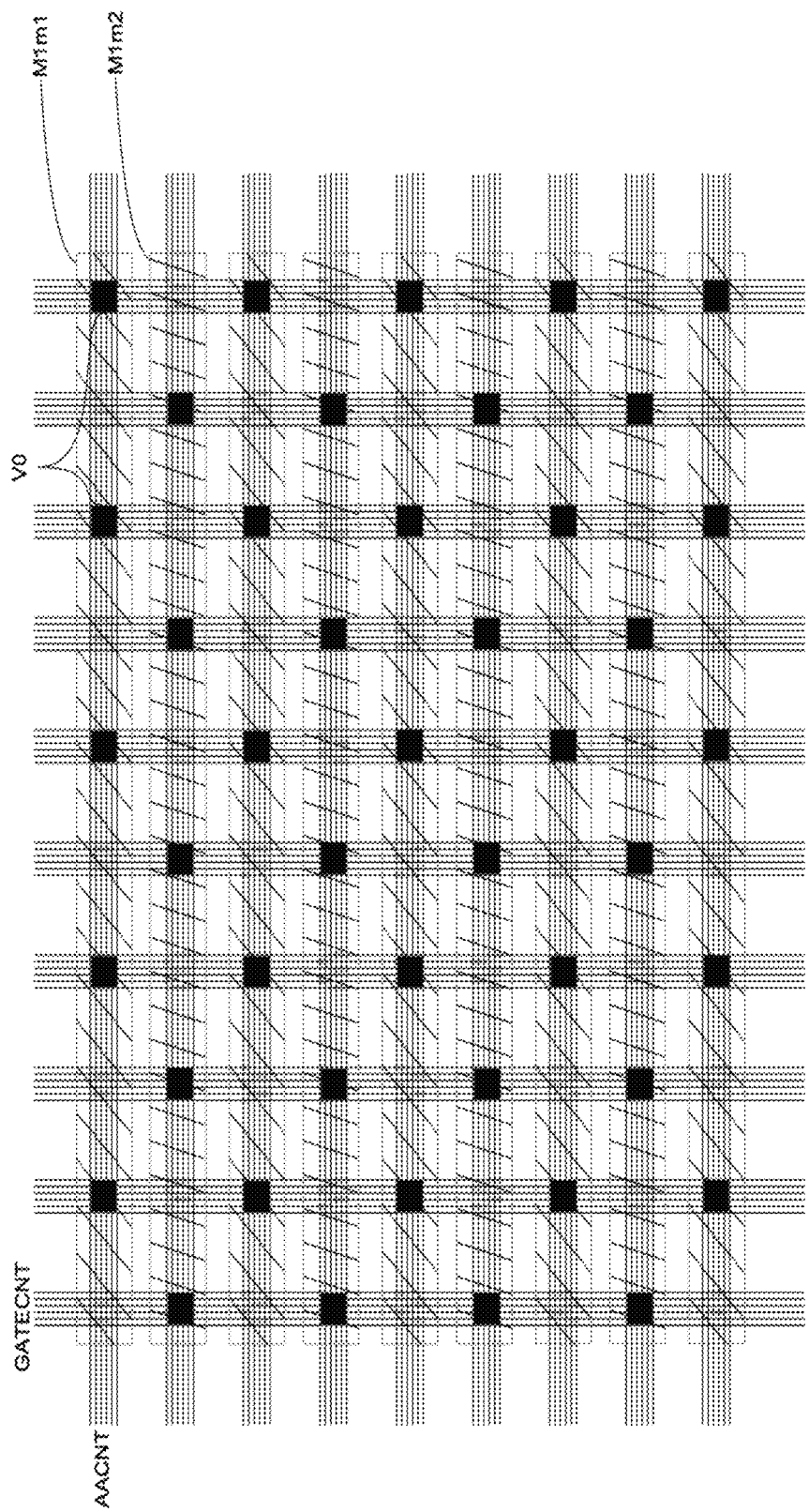
Figure 9J:
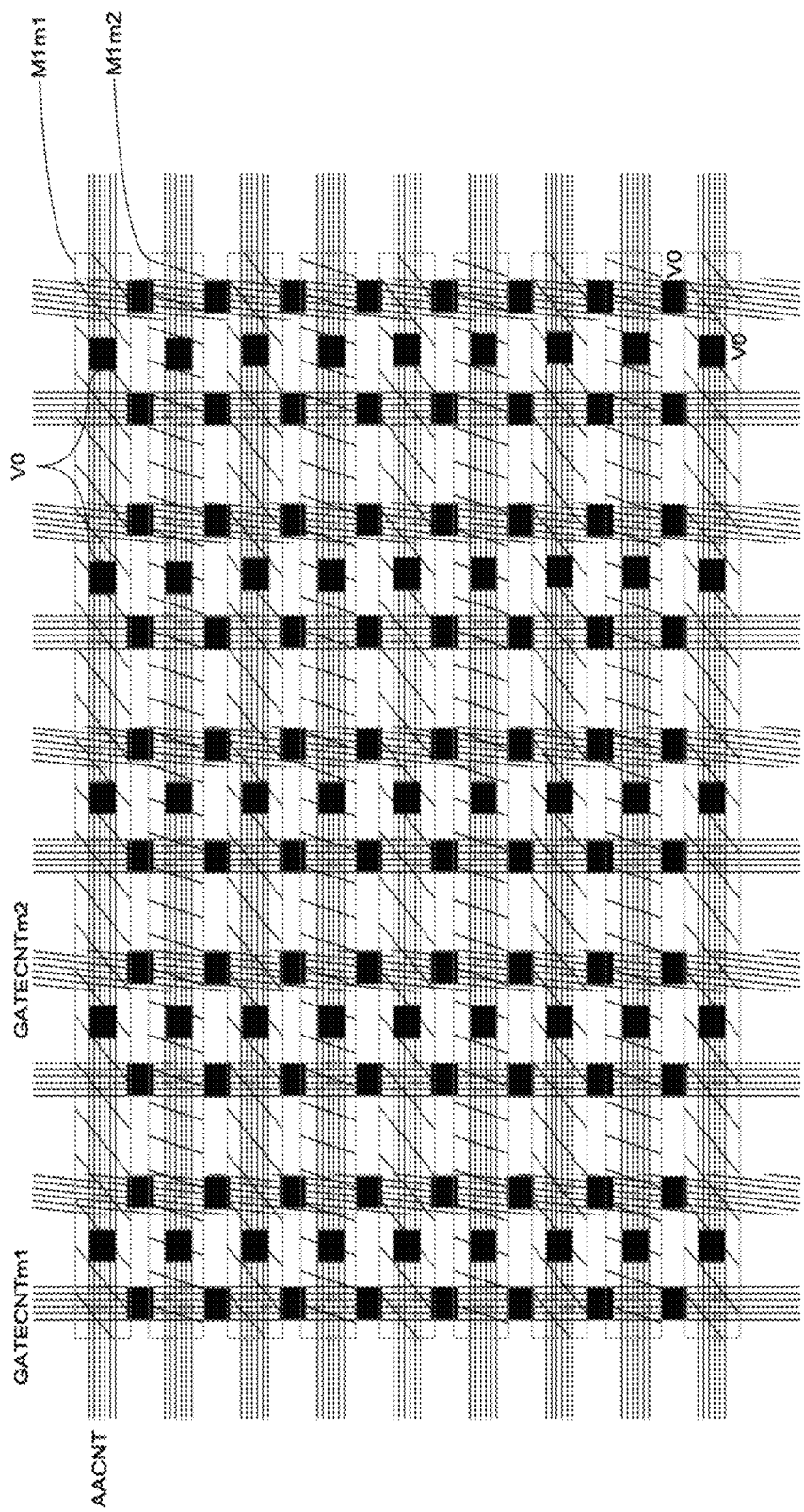

Reference is now made to FIGS. 9A-9E, which depict several illustrative designs for a NCEM pad, suitable for use in connection with embodiments of the invention. Additional NCEM pads are disclosed in the incorporated '841 application. FIG. 9A shows a simple, solid conductive pad, typically, though not necessarily, formed in M1. FIGS. 9B-9D depict several options for a non-solid, segmented, single-conductor pad. (As persons skilled in the art will appreciate, the variety of shapes for such pads is endless.) FIG. 9E depicts an example of a presently preferred, multi-conductor, mesh-style pad. Applicants' experimentation has revealed that these mesh-style pad designs—which are more space efficient and design rule friendly than single conductor pads—still produce a usable NCEM, particularly if sampled at low resolution, as taught in the incorporated '841 application. FIGS. 9F-9IIII depict additional embodiments of mesh pad structures. As persons skilled in the art will appreciate, these structures can be rendered in any size (e.g., 2×2, 2×3, 3×2, 3×3, etc.), and not just the specifically depicted 10×9 and 5×2 examples.

Design of the NCEM-Enabled Fill Cells:

Such fill cells preferably have certain common elements (e.g., height, supply rails, and GATE pitch (CPP) that is consistent with standard cells in the library), then vary according to the measurement type, layer(s) involved, and structure(s) to be evaluated/tested. NCEM-enabled fill cells come in two basic types: short[/leakage] and open[/resistance]. Relevant layers typically involve either a single process layer (e.g., GATE-to-GATE) or two process layers (e.g. GATECNT-to-GATE). Structural configurations are many, and include a set of standard structures (e.g., tip-to-tip, tip-to-side, side-to-side, etc.), as well as reference or ad hoc structures.

As depicted in FIGS. 10-11, the general structure of a short[/leakage]-configured, NCEM-enabled fill cell preferably includes four overlaid components: (i) "standard" patterning; (ii) a NCEM pad; (iii) "test gap" patterning; and (iv) pad/ground wiring. Standard patterning is that which appears in essentially all of the standard library cells, such as supply rails, and sometimes minimum contacted poly pitch (CPP) spaced rail-to-rail GATE stripes, etc. The NCEM pads can take a variety of shapes/patterns, as is non-exhaustively exemplified in FIGS. 9A-9IIII. The standard structures used for test gap patterning are depicted in FIGS. 14-30, and may include tip-to-tip, tip-to-side, side-to-side, etc. (Note that a single, short-configured NCEM-enabled fill cell may include more than one test gap, with all gaps preferably wired in parallel via the pad/ground wiring; an example with multiple test gaps appears in FIG. 45). The pad/ground wiring comprises low-resistance wiring from one side of the test gap(s) to the pad, and from the other side of the test gap(s) to a permanent or virtual ground. Points of effective ground include either supply rail, as well as any electrical structure that can conduct to the substrate under appropriate e-beam charging conditions (e.g., a p+ diode to NWELL that becomes positively charged during e-beam measurement). Virtual grounding can be accomplished by connecting to a node with sufficient capacitance to avoid discharge during e-beam measurement, and thus act as a source and/or sink for electrons during the measurement.

Figure 12:
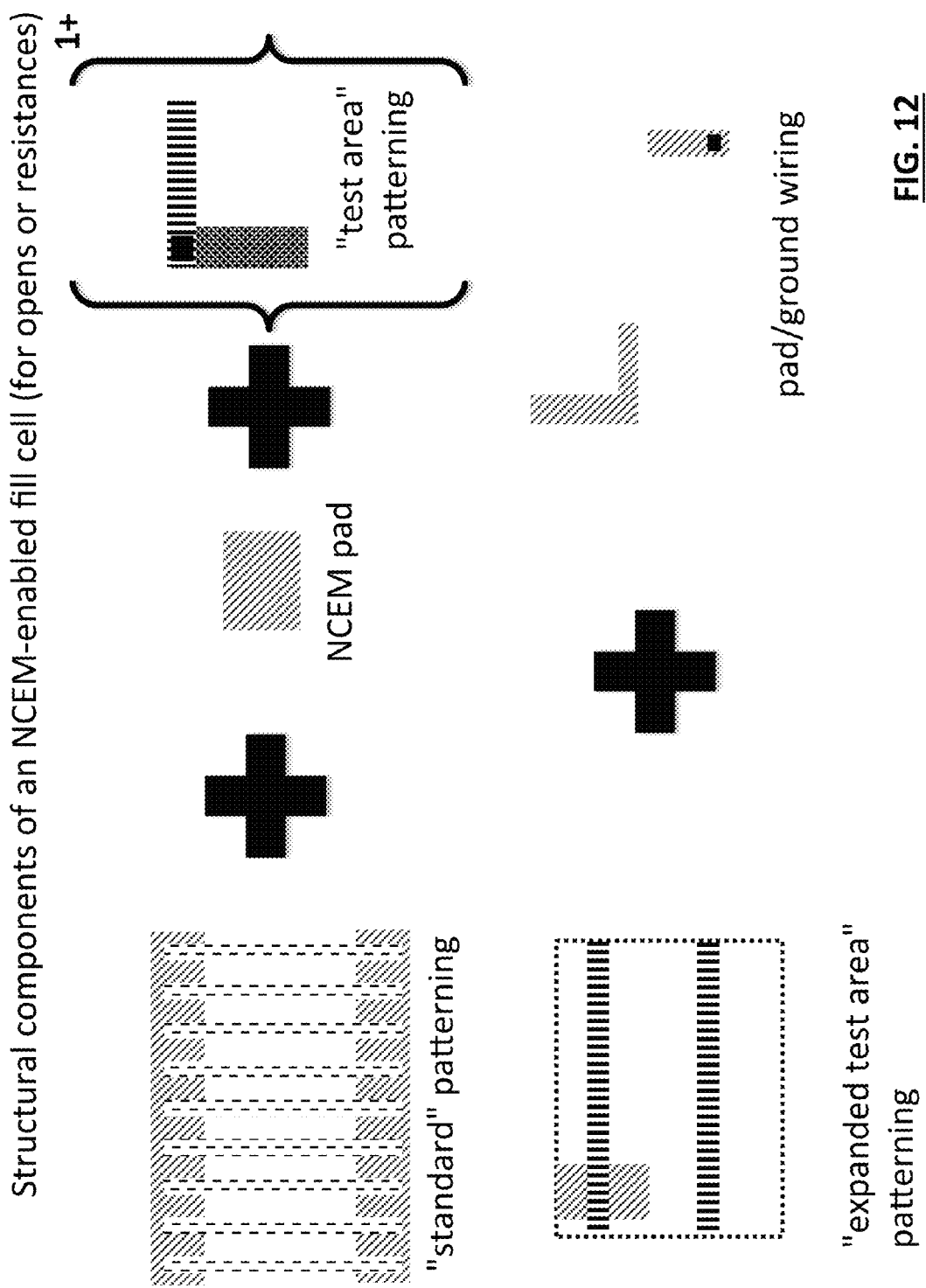
FIGS. 12-13, in conjunction with the description below, depict the overall physical structure and connectivity of open-configured (and/or resistance-configured), NCEM-enabled fill cells in accordance with certain aspects of the invention.
Figure 13:
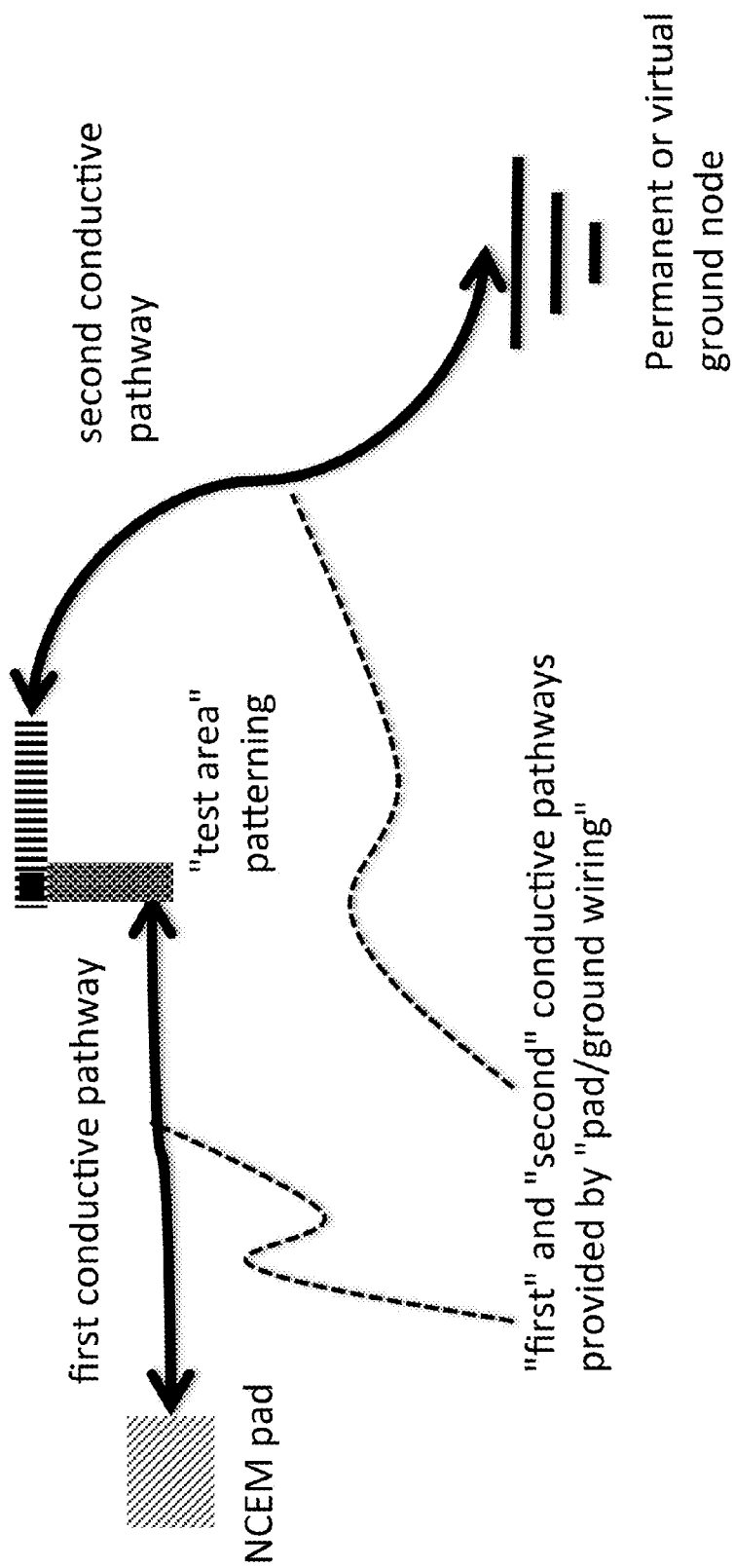

As depicted in FIGS. 12-13, the general structure of an open[/resistance]-configured, NCEM-enabled fill cell preferably includes four overlaid components: (i) "standard" patterning; (ii) a NCEM pad; (iii) "test area" patterning; and (iv) pad/ground wiring. As with the shorts, standard patterning is that which appears in essentially all of the standard library cells, such as supply rails, etc. Similarly, the NCEM pads can take a variety of shapes/patterns, as is non-exhaustively exemplified in FIGS. 9A-9IIII. Standard structures used for test structure patterning are depicted in FIGS. 28-36, and may include snake, overlap, stitch, etc. As with the shorts, the pad/ground wiring for opens comprises low-resistance wiring from one side of the test structure patterning to the pad, and from the other side of the test structure patterning to a permanent or virtual ground. Open-configured, NCEM-enabled fill cells can, and often do, include multiple test areas, in which case the pad/ground wiring connects all relevant test structures in a series-connected chain.

In cases where the NCEM-enabled fill cells will be used with a highly regular style cell library, an additional constraint on the NCEM-enabled fill cells is that they preferably conform, as closely as reasonably possible, to the regular patterns used for the library's functional cells. Preferred methods for measuring compliance with regular patterns, and/or constructing pattern-compliant cells, are described in U.S. Pat. Applic. No. 61/887,271 ("Template Based Design with LibAnalyzer") and 62/186,677 ("Template Based Design with LibAnalyzer"), both to Langnese et al., and both incorporated by reference herein. As those skilled in the art will appreciate, close, if not perfect, pattern compliance is feasible for those portions of the fill cell that do not affect the structure(s) or fail mode(s) to be evaluated. In general, however, perfect pattern compliance will prove infeasible for a several reasons. First, the structure to-be-evaluated may not, itself, be an "allowable" pattern (e.g., the pattern rules for the library may not allow any structure that spaces a GATE tip from a GATECNT side at minimum design rule dimensions, thus dictating that the "GATE-GATECNT-tip-to-side-short-configured, NCEM-enabled fill cell" will necessarily include at least one pattern violation). Second, DOEs typically involve several small variations in at least one minimum-spaced dimension, whereas regular patterning rules will typically only permit one of the variants. And third, the patterning used for the NCEM pad is preferably selected to match the operational capabilities of the scanner, but may well violate the library's pattern regularity constraints. Thus, ignoring these "necessary" pattern regularity violations, NCEM-enabled fill cells for use with highly regular libraries will preferably contain very few, if any, additional pattern regularity violations.

Figure 14:
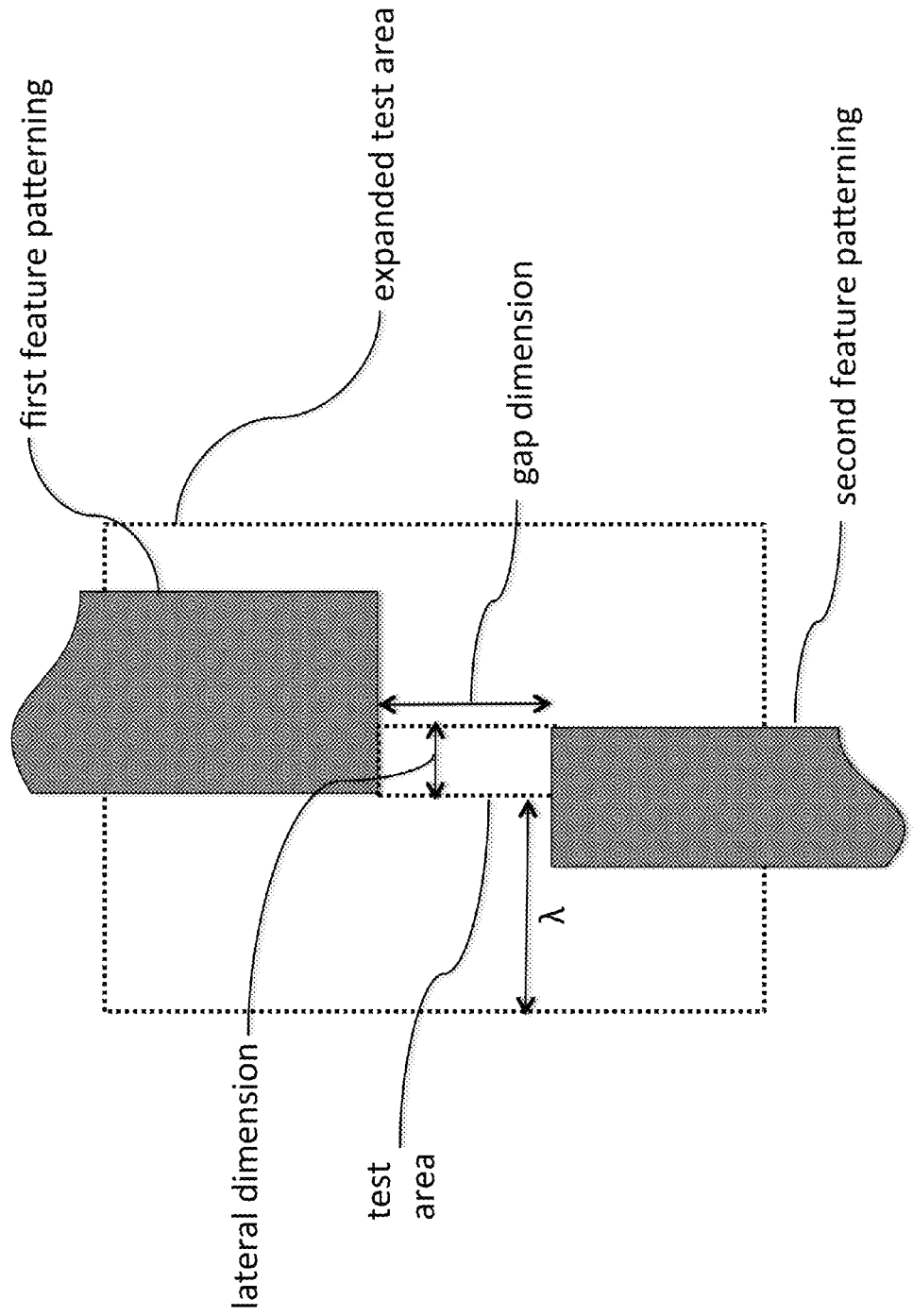
FIG. 14 depicts a plan view of exemplary test area geometry for an exemplary tip-to-tip-short-configured, NCEM-enabled fill cell.
Figure 15:
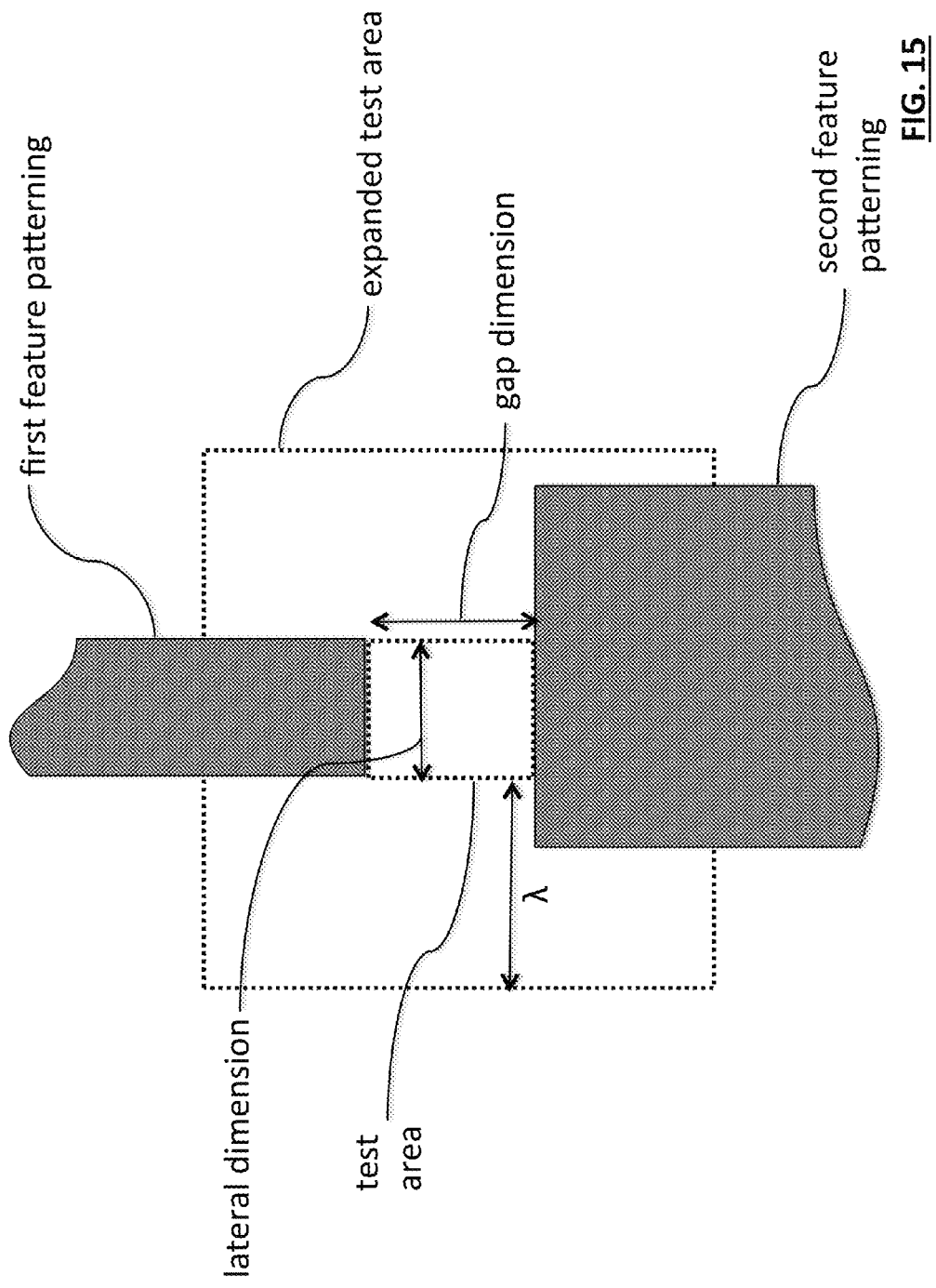
FIG. 15 depicts another plan view of exemplary test area geometry for an exemplary tip-to-tip-short-configured, NCEM-enabled fill cell.

Reference is now made to FIGS. 14-15, which depict plan views of two exemplary test area geometries for tip-to-tip-short-configured, NCEM-enabled fill cells. Cells that utilize these geometric configurations may include:

AA-tip-to-tip-short-configured, NCEM-enabled fill cells [e.g., FIGS. 1298-1326];
AACNT-tip-to-tip-short-configured, NCEM-enabled fill cells [e.g., FIGS. 1327-1405];
AACNT-AA-tip-to-tip-short-configured, NCEM-enabled fill cells;
AACNT-TS-tip-to-tip-short-configured, NCEM-enabled fill cells [e.g., FIGS. 1406-1412];
TS-tip-to-tip-short-configured, NCEM-enabled fill cells;
GATE-tip-to-tip-short-configured, NCEM-enabled fill cells [e.g., FIGS. 1413-1461];
GATECNT-GATE-tip-to-tip-short-configured, NCEM-enabled fill cells;
GATECNT-tip-to-tip-short-configured, NCEM-enabled fill cells [e.g., FIGS. 1462-1548];
GATECNT-AACNT-tip-to-tip-short-configured, NCEM-enabled fill cells;
M1-tip-to-tip-short-configured, NCEM-enabled fill cells [e.g., FIGS. 1549-1556];
V0-tip-to-tip-short-configured, NCEM-enabled fill cells;
M1-V0-tip-to-tip-short-configured, NCEM-enabled fill cells;
V1-M1-tip-to-tip-short-configured, NCEM-enabled fill cells;
V1-tip-to-tip-short-configured, NCEM-enabled fill cells;
M2-tip-to-tip-short-configured, NCEM-enabled fill cells;
M2-V1-tip-to-tip-short-configured, NCEM-enabled fill cells;
V2-M2-tip-to-tip-short-configured, NCEM-enabled fill cells;
M3-tip-to-tip-short-configured, NCEM-enabled fill cells;
V2-tip-to-tip-short-configured, NCEM-enabled fill cells; and,
M3-V2-tip-to-tip-short-configured, NCEM-enabled fill cells.

[As persons skilled in the art will understand, for interconnect layers 2 and higher, any NCEM-enabled fill cell of type "$M_x$- . . . " can also be formed as a corresponding "$M_{(x+n)}$- . . . " cell, any "$V_x$- . . . " cell can also be formed as a corresponding "$V_{(x+n)}$- . . . " cell, any "$M_x$-$V_{(x+1)}$- . . . " cell can also be formed as a corresponding "$M_{(x+n)}$-$V_{(x+n+1)}$- . . . " cell, and any "$M_x$-$V_{(x-1)}$- . . . " cell can also be formed as a corresponding "$M_{(x+n)}$-$V_{(x+n-1)}$- . . . " cell, assuming that the process-in-question supports the referenced interconnect layers. The present description should be read as including all such possible higher interconnect layer, and layer combination, cells, in all available failure types and geometric configurations.]

DOEs of these structures are preferably constructed by varying the dimensional parameters that define the test area (e.g., lateral and/or gap dimension), or by varying other, same- or adjacent-layer patterning within the expanded test area.

Figure 16:
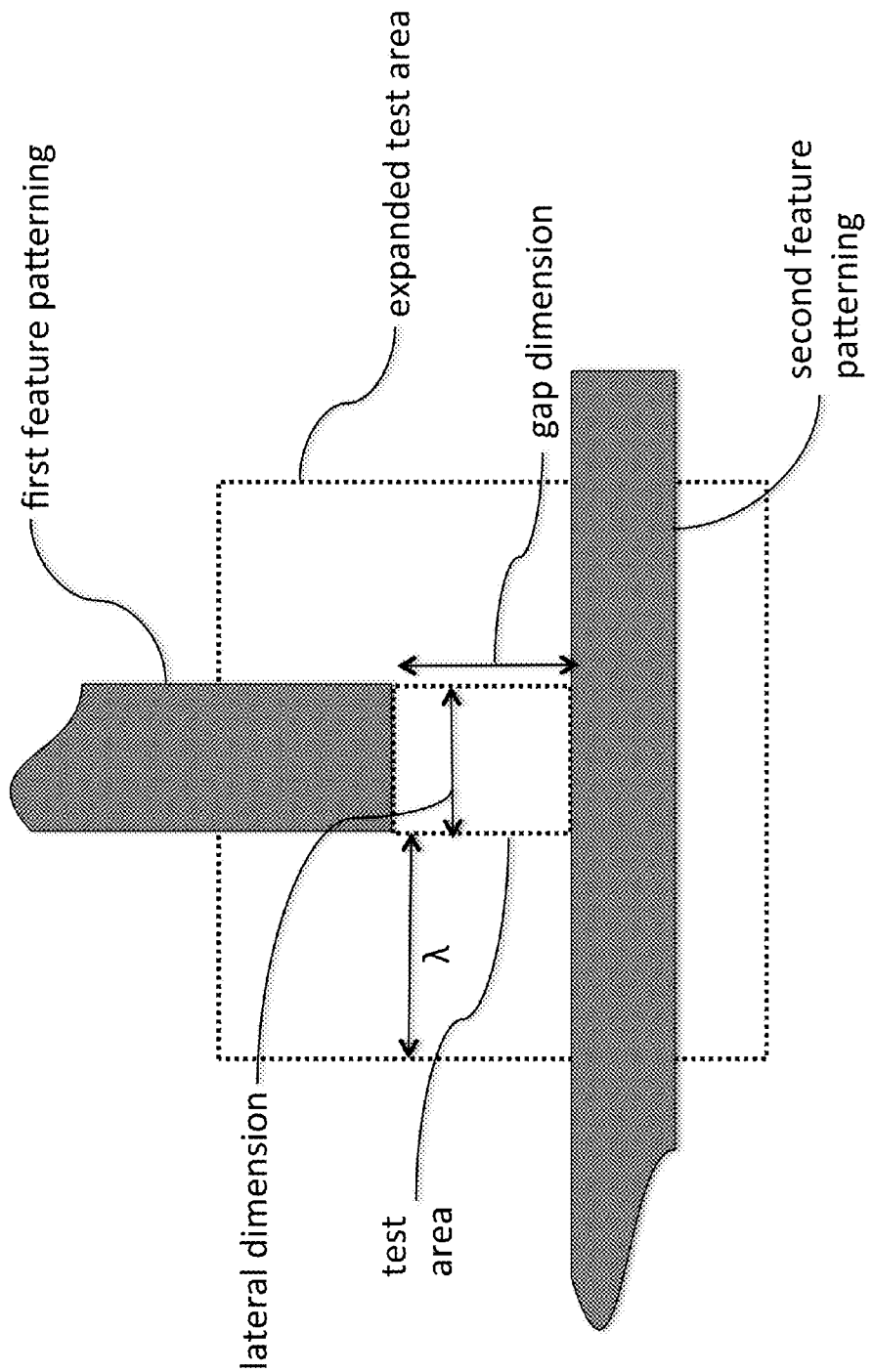
FIG. 16 depicts a plan view of exemplary test area geometry for an exemplary tip-to-side-short-configured, NCEM-enabled fill cell.

Reference is now made to FIG. 16, which depicts a plan view of exemplary test area geometry for tip-to-side-short-configured, NCEM-enabled fill cells. Cells that utilize this geometric configuration may include:

AA-tip-to-side-short-configured, NCEM-enabled fill cells;
AACNT-tip-to-side-short-configured, NCEM-enabled fill cells [e.g., FIG. 45];
AACNT-AA-tip-to-side-short-configured, NCEM-enabled fill cells;
GATE-AA-tip-to-side-short-configured, NCEM-enabled fill cells [e.g., FIGS. 49, 50, 1084-1119];
GATECNT-GATE-tip-to-side-short-configured, NCEM-enabled fill cells [e.g., FIGS. 1201-1238];
GATECNT-tip-to-side-short-configured, NCEM-enabled fill cells [e.g., FIGS. 1120-1149];
TS-GATECNT-tip-to-side-short-configured, NCEM-enabled fill cells [e.g., FIGS. 1239-1263];
GATECNT-AACNT-tip-to-side-short-configured, NCEM-enabled fill cells [FIGS. 1150-1188];
GATECNT-AACNT-TS-tip-to-side-short-configured, NCEM-enabled fill cells [FIGS. 1189-1200];
M1-tip-to-side-short-configured, NCEM-enabled fill cells [e.g., FIGS. 1264-1297];
V0-tip-to-side-short-configured, NCEM-enabled fill cells;
M1-V0-tip-to-side-short-configured, NCEM-enabled fill cells;
V1-M1-tip-to-side-short-configured, NCEM-enabled fill cells;
V1-tip-to-side-short-configured, NCEM-enabled fill cells;
M2-tip-to-side-short-configured, NCEM-enabled fill cells;

M2-V1-tip-to-side-short-configured, NCEM-enabled fill cells;
V2-M2-tip-to-side-short-configured, NCEM-enabled fill cells;
M3-tip-to-side-short-configured, NCEM-enabled fill cells;
V2-tip-to-side-short-configured, NCEM-enabled fill cells; and,
M3-V2-tip-to-side-short-configured, NCEM-enabled fill cells.

DOEs of these structures are preferably constructed by varying the dimensional parameters that define the test area (e.g., lateral and/or gap dimension), or by varying other, same- or adjacent-layer patterning within the expanded test area.

Figure 17:
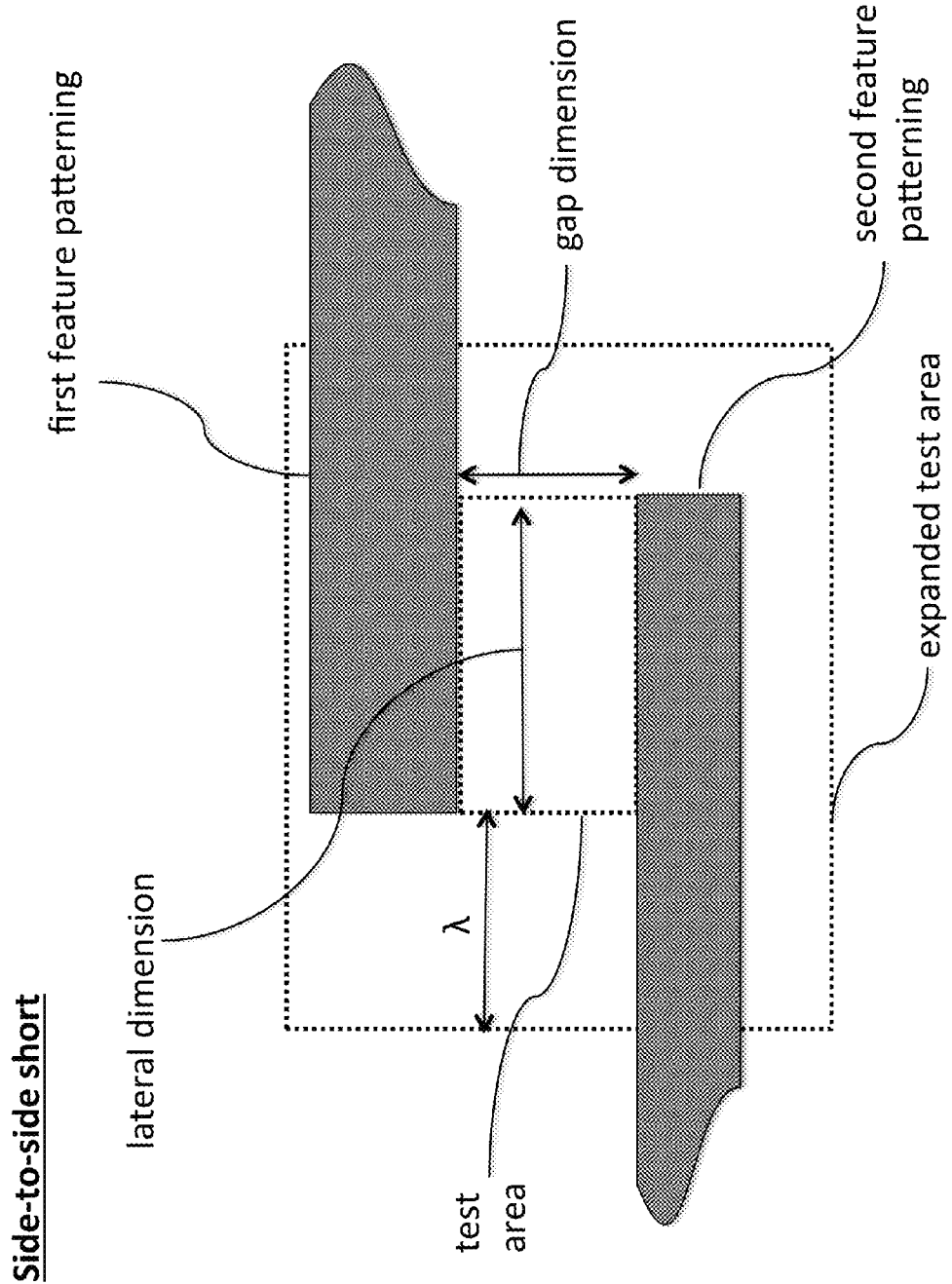
FIG. 17 depicts a plan view of exemplary test area geometry for an exemplary side-to-side-short-configured, NCEM-enabled fill cell.
Figure 18:
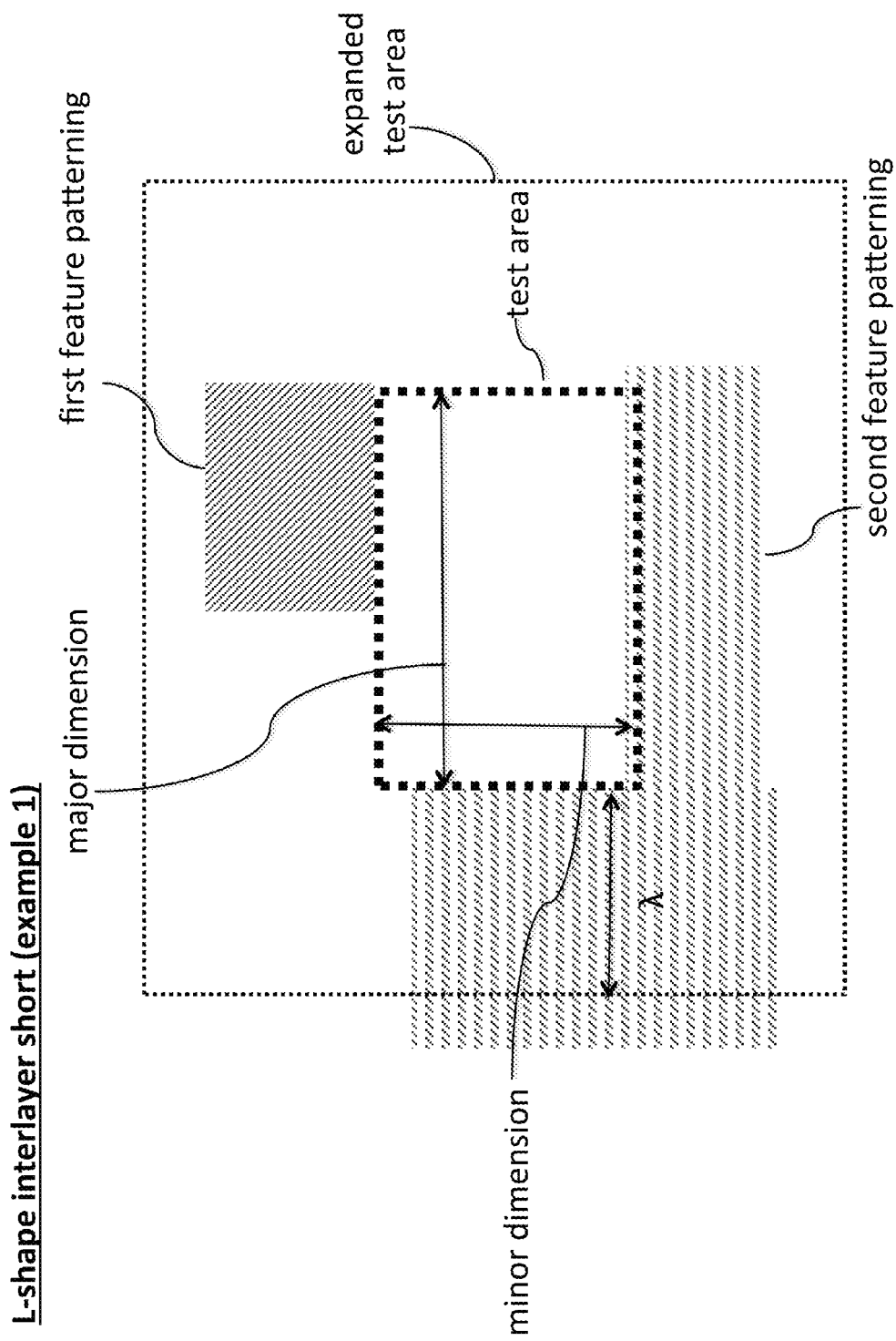
FIG. 18 depicts a plan view of exemplary test area geometry for an exemplary L-shape-interlayer-short-configured, NCEM-enabled fill cell.
Figure 19:
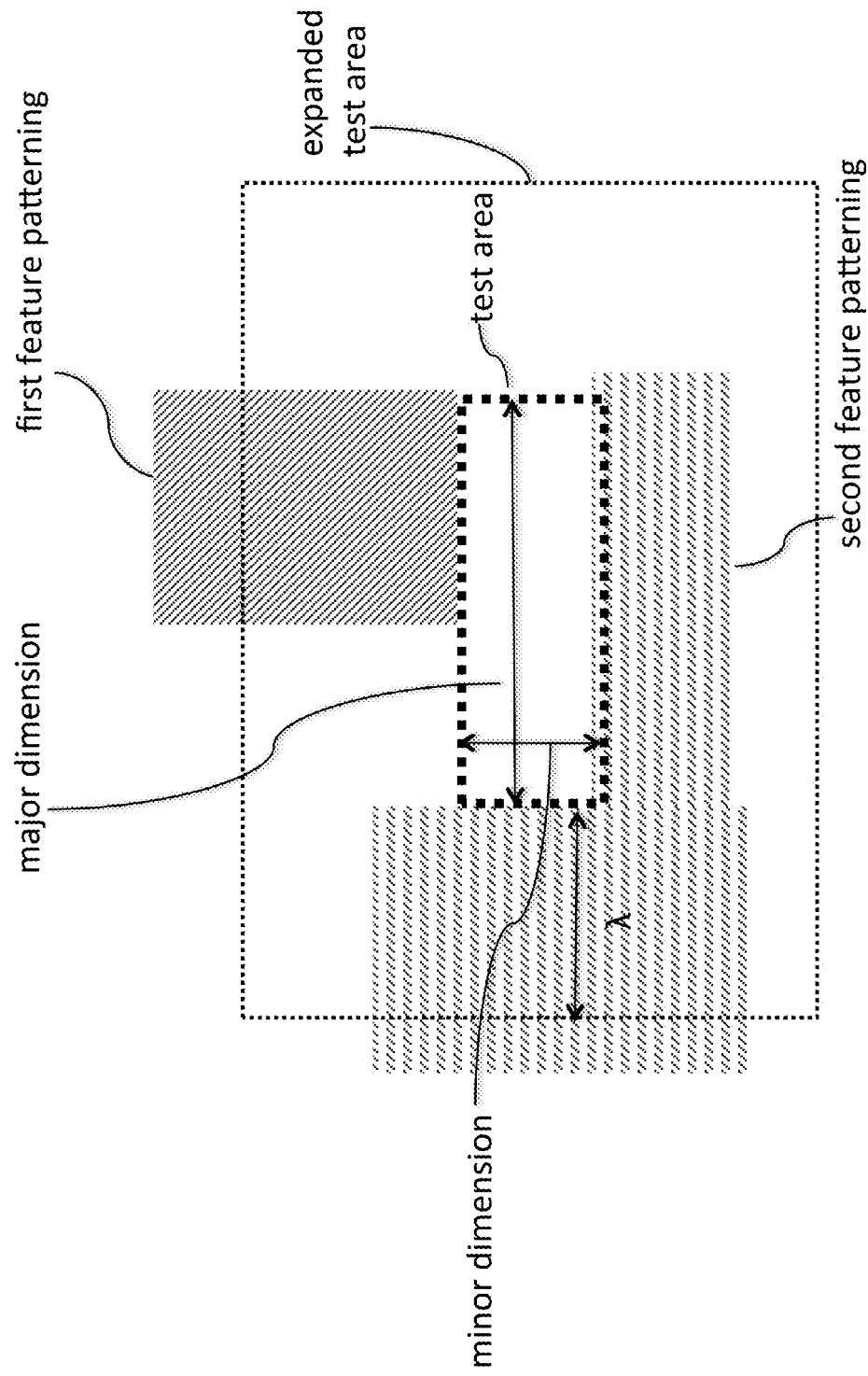
FIG. 19 depicts a plan view of exemplary test area geometry for another exemplary L-shape-interlayer-short-configured, NCEM-enabled fill cell.
Figure 20:
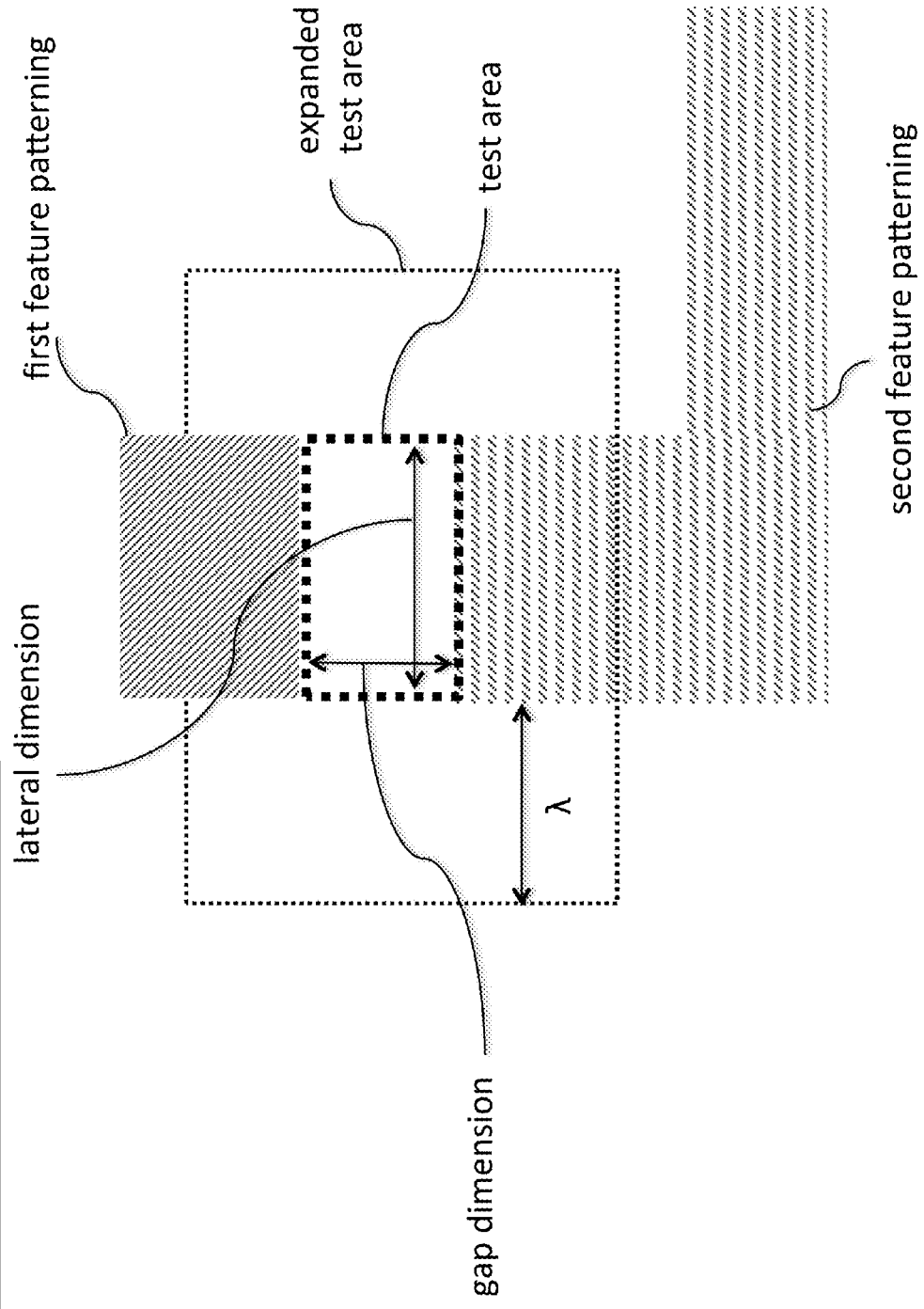
FIG. 20 depicts a plan view of exemplary test area geometry for another exemplary L-shape-interlayer-short-configured, NCEM-enabled fill cell.
Figure 21:
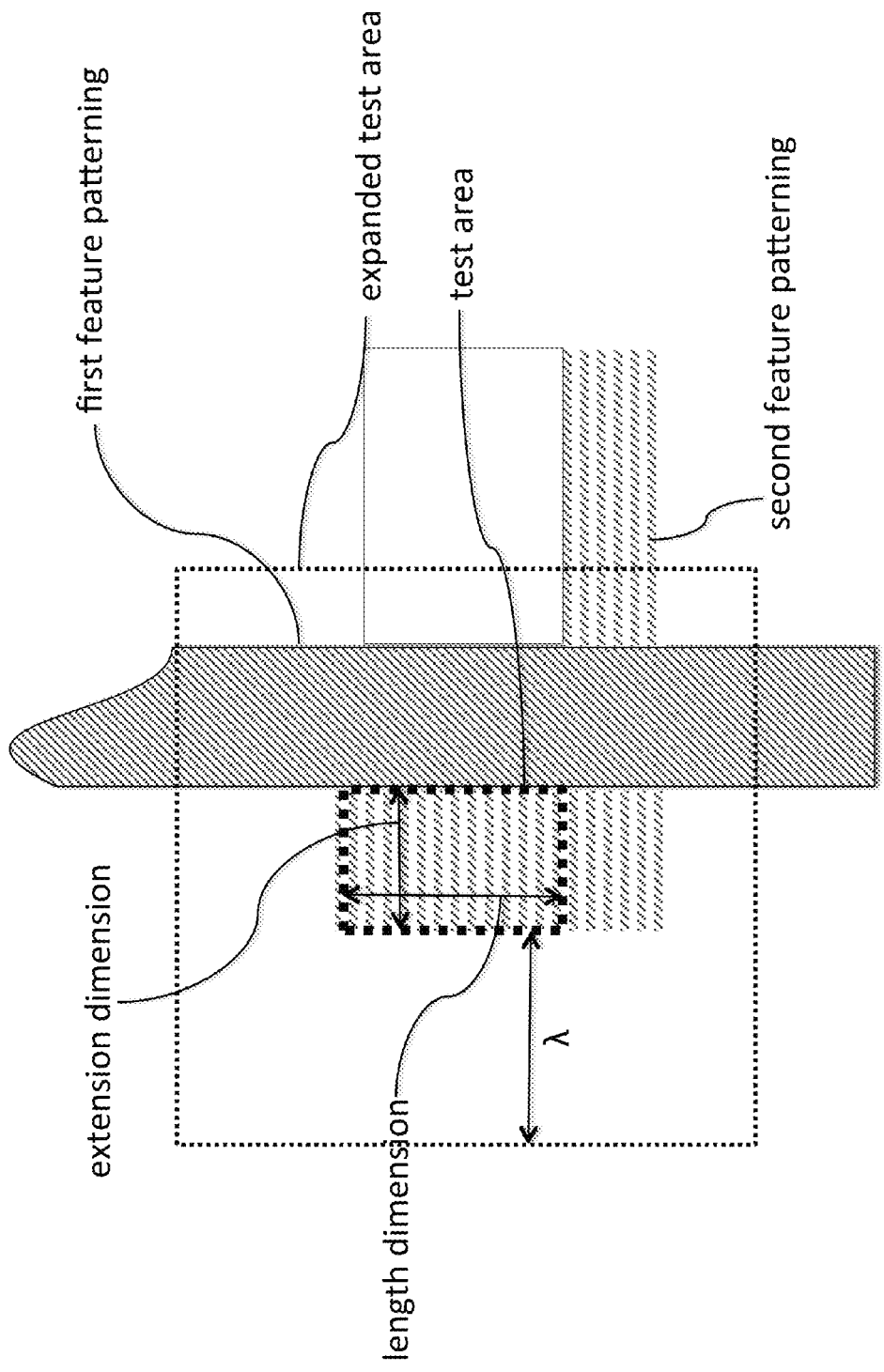
FIG. 21 depicts a plan view of exemplary test area geometry for another exemplary L-shape-interlayer-short-configured, NCEM-enabled fill cell.
Figure 22:
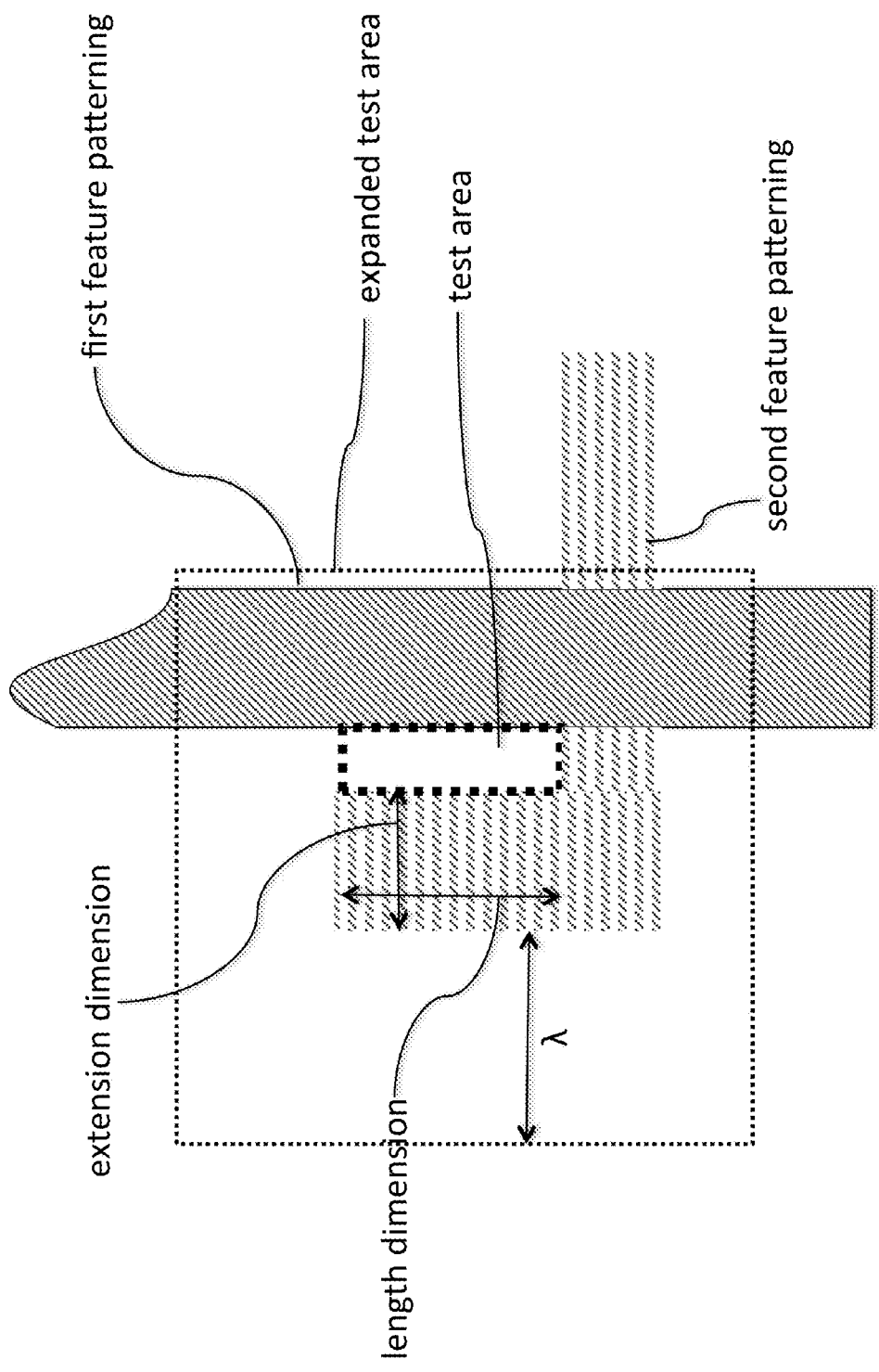
FIG. 22 depicts a plan view of exemplary test area geometry for another exemplary L-shape-interlayer-short-configured, NCEM-enabled fill cell.

Reference is now made to FIG. 17, which depicts a plan view of exemplary test area geometry for side-to-side-short-configured, NCEM-enabled fill cells. Cells that utilize this geometric configuration may include:
AA-side-to-side-short-configured, NCEM-enabled fill cells;
AACNT-side-to-side-short-configured, NCEM-enabled fill cells [e.g., FIGS. 786-804];
AACNT-AA-side-to-side-short-configured, NCEM-enabled fill cells;
AACNT-GATE-side-to-side-short-configured, NCEM-enabled fill cells [e.g., FIGS. 805-832];
GATE-side-to-side-short-configured, NCEM-enabled fill cells [e.g., FIG. 833-859];
GATECNT-GATE-side-to-side-short-configured, NCEM-enabled fill cells [e.g., FIGS. 886-903];
TS-GATE-side-to-side-short-configured, NCEM-enabled fill cells [e.g., FIGS. 937-1040];
GATECNT-side-to-side-short-configured, NCEM-enabled fill cells [e.g., FIGS. 860-872];
GATECNT-AACNT-side-to-side-short-configured, NCEM-enabled fill cells [e.g., FIGS. 47(*a*)-(*c*), 873-885];
M1-side-to-side-short-configured, NCEM-enabled fill cells [e.g., FIGS. 904-928];
V0-side-to-side-short-configured, NCEM-enabled fill cells;
M1-V0-side-to-side-short-configured, NCEM-enabled fill cells [e.g., FIGS. 929-936];
V1-M1-side-to-side-short-configured, NCEM-enabled fill cells;
V1-side-to-side-short-configured, NCEM-enabled fill cells;
M2-side-to-side-short-configured, NCEM-enabled fill cells;
M2-V1-side-to-side-short-configured, NCEM-enabled fill cells;
V2-M2-side-to-side-short-configured, NCEM-enabled fill cells;
M3-side-to-side-short-configured, NCEM-enabled fill cells;
V2-side-to-side-short-configured, NCEM-enabled fill cells; and,
M3-V2-side-to-side-short-configured, NCEM-enabled fill cells.

DOEs of these structures are preferably constructed by varying the dimensional parameters that define the test area (e.g., lateral and/or gap dimension), or by varying other, same- or adjacent-layer patterning within the expanded test area.

Reference is now made to FIGS. 18, 19, 20, 21, and 22, each of which depicts a plan view of exemplary test area geometry for L-shape-interlayer-short-configured, NCEM-enabled fill cells. Cells that utilize these geometric configurations may include:
AA-L-shape-interlayer-short-configured, NCEM-enabled fill cells;
AACNT-L-shape-interlayer-short-configured, NCEM-enabled fill cells;
AACNT-AA-L-shape-interlayer-short-configured, NCEM-enabled fill cells;
GATE-AA-L-shape-interlayer-short-configured, NCEM-enabled fill cells;
GATE-TS-L-shape-interlayer-short-configured, NCEM-enabled fill cells;
GATECNT-GATE-L-shape-interlayer-short-configured, NCEM-enabled fill cells;
GATECNT-AA-L-shape-interlayer-short-configured, NCEM-enabled fill cells;
GATECNT-TS-L-shape-interlayer-short-configured, NCEM-enabled fill cells;
GATECNT-AACNT-L-shape-interlayer-short-configured, NCEM-enabled fill cells;
V0-AA-L-shape-interlayer-short-configured, NCEM-enabled fill cells;
V0-TS-L-shape-interlayer-short-configured, NCEM-enabled fill cells;
V0-AACNT-L-shape-interlayer-short-configured, NCEM-enabled fill cells;
V0-GATE-L-shape-interlayer-short-configured, NCEM-enabled fill cells;
V0-GATECNT-L-shape-interlayer-short-configured, NCEM-enabled fill cells;
M1-AACNT-L-shape-interlayer-short-configured, NCEM-enabled fill cells;
M1-GATECNT-L-shape-interlayer-short-configured, NCEM-enabled fill cells;
M1-V0-L-shape-interlayer-short-configured, NCEM-enabled fill cells;
V1-M1-L-shape-interlayer-short-configured, NCEM-enabled fill cells;
V1-V0-L-shape-interlayer-short-configured, NCEM-enabled fill cells;
M2-M1-L-shape-interlayer-short-configured, NCEM-enabled fill cells;
M2-V1-L-shape-interlayer-short-configured, NCEM-enabled fill cells;
V2-V1-L-shape-interlayer-short-configured, NCEM-enabled fill cells;
V2-M2-L-shape-interlayer-short-configured, NCEM-enabled fill cells;
M3-M2-L-shape-interlayer-short-configured, NCEM-enabled fill cells; and,
M3-V2-L-shape-interlayer-short-configured, NCEM-enabled fill cells.

DOEs of these structures are preferably constructed by varying the dimensional parameters that define the test area, or by varying other, same- or adjacent-layer patterning within the expanded test area.

Figure 23:
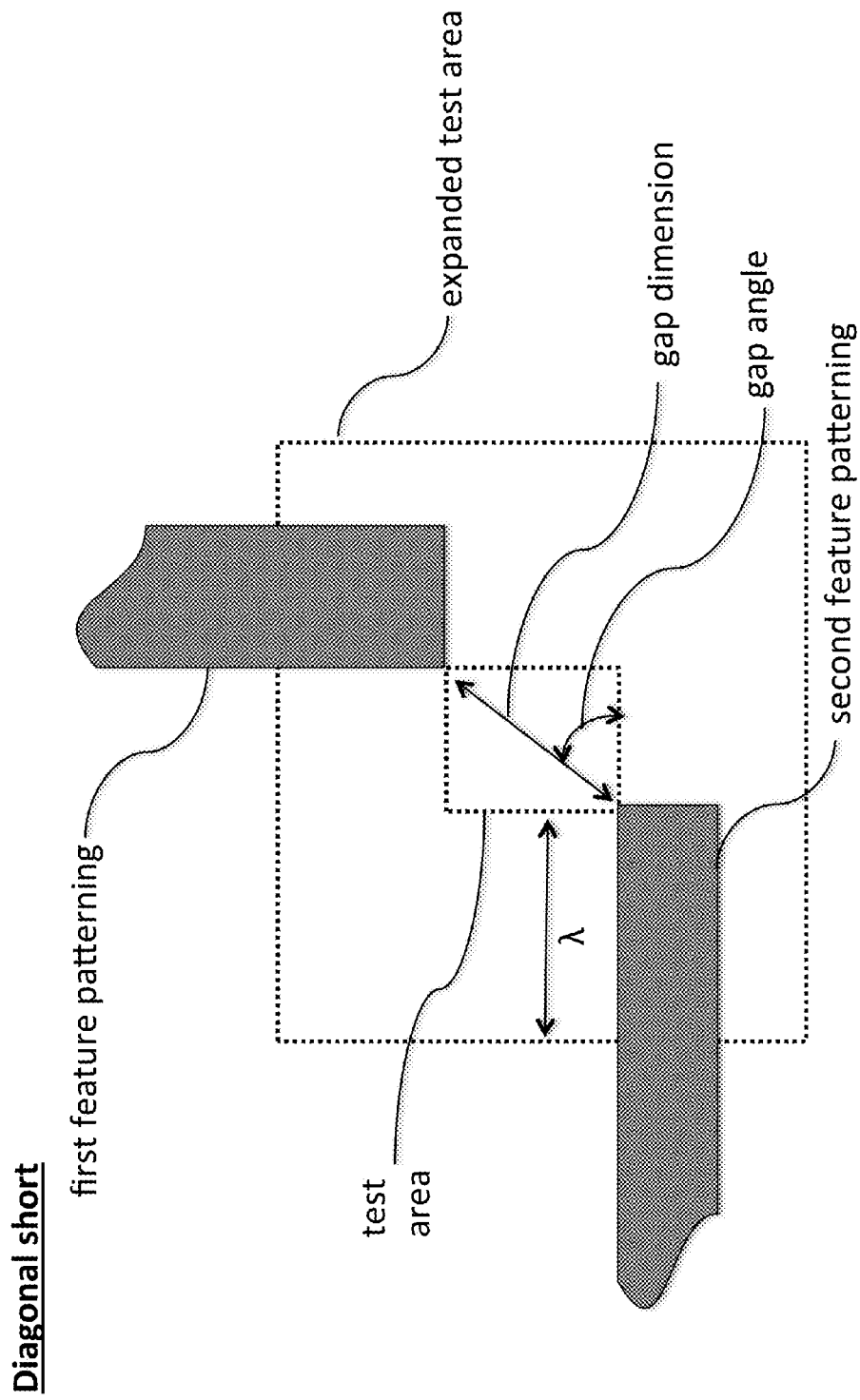
FIG. 23 depicts a plan view of exemplary test area geometry for an exemplary diagonal-short-configured, NCEM-enabled fill cell.

Reference is now made to FIG. 23, which depicts a plan view of exemplary test area geometry for diagonal-short-configured, NCEM-enabled fill cells. Cells that utilize this geometric configuration may include:
AA-diagonal-short-configured, NCEM-enabled fill cells;
TS-diagonal-short-configured, NCEM-enabled fill cells;
AACNT-diagonal-short-configured, NCEM-enabled fill cells;
AACNT-AA-diagonal-short-configured, NCEM-enabled fill cells;

GATE-diagonal-short-configured, NCEM-enabled fill cells;
GATE-AACNT-diagonal-short-configured, NCEM-enabled fill cells;
GATECNT-GATE-diagonal-short-configured, NCEM-enabled fill cells;
GATECNT-diagonal-short-configured, NCEM-enabled fill cells [e.g., FIGS. 495-554];
GATECNT-AACNT-diagonal-short-configured, NCEM-enabled fill cells [e.g., FIGS. 555-632];
M1-diagonal-short-configured, NCEM-enabled fill cells;
V0-diagonal-short-configured, NCEM-enabled fill cells;
M1-V0-diagonal-short-configured, NCEM-enabled fill cells;
V1-M1-diagonal-short-configured, NCEM-enabled fill cells;
V1-diagonal-short-configured, NCEM-enabled fill cells;
M2-diagonal-short-configured, NCEM-enabled fill cells;
M2-V1-diagonal-short-configured, NCEM-enabled fill cells;
M3-diagonal-short-configured, NCEM-enabled fill cells;
V2-M2-diagonal-short-configured, NCEM-enabled fill cells;
V2-diagonal-short-configured, NCEM-enabled fill cells; and,
M3-V2-diagonal-short-configured, NCEM-enabled fill cells.

DOEs of these structures are preferably constructed by varying the dimensional parameters that define the test area (e.g., gap dimension and/or gap angle), or by varying other, same- or adjacent-layer patterning within the expanded test area.

Figure 24:
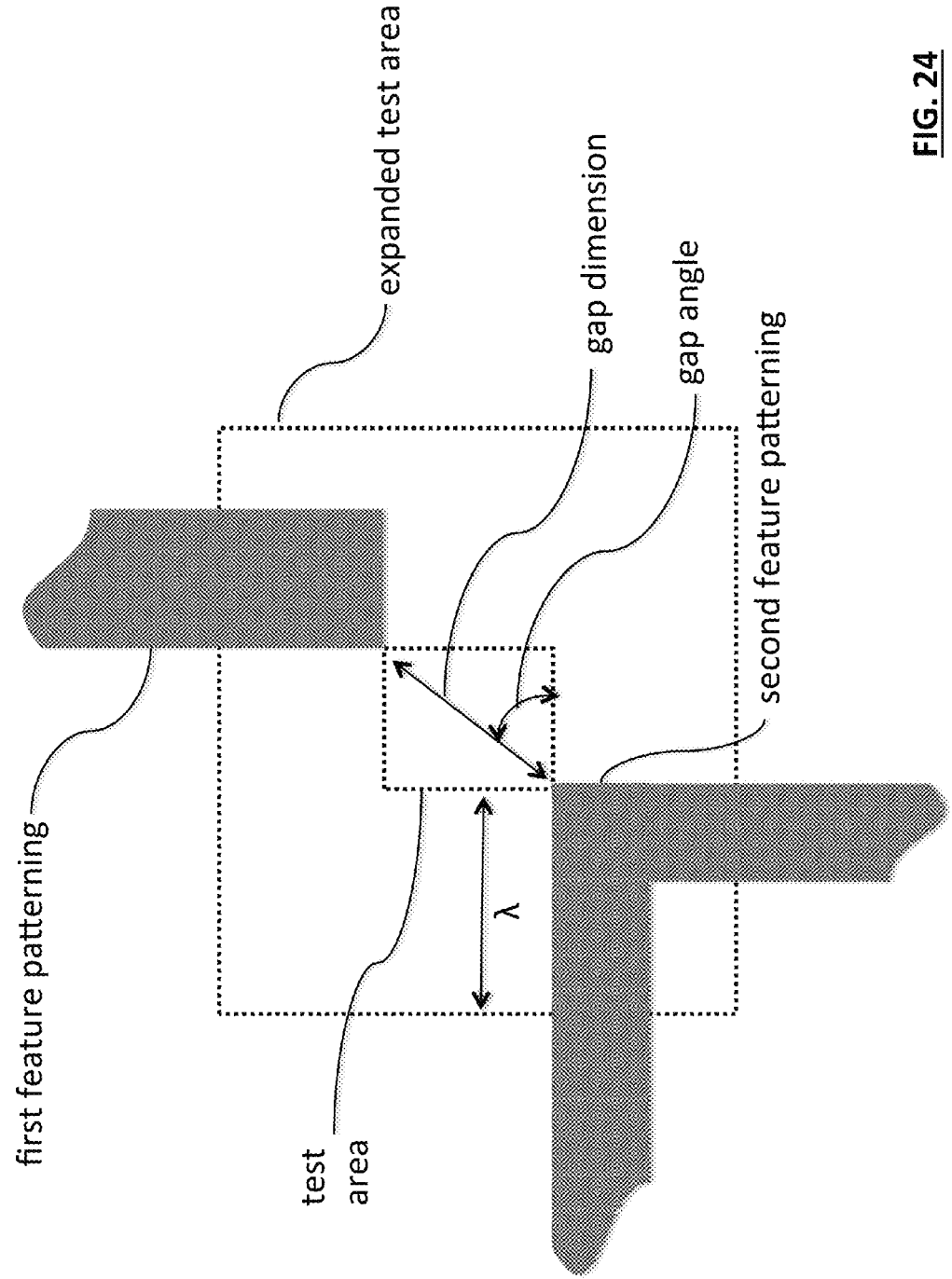
FIG. 24 depicts a plan view of exemplary test area geometry for an exemplary corner-short-configured, NCEM-enabled fill cell.
Figure 25:
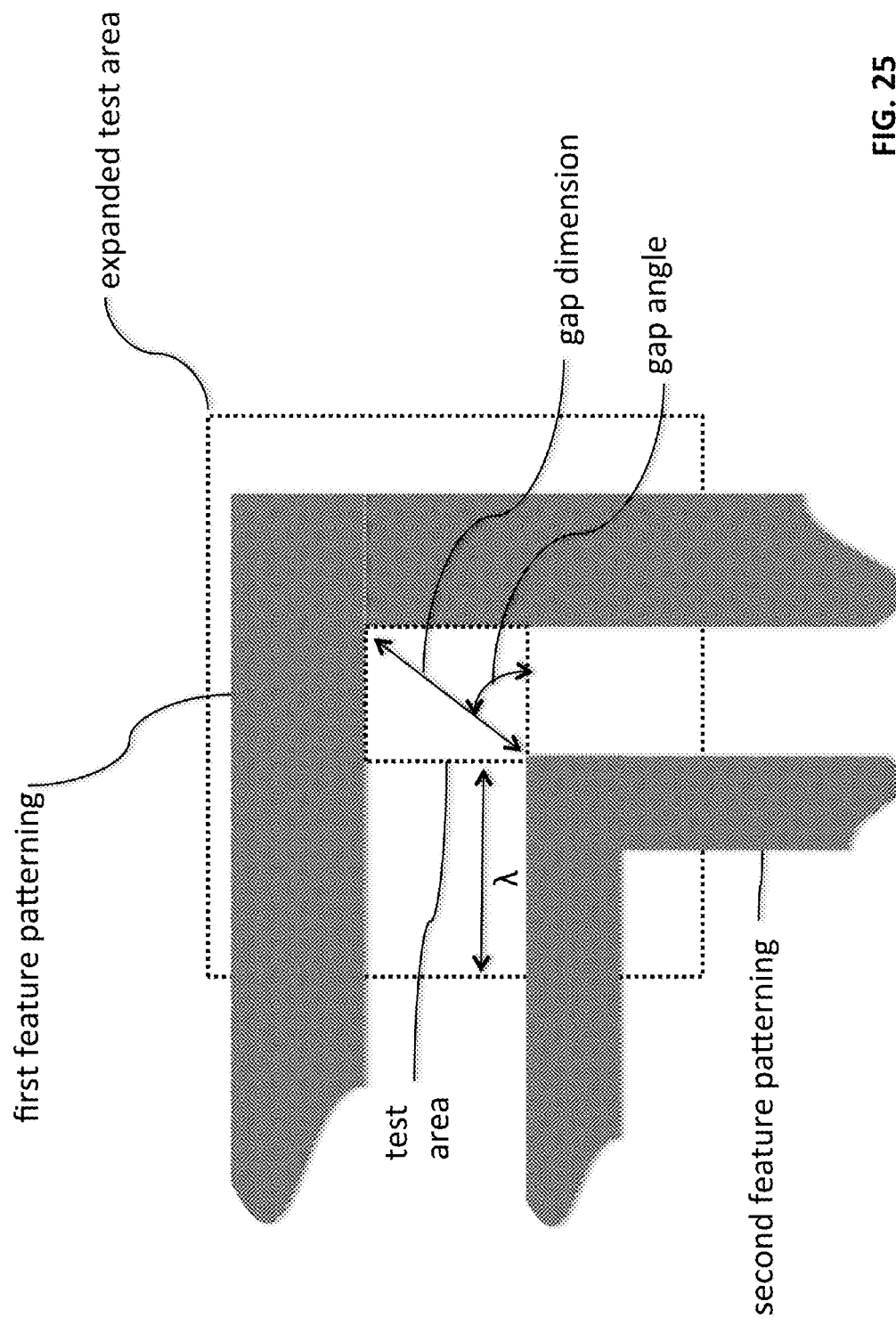
FIG. 25 depicts a plan view of exemplary test area geometry for another exemplary corner-short-configured, NCEM-enabled fill cell.
Figure 26:
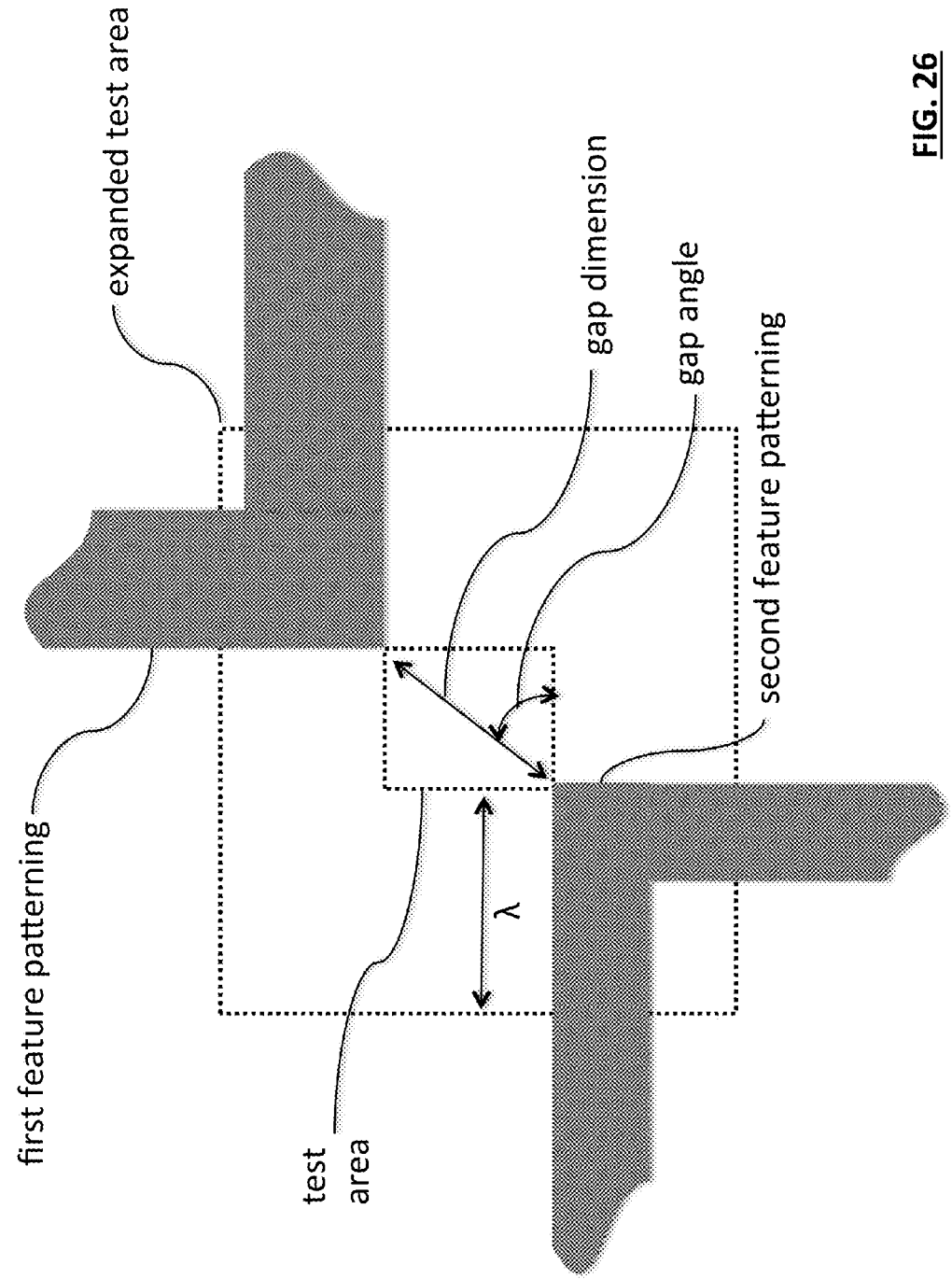
FIG. 26 depicts a plan view of exemplary test area geometry for another exemplary corner-short-configured, NCEM-enabled fill cell.

Reference is now made to FIGS. 24, 25, and 26, each of which depicts a plan view of exemplary test area geometry for corner-short-configured, NCEM-enabled fill cells. These configurations differ from the diagonal configuration because, in these corner configurations, at least one of the first and/or second features is non-rectangular. Cells that utilize these geometric configurations may include:
AA-corner-short-configured, NCEM-enabled fill cells;
AACNT-corner-short-configured, NCEM-enabled fill cells;
AACNT-AA-corner-short-configured, NCEM-enabled fill cells;
GATE-corner-short-configured, NCEM-enabled fill cells;
GATECNT-GATE-corner-short-configured, NCEM-enabled fill cells;
GATECNT-TS-corner-short-configured, NCEM-enabled fill cells [e.g., FIGS. 287-685];
GATECNT-corner-short-configured, NCEM-enabled fill cells;
GATECNT-AA-corner-short-configured, NCEM-enabled fill cells [e.g., FIGS. 263-286];
GATECNT-AACNT-corner-short-configured, NCEM-enabled fill cells;
M1-corner-short-configured, NCEM-enabled fill cells [e.g., FIGS. 416-494];
V0-corner-short-configured, NCEM-enabled fill cells;
M1-V0-corner-short-configured, NCEM-enabled fill cells;
V1-M1-corner-short-configured, NCEM-enabled fill cells;
V1-corner-short-configured, NCEM-enabled fill cells;
M2-corner-short-configured, NCEM-enabled fill cells;
M2-V1-corner-short-configured, NCEM-enabled fill cells;
M3-corner-short-configured, NCEM-enabled fill cells;
V2-M2-corner-short-configured, NCEM-enabled fill cells;
V2-corner-short-configured, NCEM-enabled fill cells; and,
M3-V2-corner-short-configured, NCEM-enabled fill cells.

DOEs of these structures are preferably constructed by varying the dimensional parameters that define the test area (e.g., gap dimension and/or gap angle), or by varying other, same- or adjacent-layer patterning within the expanded test area.

Figure 27:
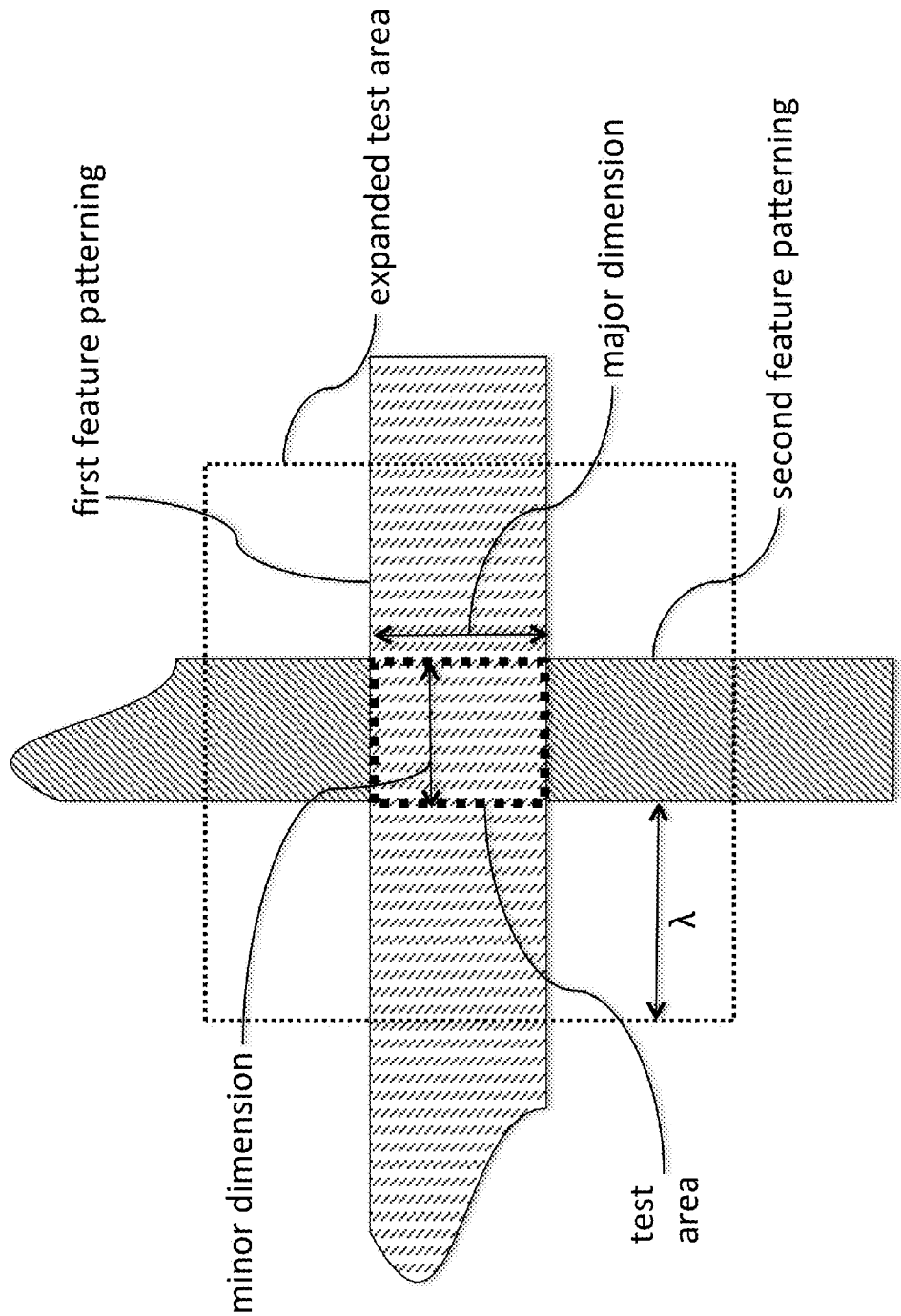
FIG. 27 depicts a plan view of exemplary test area geometry for an exemplary interlayer-overlap-short-configured, NCEM-enabled fill cell.

Reference is now made to FIG. 27, which depicts a plan view of exemplary test area geometry for interlayer-overlap-short-configured, NCEM-enabled fill cells. Cells that utilize this geometric configuration may include:
GATE-AA-interlayer-overlap-short-configured, NCEM-enabled fill cells [e.g., FIGS. 692-734];
GATE-AACNT-interlayer-overlap-short-configured, NCEM-enabled fill cells [e.g., FIGS. 633-691];
GATE-TS-interlayer-overlap-short-configured, NCEM-enabled fill cells;
GATECNT-TS-interlayer-overlap-short-configured, NCEM-enabled fill cells;
GATECNT-AA-interlayer-overlap-short-configured, NCEM-enabled fill cells;
V0-AA-interlayer-overlap-short-configured, NCEM-enabled fill cells;
V0-AACNT-interlayer-overlap-short-configured, NCEM-enabled fill cells;
V0-TS-interlayer-overlap-short-configured, NCEM-enabled fill cells;
V0-GATE-interlayer-overlap-short-configured, NCEM-enabled fill cells;
M1-GATECNT-interlayer-overlap-short-configured, NCEM-enabled fill cells;
M1-AACNT-interlayer-overlap-short-configured, NCEM-enabled fill cells;
V1-V0-interlayer-overlap-short-configured, NCEM-enabled fill cells;
M2-M1-interlayer-overlap-short-configured, NCEM-enabled fill cells;
V2-V1-interlayer-overlap-short-configured, NCEM-enabled fill cells; and,
M3-M2-interlayer-overlap-short-configured, NCEM-enabled fill cells.

DOEs of these structures are preferably constructed by varying the dimensional parameters that define the test area (e.g., major and/or minor dimension), or by varying other, same- or adjacent-layer patterning within the expanded test area.

Figure 28:
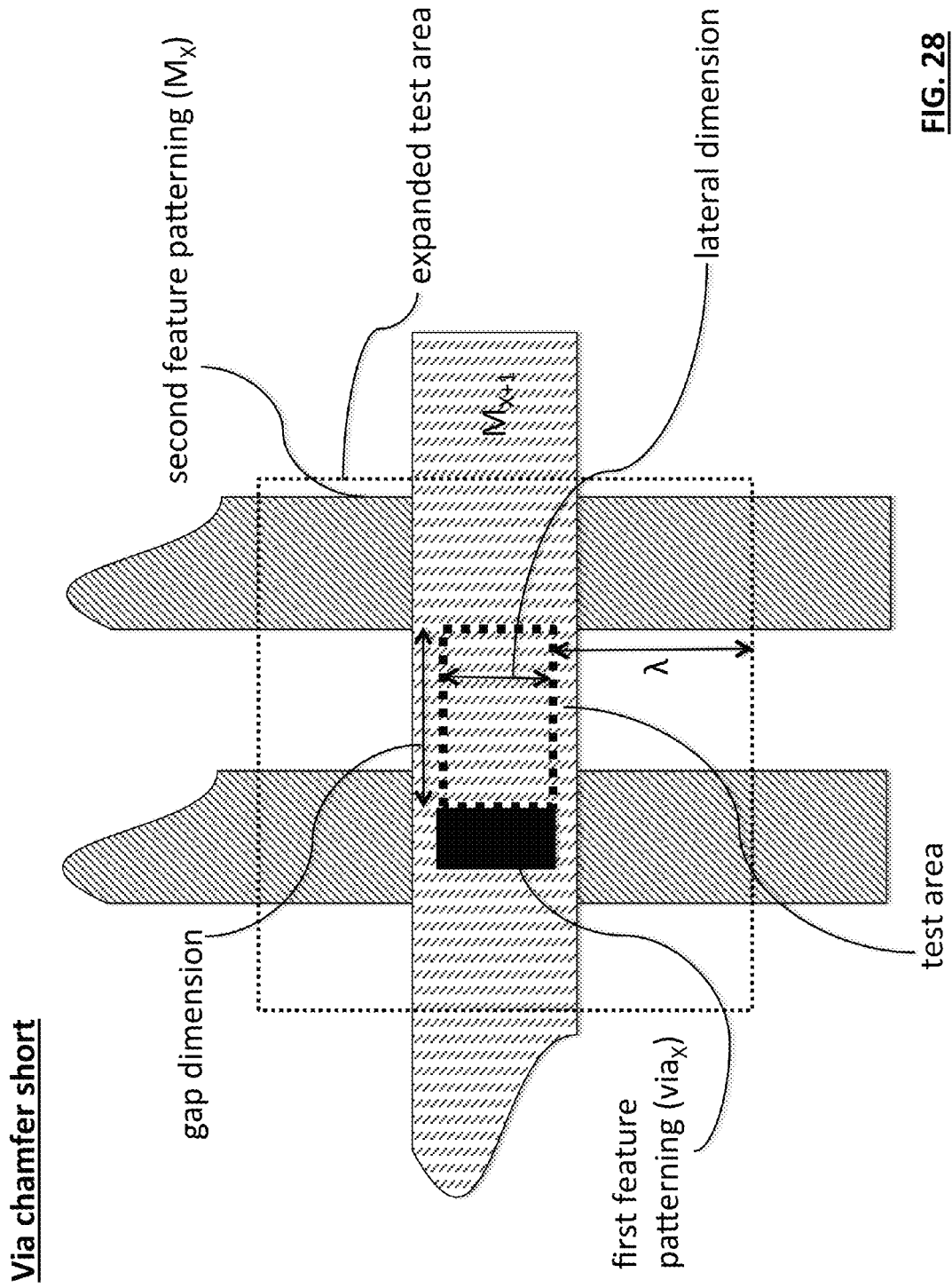
FIG. 28 depicts a plan view of exemplary test area geometry for an exemplary via-chamfer-short-configured, NCEM-enabled fill cell.

Reference is now made to FIG. 28, which depicts a plan view of exemplary test area geometry for via-chamfer-short-configured, NCEM-enabled fill cells. Cells that utilize this geometric configuration may include:
V0-GATECNT-via-chamfer-short-configured, NCEM-enabled fill cells;
V0-AACNT-via-chamfer-short-configured, NCEM-enabled fill cells [e.g., FIGS. 52-256];
V1-M1-via-chamfer-short-configured, NCEM-enabled fill cells;
V2-M2-via-chamfer-short-configured, NCEM-enabled fill cells; and,
V3-M3-via-chamfer-short-configured, NCEM-enabled fill cells [e.g., FIGS. 257-262].

DOEs of these structures are preferably constructed by varying the dimensional parameters that define the test area (e.g., gap and/or lateral dimension), or by varying other, same- or adjacent-layer patterning within the expanded test area.

Figure 29:
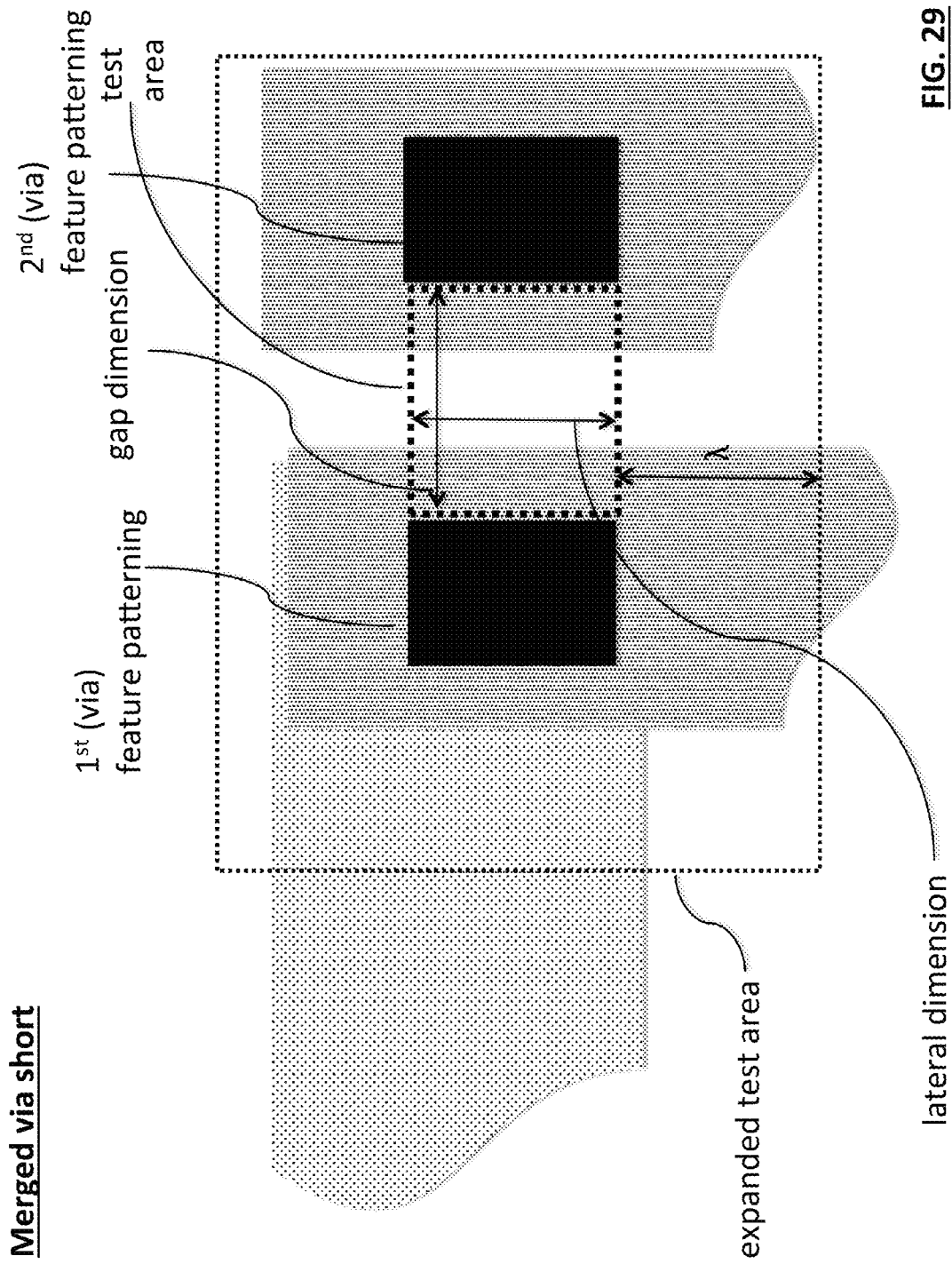
FIG. 29 depicts a plan view of exemplary test area geometry for an exemplary merged-via-short-configured, NCEM-enabled fill cell.

Reference is now made to FIG. 29, which depicts a plan view of exemplary test area geometry for merged-via-short-configured, NCEM-enabled fill cells. Cells that utilize this geometric configuration may include:
- V0-merged-via-short-configured, NCEM-enabled fill cells;
- V1-merged-via-short-configured, NCEM-enabled fill cells; and,
- V2-merged-via-short-configured, NCEM-enabled fill cells.

DOEs of these structures are preferably constructed by varying the dimensional parameters that define the test area (e.g., gap and/or lateral dimension), or by varying other, same- or adjacent-layer patterning within the expanded test area.

Figure 30:
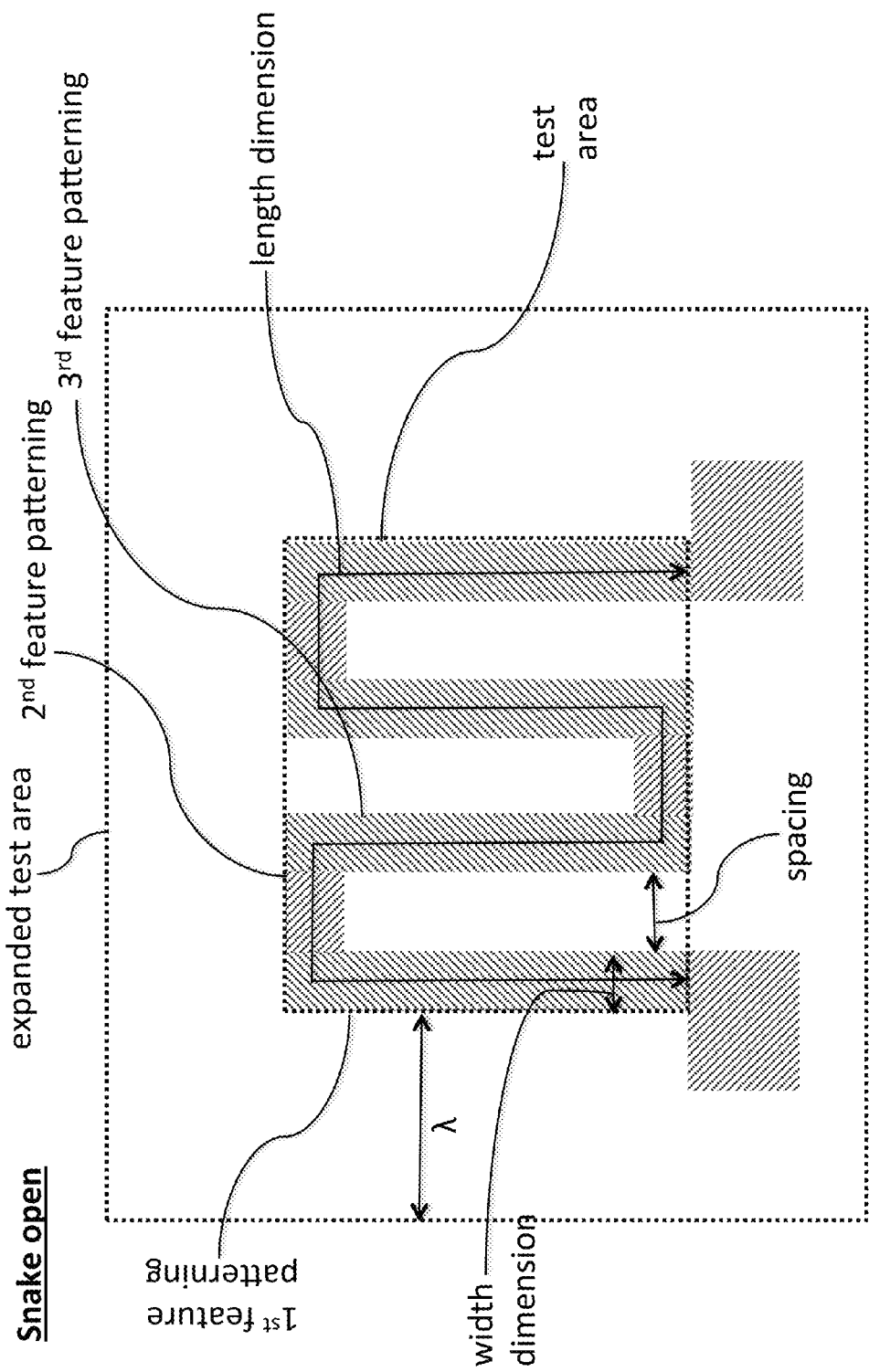
FIG. 30 depicts a plan view of exemplary test area geometry for an exemplary snake-open-configured, NCEM-enabled fill cell.

Reference is now made to FIG. 30, which depicts a plan view of exemplary test area geometry for snake-open-configured, NCEM-enabled fill cells. Cells that utilize this geometric configuration may include:
- AA-snake-open-configured, NCEM-enabled fill cells;
- TS-snake-open-configured, NCEM-enabled fill cells;
- AACNT-snake-open-configured, NCEM-enabled fill cells;
- GATE-snake-open-configured, NCEM-enabled fill cells [e.g., FIGS. 1041-1048];
- GATECNT-snake-open-configured, NCEM-enabled fill cells;
- V0-snake-open-configured, NCEM-enabled fill cells;
- M1-snake-open-configured, NCEM-enabled fill cells [e.g., FIGS. 44, 1049-1066];
- M1-V0-AACNT-snake-open-configured, NCEM-enabled fill cells [e.g., FIGS. 1067-1071];
- V1-snake-open-configured, NCEM-enabled fill cells;
- M2-snake-open-configured, NCEM-enabled fill cells;
- V2-snake-open-configured, NCEM-enabled fill cells; and,
- M3-snake-open-configured, NCEM-enabled fill cells.

DOEs of these structures are preferably constructed by varying the dimensional parameters that define the test area (e.g., length, width, spacing, etc.), or by varying other, same- or adjacent-layer patterning within the expanded test area.

Figure 31:
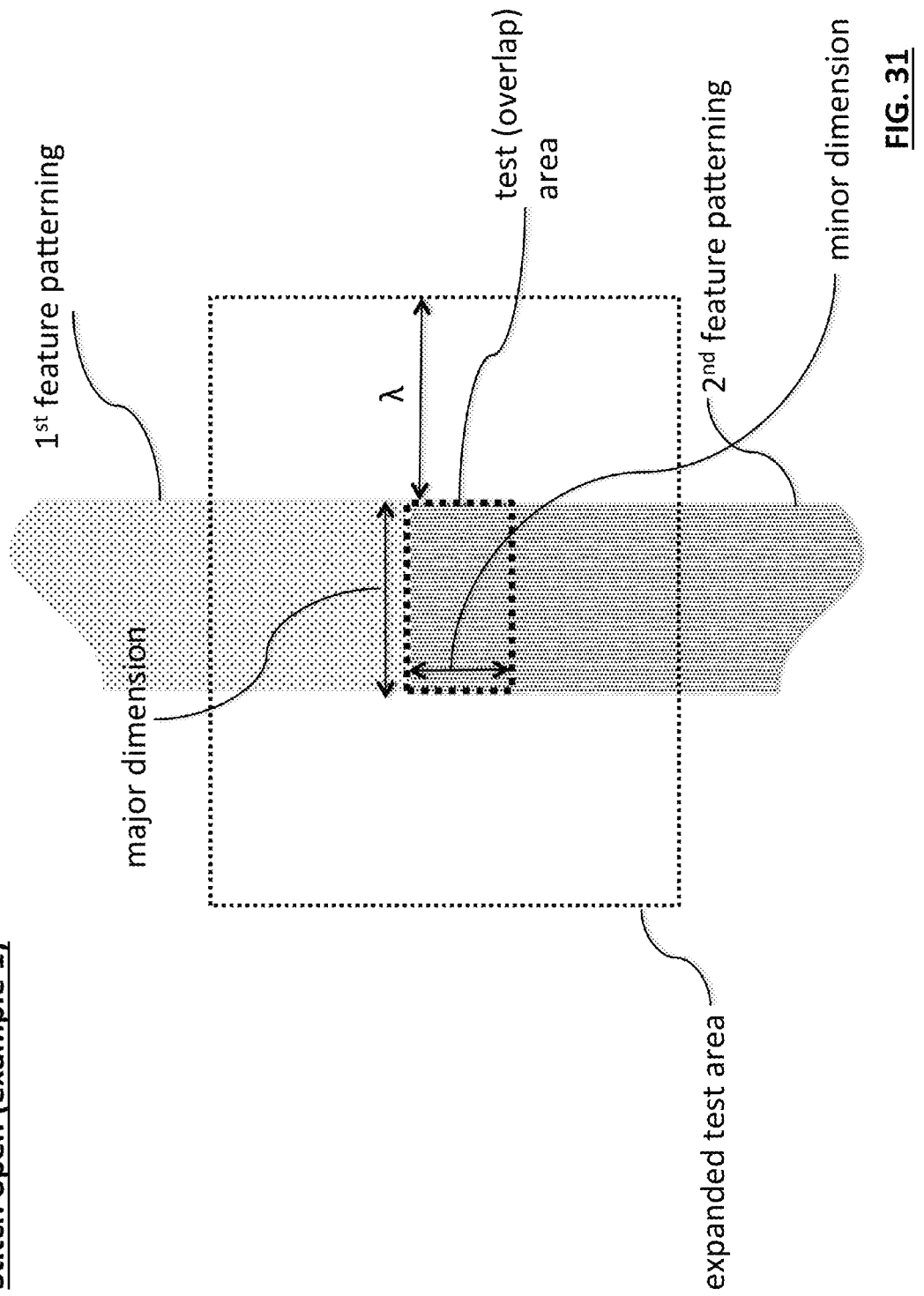
FIG. 31 depicts a plan view of exemplary test area geometry for an exemplary stitch-open-configured, NCEM-enabled fill cell.
Figure 32:
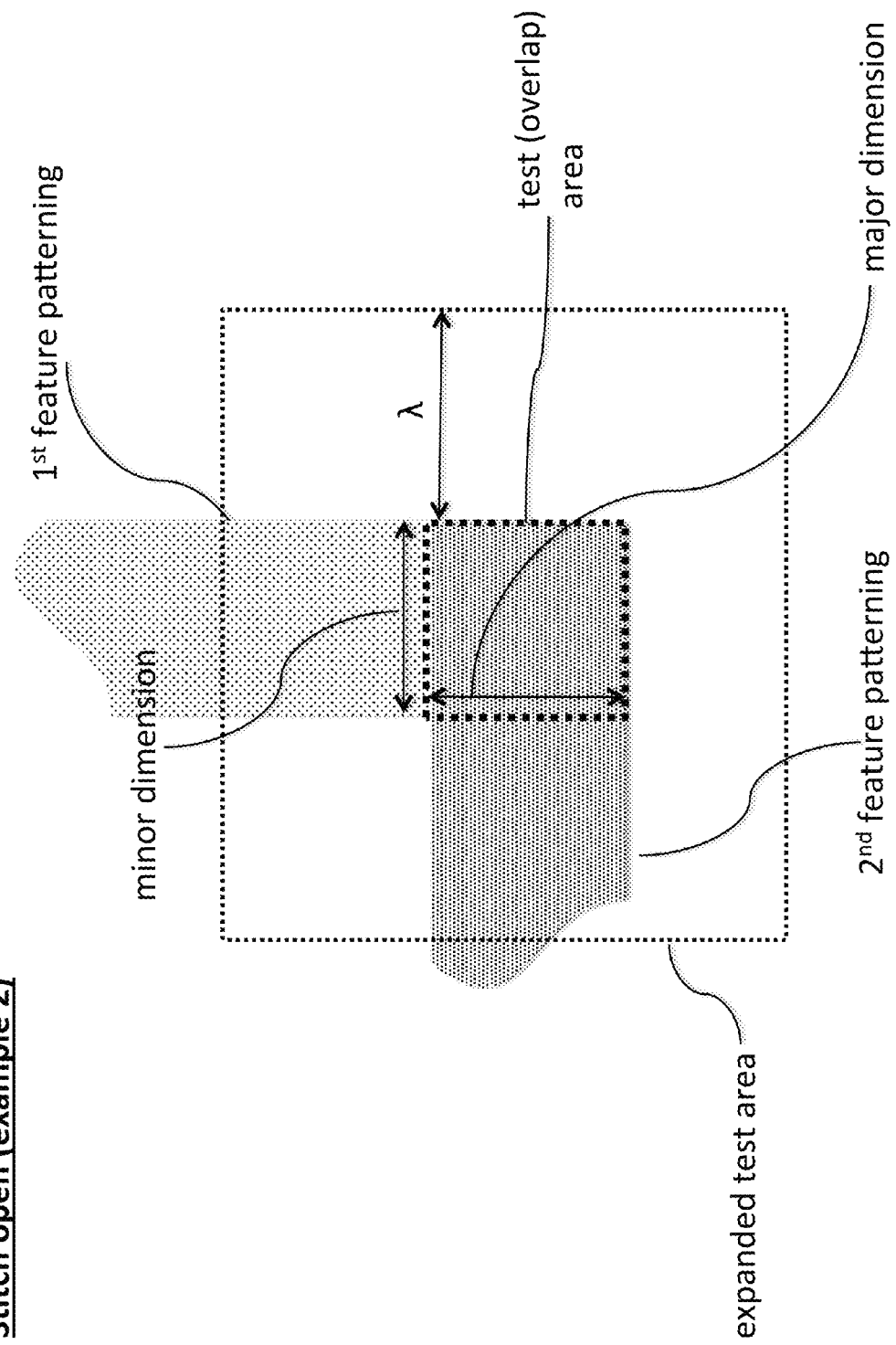
FIG. 32 depicts a plan view of exemplary test area geometry for another exemplary stitch-open-configured, NCEM-enabled fill cell.

Reference is now made to FIGS. 31-32, which each depict plan views of exemplary test area geometries for stitch-open-configured, NCEM-enabled fill cells. Cells that utilize these geometric configurations may include:
- AA-stitch-open-configured, NCEM-enabled fill cells;
- TS-stitch-open-configured, NCEM-enabled fill cells;
- AACNT-stitch-open-configured, NCEM-enabled fill cells;
- GATECNT-stitch-open-configured, NCEM-enabled fill cells;
- V0-stitch-open-configured, NCEM-enabled fill cells;
- M1-stitch-open-configured, NCEM-enabled fill cells [e.g., FIGS. 1072-1083];
- V1-stitch-open-configured, NCEM-enabled fill cells;
- M2-stitch-open-configured, NCEM-enabled fill cells;
- V2-stitch-open-configured, NCEM-enabled fill cells; and,
- M3-stitch-open-configured, NCEM-enabled fill cells.

DOEs of these structures are preferably constructed by varying the dimensional parameters that define the test area (e.g., major and/or minor dimension), or by varying other, same- or adjacent-layer patterning within the expanded test area.

Figure 33:
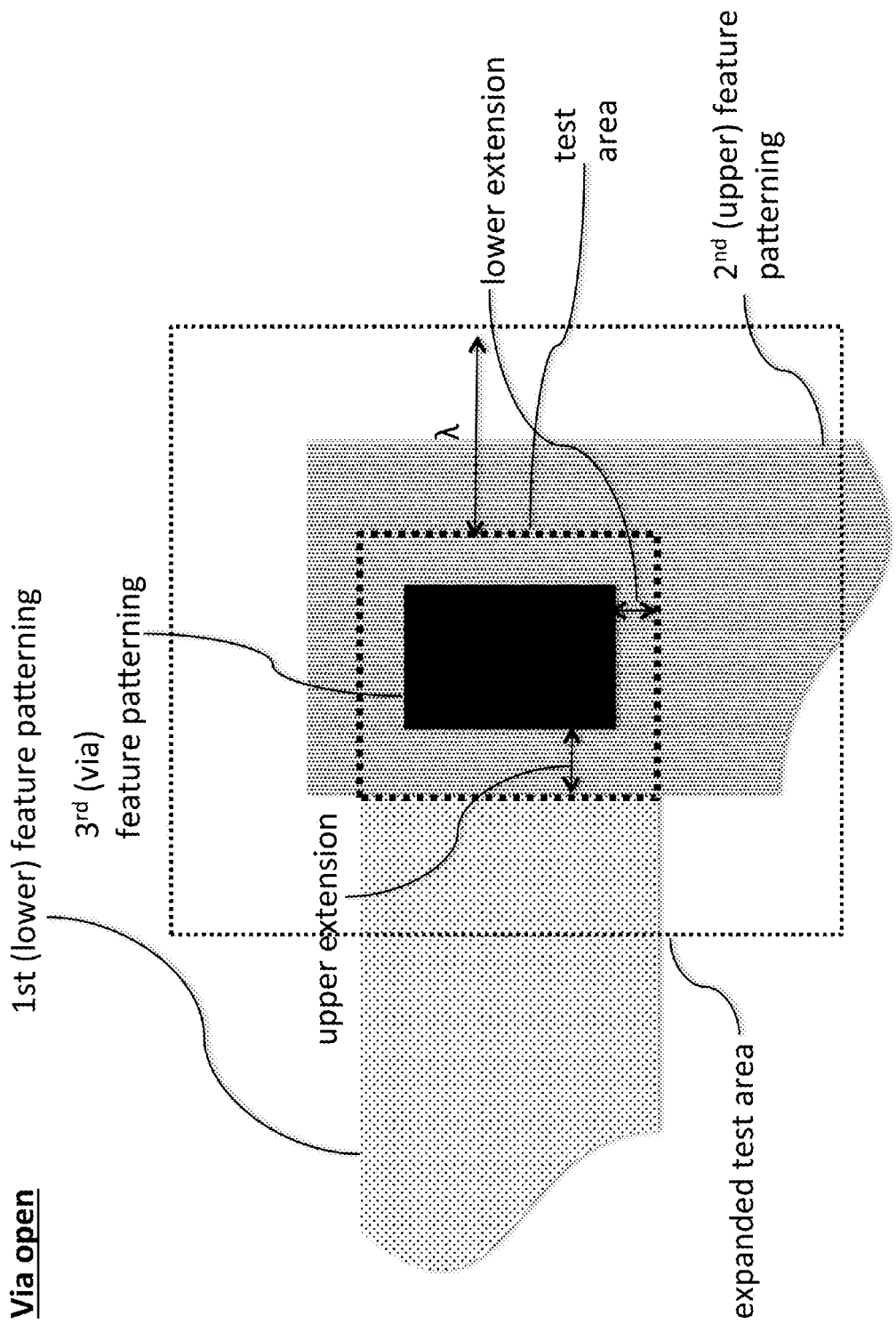
FIG. 33 depicts a plan view of exemplary test area geometry for an exemplary via-open-configured, NCEM-enabled fill cell.

Reference is now made to FIG. 33, which depicts a plan view of exemplary test area geometry for via-open-configured, NCEM-enabled fill cells. Cells that utilize this geometric configuration may include:
- AACNT-TS-via-open-configured, NCEM-enabled fill cells [e.g., FIGS. 1629-1673];
- AACNT-AA-via-open-configured, NCEM-enabled fill cells [FIGS. 1557-1628];
- TS-AA-via-open-configured, NCEM-enabled fill cells [e.g., FIGS. 2315-2330];
- GATECNT-GATE-via-open-configured, NCEM-enabled fill cells [e.g., FIGS. 48, 1699-2005];
- GATECNT-AACNT-via-open-configured, NCEM-enabled fill cells [e.g., FIGS. 1674-1682];
- GATECNT-AACNT-GATE-via-open-configured, NCEM-enabled fill cells [e.g., FIGS. 1683-1698];
- V0-GATECNT-via-open-configured, NCEM-enabled fill cells [e.g., FIGS. 2375-2439];
- V0-AA-via-open-configured, NCEM-enabled fill cells;
- V0-TS-via-open-configured, NCEM-enabled fill cells;
- V0-AACNT-via-open-configured, NCEM-enabled fill cells [e.g., FIGS. 2345-2374];
- V0-GATE-via-open-configured, NCEM-enabled fill cells;
- V0-via-open-configured, NCEM-enabled fill cells [e.g., FIGS. 2331-2344];
- M1-V0-via-open-configured, NCEM-enabled fill cells [e.g., FIGS. 2006-2200];
- V1-via-open-configured, NCEM-enabled fill cells [e.g., FIGS. 2440-2441];
- V1-M1-via-open-configured, NCEM-enabled fill cells [e.g., FIGS. 2442-2459];
- V1-M2-via-open-configured, NCEM-enabled fill cells [e.g., FIGS. 2221-2256];
- M1-GATECNT-via-open-configured, NCEM-enabled fill cells;
- M1-AANCT-via-open-configured, NCEM-enabled fill cells;
- V2-M2-via-open-configured, NCEM-enabled fill cells;
- V2-M3-via-open-configured, NCEM-enabled fill cells [e.g., FIGS. 2257-2274];
- V3-via-open-configured, NCEM-enabled fill cells [e.g., FIGS. 2460-2461];
- M4-V3-via-open-configured, NCEM-enabled fill cells [e.g., FIGS. 2275-2296]; and,
- M5-V4-via-open-configured, NCEM-enabled fill cells [e.g., FIGS. 2297-2314].

DOEs of these structures are preferably constructed by varying the dimensional parameters that define the test area (e.g., upper extension, lower extension, and/or via size/shape), or by varying other, same- or adjacent-layer patterning within the expanded test area.

Figure 34:
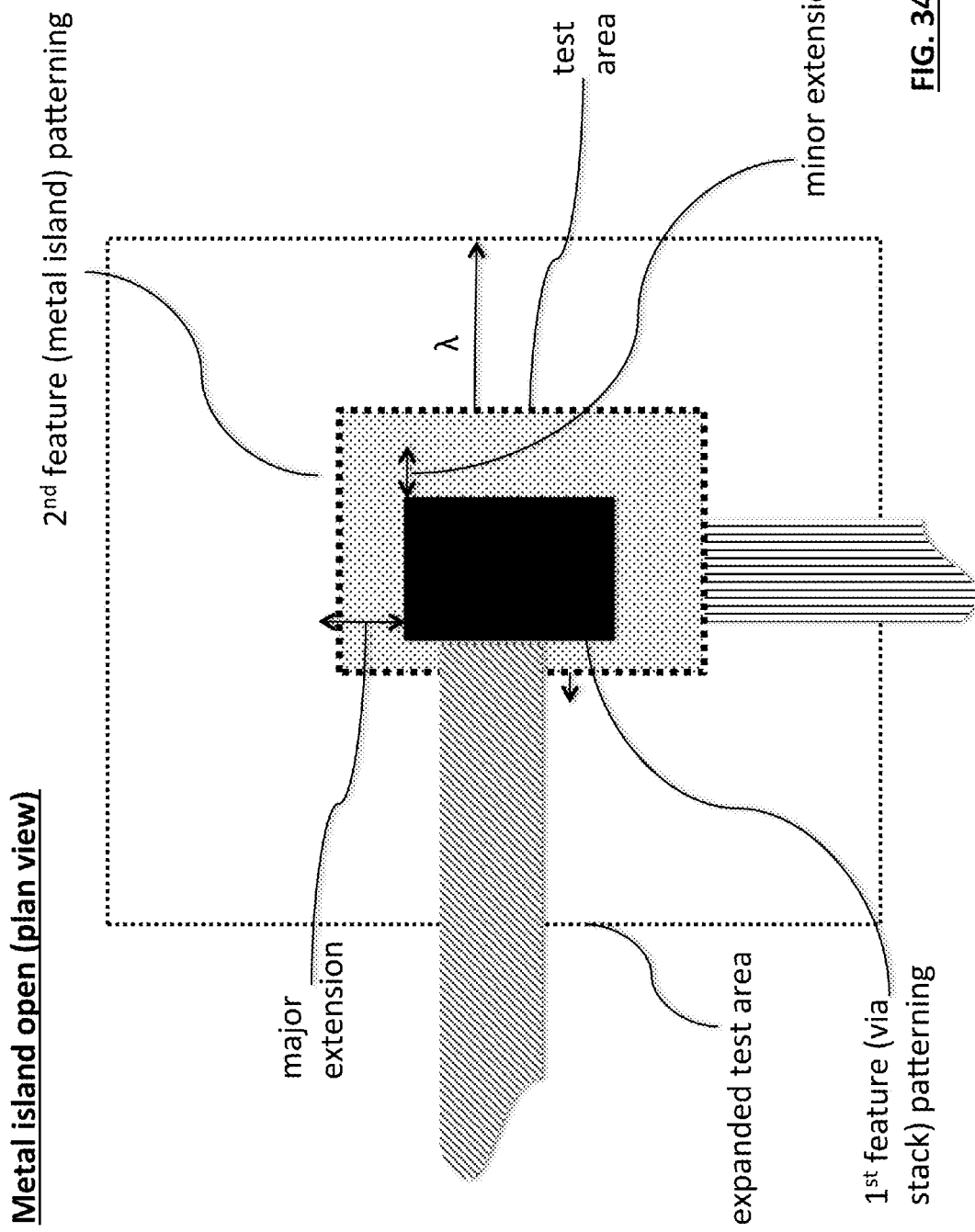
FIG. 34 depicts a plan view of exemplary test area geometry for an exemplary metal-island-open-configured, NCEM-enabled fill cell.
Figure 35:
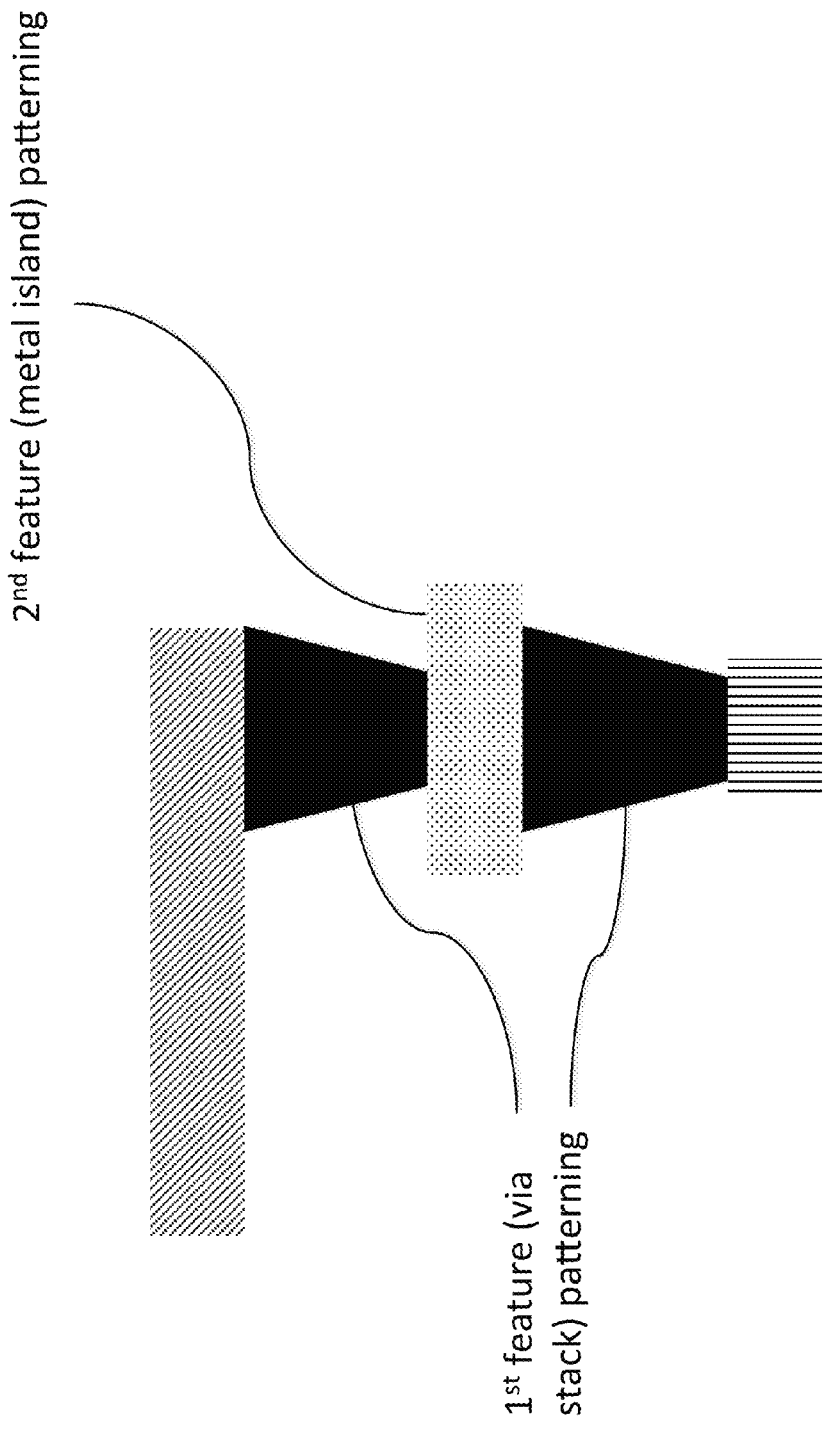
FIG. 35 depicts a cross-sectional view of exemplary test area geometry for the exemplary metal-island-open-configured, NCEM-enabled fill cell.

Reference is now made to FIGS. 34 and 35, which respectively depict plan and cross-sectional views of exemplary test area geometry for metal-island-open-configured, NCEM-enabled fill cells. Cells that utilize this geometric configuration may include:
- M1-metal-island-open-configured, NCEM-enabled fill cells;
- M2-metal-island-open-configured, NCEM-enabled fill cells; and,
- M3-metal-island-open-configured, NCEM-enabled fill cells.

DOEs of these structures are preferably constructed by varying the dimensional parameters that define the test area (e.g., major extension, minor extension, and/or size(s)/ shape(s) of lower and/or upper stacked vias), or by varying other, same- or adjacent-layer patterning within the expanded test area.

Figure 36:
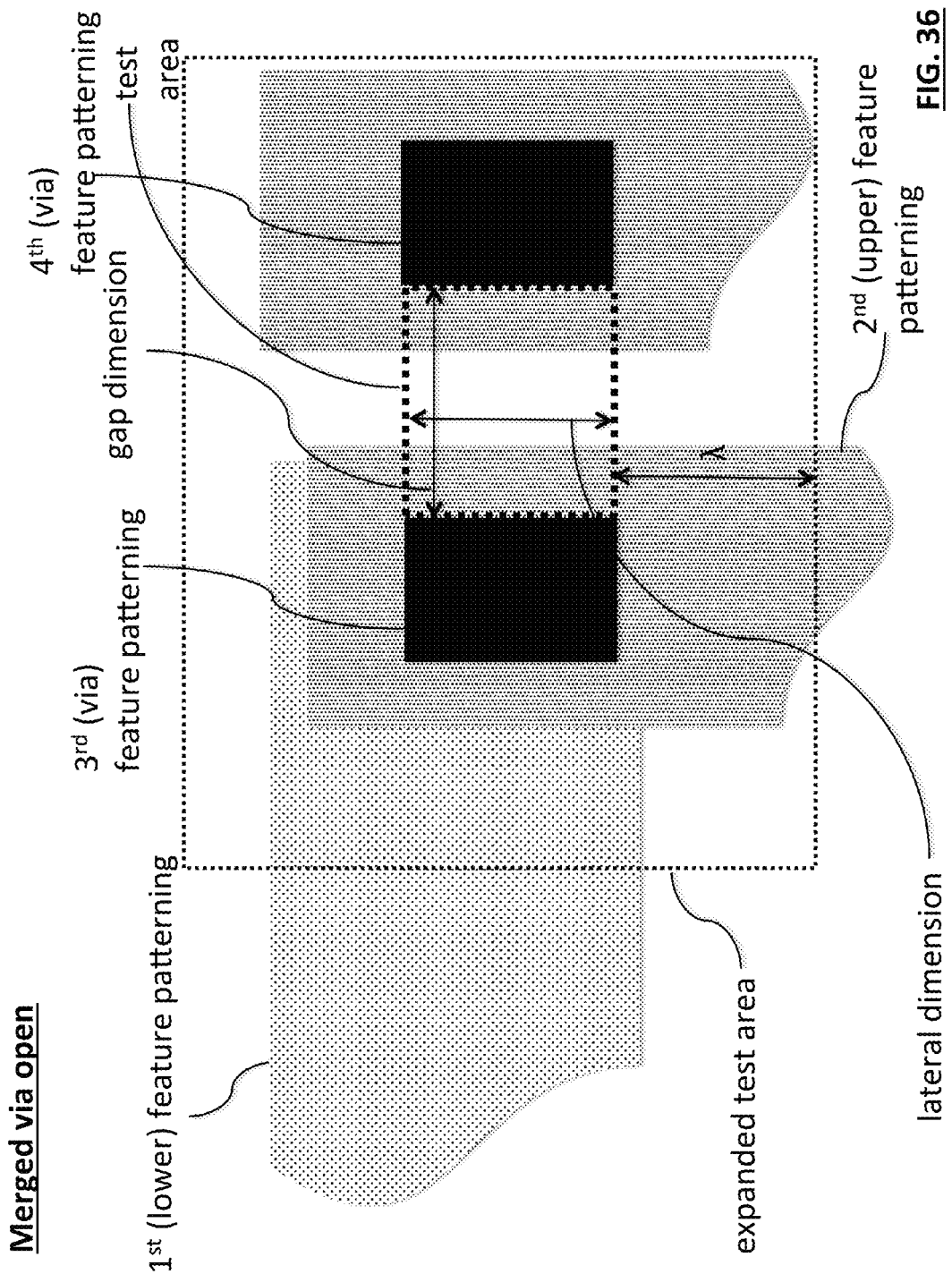
FIG. 36 depicts a plan view of exemplary test area geometry for an exemplary merged-via-open-configured, NCEM-enabled fill cell.

Reference is now made to FIG. 36, which depicts a plan view of exemplary test area geometry for merged-via-open-configured, NCEM-enabled fill cells. Cells that utilize this geometric configuration may include:

V0-merged-via-open-configured, NCEM-enabled fill cells [e.g., FIGS. 735-785];
V0-AACNT-merged-via-open-configured, NCEM-enabled fill cells;
V0-GATECNT-merged-via-open-configured, NCEM-enabled fill cells;
V1-merged-via-open-configured, NCEM-enabled fill cells;
V2-merged-via-open-configured, NCEM-enabled fill cells;
V1-M1-merged-via-open-configured, NCEM-enabled fill cells; and,
V2-M2-merged-via-open-configured, NCEM-enabled fill cells.

DOEs of these structures are preferably constructed by varying the dimensional parameters that define the test area (e.g., gap dimension, lateral dimension, and/or size/shape of one or both vias), or by varying other, same- or adjacent-layer patterning within the expanded test area.

Figure 37:
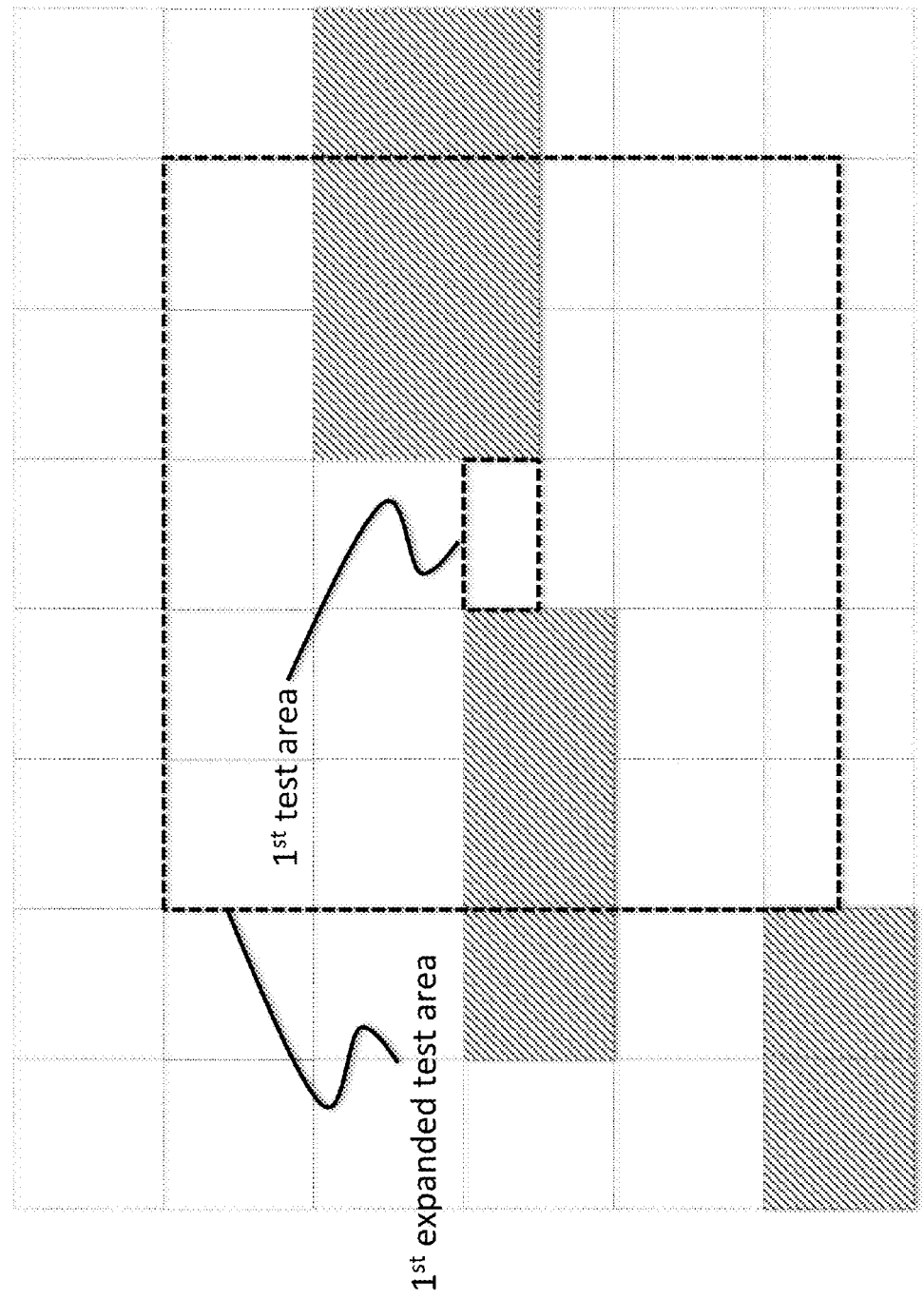
FIG. 37 shows exemplary expanded test area geometry from a $1^{st}$ variant of a NCEM-enabled fill cell.
Figure 38:
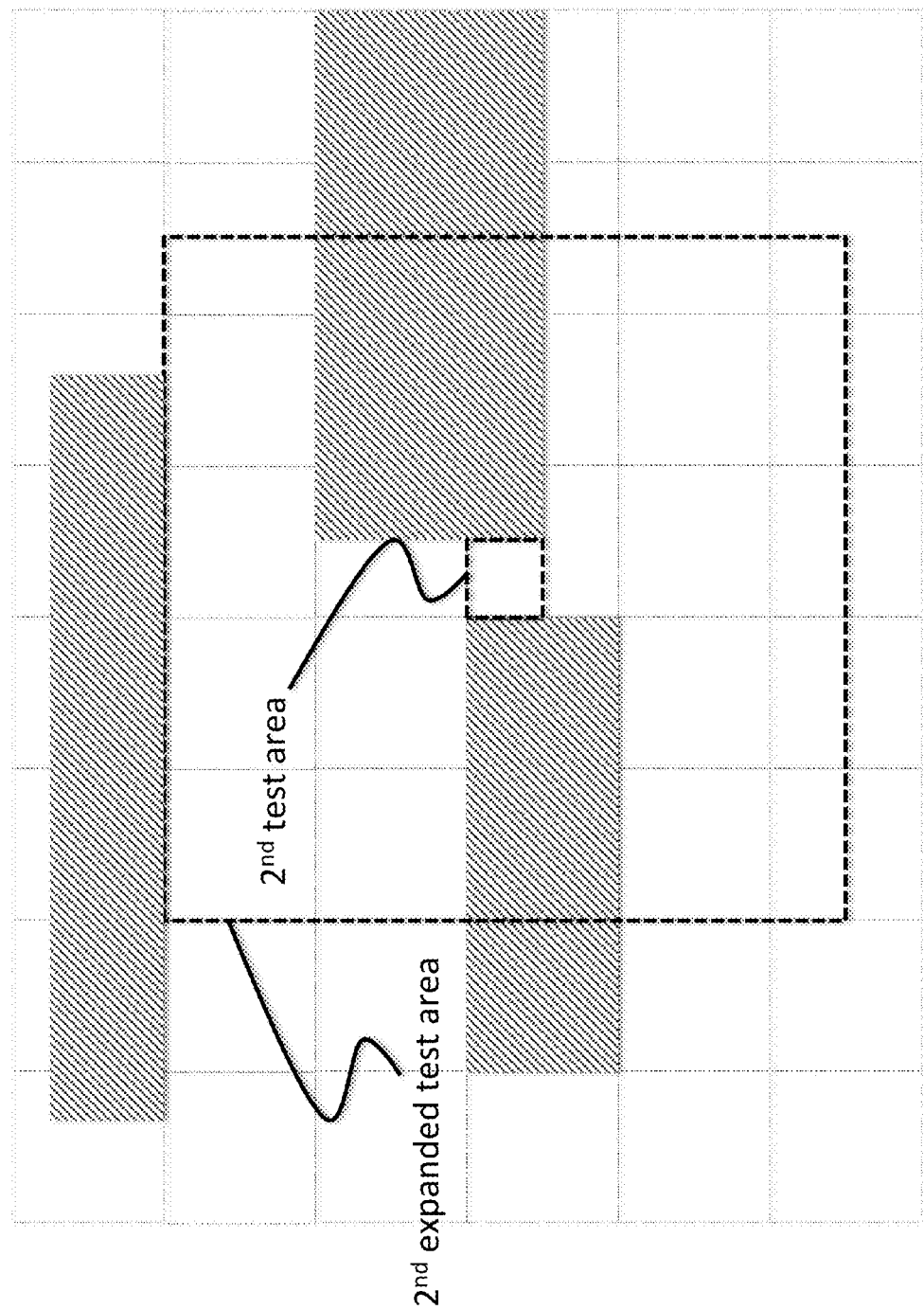
FIG. 38 shows exemplary expanded test area geometry from a $2^{nd}$ variant of a NCEM-enabled fill cell.
Figure 39:
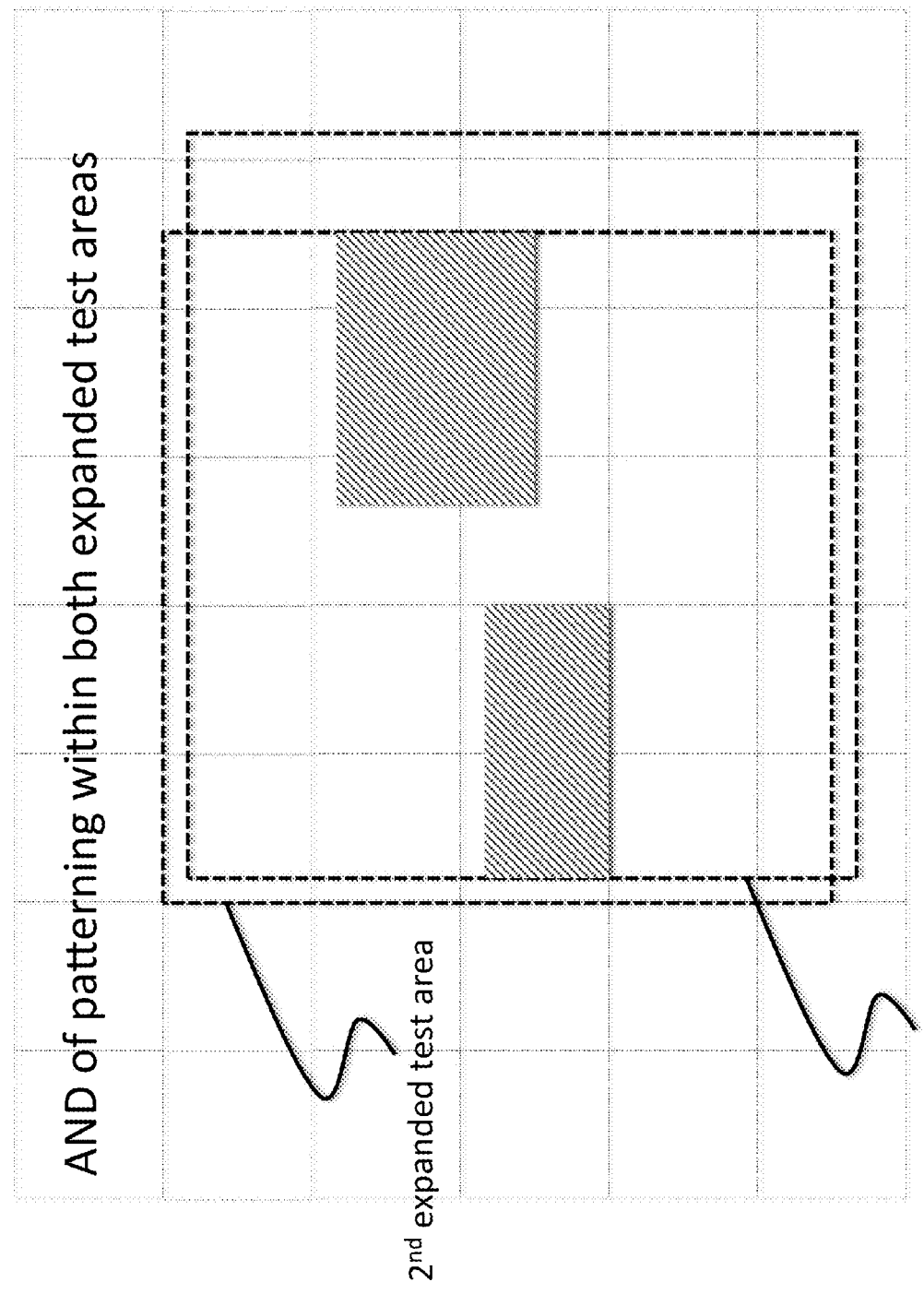
FIG. 39 shows the logical AND of patterning within both expanded test areas (of FIGS. 37 & 38)
Figure 40:
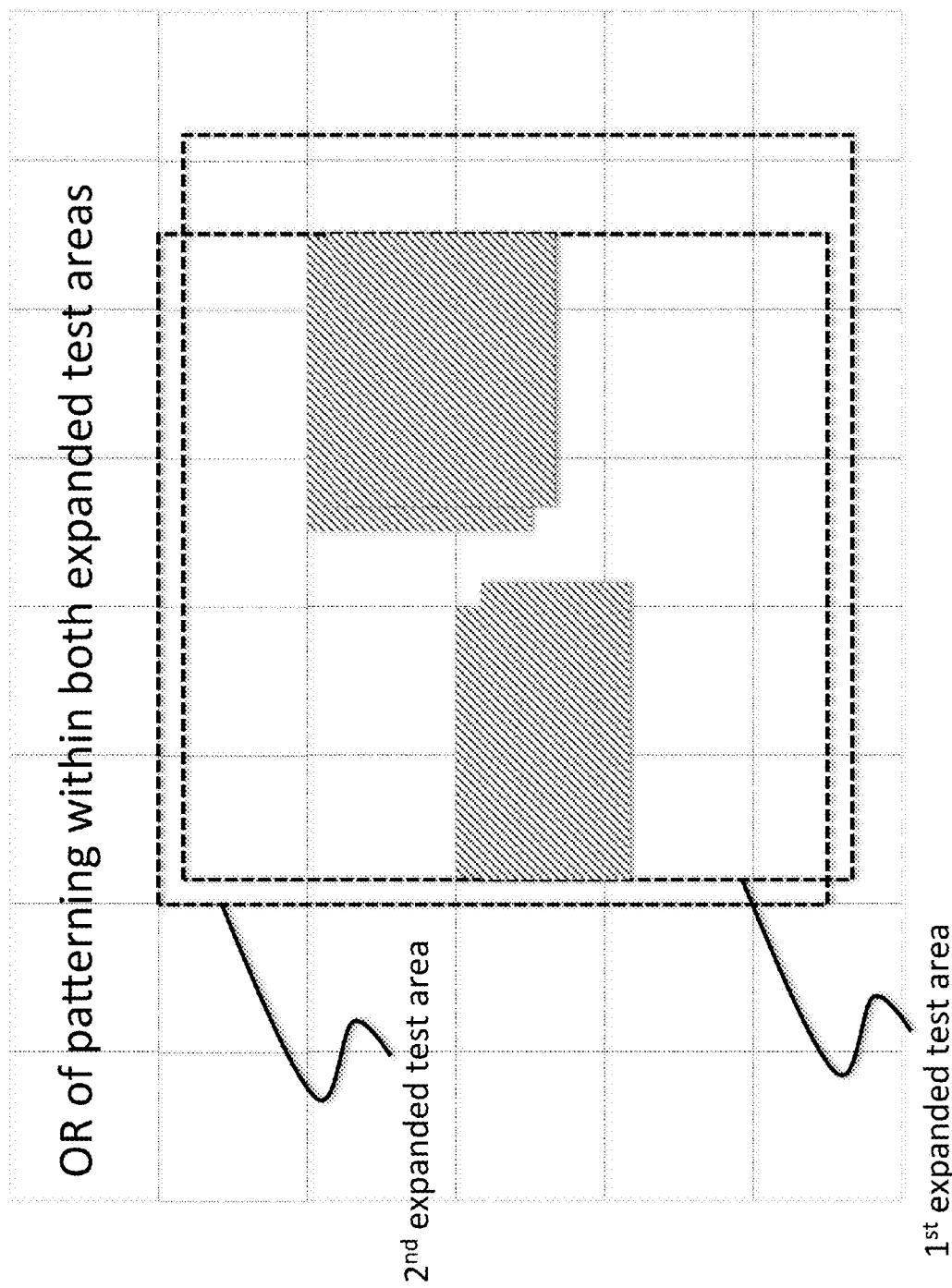

Reference is now made to FIG. 37, which shows exemplary expanded test area geometry from a $1^{st}$ variant of a NCEM-enabled fill cell, and to FIG. 38, which shows exemplary expanded test area geometry from a $2^{nd}$ variant of a NCEM-enabled fill cell. These figures, and the two that follow, illustrate the computation of the PSR between (the depicted layer, which could be any layer, of) the $1^{st}$ variant and the $2^{nd}$ variant. FIG. 39 shows the logical AND of (depicted layer) patterning within both expanded test areas (of FIGS. 37 & 38). FIG. 40 shows the logical OR of patterning within both expanded test areas (of FIGS. 37 & 38). The PSR (pattern similarity ratio) is then defined as the area ratio of the AND patterns to the OR patterns. Conceptually, PSR is a measure of how much of the patterning within the common expanded test areas is new. In other words, if the two cells are identical (within the layer(s)-at-issue, and within the common expanded test area), then the PSR will be 1.0. Conversely, if they share no common patterning (within the layer(s)-at-issue, and within the common expanded test area), then the AND patterns will be nil, and the PSR will be 0.0.

Figure 41:
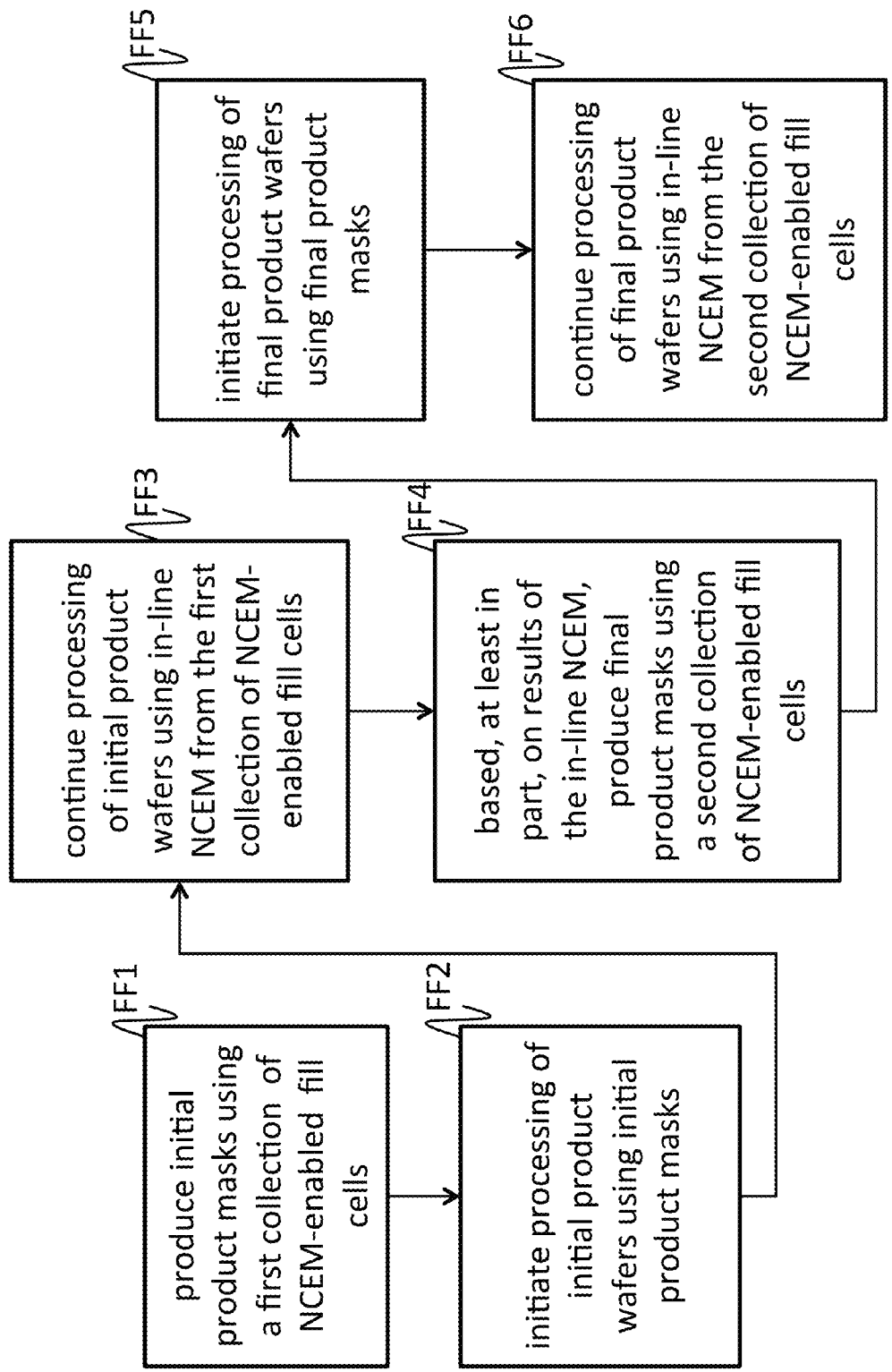

Reference is now made to FIG. 41, which depicts an exemplary process flow, suitable for use in connection with certain embodiments of the invention. At FF1, an initial set of product masks is produced (or otherwise obtained); these initial product masks include a first collection of NCEM-enabled fill cells.

At FF2, processing of wafers is initiated using the initial product masks. Such processing preferably includes at least FEOL and/or MOL processing, but may also include BEOL processing. Before FF3, NCEM measurements are preferably obtained from some or all of the NCEM-enabled fill cells on the partially-processed initial product wafers.

At FF3, some or all of the obtained NCEM measurements are "used" to continue processing of the initial product wafers. Such "use" may include determining whether to continue or abandon processing of one or more of the wafers, modifying one or more processing, inspection or metrology steps in the continued processing of one or more of the wafers (and/or other product wafers currently being manufactured using process flows relevant to observed manufacturing failures), and/or performing additional processing, metrology or inspection steps on one or more of the wafers (and/or other product wafers currently being manufactured using process flows relevant to observed manufacturing failures).

At FF4, final product masks are produced (or otherwise obtained) "using" at least some of the NCEM measurements obtained during the processing of initial product wafers. Here, such "use" preferably includes selecting and instantiating a second collection of NCEM-enabled fill cells that is better and/or optimally matched to failure modes observed during processing of the initial product wafers. For example, if the first collection of NCEM-enabled fill cells included GATE-side-to-side-short-configured cells, yet no GATE side-to-side shorts were observed during processing of the initial product wafers, then the second collection of NCEM-enabled fill cells would preferably omit GATE-side-to-side-short-configured cells, and instead replace them with other NCEM-enabled fill cells that are better matched to the observed or expected failure modes on the final product wafers.

At FF5, processing of wafers is initiated using the final product masks. Such processing preferably includes at least FEOL and/or MOL processing, but may also include BEOL processing. Before FF6, NCEM measurements are preferably obtained from some or all of the NCEM-enabled fill cells on the partially-processed final product wafers.

At FF6, some or all of the obtained NCEM measurements are "used" to continue processing of the final product wafers. Such "use" may include determining whether to continue or abandon processing of one or more of the wafers, modifying one or more processing, inspection or metrology steps in the continued processing of one or more of the wafers (and/or other product wafers currently being manufactured using process flows relevant to observed manufacturing failures), and/or performing additional processing, metrology or inspection steps on one or more of the wafers (and/or other product wafers currently being manufactured using process flows relevant to observed manufacturing failures).

Figure 42:
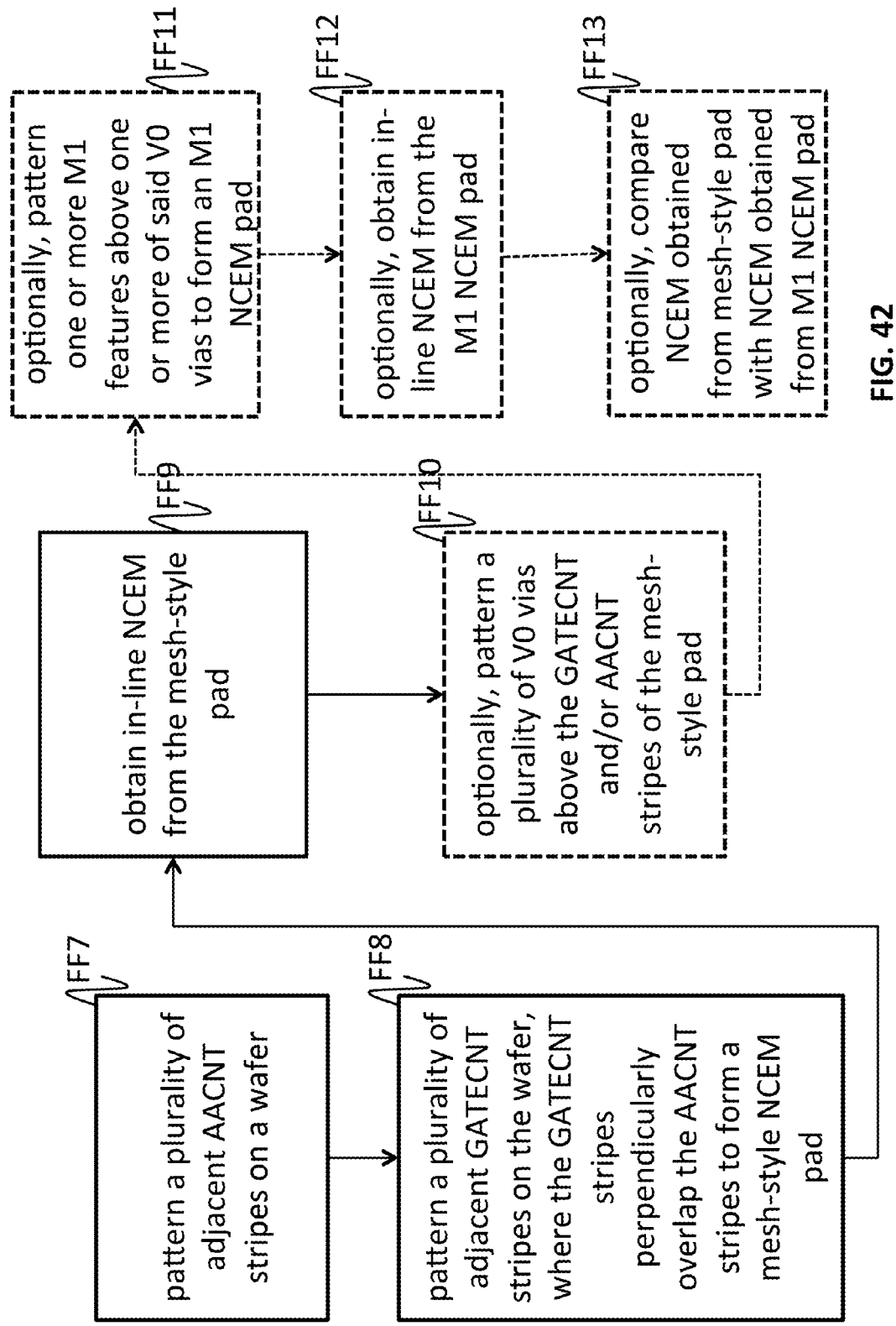

Reference is now made to FIG. 42, which depicts an exemplary process flow for obtaining and (optionally) using measurements from mesh-style NCEM pads. As persons skilled in the art will appreciate, this process can be utilized either with or without NCEM-enabled fill cells; in other words, the mesh-style NCEM pads can be instantiated within NCEM-enabled fill cells, but can also be instantiated anywhere on a chip, die, or wafer. Furthermore, as persons skilled in the art will also appreciate, the order of steps FF7 & FF8 can be reversed, or performed simultaneously, to accommodate processes where the order of AACNT & GATECNT patterning is different.

Figure 43:
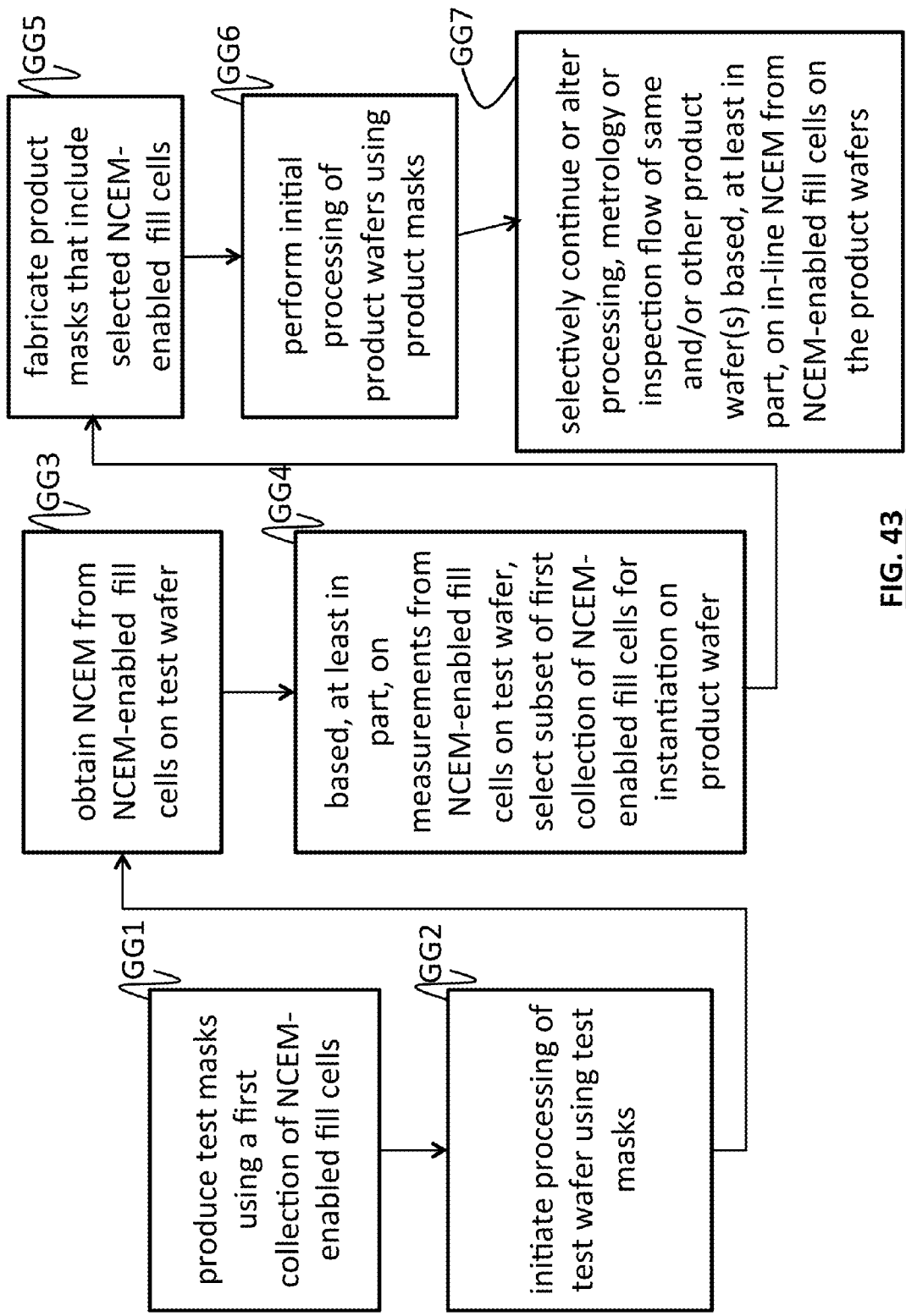

Reference is now made to FIG. 43, which depicts another exemplary process flow, suitable for use in accordance with certain embodiments of the invention. At GG1, test mask (e.g., masks to produce a "test" or "engineering" wafer) are produced or otherwise obtained; such test masks include a first collection of NCEM-enabled fill cells.

At GG2, processing of the test wafer(s) is initiated. Such processing preferably includes FEOL and/or MOL processing, but may also include BEOL processing.

At GG3, NCEM measurements are obtained from NCEM-enabled fill cells on the partially-processed test wafer(s).

At GG4, the obtained measurements are "used" to select a second collection of NCEM-enabled fill cells (preferably a subset of the first collection) for instantiation on product wafers. Here, such "use" preferably includes selecting a second collection of NCEM-enabled fill cells that, given the available fill cell space on the product wafers, is optimally matched to failure modes observed during processing of the test product wafers. For example, if the first collection of NCEM-enabled fill cells included GATE-side-to-side-short-configured cells, yet no GATE side-to-side shorts were observed during processing of test wafers, then the second collection of NCEM-enabled fill cells would preferably omit GATE-side-to-side-short-configured cells.

At GG5, product masks that include the second collection of NCEM-enabled fill cells are produced, or otherwise obtained.

At GG6, processing of the product wafer(s) is initiated. Such processing preferably includes at least FEOL and/or MOL processing, but may also include BEOL processing. Prior to GG7, NCEM measurements are obtained from at least some of the NCEM-enabled fill cells on the partially-processed product wafer(s).

At GG7, some or all of the obtained NCEM measurements are "used" to continue processing of the product wafer(s). Such "use" may include determining whether to continue or abandon processing of one or more of the product wafers, modifying one or more processing, inspection or metrology steps in the continued processing of one or more of the product wafers (and/or other product wafers currently being manufactured using process flows relevant to observed manufacturing failures), and/or performing additional processing, metrology or inspection steps on one or more of the product wafers (and/or other product wafers currently being manufactured using process flows relevant to observed manufacturing failures).

In certain embodiments, FF1-3 and/or GG5-7 could be practiced as stand-alone process flows.

Figure 44:
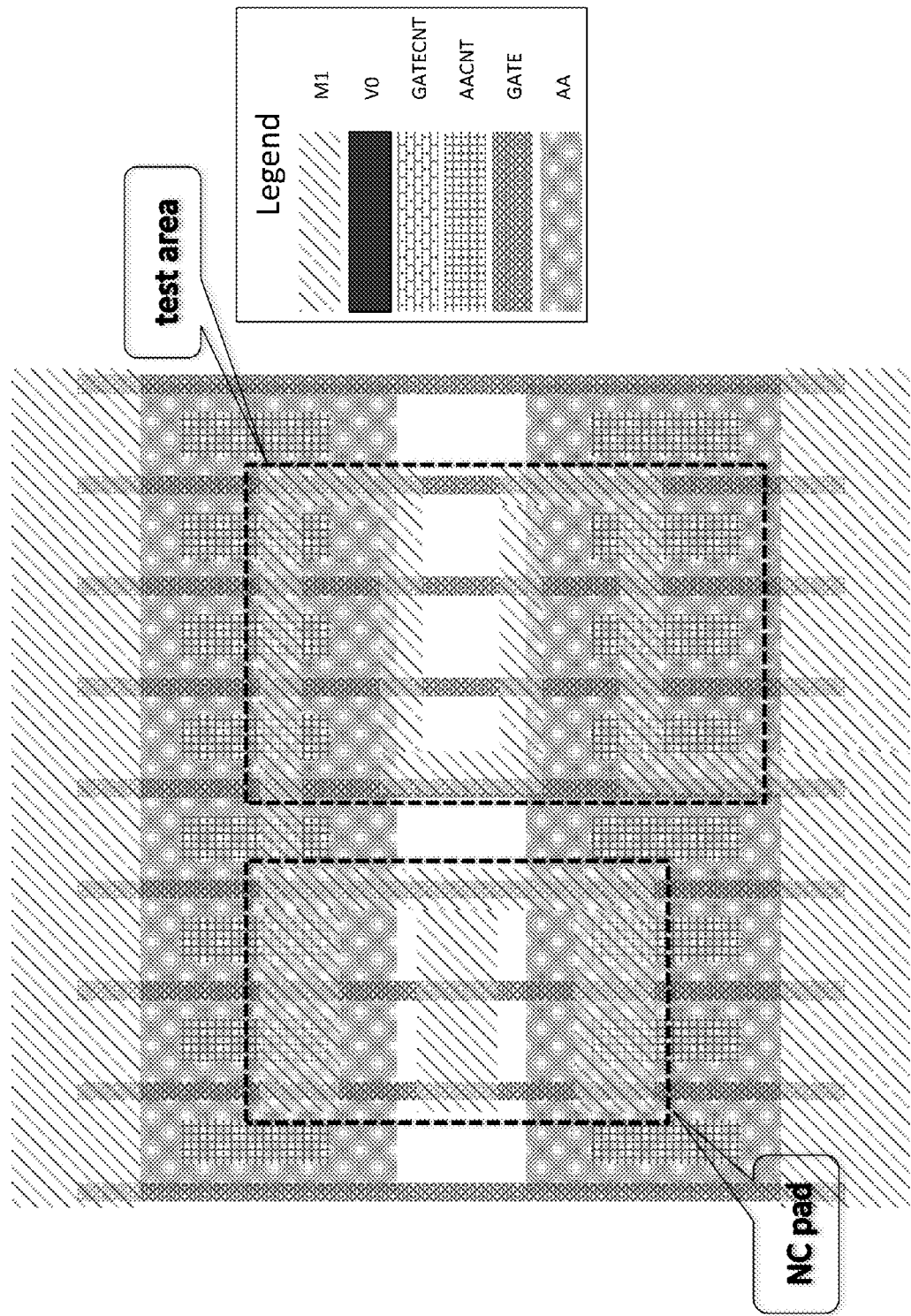

Reference is now made to FIG. 44, which depicts a plan view of an exemplary M1-snake-open-configured, NCEM-enabled fill cell. This cell contains a left-facing-E-shaped NCEM pad, a snake-open-configured test area, and is NCEM-enabled to detect the following failure mode: M1 snake open. In the depicted configuration, a passing response is grounded metal=bright NCEM, whereas a failing response is floating pad=dark NCEM.

Figure 45:
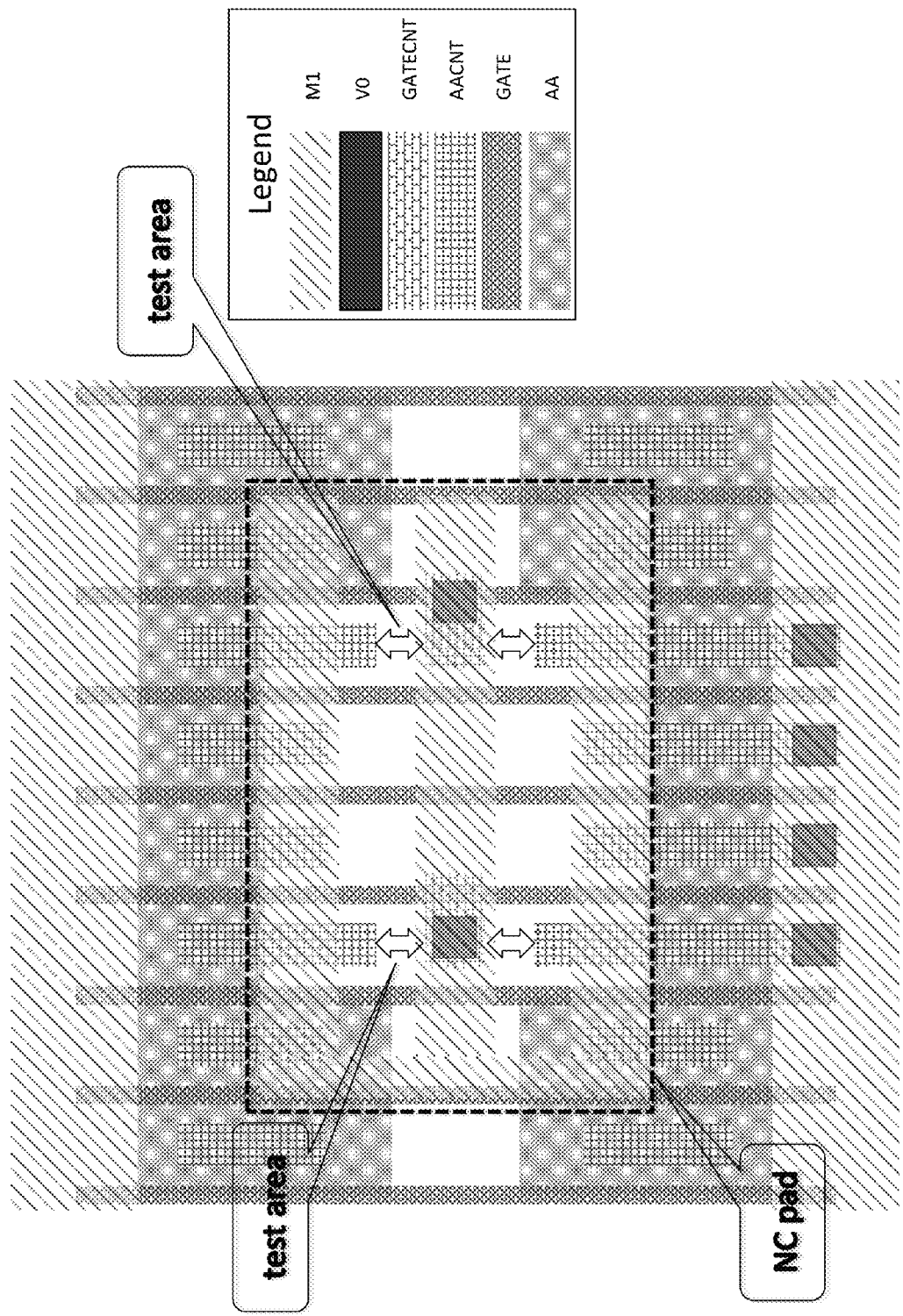

Reference is now made to FIG. 45, which depicts a plan view of an exemplary AACNT-tip-to-side-short-configured, NCEM-enabled fill cell. This cell contains four test areas, and an E-shaped NCEM pad that overlies the test areas. It is NC-configured for inline measurement of the following failure mode: AACNT tip-to-side short. In the depicted configuration, a passing response is floating AA contacts=dark NCEM, whereas a failing response is a short to grounded contact layer=bright NCEM.

Reference is now made to FIGS. 46A-C, which respectively depict plan views of—(A) all layers; (B) NWELL, AA, GATE, GATECNT, TS, and AACNT layers; (C) V0 and M1 layers—of an exemplary TS-GATE-side-to-side-short-configured, NCEM-enabled fill cell of type PDF_D_VCI_V16_14S1_01. This cell utilizes a composite NCEM pad, as depicted in FIG. 9E.

Reference is now made to FIGS. 47A-C, which respectively depict plan views of—(A) all layers; (B) NWELL, AA, GATE, GATECNT, TS, and AACNT layers; (C) V0 and M1 layers—of an exemplary GATECNT-AACNT-side-to-side-short-configured, NCEM-enabled fill cell of type PDF_D_VCI_V16_14S1_05. This cell also utilizes a composite NCEM pad.

Reference is now made to FIGS. 48A-C, which respectively depict plan views of—(A) all layers; (B) NWELL, AA, GATE, GATECNT, TS, and AACNT layers; (C) V0 and M1 layers—of an exemplary GATECNT-GATE-via-open-configured, NCEM-enabled fill cell of type PDF_D_VCI_V16_14S1_08. This cell also utilizes a composite NCEM pad.

Reference is now made to FIGS. 49A-C, which respectively depict plan views of—(A) all layers; (B) NWELL, AA, GATE, GATECNT, TS, and AACNT layers; (C) V0 and M1 layers—of an exemplary GATE-AA-tip-to-side-short-configured, NCEM-enabled fill cell of type PDF_D_VCI_V16_14S1_11. This cell also utilizes a composite NCEM pad.

Reference is now made to FIGS. 50(A)-(C), which respectively depict plan views of—(A) all layers; (B) NWELL, AA, GATE, GATECNT, TS, and AACNT layers; (C) V0 and M1 layers—of another exemplary GATE-AA-tip-to-side-short-configured, NCEM-enabled fill cell of type PDF_D_VCI_V16_14S1_12. This cell also utilizes a composite NCEM pad.

Certain of the claims that follow may contain one or more means-plus-function limitations of the form, "a<cell name> means for enabling NC detection of a GATE-tip-to-tip short." It is applicant's intent that such limitations be construed, pursuant to 35 U.S.C. § 112(f), as "the structure of the named cell, or an equivalent structure, that enables detection of a GATE-tip-to-tip short by non-contact measurement."

Additionally, certain of the claims that follow may contain one or more step-plus-function limitations of the form, "a<cell name> step for enabling NC detection of a GATE-tip-to-tip short." It is applicant's intent that such limitations be construed, pursuant to 35 U.S.C. § 112(f), as "enabling voltage contrast detection of a GATE-tip-to-tip short by patterning an instance of the named cell, or an equivalent cell."

While the invention has been illustrated with respect to one or more specific implementations, numerous alterations and/or modifications can be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular application. Furthermore, to the extent that the terms "including," "includes," "having," "has," "with," or variants thereof are used in either the detailed description or the claims, such terms are intended to be inclusive in a manner similar to the term "comprising." As used herein, the phrase "X comprises one or more of A, B, and C" means that X can include any of the following: either A, B, or C alone; or combinations of two, such as A and B, B and C, and A and C; or combinations of three A, B and C.

What we claim in this application is:

1. A method for processing a semiconductor substrate, comprising at least the following steps:
   using one or more mask(s) to pattern a plurality of adjacent source/drain contact (AACNT) stripes on the substrate;
   using one or more mask(s) to pattern a plurality of adjacent gate contact (GATECNT) stripes on the substrate;
   wherein the GATECNT stripes perpendicularly intersect the AACNT stripes to form a mesh-style non-contact electrical measurement (NCEM) pad; and
   after forming the NCEM pad, obtaining in-line NCEM from the mesh-style NCEM pad.

2. A method for processing a semiconductor substrate, as defined in claim 1, further comprising at least the following additional steps:
- using one or more mask(s) to pattern a plurality of via to interconnect stack (V0) vias above at least some of the GATECNT and/or AACNT stripes of the mesh-style NCEM pad; and,
- using one or more mask(s) to pattern one or more first wiring layer (M1) features above one or more of said V0 vias to form an M1 NCEM pad.

3. A method for processing a semiconductor substrate, as defined in claim 2, further comprising at least the following additional step:
- obtaining in-line NCEM from the M1 NCEM pad.

* * * * *